(12) United States Patent
Curtis et al.

(10) Patent No.: US 6,727,249 B2
(45) Date of Patent: Apr. 27, 2004

(54) AZABICYCLIC ETHER DERIVATIVES AND THEIR USE AS THERAPEUTIC AGENTS

(75) Inventors: Neil Roy Curtis, Buntingford (GB); Ian Thomas Huscroft, Bishops Stortford (GB); Janusz Jozef Kulagowski, Sawbridgeworth (GB); Piotr Antoni Raubo, Bishops Stortford (GB)

(73) Assignee: Merck Sharp & Dohme Ltd., Hoddesdon (GB)

( * ) Notice: Subject to any disclaimer, the term of this patent is extended or adjusted under 35 U.S.C. 154(b) by 33 days.

(21) Appl. No.: 10/113,117

(22) Filed: Apr. 1, 2002

(65) Prior Publication Data

US 2002/0193402 A1 Dec. 19, 2002

(30) Foreign Application Priority Data

Apr. 10, 2001 (GB) .............................. 0108982

(51) Int. Cl.[7] .................... A61K 31/535; A61K 31/445; A61K 31/497; A61K 31/47; C07D 401/00
(52) U.S. Cl. ............... 514/237.2; 514/323; 514/252.18; 514/318; 544/362; 544/323; 546/183
(58) Field of Search ................................ 546/112, 183; 514/323, 318, 252.18, 273, 237.2; 544/323, 326, 362, 111

(56) References Cited

U.S. PATENT DOCUMENTS

| 5,242,930 A | 9/1993 | Baker et al. |
| 5,288,730 A | 2/1994 | Baker et al. |

FOREIGN PATENT DOCUMENTS

| GB | 2268 931 | 1/1994 |
| GB | 2269 170 | 2/1994 |
| WO | WO 97/03066 | 1/1997 |
| WO | WO 00/68224 | 11/2000 |

OTHER PUBLICATIONS

"N–Heteroaryl–2–phenyl–3–(benzyloxy)piperidines: A Novel Class of Potent Orally Active Human NK1 Antagonists", J. Med. Chem. 1996, 39, pp. 2907–2914.*
U.S. patent application Ser. No. 10/115,629, Muscroft et al. filed Apr. 01, 2002.
U.S. patent application Ser. No. 10/113,965, Kulagwski et al. Apr. 01, 2002.

* cited by examiner

Primary Examiner—D. Margaret Seaman
Assistant Examiner—Kinta Robinson
(74) Attorney, Agent, or Firm—J. Eric Thies; Melvin Winokur

(57) ABSTRACT

The present invention relates compounds of the formula (I):

(I)

wherein
X represents hydrogen, $C_{1-4}$alkyl optionally substituted by a hydroxy, methoxy or benzyloxy group, or $CO_2$ ($C_{1-2}$alkyl);
Z is —$CR^9R^{10}CH_2$— or —$CH_2CR^9R^{10}$—;
and $R^1$, $R^2$, $R^3$, $R^4$, $R^5$ and $R^6$ are as defined herein.

The compounds are of particular use in the treatment or prevention of depression, anxiety, pain, inflammation, migaine, emesis or postherpetic neuralgia.

16 Claims, No Drawings

AZABICYCLIC ETHER DERIVATIVES AND THEIR USE AS THERAPEUTIC AGENTS

CROSS REFERENCE TO RELATED APPLICATIONS

This application claims priority under 35 U.S.C. §119 from GB Application No. 0108982.0, filed Apr. 10, 2001.

This invention relates to a class of azabicyclic compounds which are useful as tachykinin antagonists. More particularly, the compounds of the invention are substituted benzylether derivatives of 1-phenyl-8-azabicyclo[3.2.1] octane, which are useful as neurokinin 1 (NK-1) receptor antagonists.

The present invention provides compounds of the formula (I):

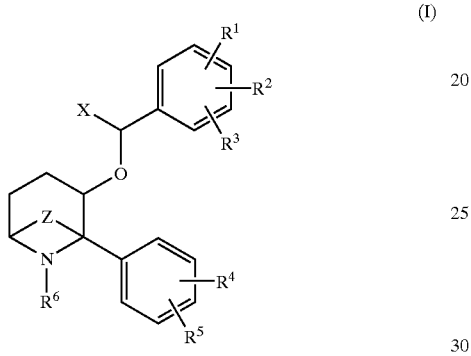

wherein

X represents hydrogen, $C_{1-4}$alkyl optionally substituted by a hydroxy, methoxy or benzyloxy group, or $CO_2$($C_{1-2}$alkyl);

Z is —$CR^9R^{10}CH_2$— or —$CH_2CR^9R^{10}$—;

$R^1$ is hydrogen, halogen, $C_{1-6}$alkyl, $C_{1-6}$alkoxy, fluoro$C_{1-6}$alkyl, fluoro$C_{1-6}$alkoxy, $C_{3-7}$cycloalkyl, $C_{3-7}$cycloalkyl$C_{1-4}$alkyl, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, wherein $R^a$ and $R^b$ each independently represent hydrogen or $C_{1-4}$alkyl;

$R^2$ is hydrogen, halogen, $C_{1-6}$alkyl, fluoro$C_{1-6}$alkyl or $C_{1-6}$alkoxy substituted by $C_{1-4}$alkoxy;

$R^3$ is hydrogen, halogen or fluoro$C_{1-6}$alkyl;

$R^4$ represents hydrogen, halogen, $C_{1-6}$alkyl, $C_{1-6}$alkoxy, $CF_3$, $OCF_3$, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, where $R^a$ and $R^b$ are as previously defined;

$R^5$ represents hydrogen, halogen, $C_{1-6}$alkyl, $CF_3$ or $C_{1-6}$alkoxy substituted by $C_{1-4}$alkoxy;

$R^6$ represents hydrogen, hydroxy, $COR^a$, $CO_2R^a$, $COCONR^aR^b$, $COCO_2R^a$, $C_{1-6}$alkyl, $C_{2-6}$alkenyl, or $C_{1-6}$alkyl substituted by a group selected from $CO_2R^a$, $CONR^aR^b$, hydroxy, CN, $COR^a$, $NR^aR^b$, C(NOH) $NR^aR^b$, CONHphenyl($C_{1-4}$alkyl), $COCO_2R^a$, $CONHNR^aR^b$, $C(S)NR^aR^b$, $CONR^aC_{1-6}$alkyl$R^{14}$, $CONR^{11}C_{2-6}$alkenyl, $CONR^{11}C_{2-6}$alkynyl, $COCONR^aR^b$, $CONR^aC(NR^b)NR^aR^b$, $CONR^a$heteroaryl, and phenyl optionally substituted by one, two or three substituents selected from $C_{1-6}$alkyl, $C_{1-6}$alkoxy, halogen and trifluoromethyl;

or $R^6$ represents a group of the formula —$CH_2C\equiv CCH_2NR^7R^8$ where $R^7$ and $R^8$ are as defined below;

or $R^6$ represents $C_{1-6}$alkyl, optionally substituted by oxo, substituted by a 5-membered or 6-membered heterocyclic ring containing 1, 2 or 3 nitrogen atoms optionally substituted by =O or =S and optionally substituted by a group of the formula —Y—$NR^7R^8$ where Y is $C_{1-6}$alkylene or $C_{3-6}$cycloalkyl;

$R^7$ represents hydrogen or $C_{1-4}$alkyl, $C_{3-7}$cycloalkyl, $C_{3-7}$cycloalkyl$C_{1-4}$alkyl, or $C_{2-4}$alkyl substituted by $C_{1-4}$alkoxy or hydroxyl;

$R^8$ represents hydrogen or $C_{1-6}$alkyl, $C_{1-6}$alkoxy, $C_{3-7}$cycloalkyl, $C_{3-7}$cycloalkyl$C_{1-4}$alkyl, phenyl or $C_{1-4}$alkyl substituted by a group selected from $C_{1-4}$alkoxy, hydroxyl, $CO_2R^a$, $NR^aR^b$, aryl, aryloxy, heteroaryl or a 4, 5 or 6 membered heteroaliphatic ring containing one or two heteroatoms selected from N, O and S;

or $R^7$, $R^8$ and the nitrogen atom to which they are attached form a heteroaliphatic ring of 4 to 7 ring atoms, optionally substituted by one or two groups selected from methyl, hydroxy, $CO_2(C_{1-2}$alkyl), phenyl, benzyl or $C_{1-4}$alkoxy optionally substituted by a $C_{1-4}$alkoxy or hydroxyl group, and optionally containing a double bond, which ring may optionally contain an oxygen or sulphur ring atom, a group S(O) or $S(O)_2$ or a second nitrogen atom which will be part of a NH or $NR^c$ moiety where $R^c$ is $C_{1-4}$alkyl, hydroxy$C_{1-4}$alkyl, $C_{1-4}$alkoxy$C_{1-4}$alkyl, phenyl or benzyl;

or $R^7$, $R^8$ and the nitrogen atom to which they are attached form a non-aromatic azabicyclic ring system of 6 to 12 ring atoms;

or Y, $R^7$ and the nitrogen atom to which they are attached form a heteroaliphatic ring to 4 to 7 ring atoms which may optionally contain an oxygen ring atom;

$R^9$ represents hydrogen, hydroxy, oxo, $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, fluoro$C_{1-6}$alkyl, $C_{1-6}$alkoxy, fluoro$C_{1-6}$alkoxy, hydroxy$C_{1-6}$alkyl, $C_{1-6}$alkoxy $C_{1-4}$alkyl, $C_{1-6}$alkoxy$C_{1-4}$alkoxy, fluoro$C_{1-6}$alkoxy $C_{1-4}$alkyl, $C_{2-6}$alkenyloxy, $C_{2-6}$alkynyloxy, $C_{3-7}$cycloalkoxy, $C_{3-7}$cycloalkyl$C_{1-4}$alkoxy, aryl, aryl ($CH_2$), aryloxy, aryl($CH_2$)oxy, cyano, halogen, $NR^7R^8$, $CH_2NR^7R^8$, $SR^{12}$, $SOR^{12}$, $SO_2R^{12}$, $OSO_2R^{12}$, $NR^aCOR^{12}$, $CH(OH)R^{12}$, $COR^{12}$, $CO_2R^{12}$, $CONR^7R^8$, $CONHNH_2$, $CH_2OR^{13}$, heteroaryl or heteroaryl $C_{1-4}$alkyl, wherein $R^a$ is as previously defined;

$R^{10}$ represents hydrogen, halogen or hydroxy;

$R^{11}$ represents hydrogen or $C_{1-6}$alkyl;

$R^{12}$ represents hydrogen, $C_{1-6}$alkyl, $C_{1-6}$alkoxy, fluoro $C_{1-6}$alkyl or phenyl optionally substituted by one, two or three substituents selected from $C_{1-6}$alkyl, $C_{1-6}$alkoxy, halogen or trifluoromethyl;

$R^{13}$ represents $C_{1-4}$alkyl substituted by a group selected from hydroxy, $COR^a$, $CO_2R^a$, $CONR^aR^b$ and heteroaryl, where $R^a$ is as previously defined;

$R^{14}$ represents $OR^a$, $CONR^aR^b$ or heteroaryl;

and pharmaceutically acceptable salts or N-oxides thereof.

A preferred class of compound of formula (I) is that wherein X is hydrogen, methyl or hydroxymethyl.

Another preferred class of compound of formula (I) is that wherein $R^1$ is hydrogen, $C_{1-4}$alkyl, $C_{1-4}$alkoxy, halogen or $CF_3$.

Another preferred class of compounds of formula (I) is that wherein $R^2$ is hydrogen, $C_{1-4}$alkyl, $C_{1-4}$alkoxy, halogen or $CF_3$.

Also preferred is the class of compounds of formula (I) wherein $R^3$ is hydrogen, fluorine, chlorine or $CF_3$.

A particularly preferred class of compounds of formula (I) is that wherein $R^1$ is fluorine, chlorine or $CF_3$.

Another particularly preferred class of compounds of formula (I) is that wherein $R^2$ is hydrogen, fluorine, chlorine or $CF_3$.

Also particularly preferred is the class of compounds of formula (I) wherein $R^3$ is hydrogen, fluorine, chlorine or $CF_3$.

Preferably $R^1$ and $R^2$ are in the 3 and 5 positions of the phenyl ring.

More preferably $R^1$ is 3-fluoro or 3-$CF_3$.
More preferably $R^2$ is 5-fluoro or 5-$CF_3$.
More preferably $R^3$ is hydrogen.
Most preferably $R^1$ is 3-F or 3-$CF_3$, $R^2$ is 5-$CF_3$ and $R^3$ is hydrogen.

A further preferred class of compound of formula (I) is that wherein $R^4$ is a hydrogen atom or a fluorine atom.

Another preferred class of compound of formula (I) is that in which $R^5$ is a hydrogen atom.

A further preferred class of compound of formula (I) is that wherein $R^6$ is a hydrogen atom or a $C_{1-6}$alkyl group (especially methyl) or a $C_{1-3}$alkyl group, in particular $CH_2$, $CH(CH_3)$ and $CH_2CH_2$ and especially $CH_2$, substituted by a 5-membered heterocyclic ring containing 2 or 3 nitrogen atoms as previously defined.

In particular, the 5-membered ring is a heterocyclic ring selected from 1,3-imidazol-4-yl, 1,2,4-triazol-3-yl, 1,2,3-triazol-4-yl, 2-oxo-1,3-imidazol-4-yl and 3-oxo-1,2,4-triazol-5-yl, any of which rings being optionally substituted by the group —Y—$NR^7R^8$.

Particularly preferred heterocyclic rings are selected from:

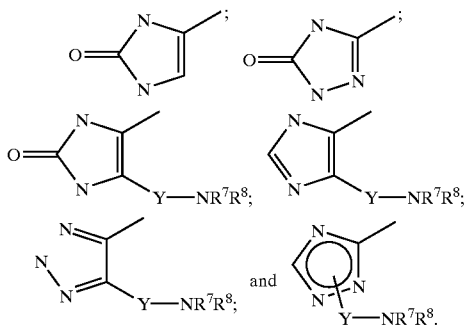

Most especially, the 5-membered heterocyclic ring is a 1,2,4-triazol-3-yl or 3-oxo-1,2,4-triazol-5-yl group.

Another preferred class of compound of formula (I) is that wherein $R^9$ represents hydrogen, hydroxy, oxo, $C_{1-6}$alkoxy, $C_{1-6}$alkoxyC_{1-4}$alkyl, hydroxyC_{1-4}$alkyl, cyano, $NR^7R^8$, $CH_2NR^7R^8$, $SO_2R^d$, $CH(OH)R^{12}$, $COR^{12}$, $CO_2R^{12}$, $CONR^7R^8$, phenyl, heteroaryl, heteroarylC$_{1-4}$alkyl or $CH_2OR^{13}$, where said phenyl is optionally substituted by one or two substituents selected from $C_{1-4}$alkyl, $C_{1-4}$alkoxy, halogen or trifluoromethyl.

A further preferred class of compound of formula (I) is that wherein $R^9$ represents hydrogen, hydroxy, $C_{1-4}$alkoxyC$_{1-2}$alkyl (especially methoxymethyl), hydroxyC$_{1-2}$alkyl (especially hydroxymethyl), cyano, $CH_2NR^7R^8$, $SO_2R^{12}$ (especially where $R^{12}$ is phenyl), $CH(OH)R^{12}$ (especially where $R^{12}$ is phenyl), $COR^{12}$ (especially where $R^{12}$ is phenyl), $CO_2R^{12}$ (especially where $R^{12}$ is $C_{1-2}$alkyl, e.g. methyl), $CONR^7R^8$, heteroaryl, or $CH_2OR^{13}$.

When the group $R^9$ represents $NR^7R^8$, $CH_2NR^7R^8$ or $CONR^7R^8$, $R^7$ is preferably hydrogen, or $C_{1-4}$alkyl (especially methyl); and $R^8$ is preferably hydrogen, $C_{1-6}$alkyl, $C_{1-4}$alkoxy or $C_{1-3}$alkyl substituted by a group selected from methoxy, hydroxy, amino, methylamino, dimethylamino, phenyl, phenyloxy, or heteroaryl, wherein said phenyl or phenyloxy groups may be optionally substituted by one, two or three halogen atoms or methoxy groups, and wherein said heteroaryl group is preferably furanyl, thienyl, imidazolyl, pyrazolyl, oxazolyl, isoxazolyl, thiazolyl, triazolyl, pyridyl or quinolinyl, each of which heteroaryl groups may be optionally substituted by a methyl or phenyl group; or $R^7$ and $R^8$, together with the nitrogen atom to which they are attached, represent a heteroaliphatic ring selected from azetidinyl, pyrolidinyl, piperidinyl, morpholinyl, or piperazinyl, wherein said piperidinyl group may be optionally substituted by a methyl, $CO_2(C_{1-2}$alkyl), phenyl or benzyl group and, optionally, a hydroxy group, and wherein said piperazinyl group may be optionally substituted on the free nitrogen atom by a phenyl or benzyl group.

When the group $R^9$ represents a heteroaryl group, said group is preferably oxazolyl, thiazolyl, triazolyl or tetrazolyl, each of which groups may be optionally substituted by $C_{1-4}$alkyl, $C_{1-2}$alkoxyC$_{1-2}$alkyl, hydroxyC$_{1-4}$alkyl, fluoroC$_{1-4}$alkyl, $CH_2CONR^aR^b$, $CH_2COR^a$, $CH_2CO_2R^a$, $CH_2SR^{12}$, $CH_2SOR^{12}$ or $CH_2SO_2R^{12}$.

Another preferred class of compounds of formula (I) is that wherein $R^{10}$ represents hydrogen, fluorine or hydroxy, and in particular that wherein $R^{10}$ is hydrogen.

One favoured group of compounds of the present invention are of the formula (Ia) and pharmaceutically acceptable salts thereof:

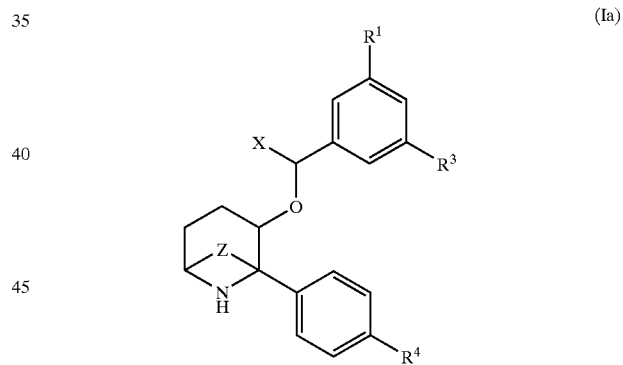

wherein $R^1$, $R^3$, $R^4$ and X are as defined in relation to formula (I) and Z is preferably —$CR^9R^{10}OCH_2$—.

With respect to compounds of the formula (I), Y (where present), may be a linear, branched or cyclic group. Favourably Y contains 1 to 4 carbon atoms and most favourably 1 or 2 carbon atoms. A particularly favourable group Y is $CH_2$.

Where the group $NR^7R^8$ represents a heteroaliphatic ring of 4 to 7 ring atoms and said ring contains a double bond, a particularly preferred group is 3-pyrroline.

Where the group $NR^7R^8$ represents a non-aromatic azabicyclic ring system, such a system may contain between 6 and 12, and preferably between 7 and 10, ring atoms. Suitable rings include 5-azabicyclo[2.1.1]hexyl, 5-azabicyclo[2.2.1]heptyl, 6-azabicyclo[3.2.1]octyl,
2-azabicyclo[2.2.2]octyl, 6-azabicyclo[3.2.2]nonyl, 6-azabicyclo[3.3.1]nonyl,
6-azabicyclo[3.2.2]decyl, 7-azabicyclo[4.3.1]decyl, 7-azabicyclo[4.4.1]undecyl and 8-azabicyclo[5.4.1]dodecyl, especially 5-azabicyclo[2.2.1]heptyl and 6-azabicyclo[3.2.1]octyl.

Where $R^8$ represents a $C_{1-4}$alkyl group substituted by a 4, 5 or 6 membered heteroaliphatic ring containing one or two heteroatoms selected from N, O and S, suitable rings include azetidinyl, pyrrolidino, piperidino, piperazino, morpholino, or thiomorpholino. Particularly preferred are nitrogen containing heteroaliphatic rings, especially pyrrolidino and morpholino rings.

Particularly suitable moieties —Y—$NR^7R^8$ include those wherein Y is $CH_2$ or $CH_2CH_2$ and —$NR^7R^8$ is amino, methylamino, dimethylamino, diethylamino, azetidinyl, pyrrolidino and morpholino.

In particular, Y is preferably $CH_2$ and $NR^7R^8$ is preferably dimethylamino, azetidinyl or pyrrolidino, especially dimethylamino.

When any variable occurs more than one time in formula (I) or in any substituent, its definition on each occurrence is independent of its definition at every other occurrence.

It will be appreciated that, where $R^9$ represents an oxo (=O) group, then $R^{10}$ will be absent and the group Z will in fact represent —C(O)$CH_2$— or —$CH_2$C(O)—.

As used herein, the term "alkyl" or "alkoxy" as a group or part of a group means that the group is straight or branched. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

As used herein, the terms "fluoro$C_{1-6}$alkyl" and fluoro $C_{1-6}$alkoxy" mean a $C_{1-6}$alkyl or $C_{1-6}$alkoxy group in which one or more (in particular, 1 to 3) hydrogen atoms have been replaced by fluorine atoms. Similarly, the term "fluoro $C_{1-4}$alkyl" means a $C_{1-4}$alkyl group in which one or more (in particular 1 to 3) hydrogen atoms have been replaced by fluorine atoms. Particularly preferred are fluoro$C_{13}$alkyl and fluoro$C_{13}$alkoxy groups, for example, $CF_3$, $CH_2CH_2F$, $CH_2CHF_2$, $CH_2CF_3$, $OCF_3$, $OCH_2CH_2F$, $OCH_2CHF_2$ or $OCH_2CF_3$, and most especially $CF_3$, $OCF_3$ and $OCH_2CF_3$.

As used herein, the term "hydroxy$C_{1-6}$alkyl" means a $C_{1-6}$alkyl group, in which one or more (in particular 1 to 3) hydrogen atoms have been replaced by a hydroxy group. Preferred are hydroxy$C_{1-3}$alkyl groups, especially where one hydrogen atom has been replaced by a hydroxy group, for example, $CH_2OH$, $CH_2CH_2OH$ and $C(CH_3)_2OH$.

The cycloalkyl groups referred to herein may represent, for example, cyclopropyl, cyclobutyl, cyclopentyl or cyclohexyl. A suitable cycloalkylalkyl group may be, for example, cyclopropylmethyl.

Similarly cycloalkoxy groups referred to herein may represent, for example, cyclopropoxy or cyclobutoxy.

As used herein, the terms "alkenyl" and "alkynyl" as a group or part of a group means that the group is straight or branched. Examples of suitable alkenyl groups include vinyl and allyl. A suitable alkynyl group is propargyl.

As used herein, the term "aryl" as a group or part of a group means a monocyclic, fused-bicyclic or linear bicyclic aromatic ring containing 6, 10 or 12 carbon atoms, any of which rings is optionally substituted by one, two or three substituents selected from halogen, $C_{1-6}$alkyl, $C_{1-6}$alkoxy, or trifluoromethyl. Particular examples of such groups include phenyl, naphthyl and biphenyl. Phenyl is especially preferred.

As used herein, the term "heteroaryl" as a group or part of a group means a monocyclic or fused-bicylic heteroaromatic ring containing between 5 and 10 ring members, of which 1 to 4 may be heteroatoms selected from N, O and S, and wherein any of which rings is optionally substituted by one or two substituents selected from halogen, $C_{1-6}$alkyl, $C_{1-6}$alkoxy, $CO_2R^a$, trifluoromethyl or phenyl. Particular examples of such groups include pyrrolyl, furanyl, thienyl, pyridyl, pyrazolyl, imidazolyl, oxazolyl, isoxazolyl, thiazolyl, isothiazolyl, pyrazinyl, pyrimidinyl, pyridazinyl, triazolyl, oxadiazolyl, thiadiazolyl, triazinyl, tetrazolyl, indole, benzofuran, benzthiophene, benzimidazole, benzoxazole, benzthiazole and quinolinyl. Furanyl, thienyl, imidazolyl, oxazolyl, isoxazolyl, thiazolyl, triazolyl, tetrazolyl and pyridyl are particularly preferred. Where said rings are substituted, preferred substituents include methyl and phenyl groups.

When used herein the term "halogen" means fluorine, chlorine, bromine and iodine. The most apt halogens are fluorine and chlorine of which fluorine is preferred, unless otherwise stated.

In a further aspect of the present invention, the compounds of formula (I) may be prepared in the form of a pharmaceutically acceptable salt, especially an acid addition salt.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulphonic acid, maleic acid, succinic acid, acetic acid, citric acid, tartaric acid, carbonic acid, phosphoric acid or sulphuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula (I) and salts thereof, for example, hydrates.

The compounds according to the invention have at least three asymmetric centres, and may accordingly exist both as enantiomers and as diastereoisomers. It is to be understood that all such isomers and mixtures thereof are encompassed within the scope of the present invention.

The preferred compounds of formula (I) and (Ia) will have the stereochemistry of the 1, 2 and 5 positions as possessed by, for instance, the compound of Example 1, i.e. as shown in formula (Ib)

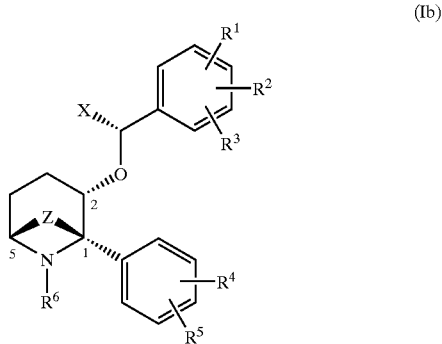

(Ib)

It will be appreciated that the preferred definitions of the various substituents recited herein may be taken alone or in combination and, unless otherwise stated, apply to the generic formula for compounds of the present invention as well as to the preferred class of compound represented by formula (Ia) and formula (Ib).

The present invention further provides pharmaceutical compositions comprising one or more compounds of formula (I) in association with a pharmaceutically acceptable carrier or excipient.

Preferably the compositions according to the invention are in unit dosage forms such as tablets, pills, capsules, powders, granules, solutions or suspensions, or suppositories, for oral, parenteral or rectal administration, or administration by inhalation or insufflation. Oral compositions such as tablets, pills, capsules or wafers are particularly preferred.

A more detailed description of pharmaceutical compositions that are suitable for the formulation of compounds of the present invention is disclosed in U.S. Pat. No. 6,071,927, the content of which is incorporated herein by reference (see in particular, column 8, line 50 to column 10, line 4).

The present invention further provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity. A comprehensive listing of clinical conditions, uses and methods of treatment for which the compounds of the present invention will be useful is disclosed in U.S. Pat. No. 6,071,927, the content of which is incorporated herein by reference (see, in particular, column 10, line 14 to column 22, line 18).

In particular, the compounds of the present invention are useful in the treatment of a variety of disorders of the central nervous system. Such disorders include mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; and anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders.

The compounds of the present invention are also particularly useful in the treatment of nociception and pain. Diseases and conditions in which pain predominates, include soft tissue and peripheral damage, such as acute trauma, osteoarthritis, rheumatoid arthritis, musculo-skeletal pain, particularly after trauma, spinal pain, myofascial pain syndromes, headache, migraine, episiotomy pain, and burns.

The compounds of the present invention are also particularly useful in the treatment of respiratory diseases, particularly those associated with excess mucus secretion, such as chronic obstructive airways disease, bronchopneumonia, chronic bronchitis, cystic fibrosis and asthma, adult respiratory distress syndrome, and bronchospasm; in the treatment of inflammatory diseases such as inflammatory bowel disease, psoriasis, fibrositis, osteoarthritis, rheumatoid arthritis, pruritis and sunburn; and in the treatment of allergic disorders such as eczema and rhinitis.

The compounds of the present invention are also particularly useful in the treatment of gastrointestinal (GI) disorders, including inflammatory disorders and diseases of the GI tract such as ulcerative colitis, Crohn's disease and irritable bowel syndrome.

The compounds of the present invention are also particularly useful in the treatment of emesis, including acute, delayed or anticipatory emesis, such as emesis induced by chemotherapy, radiation, toxins, pregnancy, vestibular disorders, motion, surgery, migraine, and variations in intercranial pressure. Most especially, the compounds of formula (I) are of use in the treatment of emesis induced by antineoplastic (cytotoxic) agents, including those routinely used in cancer chemotherapy; by radiation including radiation therapy such as in the treatment of cancer; and in the treatment of post-operative nausea and vomiting.

The excellent pharmacological profile of the compounds of the present invention offers the opportunity for their use in therapy at low doses thereby minimising the risk of unwanted side effects.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

In the treatment of emesis, a suitable dosage level is about 0.001 to 10 mg/kg per day, preferably about 0.005 to 5 mg/kg per day, and especially 0.01 to 3 mg/kg per day. The compounds may be administered on a regimen of 1 to 4 times per day, preferably once or twice per day.

In the treatment of psychiatric disorders, a suitable dosage level is about 0.001 to 10 mg/kg per day, preferably about 0.005 to 5 mg/kg per day, and especially 0.01 to 3 mg/kg per day. The compounds may be administered on a regimen of 1 to 4 times per day, preferably once or twice per day.

It will be appreciated that the amount of a compound of formula (I) required for use in any treatment will vary not only with the particular compounds or composition selected but also with the route of administration, the nature of the condition being treated, and the age and condition of the patient, and will ultimately be at the discretion of the attendant physician.

As used herein, the term "treatment" includes prophylactic use to prevent the occurrence or recurrence of any of the aforementioned conditions.

According to a general process (A), compounds of formula (I) may be prepared by the reaction of a compound of formula (II) with a compound of formula (III)

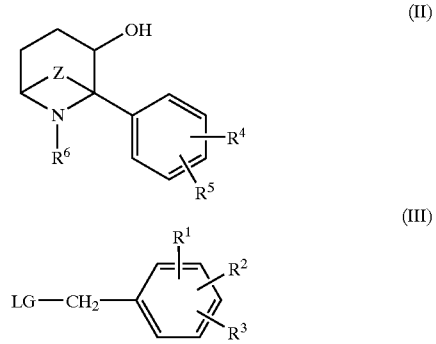

(II)

(III)

wherein LG represents a leaving group; in the presence of a base, followed by deprotection, if required.

Suitable leaving groups include halo, for example, chloro, bromo or iodo, or sulphonate derivatives such as tosylate, mesylate or triflate.

Favoured bases of use in the reaction include alkali metal amides and hydrides, such as potassium bis(trimethylsilyl)amide, sodium hydride or potassium hydride.

The reaction is conveniently carried out in a suitable organic solvent, such as dimethylformamide or an ether, for example, 1,2-dimethoxyethane, at a temperature in the region of 0° C.

According to another general process (B), compounds of formula (I), in which X is methyl or hydroxymethyl, may be prepared by the reaction of a compound of formula (IV)

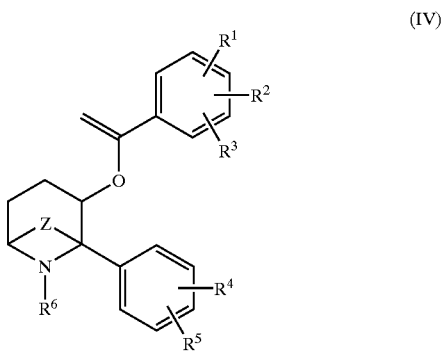

(IV)

under either:
(a) (where $R^6$ is methyl) catalytic hydrogenation conditions (e.g. $H_2$, $Pd(OH)_2$ on carbon) in a suitable solvent such as an ester, for example, ethyl acetate or an alcohol, for example, ethanol, or a mixture thereof; or
(b) (where $R^6$ is hydroxymethyl) reducing conditions (e.g. borane or $BH_3$.THF) followed by treatment with hydrogen peroxide and a base such as sodium hydroxide, conveniently in a solvent such as an ether, for example, tetrahydrofuran, or water, or a mixture thereof.

According to another general process (C), compounds of formula (I) may be prepared by the interconversion of a corresponding compound of formula (I) in which $R^6$ is H, hereinafter referred to as formula (V)

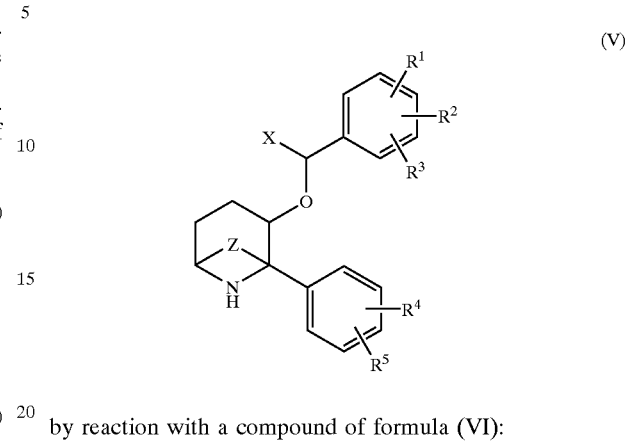

(V)

by reaction with a compound of formula (VI):

LG-$R^{6a}$ (VI)

where $R^{6a}$ is a group of the formula $R^6$ as defined in relation to formula (I) (other than H) or a precursor therefor and LG is a leaving group such as an alkyl- or arylsulphonyloxy group (e.g. mesylate or tosylate) or a halogen atom (e.g. bromine, chlorine or iodine); and, if $R^{6a}$ is a precursor group, converting it to a group $R^6$ (in which process any reactive group may be protected and thereafter deprotected if desired).

This reaction may be performed in conventional manner, for example in an organic solvent such as dimethylformamide in the presence of an acid acceptor such as potassium carbonate.

Suitable alternative methods for introducing the group $R^6$ are described, for instance, in International Patent Specification No. WO 95/18124.

According to another general process (D), compounds of formula (I), wherein X is hydrogen, may be prepared by the reduction of a compound of formula (VII)

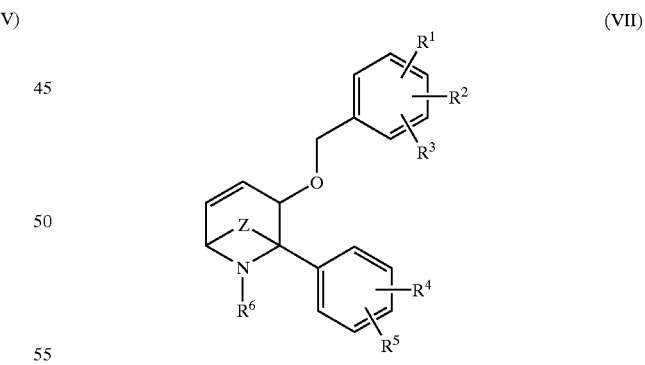

(VII)

Suitable reducing conditions include: catalytic hydrogenation using a metal catalyst such as palladium or platinum or hydroxides or oxides thereof, preferably in a suitable solvent such as alcohol, e.g. methanol or ethanol, or an ester, e.g. ethyl acetate, or an organic acid e.g. acetic acid, or a mixture thereof; or reduction using trifluoroacetic acid and triethylsilane.

According to another general process (E), compounds of formula (I), wherein X is $CO_2CH_3$ may be prepared by the reaction of a compound of formula (II) with a diazo compound of formula (VIII)

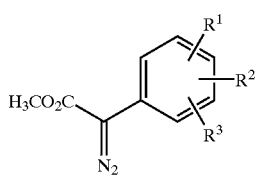

(VIII)

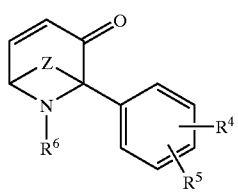

(X)

The reaction is conveniently effected in the presence of a rhodium catalyst such as rhodium (II) acetate dimer, in a suitable solvent such as a halogenated hydrocarbon, for example, 1,2-dichloroethane, or an aromatic hydrocarbon, for example, benzene. The reaction is preferably effected at an elevated temperature, for example at the reflux temperature of the solvent.

Compounds of formula (I) wherein X is $CH_2OH$ or $CH_3$ may be prepared from a corresponding compound of formula (I) wherein X is $CO_2CH_3$ by convention methodology. For instance, by reduction to the primary alcohol using a borohydride such as sodium borohydride in a suitable solvent such as an alcohol, for example, methanol, at a reduced temperature, for example, at between 0° C. and 15° C., preferably at between 5° C. and 10° C. The corresponding compound of formula (I) wherein X is $CH_3$ may be prepared from the primary alcohol by a two-step reaction. Firstly, reaction with iodine in the presence of imidazole and triphenylphosphine converts the $CH_2OH$ group to a $CH_2I$ group. The desired compound is then obtained by treatment of the iodide under conditions of catalytic hydrogenation, for instance, hydrogen in the presence of palladium on charcoal catalyst and triethylamine, in a suitable solvent such as methanol.

Further details of suitable procedures will be found in the accompanying Examples.

Intermediates of formula (II) may be prepared by reduction of a corresponding compound of formula (IX):

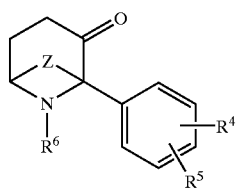

(IX)

Suitable reducing agents will be readily apparent to one skilled in the art and include, for example, metallic hydrides, such as lithium aluminium hydride or, preferably, sodium borohydride. The reduction is conveniently effected in a suitable solvent such as an ether, for example, tetrahydrofuran, or an alcohol, for example, methanol, or a mixture thereof.

Where they are not commercially available, the intermediates of formula (III) above may be prepared by the procedures described in the accompanying Examples or by alternative procedures which will be readily apparent to one skilled in the art.

Compounds of formula (IX) may be prepared from a compound of formula (X)

by catalytic hydrogenation using a metal catalyst such as palladium or platinum or hydroxides or oxides thereof, preferably in a suitable solvent such as alcohol, for example, methanol or ethanol, or an ester, for example, ethyl acetate, or an organic acid, for example, acetic acid, or a mixture thereof.

Intermediates of formula (II) may also be prepared from a compound of formula (X) by treatment with K-Selectride™ (potassium tri-sec-butylborohydride) in tetrahydrofuran.

Compounds of formula (X), wherein $R^6$ is α-methylbenzyl, benzyl or allyl, may be prepared from a compound of formula (XI)

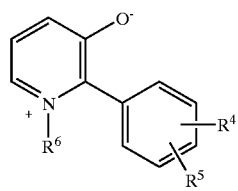

(XI)

(or a corresponding compound wherein the $O^-$ is OH, and the compound is associated with a counterion, such as a bromide or chloride ion) by reaction with a vinyl compound of the formula $R^9CH\!=\!CH_2$, in particular where $R^9$ is cyano, $SO_2R^{13}$ (especially where $R^{13}$ is phenyl) or $CO_2R^{13}$ (especially where $R^{13}$ is tert-butyl), in the presence of an organic base such as a trialkylamine, for example, triethylamine. The reaction is conveniently effected in an aprotic solvent such as an aromatic hydrocarbon, for example, toluene.

The reaction of a compound of formula (XI) with acrylonitrile is particularly suitable for preparing compounds where the $R^9$ substituent is situated on either of the carbon atoms of the two-carbon bridge.

Compounds of formula (IV) may be prepared from a compound of formula (XII)

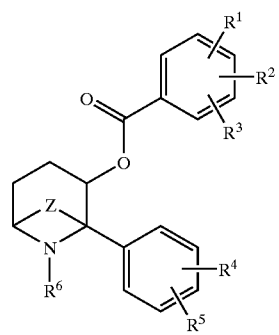

(XII)

by reaction with dimethyltitanocene in a solvent such as toluene, pyridine or tetrahydrofuran, or a mixture thereof.

Compounds of formula (XII) may be prepared by the reaction of a compound of formula (II) with L-Selectride™

(lithium tri-sec-butylborohydride) followed by treatment with a compound of formula (XIII)

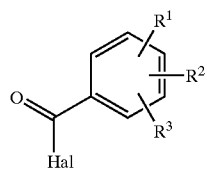

(XIII)

wherein Hal is a halogen atom, preferably chlorine.

Compounds of formula (VII) may be prepared by reaction of a compound of formula (XIV)

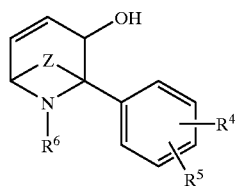

(XIV)

with a compound of formula (III) according to the method of general process (A), above.

Compounds of formula (XIII) may be prepared from the corresponding compound of formula (X) by reduction using, for example, metallic hydrides, such as lithium aluminium hydride or, preferably, sodium borohydride. The reduction is conveniently effected in a suitable solvent such as an ether, for example, tetrahydrofuran, or an alcohol, for example, methanol, or a mixture thereof.

In a preferred embodiment of the aforementioned processes, $R^6$ is a benzyl group. The various reduction reactions described above may conveniently replace the benzyl group with a hydrogen atom. It will be appreciated from the discussion above that compounds of formula (I) wherein $R^6$ is a hydrogen atom are particularly preferred precursors to other compounds of formula (I).

Compounds of formula (VIII) are either known compounds or may be prepared by methods analogous to those known in the literature (see, for instance, R. T. Lewis et al., *J. Org. Chem.* (2000) 65:2615).

Compounds of formula (XI) and (XIII) are either known compounds or may be prepared by methods analogous to those described herein.

It will be appreciated that the general methodology described above may be adapted, using methods that are readily apparent to one of ordinary skill in the art, in order to prepare further compounds of the present invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The exemplified compounds of this invention were tested by the methods set out at pages 36 to 39 of International Patent Specification No. WO 93/01165. The compounds were found to be active with $IC_{50}$ at the human $NK_1$ receptor of less than 100 nM on said test method.

The following non-limiting Examples serve to illustrate the preparation of compounds of the present invention:

DESCRIPTION 1

N-Benzyl-3-hydroxy-2-phenylpyridinium bromide

A suspension of 3-hydroxy-2-phenylpyridine (20 g, 116 mmol) in toluene (250 ml) was heated at reflux for 30 minutes. Benzyl bromide (20 ml) was added and the reaction mixture was heated at reflux for 6 hours then cooled using an ice bath. The solid residue was collected by filtration and washed twice with ether to give crude N-benzyl-3-hydroxy-2-phenylpyridinium bromide (36.5 g, 91%) which was used in the next step without further purification.

$\delta_H$(360 MHz, CDCl$_3$): 11.88 (1H, s), 9.47 (1H, d, J 7.2 Hz), 8.16 (1H, d, J 8.1 Hz), 8.05 (1H, dd, J 6.0 Hz, 8.8 Hz), 7.60–7.45 (3H, m), 7.37–7.22 (5H, m), 6.88 (2H, dd, J 6.2 Hz, 7.9 Hz), 5.61 (2H, s).

DESCRIPTION 2

(1R*,5S*,6R*)-8-Benzyl-1-phenyl-6-phenylsulphonyl-8-azabicyclo[3.2.1]oct-3-en-2-one A mixture of N-benzyl-3-hydroxy-2-phenylpyridinium bromide (Description 1; 4.91 g, 14.3 mmol), phenyl vinyl sulphone (4.2 g, 25 mmol), triethylamine (2.8 ml, 20 mmol) and 1,4-dioxane (50 ml) was heated at reflux overnight. After cooling to room temperature, the reaction mixture was poured onto saturated aqueous NaHCO$_3$ and extracted with ethyl acetate (3×100 ml). The combined organic extracts were dried (Na$_2$SO$_4$) and concentrated. The residue was purified by chromatography on silica gel (isohexane:diethyl ether 10–70%) to give the title compound (4.84 g, 78%) as a yellow-orange foam. Crystallisation from iso-hexane:diethyl ether gave the product as yellow rhombs.

$\delta_H$(360 MHz, CDCl$_3$): 7.75–7.60 (5H, m), 7.48 (2H, t, J 7.7 Hz), 7.41–7.25 (8H, m), 6.86 (1H, dd, J 4.8 Hz, 9.6 Hz), 6.23 (1H, d, J 9.6 Hz), 4.25 (1H, d, J 4.8 Hz), 3.65 (1H, d, J 13.4 Hz), 3.56 (1H, dd, J 4.0 Hz, 9.4 Hz), 3.43 (1H, d, J 13.5 Hz), 2.83 (1H, dd, J 3.9 Hz, 14.9 Hz), 2.56 (1H, dd, J 9.4 Hz, 15.0 Hz).

DESCRIPTION 3

(1R*,5S*,6R*)-8-Benzyl-1-phenyl-6-phenylsulphonyl-8-azabicyclo[3.2.1]octan-2-one 10% Palladium on carbon (1 g) was added as a slurry in water (2 ml) to a solution of (1R*,5S*,6R*)-8-benzyl-1-phenyl-6-phenylsulphonyl-8-azabicyclo[3.2.1]oct-3-ene-2-one (Description 2; 11 g, 25.6 mmol) in methanol (50 ml) and ethyl acetate (50 ml). The mixture was hydrogenated at 30 psi for one hour. The reaction mixture was filtered through a pad of Celite™. The filter cake was washed with dichloromethane (1 L) and the combined filtrates concentrated in vacuo to give the title compound (10.8 g, 98%).

$\delta_H$(400 MHz, CDCl$_3$): 7.79 (2H, d, J 7.2 Hz), 7.68 (1H, t, J 6.4 Hz), 7.51 (2H, t, J 7.6 Hz), 7.41–7.25 (10H, m), 3.94 (1H, br s), 3.73–3.69 (1H, d, J 14.0 Hz), 3.63 (1H, t, J 7.7 Hz), 3.36 (1H, d, J 14.0 Hz), 2.71–2.54 (5H, m), 1.77 (1H, m).

DESCRIPTION 4

(1R*,2R*,5S*,6R*)-8-Benzyl-1-phenyl-6-phenylsulphonyl-8-azabicyclo[3.2.1]octan-2-ol (1R*,5S*,6R*)-8-Benzyl-1-phenyl-6-phenylsulphonyl-8-azabicyclo[3.2.1]octan-2-one (Description 3; 3.05 g, 7.03 mmol) was dissolved in hot THF (10 ml) and methanol (150 ml) was added. The mixture was heated at reflux for 2 minutes and cooled to +5° C. Sodium borohydride (600 mg, 15.8 mmol) was added. The reaction mixture was stirred for 20 minutes at +5° C. The cooling bath was removed and the mixture was stirred for 90 minutes at ambient temperature. Saturated aqueous NaHCO$_3$ (10 ml) was added and the mixture was concentrated in vacuo. The residue was treated with water and extracted with ethyl acetate (3×50 ml). The combined organic extracts were dried (Na$_2$SO$_4$) and concentrated. The solid residue was crystallised from acetone:iso-hexane to give the title compound (2.95 g, 97%) as white crystals.

$\delta_H$(360 MHz, CDCl$_3$): 7.71 (2H, dm, J 8.1 Hz), 7.60 (3H, m), 7.50–7.35 (8H, m), 7.29 (2H, m), 4.35 (1H, br s), 4.15 (1H, d, J 14.7 Hz), 3.84 (1H, br s), 3.79 (1H, d, J 14.6 Hz), 3.47 (1H, dd, J 5.5 Hz, 9.3 Hz), 2.43 (1H, dd, J 5.5 Hz, 14.0 Hz), 2.29 (1H, m), 2.23 (1H, dd, J 9.3 Hz, 14.1 Hz), 1.98 (3H, m), 1.04 (1H, m).

DESCRIPTIONS 5a AND 5b (1R*,2RS,5S*,6R*)-8-Benzyl-1-phenyl-6-phenylsulphonyl-8-azabicyclo[3.2.1]oct-3-en-2-ol Sodium borohydride (450 mg, 11.8 mmol) was added to a stirred suspension of (1R*,5S*,6R*)-8-benzyl-1-phenyl-6-phenylsulphonyl-8-azabicyclo[3.2.1]oct-3-en-2-one (Description 2; 3.5 g, 8.1 mmol) in methanol (40 ml) at +5° C. The reaction mixture was stirred for 1 hour and quenched with saturated NaHCO$_3$ and concentrated in vacuo to removed methanol. The aqueous phase was extracted with ethyl acetate (3×50 ml). The combined organic extracts were dried (Na$_2$SO$_4$) and concentrated to give a 4.4:1 mixture of epimeric alcohols. The diastereoisomers were separated by flash chromatography followed by crystallisation.

DESCRIPTION 5a (1R*,2R*,5S*,6R*) isomer $\delta_H$(360 MHz, CDCl$_3$): 7.7–7.2 (15H, m), 6.16 (1H, dd, J 4.1 Hz, 9.5 Hz), 5.96 (1H, dd, J 4.8 Hz, 9.5 Hz), 4.37 (1H, d, J 4.0 Hz), 4.04 (1H, d, J 4.9 Hz), 3.82 (1H, d, J 14.1 Hz), 3.74 (1H, d, J 14.1 Hz), 3.39 (1H, dd, J 3.5 Hz, 9.4 Hz), 2.39 (1H, dd, J 3.6 Hz, 14.8 Hz), 2.14 (1H, dd, J 9.4 Hz, 14.8 Hz), 1.81 (1H, br s).

DESCRIPTION 5b (1R*,2S*5S*,6R*) isomer $\delta_H$(360 MHz, CDCl$_3$): 7.8–7.2 (15H, m), 5.85 (2H, m), 4.98 (1H, d, J 4.4 Hz), 3.81 (1H, d, J 3.6 Hz), 3.53 (1H, dd, J 3.8 Hz, 9.5 Hz), 3.45 (2H, s), 3.08 (1H, dd, J 9.6 Hz, 14.9 Hz), 2.45 (1H, dd, J 3.6 Hz, 15.1 Hz), 1.70 (1H, d, J 5.1 Hz).

DESCRIPTION 6

(1R*,2S*,5S*,6R*)-8-Benzyl-2-{[3,5-bis(trifluoromethyl)phenyl]methoxy}-1-phenyl-6-phenylsulphonyl-8-azabicyclo[3.2.1]oct-3-ene Sodium hydride (94 mg, 60% in oil, 2.45 mmol) was added to a stirred solution of (1R*,2S*,5S*,6R*)-8-benzyl-1-phenyl-6-phenylsulphonyl-8-azabicyclo[3.2.1]oct-3-en-2-ol (Description 5b; 256 mg, 0.6 mmol) and 3,5-bis(trifluoromethyl)benzyl bromide (0.8 ml) in dry THF (3 ml) at room temperature. The reaction mixture was stirred at +50° C. for 30 minutes, then cooled to room temperature and treated with diethyl ether (70 ml). The mixture was washed twice with water, brine. The combined organic extracts were dried (Na$_2$SO$_4$) and concentrated. The combined organic extracts were dried (Na$_2$SO$_4$) and concentrated. The residue was purified by chromatography on silica gel (iso-hexane:diethyl ether 0–30%) to give the title compound (400 mg, quant.).

$\delta_H$(400 MHz, CDCl$_3$): 7.81 (3H, s), 7.72 (2H, dd, J 1.0 Hz, 6.3 Hz), 7.60 (3H, m), 7.45 (2H, t, J 8.1 Hz), 7.36 (4H, d, J 8.1 Hz), 7.34–7.23 (4H, m), 6.15 (1H, dd, J 2.3 Hz, 9.8 Hz), 5.97 (1H, dd, J 4.6 Hz, 9.8 Hz), 4.99 (1H, d, J 12.3 Hz), 4.79 (1H, d, J 12.3 Hz), 4.69 (1H, br s), 3.90 (1H, d, J 4.6 Hz), 3.52 (1H, dd, J 3.8 Hz, 9.7 Hz), 3.54 (1H, d, J 13.2 Hz), 3.48 (1H, d, J 13.2 Hz), 3.21 (1H, dd, J 9.6 Hz, 14.8 Hz), 2.48 (1H, dd, J 3.8 Hz, 14.8 Hz).

DESCRIPTION 7

(1R*,2R*,5S*,6R*)-8-Benzyl-2-[3,5-bis(trifluoromethyl)benzoyloxy]-1-phenyl-6-phenylsulphonyl-8-azabicyclo[3.2.1]octane A solution of (1R*,2R*,5S*,6R*)-8-benzyl-1-phenyl-6-phenylsulphonyl-8-azabicyclo[3.2.1]octan-2-ol (Description 4; 0.98 g, 2.25 mmol), triethylamine (0.6 ml), N,N-dimethylaminopyridine (100 mg) and 3,5-bis(trifluoromethyl)benzoyl chloride (0.6 ml, 3.33 mmol) in dry dichloromethane (10 ml) was stirred at room temperature for 6 days. The reaction mixture treated with saturated aqueous NaHCO$_3$ and extracted with dichloromethane. The combined organic extracts were dried (Na$_2$SO$_4$) and concentrated. The residue was purified by chromatography on silica gel (iso-hexane:ethyl acetate 5–30%) to give the title compound (1.05 g, 69%).

$\delta_H$(400 MHz, CDCl$_3$): 8.38 (2H, s), 8.03 (1H, s), 7.77 (2H, dd, J 1.3 Hz, 7.2 Hz), 7.64–7.59 (3H, m), 7.50–7.43 (5H, m), 7.37–7.22 (4H, m), 5.83 (1H, m), 4.19 (1H, d, J 14.6 Hz), 4.06 (1H, d, J 14.6 Hz), 3.97 (1H, br s), 3.51 (1H, dd, J 5.4 Hz, 9.3 Hz), 2.58 (1H, dd, J 5.4 Hz, 14.4 Hz), 2.34 (1H, dd, J 9.3 Hz, 14.4 Hz 2.32–2.00 (3H, m), 1.11 (1H, m).

DESCRIPTION 8

(1R*,2R*,5R*)-8-Benzyl-2-[3,5-bis(trifluoromethyl)benzoyloxy]-1-phenyl-8-azabicyclo[3.2.1]octane 10% sodium amalgam (6.4 g) was added in three portion to a stirred mixture of (1R*,2R*,5S*,6R*)-8-benzyl-1-phenyl-6-phenylsulphonyl-bicyclo[3.2.1]octan-2-ol (Description 4; 1.9 g, 4.36 mmol), disodium hydrogen orthophosphate (4.5 g), THF (15 ml) and methanol (30 ml) at −20° C. The reaction mixture was stirred at −20–0° C. for one hour and cooled to −20° C. prior each addition. The reaction mixture was quenched with brine, carefully decanted and extracted with ethyl acetate (4×50 ml). The combined organic extracts were dried (Na$_2$SO$_4$) and concentrated. The residue was purified by chromatography on silica gel (iso-hexane:diethyl ether 1:1) to give a 2:1 inseparable mixture (1R*,2R*,5R*)-8-benzyl-1-phenyl-8-azabicyclo[3.2.1]octan-2-ol and (1R*,2R*)-N-benzyl-1-amino-1-phenylcyclohept-5-en-2-ol. This mixture was treated with dichloromethane (10 ml), triethylamine (1.5 ml), N,N-dimethylaminopyridine (100 mg) and 3,5-bis(trifluoromethyl)benzoyl chloride (1.33 ml) and stirred at ambient temperature for 26 hours, then quenched with saturated aqueous NaHCO, and extracted into dichloromethane. The combined organic extracts were dried (Na$_2$SO$_4$) and concentrated. The residue was purified by chromatography on silica gel (iso-hexane:diethyl ether 0–4%) to give the title compound (1.13 g, 48%) and (1R*,2R*)-1-amino-N-benzyl-2-[3,5-bis(trifluoromethyl) benzoyloxy]-1-phenylcyclohept-5-ene (0.6 g, 26%).

(1R*,2R*,5R*)-8-Benzyl-2-[3,5-bis(trifluoromethyl) benzoyloxy]-1-phenyl-8-azabicyclo[3.2.1]octane $\delta_H$(400 MHz, CDCl$_3$): 8.50 (2H, s), 8.04 (1H, s), 7.49 (4H, m), 7.39 (1H, t, J 7.7 Hz), 7.30–7.18 (4H, m), 7.15 (1H, t, J 7.2 Hz), 5.52 (1H, s), 4.19 (1H, d, J 15.0 Hz), 3.71 (1H, d, J 15.0 Hz), 3.52 (1H, m), 2.30–2.05 (5H, m), 1.91 (1H, d, J 10.6 Hz), 1.73 (1H, m), 1.7 (1H, m).

(1R*,2R*)-1-Amino-N-benzyl-2-[3,5-bis(trifluoromethyl)benzoyloxy]-1-phenylcyclohept-5-ene $\delta_H$(360 MHz, CDCl$_3$): 8.13 (2H, s), 8.00 (1H, s), 7.60 (1H, dd, J 1.3 Hz, 8.5 Hz), 7.47 (1H, d, J 7.4 Hz), 7.36 (1H, t, J 7.7 Hz), 7.30–7.18 (3H, m), 7.13 (1H, m), 6.09 (1H, m), 5.90 (1H, m), 5.47 (1H, m), 3.75 (1H, d, J 13.1 Hz), 3.65 (1H, d, J 13.1 Hz), 2.89 (1H, dd, J 4.3 Hz, 15.0 Hz), 2.71 (1H, dd, J 8.0 Hz, 15.0 Hz), 2.45–2.30 (2H, m), 2.04 (1H, m), 2.00–1.87 (2H, m). m/z (ES$^+$) 534 [M+H]$^+$.

DESCRIPTION 9

(1R*,2R*,5R*)-8-Benzyl-1-phenyl-8-azabicyclo[3.2.1]octan-2-ol

Lithium naphthalenide (200 ml, 0.6M in teterahydrofuran) was added dropwise into a −78° C. solution of (1R*,2R*,5S*,6R*)-8-benzyl-1-phenyl-6-phenylsulphonyl-8-azabicyclo[3.2.1]octan-2-ol (Description 4; 25 g, 57.7 mmol) in THF (350 ml). The mixture was quenched by addition of saturated ammonium chloride and warmed to room temperature The reaction mixture was partitioned between ethyl acetate and saturated ammonium chloride. The organic layer was washed (×2) with water then dried (MgSO$_4$), filtered and concentrated in vacuo. The residue was chromatographed on silica gel eluting with 5, 15 and 40% ethyl acetate/iso-hexanes to yield the title compound (14.3 g, 84.6%).

m/z (ES$^+$) 294 ([M+H]$^+$).

DESCRIPTION 10

2-(4-Fluorophenyl)-3-hydroxypyridine

2-Bromo-3-hydroxypyridine (50 g, 0.29 mol), sodium carbonate (64 g, 0.60 mol), toluene (600 ml), and water (300 ml) were combined in a 2 liter 3-necked flask with condenser and N$_2$ bubbler. A steady stream of N$_2$ was passed over the reaction mixture while warming to 50° C. over 30 minutes. Tetrakis(triphenylphosphine) palladium(0) (10 g) was slurried in water then added to the reaction mixture then 4-fluorobenzeneboronic acid (46 g, 0.33 mol) was slurried in ethanol (100 ml) and added. The reaction mixture was refluxed for 5 hours then cooled and stirred at room temperature for 3 days. The organic layer was decanted off and concentrated in vacuo and the aqueous layer saturated with potassium carbonate and extracted with ethyl acetate (×4). The organics were combined and concentrated in vacuo then ethyl acetate (200 ml) added and the mixture heated. A yellow powder settled in the flask which was filtered off to give the title compound (25.1 g, 46%).

m/z (ES$^+$) 191 ([M+H]$^+$).

DESCRIPTION 11

1-Benzyl-2-(4-fluorophenyl)-3-oxypyridinium betaine 2-(4-Fluorophenyl)-3-hydroxypyridine (Description 10; 24.25 g, 0.13 mol) was heated in toluene (300 ml) to 80° C. under N$_2$ then benzyl bromide (15.46 ml, 0.13 mol) added and the mixture stirred at 115° C. for 16 hours. The reaction mixture was then cooled in ice and the solid filtered off and washed with diethyl ether (×2) to give the title compound as a yellow solid (30.33 g, 66%).

m/z (ES$^+$) 281 ([M+H]$^+$).

DESCRIPTION 12

(1R*,5S*,6R*)-8-Benzyl-1-(4-fluorophenyl)-6-phenylsulphonyl-8-azabicyclo[3.2.1]oct-3-ene-2-one 1-Benzyl-2-(4-fluorophenyl)-3-oxypyridinium betaine (Description 11; 30.33 g) was stirred in methanol (500 ml) with Amberlite™ ISA 400(Cl) resin (prewashed with 4N sodium hydroxide, water and methanol) for 1 hour at room temperature. The resin was filtered off and the filtrate concentrated in vacuo to give a brown oil (24.35 g, 87.28 mmol). The oil was dissolved in 1,4 dioxane (150 ml) and phenyl vinyl sulphone (24.96 g, 148.38 mmol) added and the mixture stirred under N$_2$ at reflux for 24 hours. The reaction mixture was diluted with ethyl acetate (100 ml) and washed with saturated sodium hydrogen carbonate solution. The organics were removed and the aqueous further extracted with ethyl acetate (×2). The combined organics were dried (MgSO$_4$) then concentrated in vacuo to give a brown oil. The reaction mixture was purified by flash column chromatography [30% diethyl ether in iso-hexane] to give the title compound as an orange oil (13.88 g, 23%).

m/z (ES$^+$) 448 ([M+H]$^+$).

DESCRIPTION 13

(1R*,5S*,6R*)-8-Benzyl-1-(4-fluorophenyl)-6-phenylsulphonyl-8-azabicyclo[3.2.1]octan-2-one (1R*,5S*,6R*)-8-Benzyl-1-(4-fluorophenyl)-6-phenylsulphonyl-8-azabicyclo[3.2.1]oct-3-ene-2-one (Description 12; 13.88 g, 31.05 mmol) was dissolved in methanol (25 ml) and ethyl acetate (25 ml) and 10% palladium hydroxide (1.80 g) added and the mixture hydrogenated at 30 psi for 30 minutes. The mixture was filtered and concentrated in vacuo to give the title compound as a yellow oil (11.65 g, 84%).

m/z (ES$^+$) 450 ([M+H]$^+$).

DESCRIPTION 14

(1R*,2R*,5S*,6R*)-8-Benzyl-1-(4-fluorophenyl)-6-phenylsulphonyl-8-azabicyclo[3.2.1]octan-2-ol (1R*,5S*,6R*)-8-Benzyl-1-(4-fluorophenyl)-6-phenylsulphonyl-8-azabicyclo[3.2.1]octan-2-one (Description 13; 11.65 g, 25.95 mmol) was stirred in methanol (100 ml) then sodium borohydride (981 mg, 25.95 mmol) added and the mixture stirred at room temperature for 2 hours. The reaction mixture was quenched with water then concentrated in vacuo and partitioned between water and ethyl acetate. The organics were collected, dried (MgSO$_4$), and concentrated in vacuo to give a cream solid which was triturated in diethyl ether and filtered to give the title compound as a cream-coloured solid (7.26 g, 62%).

m/z (ES$^+$) 452 ([M+H]$^+$).

DESCRIPTION 15

(1R*,2R*,5R*)-8-Benzyl-1-(4-fluorophenyl)-8-azabicyclo[3.2.1]octan-2-ol (1R*,2R*,5S*,6R*)-8-Benzyl-1-(4-fluorophenyl)-6-phenylsulphonyl-8-azabicyclo[3.2.1]octan-2-ol (Description 14; 10.72 g, 23.77 mmol) was dissolved in THF (200 ml) then cooled to −78° C. and lithium naphthalenide added until a permanent green colour was observed. Each portion was then quenched with saturated ammonium chloride solution then extracted with ethyl acetate (×3) and the extracts dried (MgSO$_4$) and concentrated in vacuo. The extracts were combined to give a yellow oil/solid. This was purified by flash column chromatography [20%–40% ethyl acetate in iso-hexane] to give a yellow solid which was repurified by flash column chromatography [25% ethyl acetate in iso-hexane] to give the title compound as a clear yellow oil (5.37 g, 73%).

m/z (ES$^+$) 312 ([M+H]$^+$).

DESCRIPTION 16

(1R*,2R*,5R*)-8-Benzyl-2-(3,5-bis(trifluoromethyl)benzoyl)-1-(4-fluorophenyl)-8-azabicyclo[3.2.1]octane (1R*,2R*,5R*)-8-Benzyl-1-(4-fluorophenyl)-8-azabicyclo[3.2.1]octan-2-ol (Description 15; 1.23 g, 3.95 mmol), and triethylamine (0.61 ml, 4.35 mmol) in dichloromethane were stirred with 4-dimethylaminopyridine (5 crystals) and 3,5-bis(trifluoromethyl)benzoyl chloride at room temperature for a weekend. The reaction mixture was poured into water and extracted with dichloromethane (×3), dried (MgSO$_4$) and concentrated in vacuo to give a yellow oil. This was purified by flash column chromatography [10%–20% ethyl acetate in iso-hexane] to give the title compound as a yellow solid (1.27 g, 58%).

m/z (ES$^+$) 552 ([M+H]$^+$).

DESCRIPTION 17

(1R*,2R*,5R*)-Benzyl-2-{1-[3,5-bis(trifluoromethyl)phenyl]ethenyloxy}-1-(4-fluorophenyl)-8-azabicyclo[3.2.1]octane Dimethylbis(cyclopentadienyl)titanium (11.23 ml, 1.23M in toluene, 13.8 mmol) was added to (1R*,2R*,5R*)-benzyl-2-(3,5-bis(trifluoromethyl)benzoyl)-1-(4-fluorophenyl)-8-azabicyclo[3.2.1]octane (Description 16; 1.27 g, 2.30 mmol) and the reaction mixture stirred in the dark under N$_2$ for 3 hours at 80° C. The reaction mixture was stirred with methanol (5 ml), water (0.5 ml) and sodium hydrogen carbonate at 40° C. for 1 hour. The mixture was then cooled, filtered and concentrated in vacuo to give a green oil. This was purified by flash column chromatography [5% ethyl acetate in iso-hexane] to give the title compound as an orange oil (923 mg, 73%).

m/z (ES$^+$) 550 ([M+H]$^+$).

DESCRIPTIONS 18a and 18b (1R*,5S*,6RS)-8-Benzyl-6-(tert-butoxycarbonyl)-1-phenyl-8-azabicyclo[3.2.1]oct-3-en-2-one A mixture of N-benzyl-3-hydroxy-2-phenylpyridinium bromide (255 g, 0.745 mol), tert-butyl acrylate (470 ml), triethylamine (150 ml) and 1,4-dioxane (1 l) was heated at reflux for 15 hours and cooled to room temperature. The reaction mixture was poured onto saturated aqueous NaHCO$_3$ (1 l) and extracted into an 1:1 mixture of isohexane:diethyl ether (3×500 ml). The combined organic extracts were dried (Na$_2$SO$_4$) and concentrated. The residue was purified by chromatography on silica gel (750 g, isohexane:diethyl ether 0–20%) to give a 2:1 mixture of (1R,5S*,6R*)-8-benzyl-6-(tert-butoxycarbonyl)-1-phenyl-8-azabicyclo[3.2.1]oct-3-en-2-one and (1R*,5S*,6S*)-8-benzyl-6-(tert-butoxycarbonyl)-1-phenyl-8-azabicyclo[3.2.1]oct-3-en-2-one (205 g, 70%) as a yellow-orange foam. The isomers were separated on silica gel (isohexane:diethyl ether) and crystallised from isohexane:diethyl ether giving yellow rhombs:

DESCRIPTION 18a (1R*,5S*,6R*)-isomer

δ$_H$(360 MHz, CDCl$_3$): 7.83 (1H, dd, J 1.4 Hz, 8.6 Hz), 7.40–7.25 (8H, m), 6.91 (1H, dd, J 4.8 Hz, 9.7 Hz), 6.18 (1H, d, J 9.7 Hz), 4.10 (1H, d, J 4.8 Hz), 3.67 (1H, d, J 13.0 Hz), 3.51 (1H, d, J 14.0 Hz), 2.99 (1H, dd, J 2.6 Hz, 14.2 Hz), 2.84 (1H, dd, J 2.6 Hz, 9.0 Hz), 2.39 (1H, dd, J 9.0 Hz, 14.2 Hz), 1.43 (9H, s).

DESCRIPTION 18b (1R*,5S*,6S*)-isomer

δ$_H$(360 MHz, CDCl$_3$): 7.70 (1H, dd, J 1.3 Hz, 8.7 Hz), 7.40–7.25 (8H, m), 6.88 (1H, dd, J 4.8 Hz, 9.8 Hz), 6.25 (1H, d, J 9.8 Hz), 4.02 (1H, dd, J 5.0 Hz, 6.0 Hz), 3.65–3.50 (3H, m), 2.60 (2H, m), 1.43 (9H, s).

DESCRIPTIONS 19a and 19b (1R*,5S*,6RS)-8-Benzyl-6-(tert-butoxycarbonyl)-1-phenyl-8-azabicyclo[3.2.1]octan-2-one A mixture of (1R*,5S*,6RS)-8-benzyl-6-(tert-butoxycarbonyl)-1-phenyl-8-azabicylco[3.2.1]oct-3-en-2-one (Description 18; 26 g, 66 mmol), 10% palladium on charcoal (3.5 g, 3.3 mmol), ethyl acetate (50 ml) and methanol (100 ml) was stirred under hydrogen atmosphere (1 atm) at room temperature for 1 hour. The reaction mixture was treated with dichloromethane (500 ml), filtered through a pad of Celite™. The filter cake was well washed with dichloromethane and the filtrate was concentrated to give the title compound as a solid (26 g, 100%). The isomers were separated on silica gel (isohexane:ethyl acetate) and crystallised from acetone:isohexane yielding pure ketones as a colourless crystals.

DESCRIPTION 19a (6R*)-isomer

δ$_H$(360 MHz, CDCl$_3$): 7.50 (2H, dm, J 7.2 Hz), 7.41 (2H, d, J 7.3 Hz), 7.33 (4H, m), 7.25 (2H, m), 3.72 (1H, m), 3.70 (1H, d, J 15.0 Hz), 3.44 (1H, d, J 14.6 Hz), 2.91 (1H, dd, J 5.2 Hz, 9.5 Hz), 2.75–2.45 (5H, m), 1.97–1.87 (1H, m), 1.46 (9H, s).

DESCRIPTION 19b (6S*)-isomer

δ$_H$(360 MHz, CDCl$_3$): 7.50–7.20 (10H, m), 3.75 (1H, d, J 14.7 Hz), 3.61 (1H, dd, J 3.5 Hz, 6.3 Hz), 3.52 (1H, d, J 14.8 Hz), 3.46 (1H, dt, J 6.7 Hz, 11.6 Hz), 2.95 (1H, m), 2.90 (1H, dd, J 7.0 Hz, 14.4 Hz), 2.53–2.36 (2H, m), 2.26 (1H, dd, J 11.6 Hz, 14.0 Hz), 1.94 (1H, d, J 14.0 Hz), 1.91 (1H, m), 1.46 (9H, s).

DESCRIPTION 20

(1R*,2R*,5S*,6R*)-8-Benzyl-6-(tert-butoxycarbonyl)-1-phenyl-8-azabicyclo[3.2.1]octan-2-ol Sodium borohydride (8.7 g, 0.23 mol) was added to a stirred suspension of (1R*,5S*,6R*)-8-benzyl-6-(tertbutoxycarbonyl)-1-phenyl-8-azabicyclo[3.2.1]octan-2-one (Description 19a; 76 g, 0.23 mol) in methanol (700 ml) at room temperature. The reaction mixture was stirred overnight, quenched with water and concentrated in vacuo. The residue was extracted into ethyl acetate. The combined organic extracts were dried (MgSO$_4$) and concentrated in vacuo to give the title compound as a white solid.

$\delta_H$(400 MHz, CDCl$_3$): 7.55 (2H, dd, J 1.2 Hz, 8.6 Hz), 7.40–7.20 (8H, m), 4.08 (1H, d, J 15.2 Hz), 4.08 (1H, br s), 3.68 (1H, br s), 3.44 (1H, d, J 15.2 Hz), 2.77 (1H, dd, J 5.1 Hz, 9.4 Hz), 2.63 (1H, dd, J 5.1 Hz, 13.7 Hz), 2.21 (1H, dd, J 9.4 Hz, 13.3 Hz), 2.14 (1H, ddd, J 2.4 Hz, J 5.5 Hz, 13.3 Hz), 1.95 (1H, ddt, J 3.9 Hz, J 5.9 Hz, 13.3 Hz), 1.85 (1H, dd, J 5.5 Hz, 14.9 Hz), 1.52 (1H, d, J 6.6 Hz), 1.43 (9H, s), 1.34 (1H, m).

DESCRIPTIONS 21a and 21b (1R*,2R*,5S*,6S*)-8-Benzyl-6-(tertbutoxycarbonyl)-1-phenyl-8-aza bicyclo[3.2.1]octan-2-ol; and (1R,2S*,5S*,6S*)-8-Benzyl-6-(tert-butoxycarbonyl)-1-phenyl-8-azabicyclo[3.2.1]octan-2-ol (1R*,5S*,6S*)-8-Benzyl-6-(tert-butoxycarbonyl)-1-phenyl-8-azabicyclo[3.2.1]octan-2-one (Description 19b; 750 mg, 1.91 mmol) was dissolved in THF (5 ml) and methanol (25 ml) was added. The mixture was cooled to +5° C. and treated with sodium borohydride (184 mg, 4.8 mmol). The reaction mixture was stirred for 45 minutes, quenched with saturated aqueous NH$_4$Cl (10 ml) and concentrated in vacuo. The aqueous residue was extracted with dichloromethane. The combined organic extracts were dried (Na$_2$SO$_4$) and concentrated to give crude product as a 10:1 mixture of diastereoisomers. The residue was purified by chromatography on silica gel (iso-hexane:diethyl ether 0–30%) to give the (1R*,2R*,5S*,6S*)-isomer (710 mg, 92%) and the (1R*,2S*,5S*,6S*)-isomer (59 mg, 8%) of the title compound.

DESCRIPTION 21a (1R*,2R*,5S*,6S*)-isomer $\delta_H$(400 MHz, CDCl$_3$): 7.45–7.20(10H, m), 4.14 (1H, d, J 15.3 Hz), 3.66 (1H, s), 3.49 (1H, s), 3.46 (1H, dt, J 6.6 Hz, 12.1 Hz), 3.26 (1H, d, J 15.2 Hz), 3.05 (1H, br), 2.70 (1H, dt, J 5.5 Hz, 13.7 Hz), 2.37 (1H, d, J 11.8 Hz), 2.09 (1H, ddd, J 3.5 Hz, J 5.5 Hz, 13.0 Hz), 2.03 (1H, m), 1.75–1.50 (1H, m), 1.45 (9H, s).

DESCRIPTION 21b (1R*,2S*,5S*,6S*)-isomer $\delta_H$(360 MHz, CDCl$_3$): 7.74 (1H, d, J 7.4 Hz), 7.40–7.20 (8H, m), 3.92 (1H, dd, J 5.6 Hz, 10.2 Hz), 3.76 (1H, d, J 14.7 Hz), 3.54 (1H, dt, J 6.2 Hz, 12.6 Hz), 3.38 (1H, dt, J 2.8 Hz, 7.0 Hz), 3.04 (1H, d, J 14.7 Hz), 2.86 (1H, dd, J 5.6 Hz, 13.3 Hz), 2.35 (1H, t, J 12.6 Hz), 1.97–1.87 (1H, m), 1.84–1.75 (2H, m), 1.70–1.52 (1H, m), 1.46 (9H, s), 1.15 (1H, br s).

DESCRIPTION 22

(1R*,2R*,5S*,6S*)-8-Benzyl-2-{[3,5-bis(trifluoromethyl)phenyl]methoxy}-6-(tert-butoxycarbonyl)-1-phenyl-8-azabicyclo[3.2.1]octane Sodium hydride (60% in oil, 110 mg, 2.75 mmol) was added to a stirred mixture of (1R*,2R*,5S*,6S*)-8-benzyl-6-(tert-butoxycarbonyl)-1-phenyl-8-azabicyclo[3.2.1]octan-2-ol (Description 21a; 670 mg, 1.1 mmol), 3,5-bis(trifluoromethyl)benzyl bromide (1 ml, 5.45 mmol) in N,N-dimethylformamide (5 ml) at room temperature. The reaction mixture was stirred for 20 hours, quenched with saturated aqueous NH$_4$Cl and extracted into a 1:1 mixture of iso-hexane:diethyl ether. The combined organic extracts were washed with water, dried (Na$_2$SO$_4$) and concentrated. The residue was purified by chromatography on silica gel (iso-hexane:diethyl ether 0–5%) to give the title compound (826 mg, 78%).

$\delta_H$(360 MHz, CDCl$_3$): 7.73 (1H, s), 7.68 (2H, s), 7.52 (1H, d, J 7.6 Hz), 7.42 (1H, d, J 7.4 Hz), 7.45–7.20 (6H, m), 4.75 (1H, d, J 12.9 Hz), 4.73 (1H, s), 4.46 (1H, d, J 12.9 Hz), 4.13 (1H, d, J 15.7 Hz), 4.02 (1H, s), 3.73 (1H, d, J 15.7 Hz), 3.59 (1H, d, J 5.6 Hz), 3.33 (1H, dt, J 6.3 Hz, 12.3 Hz), 2.42 (1H, dd, J 6.3 Hz, 13.7 Hz), 3.26 (1H, d, J 15.2 Hz), 3.05 (1H, br), 2.70 (1H, dt, J 5.5 Hz, 13.7 Hz), 2.13 (3H, m), 1.94 (1H, m), 1.45 (9H, s), 1.35 (1H, m),

DESCRIPTIONS 23a, 23b, 23c and 23d (1R*,5S*,6RS)-6-Cyano-1-phenyl-8-(prop-2-enyl)-8-azabicyclo[3.2.1]oct-3-en-2-one; and (1R*,5R*,6RS)-7-cyano-1-phenyl-8-(prop-2-enyl)-8-azabicyclo[3.2.1]oct-3-en-2-one A suspension of 3-hydroxy-2-phenylpyridine (15 g, 116 mmol) in toluene (250 ml) was heated at reflux for 30 minutes. Allyl bromide (30 ml) was added and the reaction mixture was heated at reflux for 20 hours and cooled using the ice bath. Solid was filtered off and washed twice with ether to afford crude 3-hydroxy-2-phenyl-N-(prop-2-enyl)-pyridinium bromide, which was used treated with acrylonitrile (100 ml), triethylamine (15 ml) and 1,4-dioxane (200 ml) was heated at reflux for 28 hours and cooled to room temperature. The reaction mixture was poured onto saturated aqueous NaHCO$_3$ and extracted with ethyl acetate. The combined organic extracts were dried (Na$_2$SO$_4$) and concentrated to give a crude mixture of regio and stereoisomers in ratio (6R*):(6S*):(7R*):(7S*)=7:8:1:5. Isomers were separated by chromatography on silica gel (iso-hexane:ethyl acetate).

DESCRIPTION 23a (1R*,5S*,6R*)-isomer $\delta_H$(400 MHz, CDCl$_3$): 7.67 (2H, m), 7.40 (3H, m), 7.31 (2H, m), 6.91 (1H, dd, J 4.7 Hz, 9.4 Hz), 6.19 (1H, d, J 9.8 Hz), 5.83 (1H, dddd, J 4.3 Hz, 6.6 Hz, 10.2 Hz, 17.2 Hz), 5.34 (1H, dq, J 1.7 Hz, 17.2 Hz), 5.20 (1H, dm, J 10.2 Hz), 4.37 (1H, d, J 4.7 Hz), 3.20 (1H, ddt, J 2.0 Hz, 4.3 Hz, 14.9 Hz), 3.05 (1H, dd, J 6.6 Hz, 14.5 Hz), 3.01 (1H, dd, J 4.3 Hz, 7.4 Hz), 2.72–2.63 (2H, m).

DESCRIPTION 23b (1R*,5S*,6S*)-isomer $\delta_H$(400 MHz, CDCl$_3$): 7.51 (2H, m), 7.36 (3H, m), 7.28 (2H, m), 7.06 (1H, dd, J 4.7 Hz, 9.8 Hz), 6.33 (1H, d, J 9.8 Hz), 5.76 (1H, dddd, J 5.1 Hz, 6.5 Hz, 10.2 Hz, 17.2 Hz), 5.22–5.09 (2H, m), 4.29 (1H, t, J 5.1 Hz), 3.44 (1H, ddd, J 5.9 Hz, 6.7 Hz, 9.8 Hz), 3.08–2.94 (2H, m), 2.71 (1H, dd, J 10.2 Hz, 14.1 Hz), 2.47 (1H, dd, J 7.0 Hz, 14.1 Hz).

DESCRIPTION 23c (1R*,5S*,7S*)-isomer $\delta_H$(360 MHz, CDCl$_3$): 7.60 (2H, m), 7.46–7.32 (5H, m), 7.11 (1H, dd, J 4.9 Hz, 9.8 Hz), 6.29 (1H, d, J 9.8 Hz), 5.84

(1H, dddd, J 5.6 Hz, 6.0 Hz, 10.2 Hz, 17.2 Hz), 5.23 (1H, dq, J 1.7 Hz, 17.2 Hz), 5.18 (1H, dm, J 10.5 Hz), 4.12 (1H, dd, J 5.3 Hz, 6.0 Hz), 3.40 (1H, dd, J 3.2 Hz, 10.9 Hz), 3.10 (2H, dt, J 1.7 Hz, 6.0 Hz), 2.70 (1H, ddd, J 6.3 Hz, 10.9 Hz, 13.0 Hz), 2.17 (1H, dd, J 3.1 Hz, 12.6 Hz).

DESCRIPTION 23d (1R*,5S*,7R*)-isomer (distinguished signals from the mixture)

$\delta_H$(360 MHz, CDCl$_3$): 6.93 (1H, dd, J 4.6 Hz, 9.8 Hz), 6.12 (1H, d, J 9.8 Hz), 5.91 (1H, dddd, J 3.9 Hz, 7.1 Hz, 10.2 Hz, 17.2 Hz), 5.27 (1H, ddd, J 2.1 Hz, 3.5 Hz, 17.2 Hz), 4.14 (1H, dd, J 4.9 Hz, 6.0 Hz), 3.45 (1H, dd, J 7.4 Hz, 8.8 Hz), 3.31 (2H, ddt, J 2.1 Hz, 3.9 Hz, 14.7 Hz), 3.09 (1H, dd, J 7.4 Hz, 15.0 Hz), 2.55 (1H, ddd, J 6.3 Hz, 7.4 Hz, 12.3 Hz), 2.35 (1H, dd, J 9.1 Hz, 11.9 Hz).

DESCRIPTION 24

(1R*,2R*,5S*,6R*)-6-Cyano-1-phenyl-8-(prop-2-enyl)-8-azabicyclo[3.2.1]octan-2-ol A solution of K-Selectride® in THF (1M, 20 ml, 20 mmol) was added dropwise to a stirred solution of (1R*,5S*,6R*)-6-cyano-1-phenyl-8-(prop-2-enyl)-8-azabicyclo[3.2.1]oct-3-en-2-one (Description 23a; 1.6 g, 6 mmol) in THF (20 ml) at −70° C. The reaction mixture was slowly warm up to 0° C. over 90 minutes and carefully quenched with a mixture of 2M NaOH (40 ml) and H$_2$O$_2$ (35%, 10 ml). The mixture was stirred for 15 minutes and extracted into dichloromethane (3×100 ml). The combined organic extracts were dried (Na$_2$SO$_4$) and concentrated. The residue was purified by chromatography on silica gel (iso-hexane:ethyl acetate 0–4%) to give the title compound (1.1 g, 68%).

$\delta_H$(360 MHz, CDCl$_3$): 7.44–7.33 (3H, m), 7.31–7.25 (2H, m), 5.84 (1H, dddd, J 5.3 Hz, 5.6 Hz, 10.5 Hz, 17.2 Hz), 5.34 (1H, dq, J1.7 Hz, 17.2 Hz), 5.17 (1H, dq, J 1.4 Hz, 10.5 Hz), 3.97 (1H, t, J 2.8 Hz), 3.75 (1H, br s), 3.55 (1H, ddt, J 1.7 Hz, 5.3 Hz, 15.1 Hz), 3.10 (1H, ddt, J 1.4 Hz, 6.0 Hz, 15.4 Hz), 2.91 (1H, dd, J 5.3 Hz, 9.5 Hz), 2.55 (1H, br), 2.52 (1H, dd, J 9.5 Hz, 13.4 Hz), 2.38 (1H, dd, J 5.3 Hz, 13.4 Hz), 2.11 (1H, ddt, J 2.8 Hz, 6.0 Hz, 13.7 Hz), 1.87–1.68 (2H, m), 1.39 (1H, m).

DESCRIPTION 25

(1R*,2R*,5S*,7S*)-7-Cyano-1-phenyl-8-(prop-2-enyl)-8-azabicyclo[3.2.1]octan-2-ol A solution of K-Selectride® in THF (1M, 6.5 ml, 6.5 mmol) was added dropwise to a stirred solution of (1R*,5S*,7S*)-7-cyano-1-phenyl-8-(prop-2-enyl)-8-azabicyclo[3.2.1]oct-3-en-2-one (Description 23c; 295 mg, 1.11 mmol) in THF (7 ml) at −78° C. The reaction mixture was slowly warm up to +15° C. over 6 hours and carefully quenched with a mixture of 2M NaOH (8 ml) and H$_2$O$_2$ (35%, 2 ml). The mixture was stirred for 20 minutes. The mixture was treated with saturated aqueous Na$_2$SO$_3$ and extracted into dichloromethane. The combined organic extracts were dried (Na$_2$SO$_4$) and concentrated. The residue was purified by chromatography on silica gel (iso-hexane:ethyl acetate) to give the title compound (50 mg, 17%).

$\delta_H$(360 MHz, CDCl$_3$): 7.49–7.36 (4H, m), 7.36–7.28 (1H, m), 5.87 (1H, dddd, J 5.3 Hz, 5.6 Hz, 10.5 Hz, 17.2 Hz), 5.34 (1H, dm, J 17.2 Hz), 5.16 (1H, dm, J 10.2 Hz), 3.73 (1H, m), 3.70 (1H, m), 3.64 (1H, dt, J 3.4 Hz, 7.2 Hz), 3.16 (1H, dd, J 5.3 Hz, 9.5 Hz), 3.03 (1H, dd, J 5.3 Hz, 15.8 Hz), 2.62–2.46 (2H, m), 2.24 (1H, dd, J 9.5 Hz, 13.3 Hz), 2.06 (1H, m), 1.89 (2H, m), 1.87–1.68 (2H, m), 1.28 (1H, m).

DESCRIPTION 26

(1R*,2R*,5R*)-2-{[3,5-Bis(trifluoromethyl)phenyl]methoxy}-8-(4-chlorobut-2-ynyl)-1-phenyl-8-azabicyclo[3.2.1]octane A solution of (1R*,2R*,5R*)-2-{[3,5-bis(trifluoromethyl)phenyl]methoxy}-1-phenyl-8-azabicyclo[3.2.1]octane (Example 60; 400 mg, 0.93 mmol) in dimethylformamide (4 ml) was added to 1,4-dichlorobutyne (0.23 ml, 2.33 mmol) and potassium carbonate (386 mg, 2.79 mmol) in dimethylformamide (2 ml) at 60° C. The reaction mixture was stirred under N$_2$ at 60° C. overnight. The mixture was diluted with water and extracted with ethyl acetate (×3), dried (MgSO$_4$) and concentrated in vacuo to give a brown oil. This was purified by flash column chromatography [2.5%–7.5% methanol in dichloromethane] to give the title compound as a brown oil.

m/z (ES$^+$) 516/518 ([M+H]$^+$).

DESCRIPTION 27

(1R*,2R*,5R*)-8-(4-Azidobut-2-ynyl)-2-{[3,5-bis(trifluoromethyl)phenyl]-methoxy}-1-phenyl-8-azabicyclo[3.2.1]octane (1R*,2R*,5R*)-2-{[3,5-Bis(trifluoromethyl)phenyl]methoxy}-8-(4-chlorobut-2-ynyl)-1-phenyl-8-azabicyclo[3.2.1]octane (Description 26; 254 mg, 0.49 mmol) and sodium azide (35 mg, 0.54 mmol) were stirred in dimethylformamide (3 ml) at room temperature overnight. The reaction mixture was diluted with water and the product extracted with ethyl acetate (×3), dried (MgSO$_4$) and concentrated in vacuo to give the title compound as an orange oil.

m/z (ES$^+$) 523 ([M+H]$^+$).

DESCRIPTIONS 28a and 28b (1R*,2R*,5S*,6R*)-8-Benzyl-2-{(1S-1-[3,5-bis(trifluoromethyl)phenyl]-2-iodoethoxy}-6-(tert-butoxycarbonyl)-1-phenyl-8-azabicyclo[3.2.1]octane; and (1R*,2R*,5S*,6R*)-8-Benzyl-2-{(1R-1-[3,5-bis(trifluoromethyl)phenyl]-2-iodoethoxy}-6-(tert-butoxycarbonyl)-1-phenyl-8-azabicyclo[3.2.1]octane (1R*,2R*,5S*,6R*)-8-Benzyl-2-1{(1S*)-1-[3,5-bis(trifluoromethyl)phenyl]-2-hydroxyethoxy}-6-(tert-butoxycarbonyl)-1-phenyl-8-azabicyclo[3.2.1]octane and (1R*,2R*,5S*,6R*)-8-benzyl-2-{(1R*)-1-[3,5-bis(trifluoromethyl)phenyl]-2-hydroxyethoxy}-6-(tert-butoxycarbonyl)-1-phenyl-8-azabicyclo[3.2.1]octane (Example 127; 398 mg, 0.61 mmol) in dichloromethane was treated with triphenylphosphine (241 mg, 0.92 mmol), imidazole (63 mg, 0.92 mmol) and iodine (234 mg, 0.92 mmol). The mixture was concentrated in vacuo and the residue purified by flash column chromatography, eluting with hexane. The title compounds were isolated as a white solid (306 mg, 66%).

m/z (ES$^+$) 760 ([M+H]$^+$).

DESCRIPTION 29

(1R*,5S*,6R*)-8-Benzyl-6-cyano-1-phenyl-8-azabicyclo[3.2.1]oct-3-ene-2-one

N-benzyl-3-hydroxy-2-phenylpyridinium bromide (20 g, 58.3 mmol), acrylonitrile (50 ml, 755 mmol) and triethylamine (20 ml, 143 mmol) were mixed and stirred at reflux for 20 hours in 1,4-dioxane (150 ml). The mixture was partitioned between saturated sodium hydrogen carbonate and ethyl acetate. The organic layer was separated, dried (MgSO$_4$), filtered and concentrated. The residue was chromatographed on silica gel eluting with 25, 35 and 45% diethyl ether/iso-hexanes to yield the title compound (4.4 g, 24%).

$\delta_H$(400 MHz, CDCl$_3$): 7.75–7.73 (2H,m), 7.48–7.28 (8H, m), 6.83 (1H, dd, J 4.8 Hz, 9.7 Hz), 6.24 (1H, d, J 9.7 Hz), 4.12 (1H,m), 3.81 (1H, d, J 14.1 Hz), 3.52 (1H, d, J 14.1 Hz), 3.00 (1H, dd, J 3.5 Hz, 8.3 Hz), 2.80–2.69 (2H, m).

DESCRIPTION 30

(1R*,5S*,6R*)-8-Benzyl-6-cyano-1-phenyl-8-azabicyclo[3.2.1]octan-2-one

Palladium hydroxide (20%) (700 mg) was added to a solution of (1R*,5S*,6R*)-8-benzyl-6-cyano-1-phenyl-8-azabicyclo[3.2.1]oct-3-ene-2-one (Description 29; 7.1 g, 22.6 mmol) in methanol (100 ml). The mixture was transferred to the Parr™ apparatus and hydrogenated at 45 psi for 20 minutes. The mixture was filtered through Celite™ and the filtrate concentrated in vacuo. The residue was partitioned between ethyl acetate and brine. The organic layer was separated, dried (MgSO$_4$), filtered and concentrated to yield the title compound (6.9 g, 96%).

$\delta_H$(400 MHz, CDCl$_3$): 7.75–7.73 (4H,m), 7.51–7.36 (4H, m), 7.32–7.28 (2H,m), 3.86 (1H,s), 3.83 (1H, d, J 14.4 Hz), 3.51 (1H, d, J 14.4 Hz), 3.03 (1H, dd, J 4.7 Hz, 9.5 Hz), 2.91 (1H, dd, J 9.5 Hz, 14.0 Hz), 2.67–2.35 (4H,m), 1.92–1.85 (1H,m).

DESCRIPTION 31

(1R*,2R*,5S*,6R*)-8-Benzyl-6-cyano-1-phenyl-8-azabicyclo[3.2.1]octan-2-ol (1R*,5S*,6R*)-8-Benzyl-6-cyano-1-phenyl-8-azabicyclo[3.2.1]octan-2-one (Description 30; 6.9 g, 21.8 mmol) was taken up a mixture of methanol (100 ml) and THF (30 ml). To this suspension was added sodium borohydride (0.5 g, 13 mmol). The mixture was stirred for 30 minutes then concentrated in vacuo. The residue was partitioned between ethyl acetate and saturated sodium hydrogen carbonate. The organic layer was separated, dried (MgSO$_4$), filtered and concentrated. Chromatography on silica gel eluting with 35 and 50% ethyl acetate/iso-hexanes afforded the title compound (4.8 g, 70%).

$\delta_H$(400 MHz, CDCl$_3$): 7.54–7.25 (10H, m), 4.18 (1H, d, J 14.9 Hz), 3.91 (1H, br s), 3.80 (1H, s), 3.70 (1H, d, J 14.9 Hz), 2.92 (1H, dd, J 5.2 Hz, 9.4 Hz), 2.61–2.47 (2H, m), 2.18–2.09 (1H, m), 1.91–1.76 (2H, m), 1.35–1.30 (1H, m).

DESCRIPTION 32

(1R*,2R*,5S*,6R*)-8-Benzyl-2-[3,5-bis(trifluoromethyl)benzoyloxy]-6-cyano-1-phenyl-8-azabicyclo[3.2.1]octane 3,5-Bis(trifluoromethyl)benzoyl chloride (2.76 g, 10 mmol) was added dropwise to an ice-cold solution of (1R*,2R*,5S*,6R*)-8-benzyl-6-cyano-1-phenyl-8-azabicyclo[3.2.1]octan-2-ol (Description 31; 3 g, 9.4 mmol), triethylamine (2 g, 20 mmol) and 4-N,N-dimethylaminopyridine (200 mg, 1.6 mmol) in dichloromethane (30 ml). The mixture was stirred at room temperature for 20 hours. The mixture was concentrated in vacuo then partitioned between ethyl acetate and brine. The organics were separated, dried (MgSO$_4$), filtered and concentrated. The residue was chromatographed on silica gel eluting with 10 and 20% ethyl acetate/iso-hexanes to afford the title compound (4.87 g, 93%).

$\delta_H$(400 MHz, CDCl$_3$): 8.45 (2H, s), 8.07 (1H, s), 7.57–7.21 (10H, m), 5.72 (1H, s), 4.27 (1H, d, J 15.0 Hz), 4.09 (1H, d, J 15.0 Hz), 3.95 (1H, s), 2.96 (1H, dd, J 4.6 Hz, 9.4 Hz), 2.59 (1H, dd, J 9.4 Hz, 13.9 Hz), 2.42 (1H, dd, J 4.5 Hz, 13.9 Hz), 2.36–2.01 (3H, m), 1.39–1.33 (1H, m).

DESCRIPTIONS 33a and 33b (1R*,2R*,5S*,6R*)-8-Benzyl-2-[3,5-bis(trifluoromethyl)benzoyloxy]-6-(2-methyl-2H-tetrazol-5-yl)-1-phenyl-8-azabicyclo[3.2.1]octane (isomer A); and (1R*,2R*,5S*,6R*)-8-benzyl-2-[3,5-bis(trifluoromethyl)benzoyloxy]-6-(1-methyl-1H tetrazol-5-yl)-1-phenyl-8-azabicyclo[3.2.1]octane (isomer B)

Sodium azide (1 g, 14.9 mmol), (1R*,2R*,5S*,6R*)-8-benzyl-2-[3,5-bis(trifluoromethyl)benzoyloxy]-6-cyano-1-phenyl-8-azabicyclo[3.2.1]octane (Description 32; 2.76 g, 4.95 mmol) and ammonium chloride (0.8 g, 14.9 mmol) were stirred at 120° C. for 18 hours. On cooling the mixture was partitioned between brine and ethyl acetate. The organic layer was separated and washed (×3) with water, then dried (MgSO$_4$), filtered and concentrated to give (1R*,2R*,5S*16R*)-8-benzyl-2-[3,5-bis(trifluoromethyl)benzoyloxyl-6-(tetrazol-5-yl)-1-phenyl-8-azabicyclo[3.2.1]octane (60%). This was taken up in acetonitrile (60 ml). To this solution was added potassium carbonate (1.42 g, 10 mmol) and methyl iodide (1.42 g, 10 mmol). After 30 minutes the mixture was concentrated in vacuo then partitioned between ethyl acetate and water. The organic layer was dried (MgSO$_4$), filtered and concentrated. The residue was chromatographed on silica gel eluting with 10, 20 and 50% ethyl acetate/iso-hexanes to give the title compounds: isomer A (1.28 g, 43%) and isomer B (0.83 g, 27%).

DESCRIPTION 33a

Isomer A $\delta_H$(400 MHz, CDCl$_3$): 8.46 (2H, s), 8.04 (1H, s), 7.60–7.58 (2H, m), 7.37–7.35 (2H, m), 7.30–7.17 (6H, m), 5.90 (1H, s), 4.36 (3H, s), 4.26 (1H, d, J 15.1 Hz), 4.04 (1H, d, J 15.1 Hz), 3.78 (1H, s), 3.60 (1H, dd, J 4.8 Hz, 9.3 Hz), 2.72 (1H, dd, J 4.8 Hz, 13.8 Hz), 2.61 (1H, dd, J 9.3 Hz, 13.7 Hz), 2.48–2.23 (2H, m), 2.18–2.05 (1H, m), 1.50–1.42 (1H, m).

DESCRIPTION 33b

Isomer B $\delta_H$(400 MHz, CDCl$_3$): 8.46 (2H, s), 8.05 (1H, s), 7.66–7.63 (2H, m), 7.34–7.20 (8H, m), 5.90 (1H, s), 4.24 (1H, d, J 15.1 Hz), 4.08 (1H, d, J 15.2 Hz), 3.92 (3H, s), 3.60 (1H, s), 3.43 (1H, dd, J 4.7 Hz, 9.2 Hz), 3.00 (1H, dd, J 4.6 Hz, 13.7 Hz), 2.62 (1H, dd, J 9.3 Hz, 13.8 Hz), 2.50–2.28 (2H, m), 2.18–2.16 (1H, m), 1.46–1.40 (1H, m).

DESCRIPTION 34

(1R*,2R*,5S*,6R*)-8-Benzyl-2-{1-[3,5-bis(trifluoromethyl)phenyl]ethenyloxy}-6-(1-methyl-1H-tetrazol-5-yl)-1-phenyl-8-azabicyclo[3.2.1]octane Dimethylbis(cyclopentadienyl)titanium (12 ml, 0.45M solution in toluene) was added to a solution of (1R*,2R*, 5S*,6R*)-8-benzyl-2-[3,5-bis(trifluoromethyl)benzoyloxy]-6-(1-methyl-1H-tetrazol-5-yl)-1-phenyl-8-azabicyclo[3.2.1]octane (Description 33b; 0.83 g, 1.35 mmol) in toluene (20 ml). The mixture was stirred at 100° C. for 3 hours. On cooling to room temperature the mixture was poured into 100 ml of 1:1 diethyl ether:iso-hexanes. The mixture was filtered through Celite™ and the filtrate concentrated in vacuo. The residue was chromatographed on silica gel eluting with 10, 20 and 50% ethyl acetate/iso-hexanes to yield the title compound (0.57 g, 69%).

$\delta_H$(400 MHz, CDCl$_3$): 7.91 (2H, s), 7.77 (1H, s), 7.67–7.65 (2H, m), 7.36–7.15 (2H, m), 7.36–7.15 (8H, m), 5.00 (1H, d, J 3.6 Hz), 4.91 (1H, s), 4.58 (1H, d, J 3.6 Hz), 4.11 (1H, d, J 15.0 Hz), 3.98 (1H, d, J 15.1 Hz), 3.90 (3H, s), 3.50 (1H, s), 3.42 (1H, dd, J 4.6 Hz, 9.2 Hz), 2.99 (1H, dd, J 4.5 Hz, 13.7 Hz), 2.54 (1H, dd, J 9.3 Hz, 13.7 Hz), 2.44–2.12 (3H, m), 1.37–1.30 (1H, m).

DESCRIPTION 35

(1R*,2R*,5S*,6R*)-8-Benzyl-2-{1-[3,5-bis(trifluoromethyl)phenyl]ethenyloxy}-6-(2-methyl-2H-tetrazol-5-yl)-1-phenyl-8-azabicyclo[3.2.1]octane Prepared in an analogous manner to (1R*,2R*,5S*,6R*)-8-benzyl-2-{1-[3,5-bis(trifluoromethyl)phenyl]ethenyloxy}-6-(1-methyl-1H-tetrazol-5-yl)-1-phenyl-8-azabicyclo[3.2.1]octane (Description 34) from the product of Description 33a.

$\delta_H$(360 MHz, CDCl$_3$): 7.91 (2H, s), 7.76 (1H, s), 7.61–7.58 (2H, m), 7.35–7.14 (8H, m), 4.99 (1H, d, J 3.5 Hz), 4.89 (1H, s), 4.57 (1H, d, J 3.5 Hz), 4.37 (3H, s), 4.11 (1H, d, J 15.1 Hz), 3.94 (1H, d, J 15.2 Hz), 3.67 (1H, s), 3.57 (1H, dd, J 4.6 Hz, 9.25 Hz), 2.72 (1H, dd, 4.6 Hz, 13.6 Hz), 2.54 (1H, dd, J 9.4 Hz, 13.7 Hz), 2.31–2.21 (3H, m), 1.42–1.35 (1H, m).

DESCRIPTION 36

(1R*,5S*,6S*)-8-Benzyl-6-ethoxycarbonyl-6-fluoro--phenyl-8-azabicyclo[3.2.1]oct-3-en-2-one A mixture of N-benzyl-3-hydroxy-2-phenylpyridinium bromide (5 g, 14.6 mmol), ethyl 1-fluoroacrylate (7 g, 59 mmol), triethylamine (3 ml, 21 mmol), hydroquinone (50 mg) and 1,4-dioxane (20 ml) was heated at reflux for 20 hours and cooled to room temperature. The reaction mixture was poured onto saturated aqueous NaHCO$_3$ and extracted into an 1:1 mixture of iso-hexane:diethyl ether. The combined organic extracts were washed with water (3×), dried (Na$_2$SO$_4$) and concentrated. The residue was purified by chromatography on silica gel (iso-hexane:diethyl ether 0–20%) to give the title compound (470 mg, 8.5%). $\delta_H$(360 MHz, CDCl$_3$): 7.86 (2H, m), 7.38 (2H, m), 7.33–7.19 (6H, m), 6.82 (1H, ddd, J 1.7 Hz, 4.9 Hz, 9.8 Hz), 6.18 (1H, dd, J 0.7 Hz, 9.8 Hz), 4.38–4.25 (2H, m), 4.20 (1H, dd, J 1.4 Hz, 4.6 Hz), 3.72 (1H, dd, J 1.4 Hz, 14.0 Hz), 3.56 (1H, d, J 14.0 Hz), 3.22 (1H, dd, J 8.1 Hz, 15.1 Hz), 2.53 (1H, dd, J 14.7 Hz, 23.9 Hz), 1.31 (3H, t, J 7.0 Hz).

DESCRIPTION 37

(1R*,5S*,6S*)-8-Benzyl-6-ethoxycarbonyl-6-fluoro-1-phenyl-8-azabicyclo[3.2.1]octan-2-one A mixture of (1R*,5S*,6S*)-8-benzyl-6-ethoxycarbonyl-6-fluoro-1-phenyl-8-azabicyclo[3.2.1]oct-3-en-2-one (Description 36; 795 mg, 66 mmol), 10% palladium on charcoal (250 mg), ethyl acetate (5 ml) and ethanol (10 ml) was stirred under hydrogen atmosphere (1 atm) at room temperature for 1 hour. The reaction mixture was treated with dichloromethane (500 ml), filtered through a pad of Celite™. The filtrate was concentrated to give the title compound.

$\delta_H$(400 MHz, CDCl$_3$): 7.53 (2H, m), 7.44–7.24 (8H, m), 4.37–4.26 (2H, m), 3.86 (1H, d, J 14.5 Hz), 3.75 (1H, d, J 4.3 Hz), 3.50 (1H, d, J 14.5 Hz), 3.03 (1H, t, J 15.3 Hz), 2.92 (1H, dt, J 9.4 Hz, 15.3 Hz), 2.74 (1H, dd, J 15.3 Hz, 25.0 Hz), 2.61 (1H, dd, J 8.2 Hz, 15.3 Hz), 2.47 (1H, m), 1.34 (3H, t, J 7.0 Hz).

DESCRIPTION 38

(1R*,2R*,5S*6S*)-8-Benzyl-6-ethoxycarbonyl-6-fluoro-1-phenyl-8-azabicyclo[3.2.1]octan-2-ol Sodium borohydride (100 mg, 2.6 mmol) was added to a stirred mixture of (1R*,5S*,6S -8-benzyl-6-ethoxycarbonyl-6-fluoro-1-phenyl-8-azabicyclo[3.2.1]octan-2-one (Description 37), THF (2 ml) and methanol (8 ml) at room temperature. The reaction mixture was stirred for 15 minutes, quenched with saturated aqueous ammonium chloride and extracted into 1:1 mixture of iso-hexane:diethyl ether. The combined organic extracts were washed with brine, dried (MgSO$_4$) and concentrated. The residue was purified by chromatography on silica gel (iso-hexane:diethyl ether 0–25%) to give the title compound.

$\delta_H$(400 MHz, CDCl$_3$): 7.73 (2H, m), 7.42 (2H, m), 7.37 (2H, d, J 7.8 Hz), 7.29 (3H, m), 7.22 (1H, m), 4.60 (1H, d, J 3.5 Hz), 4.37–4.17 (3H, m), 3.85 (1H, d, J 15.3 Hz), 3.65 (1H, s), 2.86 (1H, dd, J 12.5 Hz, 14.9 Hz), 2.43 (1H, m), 2.92 (1H, m), 2.17 (1H, dd, J 14.5 Hz, 24.7 Hz), 1.97 (1H, dd, J 6.3 Hz, 15.2 Hz), 1.90 (1H, s), 1.52 (1H, m), 1.29 (3H, t, J 7.4 Hz).

DESCRIPTIONS 39a AND 39b

(1R*,5S*,6RS)-8-Benzyl-6-cyano-1-phenyl-8-azabicyclo[3.2.1]oct-3-en-2-one

A mixture of N-benzyl-3-hydroxy-2-phenylpyridinium bromide (150 g, 0.44 mol), acrylonitrile (300 ml), triethylamine (95 ml), hydroquinone (125 mg) and 1,4-dioxane (650 ml) was heated at reflux (80° C.) for 68 hours and cooled to room temperature. The reaction mixture was poured onto saturated aqueous NaHCO$_3$ (1 l) and extracted into an 1:1 mixture of iso-hexane:diethyl ether (3×500 ml). The combined organic extracts were dried (Na$_2$SO$_4$) and concentrated to give a mixture of regio and stereoisomers in the ratio (6R*):(6S*):(7R*):(7S*)=5:4.2:1:1.9. Isomers were separated by chromatography on silica gel (iso-hexane:diethyl ether).

DESCRIPTION 39a

(1R*,5S*,6R*)-isomer $\delta_H$(360 MHz, CDCl$_3$): 7.82 (2H, d, J 7.4 Hz), 7.46–7.23 (8H, m), 6.83 (1H, dd, J 4.9 Hz, 9.8 Hz), 6.24 (1H, d, J 9.5 Hz), 4.13 (1H, d, J 4.9 Hz), 3.81 (1H, d, J 14.0 Hz), 3.54 (1H, d, J 14.0 Hz), 3.00 (1H, dd, J 3.5 Hz, 8.1 Hz), 2.78 (1H, dd, J 3.5 Hz, 14.7 Hz), 2.72 (1H, dd, J 8.1 Hz, 14.4 Hz).

DESCRIPTION 39b

(1R*,5S*,6S*)-isomer $\delta_H$(400 MHz, CDCl$_3$): 7.68 (2H, m), 7.47–7.23 (8H, m), 7.02 (1H, dd, J 4.7 Hz, 9.8 Hz), 6.43 (1H, d, J 9.8 Hz), 4.07

(1H, dd, J 5.0 Hz, 5.7 Hz), 3.64 (1H, d, J 13.7 Hz), 3.55 (1H, d, J 14.1 Hz), 3.47 (1H, ddd, J 5.8 Hz, 7.0 Hz, 10.2 Hz), 2.84 (1H, dd, J 9.8 Hz, 13.7 Hz), 2.56 (1H, dd, J 7.0 Hz, 14.1 Hz).

DESCRIPTION 40

(1R*,5S*,6S*)-8-Benzyl-6-cyano-1-phenyl-8-azabicyclo[3.2.1]octan-2-one

A mixture of (1R*,5S*,6S*)-8-benzyl-6-cyano-1-phenyl-8-azabicyclo[3.2.1]oct-3-en-2-one (Description 39b; 44 g, 140 mmol), 10% palladium on charcoal (11 g, 10 mmol), ethyl acetate (200 ml) was stirred under hydrogen atmosphere (1 atm) at room temperature for 1.5 hours. The reaction mixture was treated with dichloromethane (500 ml), filtered through a pad of Celite™. The Celite™ cake was well washed with dichloromethane to dissolve solid product. The filtrate was concentrated to give the title compound.

$\delta_H$(360 MHz, CDCl$_3$): 7.53–7.22 (10H, m), 3.72 (1H, d, J 14.4 Hz), 3.66 (1H, m 3.49 (1H, d, J 14.4 Hz), 3.49 (1H, m), 2.93 (1H, ddd, J 9.1 Hz, 14.0 Hz, 18.2 Hz), 2.73 (1H, dd, J 6.7 Hz, 14.4 Hz), 2.67–2.53 (3H, m), 2.39 (1H, ddd, J 1.8 Hz, 9.3 Hz, 13.4 Hz).

DESCRIPTION 41

(1R*,2R*,5S*,6S*)-8-Benzyl-6-cyano-1-phenyl-8-azabicyclo[3.2.1]octan-2-ol

Sodium borohydride (1.8 g, 47 mmol) was added to a stirred, ice-cooled solution of (1R*,5S* 6S*)-8-benzyl-6-cyano-1-phenyl-8-azabicyclo[3.2.1]octan-2-one (Description 40) in methanol (300 ml). The reaction mixture was stirred for 30 minutes, quenched with saturated aqueous NaHCO$_3$ and extracted into ethyl acetate. The combined organic extracts were washed with brine, dried (Na$_2$SO$_4$) and concentrated. The residue was purified by chromatography on silica gel (iso-hexane:ethyl acetate 0–20%) to give the title compound (31 g).

$\delta_H$(400 MHz, CDCl$_3$): 7.48–7.25 (10H, m), 4.16 (1H, d, J 14.9 Hz), 3.86 (1H, br s), 3.58 (1H, dt, J 3.1 Hz, 6.7 Hz), 3.37 (1H, dt, J 5.9 Hz, 12.5 Hz), 3.24 (1H, d, J 14.9 Hz), 2.64 (1H, br), 2.61 (1H, t, J 13.0 Hz), 2.43 (1H, dd, J 5.9 Hz, 13.7 Hz), 2.29–2.12 (2H, m), 1.92 (1H, m), 1.76 (1H, m).

DESCRIPTION 42

(1R*,2R*,5S*,6S*)-8-Benzyl-2-(tert-butyldimethylsilyloxy)-6-cyano-1-phenyl-8-azabicyclo[3.2.1]octane t-Butyldimethylsilyl trifluoromethanesulphonate (23 ml, 76 mmol) was added dropwise to a stirred solution of (1R*,2R*5S*,6S*)-8-benzyl-6-cyano-1-phenyl-8-azabicyclo[3.2.1]octan-2-ol (Description 41; 31 g), triethylamine (18 ml, 243 mmol) in dichloromethane (100 ml) at room temperature over 30 minutes. The reaction mixture was stirred for 15 minutes, quenched with saturated aqueous NaHCO$_3$ and extracted into diethyl ether (3×100 ml). The combined organic extracts were washed with water, brine, dried (Na$_2$SO$_4$) and concentrated to give the title compound.

$\delta_H$(400 MHz, CDCl$_3$): 7.48 (2H, m), 7.39–7.28 (7H, m), 7.22 (1H, m), 4.35 (1H, br s), 4.23 (1H, d, J 15.6 Hz), 3.82 (1H, d, J 16.0 Hz), 3.60 (1H, dd, J 2.0 Hz, 6.7 Hz 3.23 (1H, dt, J 6.3 Hz, 11.7 Hz), 2.35–2.23 (3H, m), 2.18 (1H, dd, J 5.9 Hz, 13.3 Hz), 1.98 (1H, m), 1.58 (1H, m), 0.80 (9H, s), 0.11 (3H, s), −0.12 (3H, s).

DESCRIPTION 43

(1R*,2R*,15S*,6S*)-8-Benzyl-2-(tert-butyldimethylsilyloxy)-6-[1-(2-methoxyethoxymethyl)tetrazol-5-yl]-1-phenyl-8-azabicyclo[3.2.1]octane (isomer A); and

(1R*,2R*,5S*,6S*)-8-benzyl-2-(tert-butyldimethylsilyloxy)-6-[2-(2-methoxyethoxymethyl)tetrazol-5-yl]-1-phenyl-8-azabicyclo[3.2.1]octane (isomer B)

A mixture of (1R*,2R*,5S*,6S*)-8-benzyl-2-(tert-butyldimethylsilyloxy)-6-cyano-1-phenyl-8-azabicyclo[3.2.1]octane (Description 42; 43 g), sodium azide (27 g), triethylamine hydrochloride (55 g) and N,N-dimethylformamide (150 ml) was stirred at +130° C. for 7 hours. The reaction mixture was cooled to room temperature, treated with water (500 ml) and extracted into ethyl acetate (4×200 ml). The combined organic extracts were washed with water (3×200 ml) and brine. The combined water layers were extracted again with ethyl acetate (2×200 ml). The organic phase was washed with small amount of water (50 ml). The combined organic extracts were dried (Na$_2$SO$_4$) and concentrated to give crude (1R*, 2R*,5S*,6S*)-8-benzyl-2-(tert-butyldimethylsilyloxy)-1-phenyl-6-(tetrazol-5-yl]-8-azabicyclo[3.2.1]octane (47 g), which was mixed with potassium carbonate (25 g) and acetonitrile (220 ml), warmed up to +70° C. and finally treated with 2-methoxyethoxymethyl chloride (20 ml). The reaction mixture was stirred for 15 minutes, cooled to room temperature, then treated with water (500 ml) and extracted into ethyl acetate (3×200 ml). The combined organic extracts were dried (Na$_2$SO$_4$) and concentrated to give a 1:1.5 mixture of isomers A and B, respectively. Regioisomers were separated by chromatography on silica gel (iso-hexane:diethyl ether).

DESCRIPTION 43a

Isomer A $\delta_H$(360 MHz, CDCl$_3$): 7.59 (2H, d, J 7.0 Hz), 7.44 (2H, d, J 7.4 Hz), 7.35 (4H, m), 7.24 (2H, m), 5.65 (2H, s), 4.52 (1H, d, J 2.5 Hz), 4.24 (1H, d, J 16.1 Hz), 4.02 (1H, d, J 16.1 Hz), 3.83 (1H, dt, J 6.3 Hz, 11.9 Hz), 3.71 (1H, m), 3.63 (2H, m), 3.39 (2H, m), 3.25 (3H, s), 2.89 (1H, 6.3 Hz, 13.3 Hz), 2.61 (1H, m), 2.33 (1H, dd, J 12.3 Hz, 13.0 Hz), 2.18 (1H, m), 1.65 (1H, dd, J 5.6 Hz, 14.7 Hz), 0.78 (9H, s), 0.69 (1H, dd, J 6.0 Hz, 14.0 Hz), 0.09 (3H, s), −0.11 (3H, s).

DESCRIPTION 43b

Isomer B $\delta_H$(360 MHz, CDCl$_3$): 7.60 (2H, d, J 7.0 Hz), 7.46 (2H, d, J 7.4 Hz), 7.34 (4H, m), 7.23 (2H, m), 5.90 (2H, s), 4.47 (1H, s), 4.33 (1H, d, J 15.8 Hz), 4.00 (1H, d, J 15.8 Hz), 3.92 (1H, dt, J 6.7 Hz, 11.6 Hz), 3.79 (1H, m), 3.77 (2H, m), 3.53 (2H, m), 3.30 (3H, s), 2.71 (1H, dd, J 6.7 Hz, 13.7 Hz), 2.33 (1H, t, J 12.3 Hz), 2.26–2.10 (2H, m), 1.59 (1H, m), 0.83 (1H, m), 0.78 (9H, s), 0.08 (3H, s), −0.12 (3H, s).

DESCRIPTIONS 44a AND 44b

(1R*,2R*,5S*,6S*)-8-Benzyl-2-(tert-butyldimethylsilyloxy)-6-fluoro-6-[1-(2-methoxyethoxymethyl)-1H-tetrazol-5-yl]-1-phenyl-8-azabicyclo[3.2.1]octane; and

(1R*,2R*,5S*,6R*)-8-benzyl-2-(tert-butyldimethylsilyloxy)-6-fluoro-6-[1-(2-methoxyethoxymethyl)-1 tetrazol-5-yl]-1-phenyl-8-azabicyclo[3.2.1]octane A solution of n-butyl lithium in hexanes (1.6 M, 14 ml, 22.4 mmol) was added dropwise to a stirred solution of 1R*,2R*,5S*,6S*)-8-benzyl-2-(tert-butyldimethylsilyloxy)-6-[1-(2-methoxyethoxymethyl)-1H-tetrazol-5-yl]-1-phenyl-8-azabicyclo[3.2.1]octane (Description 43a; 10.7 g, 19 mmol) in THF (50 ml) at −78° C. over 10 minutes. The mixture was stirred for 5 minutes and a solution of N-fluorobenzenesulphonimide (10.4 g, 33 mmol) in THF (40 ml) was added over 10 minutes. The reaction mixture was stirred at −78° C. for 1 hour, quenched with brine and extracted into a 1:1 mixture iso-hexane:diethyl ether. The organic phase was washed twice with 2M NaOH, water and brine and dried ($Na_2SO_4$) and concentrated to give a 1:1 mixture of epimers, which were separated by chromatography on silica gel (iso-hexane:diethyl ether).

DESCRIPTION 44a (1R*,2R*,5S*,6S*)-isomer $\delta^H$(360 MHz, $CDCl_3$): 7.75 (2H, d, J 7.4 Hz), 7.37 (2H, t, J 8.1 Hz), 7.24 (2H, m), 7.14–6.99 (4H, m), 5.87 (1H, d, J 10.9 Hz), 5.68 (1H, dd, J 1.4 Hz, 11.2 Hz), 4.70 (1H, br s), 4.20 (1H, d, J 15.8 Hz), 3.93 (1H, d, J 15.8 Hz), 3.61 (1H, s), 3.56–3.43 (2H, m), 3.21 (3H, s), 3.07 (1H, ddd, J 2.8 Hz, 4.6 Hz, 11.2 Hz), 2.98 (1H, ddd, J 2.5 Hz, 4.6 Hz, 10.9 Hz), 2.85 (1H, ddd, J 2.5 Hz, 8.1 Hz, 10.9 Hz), 2.46 (1H, dd, J 15.1 Hz, 26.3 Hz), 2.28 (1H, m), 1.98 (1H, dd, J 4.9 Hz, 15.1 Hz), 1.62 (1H, m), 0.82 (9H, s), 0.22 (3H, s), 0.08 (3H, s).

DESCRIPTION 44b (1R*,2R*,5S*,6R*)-isomer $\delta_H$(360 MHz, $CDCl_3$): 7.62 (2H, d, J 7.7 Hz), 7.53 (2H, d, J 7.4 Hz), 7.35 (4H, m), 7.24 (2H, m), 5.88 (1H, d, J 10.9 Hz), 5.76 (1H, dd, J 1.4 Hz, 10.9 Hz), 4.61 (1H, d, J 2.5 Hz), 4.33 (1H, d, J 16.5 Hz), 4.18 (1H, d, J 16.5 Hz), 3.96 (1H, d, J 13.0 Hz), 3.70 (1H, ddd, J 3.2 Hz, 6.0 Hz, 10.9 Hz), 3.61 (1H, ddd, J 3.2 Hz, 5.6 Hz, 11.2 Hz), 3.46 (1H, dd, J 15.4 Hz, 24.2 Hz), 3.37 (2H, m), 3.21 (3H, s), 2.52 (1H, dd, J 15.8 Hz, 37.2 Hz), 2.45 (1H, m), 2.14 (1H, m), 1.66 (1H, dd, J 5.6 Hz, 15.4 Hz), 0.79 (9H, s), 0.52 (1H, dd, J 6.3 Hz, 14.7 Hz), 0.12 (3H, s), −0.03 (3H, s).

DESCRIPTION 45

(1R*,2R*,5S*,6S*)-8-Benzyl-6-fluoro-6-[1-(2-methoxyethoxymethyl)-1H-tetrazol-5-yl]-1-phenyl-8-azabicyclo[3.2.1]octan-2-ol A mixture of (1R*,2R*,5S*,6S*)-8-benzyl-2-(tert-butyldimethylsilyloxy)-6-fluoro-6-[1-(2-methoxyethoxymethyl)-1H-tetrazol-5-yl]-1-phenyl-8-azabicyclo[3.2.1]octane (Description 44a; 4.5 g, 7.7 mmol), 1 M solution of hydrogen chloride in ether (30 ml) and methanol (50 ml) was stirred at room temperature for 90 minutes. The reaction mixture was treated with saturated aqueous NaHCO, and extracted into ethyl acetate. The combined organic extracts were dried ($Na_2SO_4$) and concentrated. The residue was purified by chromatography on silica gel (iso-hexane:diethyl ether 20–80%) to give the title compound (2.5 g, 70%).

$\delta_H$(360 MHz, $CDCl_3$): 7.87 (2H, d, J 7.4 Hz), 7.47 (2H, t, J 8.1 Hz), 7.32 (2H, m), 7.15–7.00 (4H, m), 5.87 (1H, d, J 10.9 Hz), 5.69 (1H, dd, J 1.7 Hz, 11.2 Hz), 4.68 (1H, br s), 4.20 (1H, d, J 14.7 Hz), 3.82 (1H, d, J 15.1 Hz), 3.60 (1H, s), 3.58 (1H, dd, J 12.6 Hz, 15.1 Hz), 3.28 (1H, ddd, J 2.4 Hz, 7.7 Hz, 10.5 Hz), 3.21 (3H, s), 3.09 (1H, ddd, J 2.8 Hz, 4.6 Hz, 11.2 Hz), 2.96 (1H, ddd, J 2.8 Hz, 4.6 Hz, 10.9 Hz), 2.87 (1H, ddd, J 2.5 Hz, 8.1 Hz, 10.9 Hz), 2.52 (1H, dd, J 14.7 Hz, 26.3 Hz), 2.47 (1H, m), 2.31 (1H, m), 2.05 (1H, dd, J 5.6 Hz, 15.1 Hz), 1.98 (1H, br s), 1.66 (1H, m).

DESCRIPTION 46

(1R*,2R*,5S1,6S*)-8-Benzyl-2-{(1R*)-1-[3,5-bis(trifluoromethyl)phenyl]-2-iodoethoxy}-6-fluoro-6-[1-(2-methoxyethoxymethyl)-2H-tetrazol-5-yl]-1-phenyl-8-azabicyclo[3.2.1]octane (1R*,2R*,5S*,6S*)-8-Benzyl-2-{(1R*)-1-[3,5-bis(trifluoromethyl)phenyl]-2-hydroxyethoxy}-6-fluoro-6-[1-(2-methoxyethoxymethyl)-1 H-tetrazol-5-yl]-1-phenyl-8-azabicyclo[3.2.1]octane (Example 176; 0.2 g, 0.28 mmol), triphenylphosphine (0.11 g, 0.415 mmol), imidazole (28 mg, 0.415 mmol) and iodine (105 mg, 0.415 mmol) were stirred at room temperature for 18 hours. The reaction mixture was partitioned between 5% sodium thiosulfate and ethyl acetate. The organic layer was dried ($MgSO_4$), filtered and concentrated in vacuo. The residue was chromatographed on silica gel eluting with 10 and 20% ethyl acetate/iso-hexanes to afford the title compound, 193 mg, 84%.

$\delta_H$(400 MHz, $CDCl_3$): 7.80 (1H, s), 7.51 (2H, s), 7.19–6.98 (10H, m), 5.92–5.85 (2H, m), 4.71–4.69 (1H, m), 4.49 (1H, d, J 16.0 Hz), 4.07–4.04 (2H, m), 3.90 (1H, s), 3.74–3.71 (2H, m), 3.48–3.46 (2H, m), 3.36–3.34 (1H, m), 3.30 (3H, s), 3.29–3.26 (1H, m), 3.11–3.04 (1H, m), 2.55–2.30 (3H, m), 1.77–1.70 (1H, m).

DESCRIPTION 47

(1R*,2R*,5R*)-1-Phenyl-8-azabicyclo[3.2.1]octan-2-ol

10% Palladium on carbon (4 g) was added as a slurry in water (25 ml) to a solution of (1R*,2R*,5R*)-8-benzyl-1-phenyl-8-azabicyclo[3.2.1]octan-2-ol (Description 9; 29.3 g, 100 mmol) and 1,4-cyclohexadiene (80 g, 1 mol) in ethanol (250 ml). The mixture was heated at 60° C. for 6 hours. On cooling to room temperature the mixture was filtered through Celite™ and the filtrate concentrated in vacuo. The residue was chromatographed on silica gel eluting with 5 and 10% methanol/dichloromethane/1% ammonia to yield the title compound (12.2 g, 60%).

$\delta_H$(400 MHz, $CDCl_3$): 7.35–7.20 (5H, m), 3.70 (1H, s), 3.69–3.62 (1H, m), 2.22–1.34 (8H, m).

DESCRIPTION 48

(1S*,2S*,5S)-1-Phenyl-8-azabicyclo[3.2.1]octan-2-ol (−)-dibenzoyl tartrate

A solution of (−)-dibenzoyl tartaric acid (4.85 g, 13.5 mmol) in ethyl acetate (100 ml) was added dropwise to a solution of (1R*,2R*,5R*)-1-phenyl-8-azabicyclo[3.2.1]octan-2-ol (Description 47; 11 g, 54.2 mmol) in hot ethyl acetate (250 ml). Iso-propyl alcohol (500 ml) was added and the mixture heated at reflux for 1 hour. The mixture was allowed to cool slowly to room temperature then filtered to yield the title compound (4.8 g, 46%, e.e. >99%).

$\delta_H$(400 MHz, $CDCl_3$): 8.17–8.15 (4H, m), 7.57–7.53 (2H, m), 7.45–7.27 (12H, m), 5.89 (2H, s), 4.04–4.02 (2H, m), 3.88–3.87 (2H, m), 2.66–2.58 (2H, m), 2.26–1.98 (6H, m), 1.77–1.59 (2H, m), 1.25–1.14 (2H, m).

DESCRIPTION 49

(1R,2R,5R)-1-Phenyl-8-azabicyclo[3.2.1]octan-2-ol (+)-dibenzoyl tartrate

The mother liquors from the crystallisation in Description 48 were neutralised with 10% sodium carbonate and extracted with dichloromethane. The organic extracts were dried (MgSO₄), filtered and concentrated in vacuo, then treated with (+)-dibenzoyl tartaric acid in an analogous manner to Description 48 to yield the title compound (4.98 g, 48%, e.e. >99%).

DESCRIPTION 50

(1R,2R,5R)-1-Phenyl-8-azabicyclo[3.2.1]octan-2-ol

A mixture of (1R,2R,5R)-1-phenyl-8-azabicyclo[3.2.1]octan-2-ol (+)-dibenzoyl tartrate salt ((Description 49; 4.5 g, 5.9 mmol), dichloromethane (100 ml), water (100 ml) and saturated aqueous NaHCO₃ (50 ml) was stirred vigorously at room temperature for 15 minutes. The phases were separated and the aqueous phase was extracted with dichloromethane (10×50 ml). The combined organic extracts were dried (Na₂SO₄) and concentrated to give the title compound (2.2 g, 92%).

DESCRIPTION 51

(1R,2R,5R)-1-Phenyl-2-triethylsilyloxy-8-azabicyclo[3.2.1]octane

Triethylsilyl trifluoromethenesulphonate (2.6 ml, 11.5 mmol) was added dropwise to a stirred solution of (1R,2R,5R)-1-phenyl-8-azabicyclo[3.2.1]octan-2-ol (Description 50; 2.2 g, 10.7 mmol), triethylamine (4 ml, 28 mmol) and dichloromethane (20 ml) at room temperature over 10 minutes. The reaction mixture was stirred for 20 minutes and quenched with saturated aqueous NaHCO₃. The phases were separated. The aqueous phase was extracted with dichloromethane (3×50 ml). The combined organic extracts were dried (Na₂SO₄) and concentrated to give the title compound (4.33 g).

$\delta_H$(360 MHz, CDCl₃): 7.32–7.25 (2H, m), 7.24–7.16 (3H, m), 4.00 (1H, br), 3.84 (1H, dd, J 2.6 Hz, 6.6 Hz), 3.81 (1H, t, J 1.9 Hz), 2.30–2.13 (2H, m), 2.07–1.93 (2H, m), 1.75–1.59 (2H, m), 1.41 (1H, m), 0.71 (9H, d, J 8.1 Hz), 0.32–0.11 (6H, m).

DESCRIPTION 52

(1R,2R,5R)-8-Benzyl-1-phenyl-2-triethylsilyloxy-8-azabicyclo[3.2.1]octane

A mixture of (1R,2R,5R)-1-phenyl-2-triethylsilyloxy-8-azabicyclo[3.2.1]octane (Description 51; 100 mg, 0.315 mmol), benzyl bromide (0.5 ml), potassium carbonate (380 mg) and N,N-dimethylformamide (2 ml) was stirred at room temperature for 30 minutes. The reaction mixture was treated with diethyl ether, washed with water, brine, dried (Na₂SO₄) and concentrated. The residue was purified by chromatography on silica gel to give the title compound (107 mg, 83%).

$\delta_H$(360 MHz, CDCl₃): 7.53 (2H, d, J 8.1 Hz), 7.43 (2H, d, J 7.4 Hz), 7.35–7.10 (6H, m), 4.20 (1H, br s), 4.16 (1H, d, J 15.6 Hz), 3.65 (1H, d, J 15.6 Hz), 3.35 (1H, m), 2.23 (1H, tdd, J 1.9 Hz, 5.0 Hz, 13.4 Hz), 2.12–1.96 (2H, m), 1.92–1.77 (2H, m), 1.69 (1H, dd, J 4.2 Hz, 14.4 Hz), 1.57 (1H, m), 1.05 (1H, m), 0.86 (9H, d, J 7.7 Hz), 0.56–0.45 (6H, m).

DESCRIPTION 53

(1R,2R,5R)-8-Benzyl-1-phenyl-8-azabicyclo[3.2.1]octan-2-ol

A mixture of (1R,2R,5R)-8-benzyl-1-phenyl-2-triethylsilyloxy-8-azabicyclo[3.2.1]octane (Description 52; 107 mg, 0.26 mmol), 2M hydrochloric acid (3 ml) and methanol (6 ml) was stirred at +55° C. for 15 minutes, then concentrated in vacuo and quenched with saturated aqueous NaHCO₃. The mixture was extracted with dichloromethane. The combined organic extracts were dried (Na₂SO₄) and concentrated to give the title compound (79 mg, 96%).

$\delta_H$(400 MHz, CDCl₃): 7.46–7.17 (1 OH, m), 4.02 (1H, d, J 14.9 Hz), 3.06 (1H, 14.9 Hz), 3.46 (1H, br s), 3.36 (1H, br), 3.29 (1H, m), 2.27–2.13 (3H, m), 1.99 (1H, tdd, J 2.7 Hz, 5.5 Hz, 13.3 Hz), 1.87 (1H, tdd, J 3.1 Hz, 5.1 Hz, 13.7 Hz), 1.74–1.61 (2H, m), 1.30 (1H, m).

DESCRIPTION 54

(1 S,2S,5S)-1-Phenyl-8-azabicyclo[3.2.1]octan-2-ol

A mixture of (1S,2S,5S)-1-phenyl-8-azabicyclo[3.2.1]octan-2-ol (−)-dibenzoyl tartrate salt (Description 48; 614 g, 0.8 mmol), dichloromethane (50 ml), 5% aqueous NaHCO₃ (50 ml) was stirred vigorously at room temperature for 15 minutes. The phases were separated and the aqueous phase was extracted with dichloromethane (5×15 ml). The combined organic extracts were dried (Na₂SO₄) and concentrated to give the title compound (326 mg, quant.).

DESCRIPTION 55

(1S,2S,5S)-2-(tert-Butyldimethylsilyloxy)-1-phenyl-8-azabicyclo[3.2.1]octane t-Butyldimethylsilyl trifluoromethenesulphonate (0.35 ml, 1.5 mmol) was added dropwise to a stirred solution of (1S*,2S*,5S)-1-phenyl-8-azabicyclo[3.2.1]octan-2-ol (Description 54; 326 mg, 1.6 mmol), triethylamine (0.7 ml) and dichloromethane (5 ml) at room temperature over 30 minutes. The reaction mixture was stirred for 20 minutes and quenched with saturated aqueous NaHCO₃. The phases were separated. The aqueous phase was extracted with dichloromethane (3×50 ml). The combined organic extracts were dried (Na2SO₄) and concentrated to give the title compound (592 mg).

$\delta_H$(360 MHz, CDCl₃): 7.30–7.11 (5H, m), 3.74 (1H, t, J 2.5 Hz), 3.65 (1H, m), 3.05 (1H, br s), 2.20–2.07 (2H, m), 2.01 (1H, tdd, J 2.8 Hz, 5.3 Hz, 13.7 Hz), 1.93–1.80 (2H, m), 1.70–1.56 (2H, m), 1.34 (1H, m), 0.73 (9H, s), −0.19 (3H, s), −0.70 (3H, s).

DESCRIPTION 56

(1 S,2S,5S)-2-(tert-Butyldimethylsilyloxy)-1-phenyl-8-(prop-2-enyl)-8-azabicyclo[3.2.1]octane A mixture of (1S,2S,5S)-2-(tert-butyldimethylsilyloxy)-1-phenyl-8-azabicyclo[3.2.1]octane (Description 55; 237 mg), allyl bromide (0.4 ml), potassium carbonate (230 mg) and N,N-dimethylformamide (2 ml) was stirred at room temperature for 2 hours. The reaction mixture was treated with diethyl ether, washed with water and brine, then dried (Na₂SO₄) and concentrated. The residue was purified by chromatography on silica gel (iso-hexane:diethyl ether 0–25%) to give the title compound (230 mg, 98% two steps).

$\delta_H$(360 MHz, CDCl₃): 7.44 (2H, d, J 7.4 Hz), 7.31 (2H, t, J 8.1 Hz), 7.19 (1H, m), 5.90 (1H, m), 5.24 (1H, dq, J 1.8 Hz, 17.2 Hz), 5.07 (1H, d, J 10.2 Hz), 4.14 (1H, br s), 3.60 (1H, dd, J 6.3 Hz, 15.7 Hz), 3.57 (1H, t, J 6.1 Hz), 3.19 (1H, dd, J 4.4 Hz, 15.7 Hz), 2.20 (1H, m), 2.11–1.96 (2H, m), 1.86 (1H, ddd, J 4.6 Hz, 9.5 Hz, 13.7 Hz), 1.81–1.66 (2H, m), 1.60 (1H, ddd, J 4.2 Hz, 9.8 Hz, 12.3 Hz), 1.11 (1H, m), 0.78 (9H, s), 0.00 (3H, s), −0.20 (3H, s).

DESCRIPTION 57

(1S,2S,5S)-1-Phenyl-8-(prop-2-enyl)-8-azabicyclo[3.2.1]octan-2-ol

A mixture of (1S,2S,5S)-2-(tertbutyldimethylsilyloxy)-1-phenyl-8-(prop-2-enyl)-8-azabicyclo[3.2.1]octane (Description 56; 230 mg, 0.64 mmol), 2M hydrochloric acid (3 ml) and methanol (6 ml) was stirred at +55° C. over 5 days, then concentrated in vacuo and quenched with saturated aqueous NaHCO$_3$. The mixture was extracted with dichloromethane. The combined organic extracts were dried (Na$_2$SO$_4$) and concentrated. The residue was purified by chromatography on silica gel (dichloromethane:methanol:ammonia) to give the title compound (116 mg, 74%).

$\delta_H$(360 MHz, CDCl$_3$): 7.40–7.20 (5H, m), 5.90 (1H, dddd, J 4.2 Hz, 6.7 Hz, 10.3 Hz, 17.1 Hz), 5.24 (1H, dq, J 1.8 Hz, 17.2 Hz), 5.07 (1H, dm, J 10.2 Hz), 3.38–3.34 (4H, m), 2.51 (1H, dd, J 7.0 Hz, 15.1 Hz), 2.22–2.10 (3H, m), 2.02 (1H, tdd, J 2.5 Hz, 5.3 Hz, 13.0 Hz), 1.85 (1H, tdd, J 1.7 Hz, 5.6 Hz, 13.0 Hz), 1.74–1.64 (2H, m), 1.40 (1H, dddd, J 1.4 Hz, 3.2 Hz, 5.3 Hz, 13.0 Hz).

DESCRIPTION 58

N-[(R,S)-α-(2-Furyl)benzyl]-1 (S)-phenylethylamine

A mixture of 2-benzoylfuran (9.98 g, 58.0 mmol), 1(S)-phenylethylamine (9.0 ml, 70 mmol) and titanium(IV) isopropoxide (25 ml, 85 mmol) was stirred at 80° C. for two hours. The mixture was allowed to cool to room temperature, diluted with methanol (300 ml) and cooled in an ice-bath. Sodium borohydride (2.63 g, 69.5 mmol) was added portionwise, the cooling bath removed and the mixture stirred at room temperature overnight. The reaction mixture was concentrated in vacuo then the residue triturated with water (90 ml) to give a solid. Diluted with methanol (450 ml), filtered and washed the filter cake with methanol. The filtrate was evaporated, diluted with water (200 ml) and extracted with dichloromethane (3×100 ml). The combined extracts were dried (MgSO$_4$) and evaporated to give the title compound (15.30 g, 95%) as a yellow oil.

m/z (ES$^+$) 278 ([M+H]$^+$), 156 (100%).

DESCRIPTION 59

1-(1(S)-Phenylethyl)-3-oxy-2-phenylpyridinium betaine

A solution of N-[(R,S)-α-(2-furyl)benzyl]-1(S)-phenylethylamine (Description 58; 10.67 g, 38.5 mmol) in THF (80 ml) was diluted with water (40 ml) and cooled to 2° C. Bromine (2.2 ml, 43 mmol) was added dropwise over five minutes and the resulting mixture stirred at 0° C. for twenty minutes. The cooling bath was removed and the mixture stirred overnight. The reaction mixture was concentrated in vacuo, diluted with saturated aqueous sodium hydrogen carbonate (200 ml) and extracted with dichloromethane (3×50 ml). The combined extracts were dried (MgSO$_4$) and concentrated to a small volume and ethyl acetate added. The mixture was evaporated to give a solid which was triturated with ethyl acetate (20 ml), the resultant solid collected under suction, washed with ethyl acetate and dried in vacuo to afford the title compound (3.13 g, 30%). A further crop of the title compound (1.37 g, 22%) was obtained by evaporation of the ethyl acetate filtrate, purification by flash chromatography eluting with 5–20% methanol in dichloromethane and crystallisation from ethyl acetate.

$\delta_H$(400 MHz, CDCl$_3$): 7.57–7.32 (9H, m), 7.26–7.14 (3H, m), 6.98 (1H, d, J 5.8 Hz), 5.68 (1H, q, J 6.3 Hz), 1.83 (3H, d, J 6.3 Hz).

DESCRIPTION 60

(1S,5R,6S,9S)-6-(tert-Butoxycarbonyl)-1-phenyl-8-(1-phenylethyl)-8-azabicyclo[3.2.1]oct-3-en-2-one A mixture of 1-(1(S)-phenylethyl)-3-oxy-2-phenylpyridinium betaine (Description 59; 1.49 g, 5.41 mmol), tert-butyl acrylate (16 ml, 0.11 mol) and hydroquinone (21.5 mg, 0.20 mmol) in toluene (100 ml) was stirred at 95° C. for four days. The reaction mixture was concentrated in vacuo and purified by flash chromatography, eluting with 2:1 dichloromethane/iso-hexane, dichloromethane then 5% diethyl ether in dichloromethane, to give the title compound (0.463 g, 21%). A further crop of product (0.300 g, 14%) was obtained by iso-hexane recrystallization of an impure fraction from the chromatography.

m/z (ES$^+$) 404 ([M+H]$^+$).

DESCRIPTION 61

(1S,5R,6S,9S)-6-(tert-Butoxycarbonyl)-1-phenyl-8-(1-phenylethyl)-8-azabicyclo[3.2.1]octan-2-one 5% Palladium on carbon (79.8 mg) was added to a solution of (1S,5R,6S,9S)-6-(tert-butoxycarbonyl)-1-phenyl-8-(1-phenylethyl)-8-azabicyclo[3.2.1]oct-3-en-2-one (Description 60; 0.754 g, 1.87 mmol) in ethyl acetate (75 ml) and the mixture hydrogenated on a Parr™ apparatus (30 psi max.) for two hours. Filtration and evaporation gave the title compound (0.76 g, 100%) as an off-white solid.

m/z (ES$^+$) 406 ([M+H]$^+$).

DESCRIPTION 62

(1S,2S,5R,6S,9S,11S)-2-(1-(3,5-Bis(trifluoromethyl)phenyl)-2-iodo)ethoxy-6-(tertbutoxycarbonyl)-1-phenyl-8-(1-phenylethyl)-8-azabicyclo[3.2.1]octane Iodine (1.72 g, 6.78 mmol) was added to a solution of (1S,2S,5R,6S,9S,11S)-2-(1-(3,5-bis(trifluoromethyl)phenyl)-2-hydroxy)ethoxy-6-(tert-butoxycarbonyl)-1-phenyl-8-(1-phenylethyl)-8-azabicyclo[3.2.1]octane (Example 185; 3.00 g, 4.52 mmol), triphenylphosphine (1.78 g, 6.79 mmol) and imidazole (0.46 g, 6.76 mmol) in dichloromethane (60 ml). The mixture was stirred at room temperature for forty-five minutes, diluted with iso-hexane (60 ml) and filtered. The filtrate was evaporated, the residue dissolved in 10% ethyl acetate/iso-hexane and treated with silica. The mixture was filtered and the silica washed with 10% ethyl acetate/iso-hexane. The filtrate was evaporated to afford the title compound (3.07 g, 88%) as a white solid.

m/z (ES$^+$) 774 ([M+H]$^+$).

EXAMPLE 1

(1R*,2R*,5S*,6R*)-8S-8-Benzyl-2-{([3,5-bis(trifluoromethyl)phenyl]methoxy}-1-phenyl-6-phenylsulphonyl-8-azabicyclo[3.2.1]octane Sodium hydride (182 mg, 60% in oil, 4.55 mmol) was added to a stirred solution of (1R*,2R*,5S*,6R*)-8-benzyl-1-phenyl-6-phenylsulphonyl-8-azabicyclo[3.2.1]octan-2-ol (Description 4; 1.08 g, 2.5 mmol), 18-crown-6 (132 g, 0.5 mmol) and 3,5-bis(trifluoromethyl)benzyl bromide (1.5 ml, 7.8 mmol) in dry THF (10 ml) at room temperature. The reaction mixture was stirred for 4 days, then quenched with brine and extracted with dichloromethane (3×50 ml). The combined organic extracts were dried ($Na_2SO_4$) and concentrated. The residue was purified by chromatography on silica gel (iso-hexane:ethyl acetate 0–30%) to give the title compound as a solid (1.36 g, 83%).

m/z ($ES^+$) 661 $[M+H]^+$

EXAMPLE 2

(1R*,2R*,5S*,6R*)-2-{[3,5-Bis(trifluoromethyl) phenyl]methoxy}-1-phenyl-6-phenylsulphonyl-8-azabicyclo[3.2.1]octane A mixture of (1R*,2R*,5S*,6R*)-8S*)-8-benzyl-2-[3,5-bis(trifluoromethyl)-phenylmethoxy]-1-phenyl-6-phenylsulphonyl-8-azabicyclo[3.2.1]octane (Example 1; 450 mg, 0.68 mmol), 5% palladium on charcoal (1 g, 0.47 mmol) and ethanol (20 ml) was stirred under hydrogen atmosphere (1 atm) at +65° C. for 8 hours. The reaction mixture was cooled to room temperature, flushed with nitrogen gas and filtered through a pad of Celite™. The filtrate was concentrated and purified by flash chromatography to give the title compound (233 mg, 60%). The hydrochloride salt of the title compound was prepared by treatment with ethereal HCl.

m/z ($ES^+$) 430 [M+H].

EXAMPLE 3

(1R*,2R*,5R*)-2-{[3,5-Bis(trifluoromethyl)phenyl] methoxyl}-1-phenyl-8-azabicyclo[3.2.1]octane hydrochloride 10% sodium amalgam (400 mg) was added in two portion to a stirred mixture of (1R*,2R*,5S*,6R*)-2-{[3,5-bis(trifluoromethyl)phenyl]methoxy}-1-phenyl-6-phenylsulphonyl-8-azabicyclo[3.2.1]octane (Example 2; 233 mg, 0.41 mmol), disodium hydrogen orthophosphate (420 mg), THF (1 ml) and methanol (4 ml). The reaction mixture was stirred at room temperature for 2 hours, quenched with brine, carefully decanted and extracted with dichloromethane. The combined organic extracts were dried ($Na_2SO_4$) and concentrated. The residue was purified by chromatography on silica gel (dichloromethane:methanol) to give the free base of the title compound (30 mg) (contaminated by products of partial defluorination). The hydrochloride salt of the title compound was prepared by treatment with ethereal HCl.

m/z ($ES^+$) 430 $[M+H]^+$.

EXAMPLE 4

(1R*,2S*,5S*,6R*)-2-{[3,5-Bis(trifluoromethyl) phenyl]methoxy}-1-phenyl-6-phenylsulphonyl-8-azabicyclo[3.2.1]octane A mixture of (1R*,2S*,5S*,6R*)-8-benzyl-2-{[3,5-bis(trifluoromethyl)phenyl]methoxy}-1-phenyl-6-phenylsulphonyl-8-azabicyclo[3.2.1]oct-3-ene (Description 6; 390 g, 0.59mol), 10% palladium on charcoal (473 mg) and ethanol (25 ml) was stirred under hydrogen atmosphere (1 atm) at +70° C. for 2 hours and at room temperature overnight. The reaction mixture was cooled to room temperature, flushed with nitrogen gas and filtered through a pad of Celite™. The filtrate was concentrated and purified by flash chromatography to give the title compound (250 mg, 74%). The hydrochloride salt of the title compound was prepared by treatment with ethereal HCl and recrystallized from dichloromethane-ether.

m/z ($ES^+$) 430 [M+H].

EXAMPLES 5a AND 5b (1R*,2R*,5S*,6R*)-2-(1S*)-{[3,5-Bis (trifluoromethyl)phenyl]ethyloxy}-1-phenyl-6-phenylsulphonyl-8-azabicyclo[3.2.1]octane; and (1R*,2R*,5S*,6R*)-2-{(1R*-[3,5-bis (trifluoromethyl)phenyl]ethyloxy}-1-phenyl-6-phenylsulphonyl-8-azabicyclo[3.2.1]octane (1R*,2R*,5S*,6R*)-8-Benzyl-2-[3,5-bis(trifluoromethyl) benzoyloxy]-1-phenyl-6-phenylsulphonyl-8-azabicyclo [3.2.1]octane (Description 7; 595 mg, 0.88 mmol) was treated with a solution of dimethylbis(cyclopentadienyl) titanium in toluene (0.2M, 40 ml). The reaction mixture was stirred in the dark at 90° C. for 40 hours. The mixture was cooled to 40° C., than solid $NA_2CO_3$ (2.7 g) added followed by a mixture of methanol-water (9:1, 20 ml). The mixture was stirred for 2 hours and filtered through a pad of Celite™. The filtrate was dried ($Na_2SO_4$) and concentrated. The residue was purified by chromatography on silica gel (iso-hexane:ethyl acetate 0–35% containing 0.5% triethylamine) to give a 1.3:1 mixture of (1R*,2R*,5S*,6R*)-2-{1-[3,5-bis (trifluoromethyl)phenyl]ethenyloxy}-1-phenyl-6-phenylsulphonyl-8-azabicyclo[3.2.1]octane and (1R*,2R*, 5S*,6R*)-8-benzyl-2-[3,5-bis(trifluoromethyl)benzoyloxy]-1-phenyl-6-phenylsulphonyl-8-azabicyclo[3.2.1]octane (556 mg).

The crude mixture (200 mg) was treated with I-propanol (5 ml), ethyl acetate (5 ml) and 10% palladium on charcoal (450 mg) and stirred under hydrogen atmosphere (1 atm) at 50° C. for 20 hours. After cooling to room temperature, the mixture was filtered through a pad of Celite™ and concentrated. The residue was purified by chromatography on silica gel (iso-hexane:ethyl acetate) to give the title compounds (20 mg each). The hydrochloride salt of the (1S*)-isomer was prepared by treatment with ethereal HCl and recrystallised from dichloromethane: iso-hexane.

EXAMPLE 5a (1S*) isomer (HCl salt)

$\delta_H$(400 MHz, MeOH-$d_4$): 7.97 (2H, dm, J 7.8 Hz), 7.97 (1H, t, J 7.3 Hz), 7.75–7.66 (3H, m), 7.31 (5H, s), 7.15 (1H, t, J 7.3 Hz), 4.75 (1H, q, J 6.5 Hz), 4.34 (1 H, br s), 3.62 (2H, br s), 2.96 (1H, dd, J 9.1 Hz, 14.8 Hz), 2.45 (1H, m), 2.30 (1H, t, J 15.7 Hz), 2.16 (2H, d, J 10.9 Hz), 1.63 (1H, t, J 14.6 Hz), 1.79 (1H, d, J 14.0 Hz), 1.40 (3H, d, J 6.4 Hz); m/z ($ES^+$) 584 $[M+H]^+$.

EXAMPLE 5b (1R*) isomer (free base)

$\delta_H$(360 MHz, $CDCl_3$): 7.85 (2H, dd, J 1.3 Hz, 8.4 Hz), 7.71 (1H, s), 7.65 (1H, s), 7.62–7.45 (2H, m), 7.54 (2H, s), 7.40–7.25 (5H, m), 4.08 (1H, br s), 3.63 (1H, q, J 6.4 Hz), 3.53 (1H, dd, J 5.1 Hz, 8.7 Hz), 3.34 (1H, br s), 2.43 (1H, dd, J 8.8 Hz, 14.4 Hz), 2.29 (1H, dd, J 5.0 Hz, 14.7 Hz), 2.05 (1H, br s), 1.95 (1H, ddt, J 3.1 Hz, 5.7 Hz, 13.1 Hz), 1.60–1.30 (2H, m), 0.94 (3H, d, J 6.5 Hz).

EXAMPLES 6a AND 6b (1R*,2R*,5S*,6R*)-8-benzyl-2-{(1S*)-[3,5-bis (trifluoromethyl)phenyl]-2-hydroxyethyloxy}-1-phenyl-6-phenylsulphonyl-8-azabicyclo[3.2.1] octane; and (1R*,2R*,5S*,6R*)-8-benzyl-2-{(1R*)-[3,5-bis(trifluoromethyl)phenyl]-2-hydroxyethyloxy}-1-phenyl-6-phenylsulphonyl-8-azabicyclo[3.2.1]octane A solution of borane-THF complex in THF (1M, 3 ml) was added dropwise to a stirred solution of the 1.3:1 mixture of (1R*,2R*,5S*,6R*)-2-{1-[3,5-bis(trifluoromethyl) phenyl]ethenyloxy}-1-phenyl-6-phenylsulphonyl-8-azabicyclo[3.2.1]octane and (1R*,2R*, 5S*,6R*)-8-benzyl-2-[3,5-bis(trifluoromethyl)benzoyloxy]-1-phenyl-6-phenylsulphonyl-8-azabicyclo[3.2.1]octane (intermediates from preparation in Example 5; 356 mg) in THF (7 ml) at −15° C. The reaction mixture was slowly warm up to room temperature and then stirred overnight. After cooling using ice-bath, a mixture of aqueous sodium hydroxide (2M, 6 ml) and hydrogen peroxide (1.5 ml) was added dropwise to the mixture. The ice-bath was removed and the reaction mixture was stirred at ambient temperature for 30 minutes and treated with 10% aqueous sodium sulphite (60 ml). The mixture was extracted with ethyl acetate (3×30 ml). The combined organic extracts were dried ($Na_2SO_4$) and concentrated. The residue was purified by chromatography on silica gel (iso-hexane:ethyl acetate) to give the title compounds (100 mg each).

EXAMPLE 6a (1R*) isomer $\delta_H$(400 MHz, $CDCl_3$): 7.75 (1H, s), 7.55 (2H, dm, J 7.3 Hz), 7.53–7.30 (10H, m), 7.09 (1H, t, J 7.1 Hz), 7.02 (1H, t, J 7.8 Hz), 6.96 (1H, t, J 7.3 Hz), 4.57 (1H, dd, J 4.5 Hz, 7.1 Hz), 4.10 (1H, d, J 12.2 Hz), 3.94 (1H, br s), 3.91 (1H, d, J 11.2 Hz), 3.85 (1H, br s), 3.63 (1H, dd, J 7.2 Hz, 11.5 Hz), 3.55 (1H, dd, J 4.4 Hz, 11.5 Hz), 3.37 (1H, dd, J 5.5 Hz, 9.3 Hz), 2.25 (1H, dd, J 2.4 Hz, 12.0 Hz), 2.17 (1H, dd, J 5.4 Hz, 14.6 Hz), 2.03 (1H, dd, J 9.3 Hz, 14.3 Hz), 1.89 (1H, m), 1.71 (1H, m), 1.56 (1H, br s), 1.04 (1H, m).

EXAMPLE 6b (1S*) isomer:

$\delta_H$(400 MHz, $CDCl_3$): 7.86 (2H, s), 7.83 (1H, s), 7.65 (2H, dm, J 7.4 Hz), 7.47–7.28 (13H, m), 4.53 (1H, dd, J 4.0 Hz, 7.0 Hz), 4.30 (1H, s), 4.16 (1H, d, J 15.0 Hz), 4.05 (1H, d, J 15.0 Hz), 3.78 (1H, s), 3.54 (2H, m), 3.37 (1H, dd, J 5.5 Hz, 9.2 Hz), 2.39 (1H, dd, J 5.4 Hz, 14.3 Hz), 2.21 (1H, dd, J 9.3 Hz, 14.3 Hz), 1.92 (1H, m), 1.78–1.61 (3H, m), 1.49 (1H, dd, J 4.6 Hz, 15.5 Hz), 0.79 (1H, dd, J 4.1 Hz, 12.4 Hz).

EXAMPLE 7

(1R*,2R*,5S*,6R*)-2-{(1R*)-[3,5-Bis(trifluoromethyl)phenyl]-2-hydroxyethyloxy}-1-phenyl-6-phenylsulphonyl-8-azabicyclo[3.2.1]octane The mixture of (1R*,2R*,5S*,6R*)-8-benzyl-2-{(1R*-[3,5-bis(trifluoromethyl)phenyl]-2-hydroxyethyloxy}-1-phenyl-6-phenylsulphonyl-8-azabicyclo[3.2.1]octane (Example 6a; 100 mg, 0.143 mmol), 10% palladium on charcoal (300 mg) and ethanol (10 ml) was stirred under the atmosphere of hydrogen (1 atm) at 65° C. for 6 hours. After cooling to room temperature, the mixture was filtered through a pad of Celite™ and concentrated. The residue was purified by chromatography on silica gel (iso-hexane:ethyl acetate) to give the title compound (58 mg, 67%). The hydrochloride salt of the title compound was prepared by treatment with ethereal HCl.

m/z ($ES^+$) 600 $[M+H]^+$

EXAMPLE 8

(1R*,2R*,5S*,6R*)-2-{(1S*)-[3,5-Bis(trifluoromethyl)phenyl]-2-hydroxyethyloxy}-1-phenyl-6-phenylsulphonyl-8-azabicyclo[3.2.1]octane The mixture of (1R*,2R*,5S*,6R*)-8-benzyl-2-{(1S*)-[3,5-bis(trifluoromethyl)phenyl]-2-hydroxyethyloxy}-1-phenyl-6-phenylsulphonyl-8-azabicyclo[3.2.1]octane (Example 6b; 99 mg, 0.14 mmol), 10% palladium on charcoal (300 mg) and ethanol (10 ml) was stirred under hydrogen atmosphere (1 atm) at 65° C. for 6 hours. After cooling to room temperature, the mixture was filtered through a pad of Celite™ and concentrated. The residue was purified by chromatography on silica gel (iso-hexane:ethyl acetate) to give the title compound (65 mg). The hydrochloride salt of the title compound was prepared by treatment with ethereal HCl and recrystallised from dichloromethane:iso-hexane.

m/z ($ES^+$) 600 $[M+H]^+$

EXAMPLES 9a AND 9b (1R*,2R*,5R*)-2-{1-(S*)-[3,5-Bis(trifluoromethyl)phenyl]ethyloxy}-1-phenyl-8-azabicyclo[3.2.1]octane; and (1R*,2R*,5R*)-2-{1-(R*)-[3,5-bis(trifluoromethyl)phenyl]ethyloxy}-1-phenyl-8-azabicyclo[3.2.1]octane (1R*,2R*,5R*)-8-Benzyl-2-[3,5-bis(trifluoromethyl)benzoyloxy]-1-phenyl-8-azabicyclo[3.2.1]octane (Description 9; 821 mg, 1.54 mmol) was treated with a solution of dimethylbis(cyclopentadienyl)titanium in toluene (0.2M, 30 ml). The reaction mixture was stirred in the dark at 82° C. for 2.5 hours. The mixture was cooled to 40° C., than solid $Na_2CO_3$ (2 g) added followed by a mixture of methanol-water (9:1, 20 ml). The mixture was stirred for 1 hour at 40° C. and filtered through a pad of Celite™. The filtrate was dried ($Na_2SO_4$) and concentrated. The residue was purified by chromatography on silica gel (iso-hexane:ethyl acetate 0–35% containing 0.5% triethylamine) to give a 10:1 mixture of (1R*,2R*,5S*,6R*)-2-{1-[3,5-bis(trifluoromethyl)phenyl]ethenyloxy}-1-phenyl-8-azabicyclo[3.2.1]octane and (1R*,2R*,5S*,6R*)-8-benzyl-2-[3,5-bis(trifluoromethyl)benzoyloxy]-1-phenyl-8-azabicyclo[3.2.1]octane. 2/5 of this crude mixture was treated with I-propanol (8 ml), ethyl acetate (8 ml) and 10% palladium on charcoal (340 mg) and stirred under hydrogen atmosphere (1 atm) at room temperature for 12 hours. The mixture was filtered through a pad of Celite™ and concentrated to give a 7:1 (S*:R*) mixture of the title compounds. The isomers were separated by preparative TLC (dichloromethane:methanol) and converted into hydrochloride salts.

EXAMPLE 9a (S*) isomer (HCl salt)

$\delta_H$(400 MHz, MeOH-$d_4$): 7.72 (1H, s), 7.32 (2H, s), 7.30 (3H, m), 7.12 (2H, m), 4.61 (1H, q, J 6.5 Hz), 4.13 (1H, m), 3.02 (1H, s), 2.63 (1H, ddd, J 4.0 Hz, J 9.8 Hz, 14.0 Hz), 2.35–1.95 (6H, m), 1.76 (1H, m), 1.41 (3H, d, J 6.5 Hz); m/z ($ES^+$) 444 $[M+H]^+$

EXAMPLE 9b (R*) isomer (HCl salt)

$\delta_H$(360 MHz, $CDCl_3$): 10.9 (1H, s), 9.7 (1H, s), 7.74 (1H, s), 7.64 (2H, dm, J 7.8 Hz), 7.59 (2H, s), 7.52–7.37 (3H, m), 4.38 (1H, m), 3.56 (1H, q, J 6.3 Hz), 3.44 (1H, m), 2.74 (1H, m), 2.51 (1H, m), 2.36 (2H, m), 1.82 (2H, m), 1.61 (1H, m), 1.44 (1H, d, J 13.3 Hz), 1.18 (3H, d, J 5.9 Hz); m/z ($ES^+$) 444 $[M+H]^+$.

EXAMPLES 10a AND 10b (1R*,2R*,5R*)-8-Benzyl-2-{(1RS)-[3,5-bis(trifluoromethyl)phenyl]-2-hydroxyethoxy}-1-phenyl-8-azabicyclo[3.2.1]octane A solution of borane-THF complex in THF (1M, 4 ml) was added dropwise to stirred solution of (1R*,2R*,5S*, 6R*)-2-{1-[3,5-bis(trifluoromethyl)phenyl]ethenyloxy}-1-phenyl-8-azabicyclo[3.2.1]octane (from the preparation of Example 9) in THF (7 ml) at −25° C. The reaction mixture was slowly warm up to room temperature (6 hours) and then stirred overnight. After cooling using ice-bath, a mixture of aqueous sodium hydroxide (2M, 6 ml) and hydrogen peroxide (1.5 ml) was added dropwise to the mixture. The ice-bath was removed and the reaction mixture was stirred at ambient temperature for 30 minutes and treated with 10% aqueous sodium sulphite (60 ml). The mixture was extracted with ethyl acetate (3×25 ml). The combined organic extracts were dried ($Na_2SO_4$) and concentrated. The residue was purified by chromatography on silica gel (iso-hexane:diethyl ether 0–80%) to give the (1R*) isomer of the title compound (183 mg) and the (1S*) isomer of the title compound (202 mg).

EXAMPLE 10a (1R*) isomer $\delta_H$(400 MHz, $CDCl_3$): 7.71 (1H, s), 7.4 (2H, d, J 7.3 Hz), 7.40–7.25 (10H, m), 4.57 (1H, dd, J 3.8 Hz, 7.8 Hz), 4.04 (1H, d, J 14.8 Hz), 3.57 (1H, dd, J 8.6 Hz, 11.2 Hz), 3.50–3.25 (4H, m), 2.20–1.88 (5H, m), 1.82–1.70 (1H, m), 1.70–1.57 (1H, m), 1.30–1.20 (1H, m).

EXAMPLE 10b (1S*) isomer $\delta_H$(400 MHz, $CDCl_3$): 7.96 (2H, s), 7.82 (1H, s), 7.62 (2H, d, J 7.7 Hz), 7.55 (2H, d, J 7.4 Hz), 7.42–7.35 (4H, m), 7.30–7.24 (2H, m), 4.32 (1H, dd, J 3.2 Hz, 7.6 Hz), 4.14 (1H, d, J 15.3 Hz), 3.71 (1H, s), 3.48 (1H, d, J 15.4 Hz), 3.45–3.38 (1H, m), 3.38–3.27 (2H, m), 2.25–2.00 (3H, m), 1.90–1.67 (2H, m), 1.60 (1H, m), 1.41 (1H, m), 1.18 (1H, m), 1.05 (1H, m).

EXAMPLE 11

(1R*,2R*,5R*)-2-{(1R*)-[3,5-Bis(trifluoromethyl) phenyl]-2-hydroxyethoxy}-1-phenyl-8-azabicyclo [3.2.1]octane The mixture of (1R*,2R*,5R*)-8-benzyl-2-{(1R*)-[3,5-bis(trifluoromethyl)phenyl]-2-hydroxyethoxy}-1-phenylphonyl-8-azabicyclo[3.2.1]octane (Example 10a; 106 mg, 0.192 mmol), 10% palladium on charcoal (330 mg) and ethanol (10 ml) was stirred under the atmosphere of hydrogen (1 atm) at 65° C. for 1.5 hours. After cooling to room temperature, the mixture was filtered through a pad of Celite™ and concentrated to give the title compound as an oil. The hydrochloride salt of the title compound was prepared by treatment with ethereal HCl and recrystallised from dichloromethane:diethyl ether.

m/z ($ES^+$) 460 $[M+H]^+$

EXAMPLE 12

(1R*,2R*,5R*)-2-{(1S*)-[3,5-Bis(trifluoromethyl) phenyl]-2-hydroxyethoxy}-1-phenyl-8-azabicyclo [3.2.1]octane The mixture of (1R*,2R*,5R*)-8-benzyl-2-{(1S*)-[3,5-bis(trifluoromethyl)phenyl]-2-hydroxyethoxy}-1-phenyl-8-azabicyclo[3.2.1]octane (Example 10b; 100 mg, 0.18 mmol), 10% palladium on charcoal (350 mg) and ethanol (10 ml) was stirred under hydrogen atmosphere (1 atm) at 65° C. for 1 hour. After cooling to room temperature, the mixture was filtered through a pad of Celite™ and concentrated to give the title compound as an oil. The hydrochloride salt of the title compound was prepared by treatment with ethereal HCl and recrystallised from dichloromethane:isohexane.

m/z ($ES^+$) 460 $[M+H]^+$

EXAMPLE 13

(1R*,2R*,5R*)-8-Benzyl-2-[2,5-bis(trifluoromethyl) phenylmethoxy]-1-phenyl-8-azabicyclo[3.2.1]octane (1R*,2R*,5R*)-8-Benzyl-1-phenyl-8-azabicyclo[3.2.1] octan-2-ol (Description 9; 151 mg, 0.52 mmol) was treated with sodium hydride (41 mg, 60% in oil, 1.03 mmol) at 0° C. in a solution of THF (2 ml) and allowed to warm to room temperature. The mixture was recooled to 0° C. and 2,5-bis (trifluoromethyl)benzyl bromide (0.24 ml, 1.30 mmol) added and the mixture heated to 50° C. for 2 days. A further 1.30 mmol of the benzyl bromide was added and the mixture further heated for 50° C. for 2 days. The reaction mixture was poured into water and extracted with ethyl acetate (×3), dried ($MgSO_4$) and concentrated in vacuo to give a yellow solid. This was purified by flash column chromatography [25% ethyl acetate in iso-hexane] to give the title compound.

EXAMPLE 14

(1R*,2R*,5R*)-2-[2,5-Bis(trifluoromethyl) phenylmethoxy]-1-phenyl-8-azabicyclo[3.2.1]octane hydrochloride (1R*,2R*,5R*)-8-Benzyl-2-[2,5-is(trifluoromethyl) phenylmethoxy]-1-phenyl-8-azabicyclo[3.2.1]octane (Example 13; 321 mg, 0.62 mmol) was dissolved in ethyl acetate (5 ml) and glacial acetic acid (1 ml) and 10% palladium hydroxide (50 mg) added. The mixture was hydrogenated at 40 psi overnight. The reaction mixture was then filtered and concentrated in vacuo. The oil was basified (1N sodium hydroxide), extracted with ethyl acetate (x3), dried ($MgSO_4$), and concentrated in vacuo to give a yellow oil. This was purified by flash column chromatography [10% methanol in dichloromethane] to give the free base of title compound. The hydrochloride salt was made by adding 1 equivalent of 1N hydrogen chloride in diethyl ether to a solution in diethyl ether and the solid filtered off and dried at 60° C. in vacuo.

m/z ($ES^+$) 430 ($[M+H]^+$).

EXAMPLE 15

(1R*,2R*,5R*)-8-Benzyl-2-[(2-methoxy-5-trifluoromethoxyphenyl)methoxy]-1-phenyl-8-azabicyclo[3.2.1]octane (1R*,2R*,5R*)-8-Benzyl-1-phenyl-8-azabicyclo[3.2.1] octan-2-ol (Description 9; 348 mg, 1.19 mmol) was dissolved in THF then sodium hydride (71 mg, 60% in oil, 1.79 mmol) added and the reaction mixture stirred for 10 minutes. 2-methoxy-5-trifluoromethoxybenzyl bromide was added and the reaction mixture stirred at 50° C. for 2 hours. The reaction mixture was poured into water and extracted with ethyl acetate (×3), dried ($MgSO_4$) and concentrated in vacuo to give a yellow oil. This was purified by flash column chromatography [5%–15% ethyl acetate in iso-hexane] to give the title compound. (205 mg, 35%).

m/z ($ES^+$) 498 ($[M+H]^+$).

EXAMPLE 16

(1R*,2R*,5R*)-2-[(2-Methoxy-5-trifluoromethoxy) phenylmethoxy]-1-phenyl-8-azabicyclo[3.2.1]octane (1R*,2R*,5R*)-8-Benzyl-2-[(2-methoxy-5-trifluoromethoxy)phenylmethoxy]-1-phenyl-8-azabicyclo

[3.2.1]octane (Example 15; 205 mg, 0.41 mmol) was dissolved in ethyl acetate (5 ml) and glacial acetic acid (1 ml) and degassed with $N_2$ for 5 minutes. 10% palladium hydroxide (30 mg) was added and the mixture hydrogenated at 50 psi overnight. The reaction mixture was filtered, washed with methanol and concentrated in vacuo to give a clear oil. This was basified (1N sodium hydroxide) and extracted with dichloromethane (×3), dried ($MgSO_4$) and concentrated in vacuo to give a clear oil which was purified by flash column chromatography [5%–7.5% methanol in dichloromethane] to give a white solid which was triturated in diethyl ether then filtered off and dried in vacuo at 60° C. to give the title compound (20 mg, 12%).

m/z ($ES^+$) 408 ($[M+H]^+$).

EXAMPLE 17

(1R*,2R*,5R*)-8-Benzyl-2-{[3,5-bis(trifluoromethyl)phenyl]methoxy}-1-(4-fluorophenyl)-8-azabicyclo[3.2.1]octane Sodium hydride (320 mg, 60% in oil, 7.98 mmol) was washed with iso-hexane (×3) then THF (8 ml) and (1R*,2R*,5R*)-8-benzyl-1-(4-fluorophenyl)-8-azabicyclo[3.2.1]octan-2-ol (Description 15; 1.24 g, 3.99 mmol) added and the mixture stirred at room temperature for 10 minutes then 3,5-bis(trifluoromethyl) benzyl bromide added and the reaction mixture stirred at 60° C. overnight. The reaction mixture was poured into water and extracted with ethyl acetate (×3), dried ($MgSO_4$) and concentrated in vacuo to give a yellow oil. This was purified by flash column chromatography [5% ethyl acetate in iso-hexane] to give the title compound (1.51 g, 58%).

m/z ($ES^+$) 538 ($[M+H]^+$).

EXAMPLE 18

(1R*,2R*,5R*)-2-{[3,5-Bis(trifluoromethyl)phenyl]methoxy}-1-(4-fluorophenyl)-8-azabicyclo[3.2.1]octane (1R*,2R*,5R*)-8-Benzyl-2-{[3,5-bis(trifluoromethyl)phenyl]methoxy}-1-(4-fluorophenyl)-8-azabicyclo[3.2.1]octane (Example 17; 1.51 g, 2.81 mmol) was dissolved in ethyl acetate (20 ml) and glacial acetic acid (2 ml) and 10% palladium hydroxide (200 mg) added and hydrogenated at 45 psi overnight. The reaction mixture was filtered then concentrated in vacuo. The oil was basified (4N sodium hydroxide) and the solution extracted with ethyl acetate (×3). The organics were dried ($MgSO_4$) and concentrated in vacuo. The mixture was purified by flash column chromatography [7.5% methanol in dichloromethane] to give a yellow oil which solidified on standing to give the title compound (506 mg, 40%). The hydrochloride salt was made by adding 1 equivalent of 1N hydrogen chloride in diethyl ether to the title compound (31 mg, 0.06 mmol). A white solid formed which was triturated in diethyl ether and filtered then dried at 60° C. in vacuo (29.8 mg, 89%).

m/z ($ES^+$) 448 ($[M+H]^+$).

EXAMPLE 19

(1R*,2R*,5R*)-2-{[3,5-Bis(trifluoromethyl)phenyl]methoxy}-1-(4-fluorophenyl)-8-[(1,2,4-triazol-3-yl)methyl]-8-azabicyclo[3.2.1]octane hydrochloride (1R*,2R*,5R*)-2-{[3,5-Bis(trifluoromethyl)phenyl]methoxy}-1-(4-fluorophenyl)-8-azabicyclo[3.2.1]octane (Example 18; 268 mg, 0.60 mmol), potassium carbonate (332 mg, 2.40 mmol), and N-formyl-2-chloroacetamidrazone (138 mg, 1.02 mmol) were combined in dimethylformamide (3 ml) and heated at 60° C. for 45 minutes. The reaction mixture was then poured into water and extracted with ethyl acetate (×2), dried ($MgSO_4$), and concentrated in vacuo. The crude compound was then dissolved in toluene and heated overnight at 120° C. The reaction mixture was poured into water and extracted with ethyl acetate (×3), dried ($MgSO_4$) and concentrated in vacuo to give a brown foam. This was purified by flash column chromatography [5% methanol in dichloromethane] to give an orange solid (148 mg, 47%). The hydrochloride salt was made by adding 1 equivalent of 1N hydrogen chloride in diethyl ether to a solution in diethyl ether. The solid formed was triturated then filtered off and dried in vacuo at 60° C. to give the title compound as a beige solid (108 mg, 68%).

m/z ($ES^+$) 529 ($[M+H]^+$).

EXAMPLE 20

(1R*,2R*,5R*)-2-{[3,5-Bis(trifluoromethyl)phenyl]methoxy}-1-(4-fluorophenyl)-8-[(1-methyl-1,2,4-triazol-3-yl)methyl]-8-azabicyclo[3.2.1]octane hydrochloride (1R*,2R*,5R*)-2-{[3,5-Bis(trifluoromethyl)phenyl]methoxy}-1-(4-fluorophenyl)-8-azabicyclo[3.2.1]octane (Example 18; 101 mg, 0.23 mmol), potassium carbonate (159 mg, 1.15 mmol), and 1-methyl-3-chloromethyl-1,2,4 triazole (386 mg, 2.30 mmol) were combined in dimethylformamide and heated at 80° C. for 5 days. The reaction mixture was poured into water and extracted with ethyl acetate (×3), dried ($MgSO_4$) and concentrated in vacuo to give a yellow oil. This was purified by flash column chromatography [7.5% methanol in dichloromethane] to give desired product. The hydrochloride salt was made by adding 1 equivalent of 1N hydrogen chloride in diethyl ether to a solution in diethyl ether. The salt was further purified by SCX cartridge eluting with methanol then ammonia in methanol. The ammonia washings were collected and concentrated in vacuo and the hydrochloride salt made by adding 1 equivalent of 1N hydrogen chloride in diethyl ether to a solution in-diethyl ether. The solid formed was filtered and dried at 60° C. in vacuo to give the title compound.

m/z ($ES^+$) 544 ($[M+H]^+$).

EXAMPLES 21a AND 21b (1R*,2R*,5R*)-2-{(1R*)-[3,5-Bis(trifluoromethyl)phenyl]ethoxy}-1-(4-fluorophenyl)-8-azabicyclo[3.2.1]octane; and (1R*,2R*,5R*)-2-{(1S*)-[3,5-bis(trifluoromethyl)phenyl]ethoxy}-1-(4-fluorophenyl)-8-azabicyclo[3.2.1]octane (1R*,2R*,5R*)-8-benzyl-2-{1-[3,5-bis(trifluoromethyl)phenyl]ethenyloxy}-1-(4-fluorophenyl)-8-azabicyclo[3.2.1]octane (Description 17; 923 mg, 1.68 mmol) was dissolved in ethyl acetate (20 ml) and glacial acetic acid (2 ml) and 10% palladium hydroxide (100 mg) added. The reaction mixture was hydrogenated at 40 psi overnight at room temperature. The mixture was filtered then concentrated in vacuo, basified (4N sodium hydroxide) and extracted with ethyl acetate (×3), dried ($MgSO_4$) and concentrated in vacuo to give an orange oil. The mixture of 2 isomers was purified by first, flash column chromatography [5% methanol in dichloromethane] to give the undesired isomer, then by lobar chromatography [7.5% methanol in dichloromethane] to give the desired isomer.

The free base of the (1R*)-isomer (200 mg) and the (1S*)-isomer (25 mg) were made into the hydrochloride salt by adding 1 equivalent of 1N hydrogen chloride in diethyl ether to a solution in diethyl ether. The solid was filtered and dried in vacuo at 60° C. (60 mg).

EXAMPLE 21a (1R*) isomer (HCl salt)

$\delta_H$(360 MHz, MeOH-d$_4$): 7.87 (3H, s), 7.41 (2H, m), 7.26 (2H, m), 4.25 (1H, m), 4.14 (1H, m), 3.84 (1H, br s), 2.74–2.66 (1H, m), 2.32–1.93 (5H, m), 1.68 (1H, m), 1.56 (1H, m), 0.99 (3H, d, J 6.4 Hz);

m/z (ES$^+$) 462 ([M+H]$^+$).

EXAMPLE 21b (1S*) isomer (HCl salt)

$\delta_H$(360 MHz, MeOH-d$_4$): 7.74 (1H, s), 7.37 (2H, s), 7.16 (2H, m), 7.03 (1H, m), 4.68 (1H, m), 4.15 (1H, m), 3.55 (1H, br s), 2.67–2.59 (1H, m), 2.33–1.95 (6H, m), 1.77 (1H, m), 1.43 (3H, d, J 6.48Hz);

m/z (ES$^+$) 462 ([M+H]$^+$).

EXAMPLE 22

(1R*,2R*,5S*,6S*)-2-{[3,5-Bis(trifluoromethyl) phenyl]methoxy}-6-(tert-butoxycarbonyl)-1-phenyl-8-azabicyclo[3.2.1]octane A mixture of (1R*,2R*,5S*,6S*)-8-benzyl-2-{[3,5-bis(trifluoromethyl)phenyl]methoxy}-6-(tert-butoxycarbonyl)-1-phenyl-8-azabicyclo[3.2.1]octane (Description 22; 826 mg, 1.33 mmol), 10% palladium on charcoal (470 mg, 0.44 mmol), ethyl acetate (10 ml) and ethanol (10 ml) was stirred under hydrogen atmosphere (1 atm) at +60° C. for 1 hour. The reaction mixture was cooled to room temperature, flushed with nitrogen gas and filtered through a pad of Celite™. The filtrate was concentrated to give the title compound (500 g, 71%).

$\delta_H$(400 MHz, CDCl$_3$): 7.67 (1H, s), 7.45–7.25 (7H, m), 4.49 (1H, d, J 12.9 Hz), 4.32 (1H, br), 4.15 (1H, d, J 12.9 Hz), 3.81 (1H, br), 3.61 (1H, br s), 2.80 (1H, dd, J 6.2 Hz, 14.1 Hz), 2.50–2.25 (2H, m), 2.70 (1H, dt, J 5.5 Hz, 13.7 Hz), 2.00 (1H, m), 1.95–1.50 (2H, m), 1.51 (9H, s).

EXAMPLE 23

(1R*,2R*,5S*,6S*)-2-{[3,5-Bis(trifluoromethyl) phenyl]methoxy}-6-methoxycarbonyl-1-phenyl-8-azabicyclo[3.2.1]octane hydrochloride A mixture of (1R*,2R*,5S*,6S*)-2-{[3,5-bis(trifluoromethyl)phenyl]methoxy}-6-(tert-butoxycarbonyl)-1-phenyl-8-azabicyclo[3.2.1]octane (Example 22; 50 mg, 0,094 mmol), methanol (0.3 ml) and 1M HCl in diethyl ether was stirred at room temperature for 10 days and heated at reflux for 5 hours. The mixture was concentrated in vacuo to give the title compound as a white solid.

m/z (ES$^+$) 488 [M+H]$^+$

EXAMPLE 24

(1R*,2R*,5S*,6R*)-8-Benzyl-2-{[3,5-bis(trifluoromethyl)phenyl]methoxy}-6-(tertbutoxycarbonyl)-1-phenyl-8-azabicyclo[3.2.1]octane A solution of (1R*,2R*,5S*,6R*)-8-benzyl-6-(tert-butoxycarbonyl)-1-phenyl-8azabicyclo[3.2.]octan-2-ol (Description 20; 5.8 g, 14.7 mmol) and 18-crown-6 (5.3 g, 20 mmol) in THF (50 ml) was added to a stirred, ice-bath cooled suspension of sodium hydride (60% in oil, 800 mg, washed twice with THF) in THF (10 ml). The mixture was stirred for 5 minutes and 3,5-bis(trifluoromethyl)benzyl bromide (1 ml, 5.45 mmol) was added via syringe. The reaction mixture was stirred for 6 days and poured onto saturated aqueous NH$_4$Cl and extracted into a 1:1 mixture of iso-hexane:diethyl ether (3×100 ml). The combined organic extracts were washed with brine, dried (Na$_2$SO$_4$) and concentrated. The residue was purified by chromatography on silica gel (iso-hexane:diethyl ether) to give the title compound (4.92 g, 54%).

$\delta_H$(400 MHz, CDCl$_3$): 7.74 (3H,s), 7.57 (1H, d, J 7.4 Hz), 7.39 (1H, d, J 7.4 Hz), 7.35–7.15 (6H, m), 4.83 (1H, d, J 12.9 Hz), 4.59 (1H, d, J 12.8 Hz), 4.11 (1H, br s), 4.09 (1H, d, J 15.8 Hz), 3.82 (1H, d, J 15.8 Hz), 3.69 (1H, br s), 2.73 (1H, dd, 4.3 Hz, 9.0 Hz), 2.48 (1H, dd, J 4.3 Hz, 12.0 Hz), 2.20 (1H, ddd, J 2.3 Hz, J 5.1 Hz, 13.3 Hz), 2.11 (1H, dd, J 5.1 Hz, 15.2 Hz), 2.02 (1H, dd, J 9.0 Hz, 13.3 Hz), 1.44 (9H, s), 1.21 (1H, m).

EXAMPLE 25

(1R*,2R*,5S*,6R*)-2-{[3,5-Bis(trifluoromethyl) phenyl]methoxy}-6-(tert-butoxycarbonyl)-1-phenyl-8-azabicyclo[3.2.1]octane A mixture of (1R*,2R*,5S*,6R*)-8-benzyl-2-{[3,5-bis(trifluoromethyl)phenyl]methoxy}-6-(tert-butoxycarbonyl)-1-phenyl-8-azabicyclo[3.2.1]octane (Example 24; 240 mg, 0.39 mmol), 10% palladium on charcoal (470 mg, 0.40 mmol) ethanol (10 ml) was stirred under hydrogen atmosphere (1 atm) at +65° C. for 1 hour and at room temperature overnight. The reaction mixture was cooled to room temperature, flushed with nitrogen gas and filtered through a pad of Celite™. The filtrate was concentrated. The residue was purified by chromatography on silica gel (iso-hexane:ethyl acetate 0–25%) to give the title compound (135 g, 66%).

m/z (ES$^+$) 530 [M+H]$^+$

EXAMPLE 26

(1R*,2R*,5S*,6R*)-2-{[3,5-Bis(trifluoromethyl) phenyl]methoxy}-6methoxycarbonyl-1-phenyl-8-azabicyclo[3.2.1]octane hydrochloride A mixture of (1R*,2R*,5S*,6R*)-2-{[3,5-bis(trifluoromethyl)phenyl]methoxy}-6-(tert-butoxycarbonyl)-1-phenyl-8-azabicyclo[3.2.1]octane (Example 25; 44 mg, 0.08 mmol), methanol (0.1 ml), dichloromethane (0.6 ml) and 1M HCl in diethyl ether (1 ml) was kept at room temperature for 3 weeks. The mixture was concentrated to give the title compound as a white solid.

m/z (ES$^+$) 488 [M+H]$^+$

EXAMPLE 27

(1R*,2R*,5S*,6R*)-2-{[3,5-Bis(trifluoromethyl) phenyl]methoxy}-1-phenyl-8-azabicyclo[3.2.1] octan-6-carboxylic acid hydrochloride A mixture of (1R*,2R*,5S*,6R*)-2-{[3,5-bis(trifluoromethyl)phenyl]methoxy}-6-(tert-butoxycarbonyl)-1-phenyl-8-azabicyclo[3.2.1]octane (Example 25; 20 mg, 0.04 mmol), dichloromethane (1 ml) and 1M HCl in diethyl ether (0.5 ml) was kept at room temperature for 2 weeks. The white solid was filtered off, washed with a 1:1 mixture dichloromethane:diethyl ether to give the title compound (11 mg).

m/z (ES$^+$) 474 [M+H]$^+$

EXAMPLE 28

(1R*,2R*,5S*,6R*)-8-Benzyl-2-{[3,5-bis(trifluoromethyl)phenyl]methoxy}-6-hydroxymethyl-1-phenyl-8-azabicyclo[3.2.1]octane A solution of DIBAL-H in dichloromethane (1M, 1.3 ml, 1.3 mmol) was added dropwise to a stirred solution of (1R*,2R*,5S*,6R*)-2-{[3,5-bis(trifluoromethyl)phenyl]methoxy}-6-(tert-butoxycarbonyl)-1-phenyl-8-azabicyclo[3.2.1]octane (Example 25; 100 mg, 0.16 mmol) in dichloromethane (2 ml) at room temperature. The mixture was stirred for 45 minutes, then diluted with dichloromethane (25 ml) and quenched with small amount of saturated aqueous $Na_2SO_4$ and stirred for additional 1 hour. The mixture was filtered through a pad of Celite™, concentrated and purified by chromatography on silica gel (iso-hexane:ethyl acetate) to give the title compound (85 mg, 96%).

$\delta_H$(360 MHz, $CDCl_3$): 7.74 (1H, s), 7.71 (2H, s), 7.56 (2H, m), 7.36 (6H, m), 7.25 (2H, m), 4.87 (1H, d, J 12.6 Hz), 4.60 (1H, d, J 12.6 Hz), 4.22 (2H, m), 4.12 (1H, dd, J 2.1 Hz, 14.7 Hz), 3.88 (1H, d, J 15.1 Hz), 3.64 (2H, m), 3.30 (1H, br s), 2.79 (1H, br), 2.30 (1H, ddd, J 2.8 Hz, J 5.6 Hz, 13.3 Hz), 2.20–1.95 (4H, m), 1.72 (1H, d, J 11.6 Hz), 1.16 (1H, dd, J 4.2 Hz, 13.7 Hz).

EXAMPLE 29

(1R*,2R*,5S*,6R*)-2-{[3,5-Bis(trifluoromethyl)phenyl]methoxy}-6-hydroxymethyl-1-phenyl-8-azabicyclo[3.2.1]octane A mixture of (1R*,2R*,5S*,6R*)-8-benzyl-2-{[3,5-bis(trifluoromethyl)phenyl]methoxy}-6-hydroxymethyl-1-phenyl-8-azabicyclo[3.2.1]octane (Example 28; 85 mg 0.15 mmol), 10% palladium on charcoal (125 mg, 0.12 mmol) ethanol (10 ml) was stirred under hydrogen atmosphere (1 atm) at +65° C. for 45 minutes. The reaction mixture was cooled to room temperature, flushed with nitrogen gas and filtered through a pad of Celite™. The filtrate was concentrated to give the title compound. The hydrochloride salt of the title compound was prepared by treatment with ethereal HCl and recrystallised from ethylacetate:iso-hexane.

m/z ($ES^+$) 460 [M+H]$^+$

EXAMPLE 30

(1R*,2R*,5S*,6R*)-2-{[3,5-Bis(trifluoromethyl)phenyl]methoxy}-6-(1-methyl-1,2,4-triazol-3-yl)methoxymethyl-1-phenyl-8-azabicyclo[3.2.1]octane hydrochloride (1R*,2R*,5S*,6R*)-8-Benzyl-2-{[3,5-bis(trifluoromethyl)phenyl]methoxy}-6-hydroxymethyl-1-phenyl-8-azabicyclo[3.2.1]octane (Example 28; 100 mg, 0.18 mmol), 15-crown-5 (80 mg, 0.36 mmol) and sodium hydride (60% dispersion in oil; 22 mg, 0.55 mmol) in THF were treated with 3-chloromethyl-1-methyl-1,2,4-triazole hydrochloride, and stirred at 60° C. for 18 hours. The mixture was diluted with water and extracted with ethyl acetate. The organics were collected, dried ($MgSO_4$) and concentrated in vacuo. The residue was purified by flash column chromatography eluting with 50–75% ethyl acetate/hexane to afford a clear oil (75 mg, 64%). This N-benzyl compound (75 mg, 0.12 mmol), palladium, 5% on carbon (40 mg), methanol (10 ml) and 2N hydrochloric acid (0.5 ml) was hydrogenated using the Parr™ apparatus for 36 hours. The mixture was filtered and concentrated in vacuo. The residue was taken into dichloromethane and washed with water. The organics were separated and dried ($MgSO_4$) and concentrated in vacuo. The residue was treated with ethereal hydrogen chloride and the resultant salt crystallised from methanol/diethyl ether to give the title compound (38 mg, 56%).

m/z ($ES^+$) 555 ([M+H]$^+$).

Prepared in an analogous manner were the following four compounds:

EXAMPLE 31

(1R*,2R*,5S*,6R*)-2-{[3,5-Bis(trifluoromethyl)phenyl]methoxy}-6-methoxymethyl-1-phenyl-8-azabicyclo[3.2.1]octane hydrochloride m/z ($ES^+$) 474 ([M+H]$^+$).

EXAMPLE 32

(1R*,2R*,5S*,6R*)-2-{[3,5-Bis(trifluoromethyl)phenyl]methoxy}-6-(N,N-dimethylacetamidoyloxymethyl)methoxymethyl-1-phenyl-8-azabicyclo[3.2.1]octane hydrochloride m/z ($ES^+$) 545 ([M+H]$^+$).

EXAMPLE 33

(1R*,2R*,5S*,6R*)-2-{[3,5-Bis(trifluoromethyl)phenyl]methoxy}-6-(3-hydroxypropyloxymethyl)methoxymethyl-1-phenyl-8-azabicyclo[3.2.1]octane hydrochloride m/z ($ES^+$) 518 ([M+H]$^+$).

EXAMPLE 34

(1R*,2R*,5S*,6R*)-2-{[3,5-Bis(trifluoromethyl)phenyl]methoxy}-6-(3-methoxypropyloxymethyl)methoxymethyl-1-phenyl-8-azabicyclo[3.2.1]octane hydrochloride m/z ($ES^+$) 532 ([M+H]$^+$).

EXAMPLE 35

(1R*,2R*,5S*,6R*)-8-Benzyl-2-{[3,5-bis(trifluoromethyl)phenyl]methoxy}-6-(1-hydroxy-1-methylethyl)-1-phenyl-8-azabicyclo[3.2.1]octane A solution of methyl magnesium bromide in diethyl ether (3M, 1 ml, 3 mmol) was added to a stirred solution of (1R*,2R*,5S*,6R*)-2-{[3,5-bis(trifluoromethyl)phenyl]methoxy}-6-(tert-butoxycarbonyl)-1-phenyl-8-azabicyclo[3.2.1]octane (Example 25; 73 mg, 0.12 mmol) in THF (4 ml) at room temperature. The mixture was stirred for 20 hours and additional portion of methyl magnesium bromide (1 ml) was added. After next 8 hours, the reaction mixture was quenched with saturated aqueous $NH_4Cl$ (15 ml) and 25% aqueous ammonia (15 ml) solutions and extracted into ethyl acetate. The combined organic extracts were dried ($Na_2SO_4$) and concentrated. The residue was purified by chromatography on silica gel (iso-hexane:ethyl acetate 0–20%) to give the title compound (56 mg, 82%).

$\delta_H$(360 MHz, $CDCl_3$): 7.73 (1H, s), 7.76 (2H, s), 7.58 (2H, dm, J 8.1 Hz), 7.39 (2H, dm, J 7.4 Hz), 7.35–7.21 (6H, m), 4.87 (1H, d, J 12.6 Hz), 4.60 (1H, d, J 12.6 Hz), 4.24

(1H, br s), 4.07 (1H, d, J 14.0 Hz), 3.83 (1H, d, J 14.0 Hz), 3.65 (1H, br), 3.45 (1H, br s), 2.35 (1H, m), 2.14 (1H, m), 2.10–1.92 (3H, m), 1.86 (1H, t, J 7.0 Hz), 1.12 (1H, dd, J 1.1 Hz, 14.3 Hz), 1.07 (3H, s), 1.05 (3H, s).

EXAMPLE 36

(1R*,2R*,5S*,6R*)-2-{[3,5-Bis(trifluoromethyl) phenyl]methoxy}-6-(1-hydroxy-1-methylethyl)-1-phenyl-8-azabicyclo[3.2.1]octane A mixture of (1R*,2R*,5S*,6R*)-8-benzyl-2-{[3,5-bis (trifluoromethyl)phenyl]methoxy}-6-(1-hydroxy-1-methylethyl)-1-phenyl-8-azabicyclo[3.2.1]octane (Example 35; 56 mg 0.10 mmol), 10% palladium on charcoal (200 mg, 0.2 mmol) ethanol (10 ml) was stirred under hydrogen atmosphere (1 atm) at +60° C. for 2 hours. The reaction mixture was cooled to room temperature, flushed with nitrogen gas and filtered through a pad of Celite™. The filtrate was concentrated to give the title compound. The hydrochloride salt of the title compound was prepared by treatment with ethereal HCl and recrystallised from ethyl acetate:iso-hexane.

m/z (ES$^+$) 530 [M+H]$^+$.

EXAMPLE 37

(1R*,2R*,5S*,6R*)-8-Benzyl-2-{[3,5-bis (trifluoromethyl)phenyl]methoxy}-6-(N-methoxy-N-methylcarbamoyl)-1-phenyl-8-azabicyclo[3.2.1] octane A mixture of (1R*,2R*,5S*,6R*)-2-{[3,5-bis (trifluoromethyl)phenyl]methoxy}-6-(tert-butoxycarbonyl)-1-phenyl-8-azabicyclo[3.2.1]octane (Example 25; 340 mg, 0.55 mmol), dichloromethane (8 ml) and trifluoroacetic acid (2 ml) was stirred at room temperature for 24 hours and concentrated. The residue was treated with dichloromethane (2.5 ml) followed by N,O-dimethylhydroxylamine hydrochloride (204 mg, 2.1 mmol), triethylamine (0.7 ml, 5 mmol), 1-(3-dimethylaminopropyl)-3-ethylcarbodiimide hydrochloride (450 mg, 2.35 mmol), 4-N,N-dimethylaminopyridine (26 mg, 0.21 mmol). The mixture was stirred for 6 hours, quenched with saturated aqueous NaHCO$_3$ and extracted into dichloromethane. The combined organic extracts were dried (Na$_2$SO$_4$) and concentrated. The residue was purified by chromatography on silica gel (iso-hexane:ethyl acetate) to give the title compound (260 mg, 78%).

$\delta_H$(360 MHz, CDCl$_3$): 7.75 (3H, s), 7.62 (2H, dd, J 1.4 Hz, 7.4 Hz), 7.41 (2H, d, J 7.7 Hz), 7.35–7.25 (4H, m), 7.19 (2H, m), 4.84 (1H, d, J 13.0 Hz), 4.59 (1H, d, J 13.0 Hz), 4.13 (1H, br s), 4.09 (1H, d, J 16.5 Hz), 3.83 (1H, d, J 16.1 Hz), 3.62 (3H, s), 3.59 (1H, s), 3.19 (3H, s), 3.06 (1H, dd, J 4.6 Hz, 8.1 Hz), 2.68 (1H, dd, J 4.6 Hz, 13.3 Hz), 2.27–1.95 (4H, m), 1.21 (1H, m).

EXAMPLE 38

(1R*,2R*,5S*,6R*)-2-{[3,5-Bis(trifluoromethyl) phenyl]methoxy}-6-(N-methoxy-N-methylcarbamoyl)-1-phenyl-8-azabicyclo[3.2.1] octane A mixture of (1R*,2R*,5S*,6R*)-8-benzyl-2-{[3,5-bis (trifluoromethyl)phenyl]methoxy}-6-(N-methoxy-N-methylcarbamoyl)-1-phenyl-8-azabicyclo[3.2.1]octane (Example 37; 420 mg 0.69 mmol), 10% palladium on charcoal (375 mg, 0.35 mmol) ethanol (25 ml) was stirred under hydrogen atmosphere (1 atm) at +60° C. for 1 hour. The reaction mixture was cooled to room temperature, flushed with nitrogen gas and filtered through a pad of Celite™. The filtrate was concentrated to give the title compound. The hydrochloride salt of the title compound was prepared by treatment with ethereal HCl and recrystallised from ethyl acetate.

m/z (ES$^+$) 517 [M+H]$^+$

EXAMPLE 39

(1R*,2R*,5S*,6R*)-2-{[3,5-Bis(trifluoromethyl) phenyl]methoxy}-1-phenyl-6-phenylcarbonylo-8-azabicyclo[3.2.1]octane hydrochloride A solution of phenyl lithium (1.8M in cyclohexane-ether, 1.5 ml, 2.7 mmol) was added droipwise to a stirred suspension of 1R*,2R*,5S*,6R*)-2-{[3,5-bis(trifluoromethyl) phenyl]methoxy}-6-(N-methoxy-N-methylcarbamoyl)-1-phenyl-8-azabicyclo[3.2.1]octane hydrochloride (Example 38; 310 mg, 0.56 mmol) in THF (8 ml) at −78° C. The reaction mixture was stirred at −78° C. for 3 hours and the cold bath was removed. The mixture was stirred at ambient temperature for 10 minutes, then quenched with saturated aqueous NH$_4$Cl and extracted into dichloromethane. The combined organic extracts were dried (Na$_2$SO$_4$) and concentrated. The residue was purified by chromatography on silica gel (iso-hexane:ethyl acetate) to give the free base of the title compound. The hydrochloride salt was prepared by treatment the amine with ethereal HCl and recrystallised from ethyl acetate:diethyl ether.

m/z (ES$^+$) 534 [M+H]$^+$

EXAMPLES 40a AND 40b (1R*,2R*,5S*,6R*)-2-{[3,5-Bis(trifluoromethyl) phenyl]methoxy}-1-phenyl-6-[(RS)-1-phenylhydroxymethyl]-8-azabicyclo[3.2.1]octane A solution of DIBAL-H in dichloromethane (1M, 4 ml, 4 mmol) was added dropwise to a stirred solution of (1R*, 2R*,5S*,6R*)-2-{[3,5-bis(trifluoromethyl)phenyl] methoxy}-6-(tert-butoxycarbonyl)-1-phenyl-8-azabicyclo [3.2.1]octane (Example 25; 750 mg, 1.4 mmol) in dichloromethane (5 ml) at −78° C. The reaction mixture was stirred at −78° C. for 20 minutes and quenched with ethyl acetate (0.5 ml) followed by dichloromethane (30 ml) and few drops of water. The mixture was warm up to room temperature and stirred with solid Na$_2$SO$_4$ for 1 hour. The mixture was filtered through a pad of Celite™. The filtrate was concentrated to give a crude aldehyde (553 mg), which was used in the next step without purification. A solution of phenyl magnesium bromide in diethyl ether (3M, 0.5 ml, 1.5 mmol) was added dropwise to a stirred solution of aldehyde (184 mg) in THF at +5° C. the reaction mixture was stirred for 1 hour and quenched with saturated aqueous NH$_4$Cl (15 ml) and 25% aqueous ammonia (15 ml) solutions and extracted into dichloromethane. The combined organic extracts were dried (Na$_2$SO$_4$) and concentrated. The residue was purified by chromatography on silica gel (iso-hexane:ethyl acetate 0–20%) to give a 1.4:1 mixture of epimeric alcohols which were separated by preparative TLC. Hydrochloride salts were prepared by treatment amines with ethereal HCl.

EXAMPLE 40a

6-[(S)-1-phenylhydroxymethyl]-epimer (HCl salt)

$\delta_H$(400 MHz MeOH-d$_4$): 7.68 (1H, s), 7.40 (2H, dm, J 7.1 Hz), 7.35–7.20 (10 H, m), 4.82 (1H, d, J 4.7 Hz), 4.45 (1H, d, J 12.9 Hz), 4.08 (1H, d, J 12.5 Hz), 3.88 (1H, br), 3.63 (1H, s), 2.47 (1H, dt, J 4.3 Hz, 9.4 Hz), 2.39 (1H, dd, J 9.4 Hz, 13.7 Hz), 2.00 (1H, dd, J 3.9 Hz, 13.3 Hz), 1.98–1.89 (2H, m); m/z (ES$^+$) 535 [M+H]$^+$

EXAMPLE 40b

6-[(R)-1-phenylhydroxymethyl]-epimer (HCl salt)

$\delta_H$(360 MHz, MeOH-d$_4$): 7.80 (1H, s), 7.55 (2H, s), 7.46–7.23 (10 H, m), 4.92 (1H, d, J 5.0 Hz), 4.69 (1H, d, J 12.4 Hz), 4.20 (1H, d, J 12.6 Hz), 4.00 (1H, br s), 3.88 (1H, br s), 2.82 (1H, dt, J 4.7 Hz, 9.5 Hz), 2.56 (1H, dd, J 9.5 Hz, 14.5 Hz), 2.22 (1H, dd, J 4.7 Hz, 14.2 Hz), 2.18–2.04 (3H, m), 1.80 (1H, m); m/z (ES$^+$) 535 [M+H]$^+$

EXAMPLE 41

(1R*,2R*,5R*)-8-Benzyl-2-{[3,5-bis(trifluoromethyl)phenyl]methoxy}-1-phenyl-8-azabicyclo[3.2.1]octan-6-one A solution of n-butyl lithium (1.5M in hexanes, 0.45 ml, 0.67 mmol) was added dropwise to a stirred solution of (1R*,2R*,5S*,6R*,8S*)-8-benzyl-2-{[3,5-bis(trifluoromethyl)phenyl]methoxy}-1-phenyl-6-phenylsulphonyl-8-azabicyclo[3.2.1]octane (Example 1; 340 mg, 0.51 mmol) in THF (10 ml) at −75° C. The reaction mixture was stirred at −75 to −60° C. for 15 minutes and oxygen gas was passed through for 15 minutes. The reaction mixture was warm up to 0° C., quenched with saturated aqueous NH$_4$Cl and extracted into dichloromethane. The combined organic extracts were dried (Na$_2$SO$_4$) and concentrated. The residue was purified by chromatography on silica gel (iso-hexane:diethyl ether 0–100%) to give the title compound (53 mg, 20%) and starting compound (250 mg, 73%).

$\delta_H$(360 MHz, CDCl$_3$): 7.77 (1H, s), 7.70 (2H, s), 7.58 (2H, d, J 8.1 Hz), 7.44–7.19 (8H, m), 4.78 (1H, d, J 12.6 Hz), 4.44 (1H, d, J 12.6 Hz), 4.20 (1H, d, J 15.1 Hz), 4.05 (1H, br s), 3.73 (1H, d, J 15.1 Hz), 3.40 (1H, br s), 2.69 (1H, d, J 18.2 Hz), 2.48 (1H, d, J 18.2 Hz), 2.33–2.11 (2H, m), 2.02–1.85 (1H, m), 1.57 (1H, m).

EXAMPLE 42

(1R*,2R*,5S*)-2-{[3,5-Bis(trifluoromethyl)phenyl]methoxy}-1-phenyl-8-azabicyclo[3.2.1]octan-6-one A mixture of (1R*,2R*,5S*)-8-benzyl-2-{[3,5-bis(trifluoromethyl)phenyl]methoxy}-1-phenyl-8-azabicyclo[3.2.1]octan-6-one (Example 41; 53 mg 0.1 mmol), 5% palladium on charcoal (230 mg, 0.11 mmol) ethanol (10 ml) was stirred under hydrogen atmosphere (1 atm) at room temperature for 45 minutes. The reaction mixture was cooled to room temperature, flushed with nitrogen gas and filtered through a pad of Celite™. The filtrate was concentrated to give the title compound. The hydrochloride salt of the title compound was prepared by treatment with ethereal HCl and recrystallised from dichloromethane:diethyl ether.

m/z (ES$^+$) 444 [M+H]$^+$.

EXAMPLE 43

(1R*,2R*,5S*,6S*)-8-Benzyl-2-{[3,5-bis(trifluoromethyl)phenyl]methoxy}-1-phenyl-8-azabicyclo[3.2.1]octan-6-ol Sodium borohydride (55 mg, 1.44 mmol) was added to a stirred solution of (1R*,2R*,5S*)-8-benzyl-2-{[3,5-bis(trifluoromethyl)phenyl]methoxy}-1-phenyl-8-azabicyclo[3.2.1]octan-6-one (Example 41; 50 mg 0.09 mmol) in methanol (3 ml) at +5° C. The reaction mixture was stirred for 15 minutes and quenched with saturated aqueous NaHCO$_3$ and extracted into dichloromethane. The combined organic extracts were dried (Na$_2$SO$_4$) and concentrated. The residue was purified by chromatography on silica gel (iso-hexane:diethyl ether 10–45%) to give the title, compound (35 mg, 70%).

$\delta_H$(360 MHz, CDCl$_3$): 7.74 (1H, s), 7.72 (2H, s), 7.53 (2H, d, J 7.7 Hz), 7.40–7.27 (6H, m), 7.27–7.17 (2H, m), 4.87 (1H, d, J 13.0 Hz), 4.63 (1H, m), 4.58 (1H, d, J 13.0 Hz), 4.21 (1H, br s), 4.18 (1H, d, J 15.1 Hz), 3.88 (1H, d, J 15.4 Hz), 3.38 (1H, br d, J 5.3 Hz), 2.26 (1H, dd, J 10.9 Hz, 13.7 Hz), 2.31 (1H, m), 2.21–2.03 (2H, m), 1.76 (1H, dd, J 4.2 Hz, 13.7 Hz), 1.72 (1H, br), 1.46 (1H, m).

EXAMPLE 44

(1R*,2R*,5S*,6S*)-2-{[3,5-Bis(trifluoromethyl)phenyl]methoxy}-1-phenyl-8-azabicyclo[3.2.1]octan-6-ol A mixture of (1R*,2R*,5S*,6S*)-8-benzyl-2-{[3,5-bis(trifluoromethyl)phenyl]methoxy}-1-phenyl-8-azabicyclo[3.2.1]octan-6-ol (Example 43; 35 mg 0.065 mmol), 5% palladium on charcoal (150 mg, 0.07 mmol) ethanol (10 ml) was stirred under hydrogen atmosphere (1 atm) at +65° C. for 1 hour. The reaction mixture was cooled to room temperature, flushed with nitrogen gas and filtered through a pad of Celite™. The filtrate was concentrated to give the title compound. The hydrochloride salt of the title compound was prepared by treatment with ethereal HCl and recrystallised from iso-hexane:diethyl ether.

m/z (ES$^+$) 446 [M+H]$^+$.

EXAMPLE 45

(1R*,2R*,5S*,6S*)-8-Benzyl-2-{[3,5-bis(trifluoromethyl)phenyl]methoxy}-6-methoxy-1-phenyl-8-azabicyclo[3.2.1]octane A mixture of (1R*,2R*,5S*,6S*)-8-benzyl-2-{[3,5-bis(trifluoromethyl)phenyl]methoxy}-1-phenyl-8-azabicyclo[3.2.1]octan-6-ol (Example 43; 22 mg 0.041 mmol), methyl iodide (0.5 ml), sodium hydride (40 mg, 1 mmol) and THF (2 ml) was stirred at room temperature for 24 hours, quenched quenched with saturated aqueous NH$_4$Cl and extracted into dichloromethane. The combined organic extracts were dried (Na$_2$SO$_4$) and concentrated. The residue was purified by preparative TLC on silica gel (iso-hexane:diethyl ether 30%) to give the title compound (17 mg, 75%).

$\delta_H$(360 MHz, CDCl$_3$): 7.74 (1H, s), 7.72 (2H, s), 7.53 (2H, d, J 7.7 Hz), 7.41–7.18 (8H, m), 4.86 (1H, d, J 13.0 Hz), 4.58 (1H, d, J 13.0 Hz), 4.19 (1H, d, J 15.4 Hz), 4.18 (1H, br d, J 3.5 Hz), 4.11 (1H, dt, J 4.9 Hz, 10.5 Hz), 3.88 (1H, d, J 15.4 Hz), 3.50 (1H, br s), 3.33(3H, s), 2.36–2.25 (1H, m), 2.29 (1H, dd, J 10.5 Hz, 13.7 Hz), 2.18–1.99 (2H, m), 1.77 (1H, dd, J 4.2 Hz, 13.7 Hz), 1.72 (1H, br), 1.34 (1H, m).

EXAMPLE 46

(1R*,2R*,5S*,6S*)-2-{[3,5-Bis(trifluoromethyl)phenyl]methoxy}-6-methoxy-1-phenyl-8-azabicyclo[3.2.1]octane A mixture of (1R*,2R*,5S*,6S*)-8-benzyl-2-{[8,5-bis(trifluoromethyl)phenyl]methoxy}-6-methoxy-1-phenyl-8- azabicyclo[3.2.1]octane (Example 45; 17 mg, 0.031 mmol), 5% palladium on charcoal (106 mg, 0.05 mmol) ethanol (10 ml) was stirred under hydrogen atmosphere (1 atm) at +65° C. for 1 hour. The reaction mixture was cooled to room temperature, flushed with nitrogen gas and filtered through a pad of Celite™. The filtrate was concentrated to give the title compound.

$\delta_H$(400 MHz, MeOH-$d_4$): 7.80 (1H, s), 7.55 (2H, s), 7.45–7.35 (3H, m), 7.29–7.23 (2H, m), 4.70 (1H, d, J 12.6 Hz), 4.31 (1H, m), 4.21 (1H, d, J 12.6 Hz), 4.13 (1H, dt, J 2.9 Hz, 6.4 Hz), 3.91 (1H, t, J 2.0 Hz), 3.47 (3H, s), 2.62 (1H, dd, J 4.7 Hz, 14.6 Hz), 2.55 (1H, dd, J 9.9 Hz, 14.6 Hz), 2.33 (1H, tdd, J 4.1 Hz, 7.3 Hz, 13.7 Hz), 2.14–1.97 (3H, m).

EXAMPLE 47

(1R*,2R*,5S*,6R*)-2-{[3,5-Bis(trifluoromethyl) phenyl]methoxy}-6-formyl-1-phenyl-8-azabicyclo [3.2.1]octane (1R*,2R*,5S*,6R*)-2-{[3,5-Bis(trifluoromethyl)phenyl] methoxy}-6-hydroxymethyl-1-phenyl-8-azabicyclo[3.2.1] octane (Example 29; 1.38 g, 2.5 mmol) in dichloromethane (6 ml) at room temperature was treated with Dess-Martin periodinane (1.07 g, 2.5 mmol) and stirred for 1 hour. The mixture was treated with 5% sodium hydrogen sulfite (50 ml) and saturated sodium hydrogen carbonate (30 ml) and stirred for 5 minutes. The organics were collected, washed with brine, dried (MgSO$_4$) and concentrated in vacuo to afford the title compound as a yellow foam (1.24 g, 91%).

m/z (ES$^+$) 566 ([M+H$_3$O]$^+$)

EXAMPLE 48

(1R*,2R*,5S*,6R*)-2-{[3,5-Bis(trifluoromethyl) phenyl]methoxy}-6-((1-methylpyrrolid-2-on-5-yl) methyl)aminomethyl-1-phenyl-8-azabicyclo[3.2.1] octane hydrochloride (1R*,2R*,5S*,6R*)-8-Benzyl-2-{[3,5-bis (trifluoromethyl)phenyl]methoxy}-6-formyl-1-phenyl-8-azabicyclo[3.2.1]octane (benzyl derivative of Example 47; 125 mg, 0.23 mmol) and 5-aminomethyl-1-methylpyrrolidin-2-one (93 mg, 0.46 mmol) in dichloroethane were stirred for 15 minutes, and treated with sodium triacetoxyborohydride (97 mg, 0.46 mmol). The mixture was diluted with dichloromethane and washed with saturated sodium hydrogen carbonate. The organics were collected, dried (MgSO$_4$) and concentrated in vacuo. The residue was purified by flash column chromatography, eluting with 5% methanol/dichloromethane. The title compound was isolated as a clear oil and debenzylated as described previously.

m/z (ES$^+$) 570 ([M+H]$^+$).

Prepared in an analogous manner were the following four compounds:

EXAMPLE 49

(1R*,2R*,5S*,6R*)-2-{[3,5-Bis(trifluoromethyl) phenyl]methoxy}-6-(1-(3-methoxy)propyl) aminomethyl-1-phenyl-8-azabicyclo[3.2.1]octane hydrochloride m/z (ES$^+$) 531 ([M+H]$^+$).

EXAMPLE 50

(1R*,2R*,5S*,6R*)-2-{[3,5-Bis(trifluoromethyl) phenyl]methoxy}-6-(1-morpholinyl)methyl-1-phenyl-8-azabicyclo[3.2.1]octane hydrochloride m/z (ES$^+$) 529 ([M+H]$^+$).

EXAMPLE 51

(1R*,2R*,5S*,6R*)-2-{[3,5-Bis(trifluoromethyl) phenyl]methoxy}-6-(piperizin-3-on-1-yl)methyl-1-phenyl-8-azabicyclo[3.2.1]octane hydrochloride m/z (ES$^+$) 542 ([M+H]$^+$).

EXAMPLE 52

(1R*,2R*,5S*,6R*)-2-{[3,5-Bis(trifluoromethyl) phenyl]methoxy}-6-[(3-methyl-3-ethoxycarbonyl) piperidin-1-yl]methyl-1-phenyl-8-azabicyclo[3.2.1] octane hydrochloride m/z (ES$^+$) 613 ([M+H]$^+$).

EXAMPLE 53

(1R*,2R*,5S*,6R*)-8-Benzyl-2-{[3,5-bis (trifluoromethyl)phenyl]methoxy}-1-phenyl-8-azabicyclo[3.2.1]octan-6-carboxylic acid trifluoroacetate A mixture of (1R*,2R*,5S*,6R*)-8-benzyl-2-{[3,5-bis (trifluoromethyl)phenyl]methoxy}-6-(tert-butoxycarbonyl)-1-phenyl-8-azabicyclo[3.2.1]octane (Example 24; 3.37 g, 5.43 mmol), trifluoroacetic acid (4 ml) and dichloromethane (6 ml) was stirred at reflux for 4.5 hour then concentrated in vacuo to give crude title compound which crystallised from dichloromethane.

$\delta_H$(360 MHz, MeOH-$d_4$): 7.85 (1H, s), 7.69 (2H, s), 7.60–7.39 (10H, m), 74.93 (1H, br), 4.89 (1H, d, J 13.0 Hz), 4.60 (1H, d, J 12.6 Hz), 4.22 (1H, br s), 4.07 (1H, d, J 13.7 Hz), 3.83 (1H, d, J 14.0 Hz), 3.51 (1H, br s), 2.67 (1H, dd, J 3.9 Hz, 9.5 Hz), 2.41–2.30 (1H, m), 2.35 (1H, dd, J 9.8 Hz, 14.0 Hz), 2.16 (1H, dd, J 5.6 H 15.8 Hz), 2.03 (1H, dd, J 4.2 Hz, 14.0 Hz), 1.96 (1H, m), 1.27 (1H, m).

EXAMPLE 54

(1R*,2R*,5S*,6R*)-2-{[3,5-Bis(trifluoromethyl) phenyl]methoxy}-6-hydroxy-1-phenyl-8-azabicyclo [3.2.1]octane hydrochloride Triphenylthioantimonate in anhydrous ether (5 ml) under nitrogen was treated with the ester prepared from (1R*,2R*, 5S*,6R*)-8-benzyl-2-{[3,5-bis(trifluoromethyl)phenyl] methoxy}-1-phenyl-8-azabicyclo[3.2.1]octan-6-carboxylic acid (free base of Example 53) and N-hydroxy-4-methylthiazolinethione (by the procedure published in the *Journal of Organic Chemistry*, 1993, 58, 2468–2477, Overman et al) in anhydrous ether (5 ml) and stirred for 5 minutes. The flask was then opened to the atmosphere and stirred for 3 hours. The mixture was passed through a plug of Celite™, and the filtrate washed with 10% potassium carbonate solution. The organic layer was collected and the aqueous washed with ether. The combined organics were dried (MgSO$_4$), filtered and concentrated in vacuo The residue was purified by flash column chromatography eluting with 0–5% methanol/dichloromethane to afford a clear oil, 153 mg, 77%. Debenzylation by the method described previously and subsequent crystallisation from diethylether/ hexane gave the title compound.

m/z (ES$^+$) 446 ([M+H]$^+$).

EXAMPLE 55

(1R*,2R*,5S*,6R*)-2-{[3,5-Bis(trifluoromethyl) phenyl]methoxy}-6-cyano-1-phenyl-8-(prop-2-enyl)-8-azabicyclo[3.2.1]octane Sodium hydride (60% in oil, 100 mg, 2.5 mmol) was added to a stirred mixture of 1R*,2R*,5S*,6R*)-6-cyano- 1-phenyl-8-(prop-2-enyl)-8-azabicyclo[3.2.1]octan-2-ol (Description 24; 400 mg, 1.49 mmol), 3,5-bis(trifluoromethyl)benzyl bromide (1 ml, 5.45 mmol) and 18-crown-6 (87 mg, 0.33 mmol) in THF (5 ml) at room temperature. The reaction mixture was stirred for 22 hours, quenched with water and extracted into dichloromethane. The combined organic extracts were washed with water, dried (Na$_2$SO$_4$) and concentrated. The residue was purified by chromatography on silica gel (iso-hexane:ethyl acetate) to give the title compound (530 mg, 72%).

$\delta_H$(360 MHz, CDCl$_3$): 7.74 (1H, s), 7.49–7.40 (2H, m), 7.39–7.31 (2H, m), 7.27 (1H, m), 5.83 (1H, m), 5.33 (1H, dm, J 17.4 Hz), 5.13 (1H, dm, J 11.2 Hz), 4.73 (1H, d, J 12.6 Hz), 4.46 (1H, d, J 12.6 Hz), 4.00 (1H, br s), 3.97 (1H, br s), 3.50 (1H, dd, J 7.0 Hz, 16.1 Hz), 3.27 (1H, dm, J 16.1 Hz), 2.89 (1H, dd, J 4.6 Hz, 9.1 Hz), 2.36 (1H, dd, J 9.5 Hz, 13.7 Hz), 2.18 (1H, dd, J 4.6 Hz, 13.7 Hz), 2.11 (1H, m), 1.77 (1H, m), 1.30 (1H, m).

EXAMPLE 56

(1R*,2R*,5S*,6R*)-2-{[3,5-Bis(trifluoromethyl)phenyl]methoxy}-6-cyano-1-phenyl-8-azabicyclo[3.2.1]octane Tetrakis(triphenylphosphine)palladium(0) (64 mg, 0.055 mmol) was added to a stirred mixture of (1R*,2R*,5S*,6R*)-2-{[3,5-bis(trifluoromethyl)phenyl]methoxy}-6-cyano-1-phenyl-8-(prop-2-enyl)-8-azabicyclo[3.2.1]octane (Example 55; 500 mg, 1.01 mmol), 1,3-dimethylbarbituric acid (465 mg, 3.0 mmol) in dichloromethane (10 ml) at room temperature. The reaction mixture was stirred at 30–35° C. for 90 minutes and treated with 2M aqueous NaOH (10 ml). The mixture was stirred for 5 minutes, then diluted with water (30 ml) and extracted into dichloromethane. The combined organic extracts were dried (Na$_2$SO$_4$) and concentrated. The residue was purified by chromatography on silica gel (iso-hexane:ethyl acetate 10–40%) to give the title compound (392 mg, 85%). The hydrochloride salt of the title compound was prepared by treatment with ethereal HCl.

m/z (ES$^+$) 455 [M+H]$^+$.

EXAMPLE 57

(1R*,2R*,5S*,7S*)-2-{[3,5-Bis(trifluoromethyl)phenyl]methoxy}-7-cyano-1-phenyl-8-(prop-2-enyl)-8-azabicyclo[3.2.1]octane Sodium hydride (60% in oil, 28 mg, 0.7 mmol) was added to a stirred mixture of 1R*,2R*,5S*,7S*)-7-cyano-1-phenyl-8-(prop-2-enyl)-8-azabicyclo[3.2.1]octan-2-ol (Description 25; 50 mg, 0.18 mmol), 3,5-bis(trifluoromethyl)benzyl bromide (0.6 ml, 3.27 mmol) and 18-crown-6 (38 mg, 0.14 mmol) in THF (4 ml) at room temperature. The reaction mixture was stirred for 20 hours, quenched with brine and extracted into dichloromethane. The combined organic extracts were washed with water, dried (Na$_2$SO$_4$) and concentrated. The residue was purified by chromatography on silica gel (iso-hexane:ethyl acetate) to give the title compound (68 mg, 74%).

$\delta_H$(360 MHz, CDCl$_3$): 7.71 (1H, s), 7.51 (2H, s), 7.39 (2H, m), 7.39 (3H, m), 7.32 (2H, m), 5.87 (1H, dddd, J 4.3 Hz, 6.6 Hz, 10.2 Hz, 17.2 Hz), 5.26 (1H, ddt, J 1.6 Hz, 2.0 Hz, 17.2 Hz), 5.12 (1H, ddt, J 1.2 Hz, 2.0 Hz, 10.2 Hz), 4.65 (1H, d, J 12.5 Hz), 4.35 (1H, d, J 12.5 Hz), 3.98 (1H, br s), 3.75 (1H, dt, J 3.1 Hz, 6.6 Hz), 3.54 (1H, dd, J 6.6 Hz, 16.0 Hz), 3.37 (1H, dm, J 16.0 Hz), 2.99 (1H, dd, J 5.5 Hz, 9.3 Hz), 2.42 (1H, m), 2.22 (1H, dd, J 9.4 Hz, 12.9 Hz), 2.19–2.01 (2H, m), 1.82 (1H, dddd, J 3.9 Hz, 5.9 Hz, 12.9 Hz, 15.3 Hz), 1.19 (1H, ddd, J 2.0 Hz, 5.1 Hz, 13.7 Hz).

EXAMPLE 58

(1R*,2R*,5S*,7S*)-2-{[3,5-Bis(trifluoromethyl)phenyl]methoxy}-7-cyano-1-phenyl-8-azabicyclo[3.2.1]octane Tetrakis(triphenylphosphine)palladium(0) (13 mg, 0.011 mmol) was added to a stirred mixture of (1R*,2R*,5S*,7S*)-2-{[3,5-bis(trifluoromethyl)phenyl]methoxy}-7-cyano-1-phenyl-8-(prop-2-enyl)-8-azabicyclo[3.2.1]octane (Example 57; 68 mg, 0.14 mmol), 1,3-dimethylbarbituric acid (70 mg, 0.5 mmol) in dichloromethane (3 ml) at room temperature. The reaction mixture was stirred at 30–35° C. for 1 hour and treated with 2M aqueous NaOH (5 ml). The mixture was stirred for 5 minutes, then diluted with water (30 ml) and extracted into dichloromethane. The combined organic extracts were dried (Na$_2$SO$_4$) and concentrated. The residue was purified by chromatography on silica gel to give the title compound (37 mg, 60%). The hydrochloride salt of the title compound was prepared by treatment with ethereal HCl.

m/z (ES$^+$) 455 [M+H]$^+$

EXAMPLE 59

(1R*,2R*,5R*)-8-Benzyl-2-{[3,5-bis(trifluoromethyl)phenyl]methoxy}-1-phenyl-8-azabicyclo[3.2.1]octane (1R*,2R*,5R*)-8-Benzyl-1-phenyl-8-azabicyclo[3.2.1]octan-2-ol (Description 9; 1.69 g, 3.90 mmol) in THF (25 ml) at 0° C. was treated with sodium hydride (217 mg, 9.02 mmol) and allowed to warm to room temperature. The mixture was recooled to 0° C. then 3,5-bis(trifluoromethyl)benzyl bromide added and the mixture heated to 50° C. overnight. The mixture was poured into water then extracted with ethyl acetate (×2), dried (MgSO$_4$) and concentrated in vacuo to give a yellow oil. This was purified by flash column chromatography [5% ethyl acetate in iso-hexane] to give the title compound as a yellow oil (1.43 g, 61%).

m/z (ES$^+$) 520 ([M+H]$^+$).

EXAMPLE 60

(1R*,2R*,5R*)-2-{[3,5-Bis(trifluoromethyl)phenyl]methoxy}-1-phenyl-8-azabicyclo[3.2.1]octane (1R*,2R*,5R*)-8-Benzyl-2-{[3,5-bis(trifluoromethyl)phenyl]methoxy}-1-phenyl-8-azabicyclo[3.2.1]octane (Example 59; 1.21 g, 2.33 mmol) was dissolved in ethyl acetate (20 ml) then 10% palladium hydroxide(0.13 mg) added. Glacial acetic acid (2 ml) was added and the mixture hydrogenated at room temperature at 40 psi overnight. The reaction mixture was filtered then concentrated in vacuo. The yellow oil was basified (saturated sodium hydrogen carbonate solution), and the solution extracted with dichloromethane (×3), dried (MgSO$_4$) and concentrated in vacuo to give a yellow oil. The reaction mixture was purified by flash column chromatography [5%–15% methanol in dichloromethane] to give the title compound as a yellow oil (0.80 g, 80%).

m/z (ES$^+$) 430 ([M+H]$^+$).

EXAMPLE 61

(1R*,2R*,5R*)-2-{[3,5-Bis(trifluoromethyl)phenyl]methoxy}-8-methyl-1-phenyl-8-azabicyclo[3.2.1]octane hydrochloride (1R*,2R*,5R*)-2-{[3,5-Bis(trifluoromethyl)phenyl]methoxy}-1-phenyl-8-azabicyclo[3.2.1]octane (Example 60; 117 mg, 0.27 mmol) was dissolved in dimethylformamide (2 ml) and potassium carbonate (149 mg, 1.08 mmol) and methyl iodide (0.02 ml, 0.32 mmol) added and the mixture stirred at room temperature for 1 hour. The reaction mixture was poured into water then extracted with ethyl acetate (×2), dried (MgSO$_4$), and concentrated in vacuo to give a yellow oil. This was purified by flash column chromatography [7.5%–10% methanol in dichloromethane] to give a yellow oil. The oil was dissolved in diethyl ether (2 ml) and 1 equivalent of 1N hydrogen chloride in diethyl ether added to give the title compound as a yellow solid which was filtered and dried at 60° C. in vacuo.

m/z (ES$^+$) 444 ([M+H]$^+$).

EXAMPLE 62

(1R*,2R*,5R*)-2-{[3,5-Bis(trifluoromethyl)phenyl]methoxy}-1-phenyl-8-[(1,2,4-triazol-3-yl)methyl]-8-azabicyclo[3.2.1]octane hydrochloride (1R*,2R*,5R*)-2-{[3,5-Bis(trifluoromethyl)phenyl]methoxy}-1-phenyl-8-azabicyclo[3.2.1]octane (Example 60; 202 mg, 0.47 mmol), N-formyl-2-chloroacetamidrazone (82 mg, 0.82 mmol) and potassium carbonate (260 mg, 1.88 mmol) were stirred in dimethylformamide (2 ml) at 60° C. for 1 hour. The reaction mixture was poured into water and extracted with dichloromethane (×3), dried (MgSO$_4$) and concentrated in vacuo. The crude oil was dissolved in toluene and heated at 120° C. overnight. The reaction mixture was poured into water and extracted with ethyl acetate (×3), dried (MgSO$_4$), and concentrated in vacuo. The brown oil was purified by flash column chromatography [5% methanol in dichloromethane] to give an orange oil which when triturated with diethyl ether gave a cream-coloured foam. The foam was dissolved in diethyl ether and 1 equivalent of 1N hydrogen chloride in diethyl ether added to give the hydrochloride salt which was dried at 60° C. in vacuo.

m/z (ES$^+$) 511 ([M+H]$^+$).

EXAMPLE 63

(1R*,2R*,5R*)-2-{[3,5-Bis(trifluoromethyl)phenyl]methoxy}-1-phenyl-8-[(1,2,4-triazol-3-on-5-yl)methyl]-8-azabicyclo[3.2.1]octane hydrochloride (1R*,2R*,5R*)-2-{[3,5-Bis(trifluoromethyl)phenyl]methoxy}-1-phenyl-8-azabicyclo[3.2.1]octane (Example 60; 180 mg, 0.42 mmol), N-methoxycarbonyl-2-chloroacetamidrazone (122 mg, 0.74 mmol), and potassium carbonate were heated in dimethylformamide (2 ml) at 60° C. for 1 hour. The reaction mixture was poured into water then extracted with dichloromethane (×3), dried (MgSO$_4$), and concentrated in vacuo. The crude oil was dissolved in toluene and heated at 120° C. overnight. The reaction mixture was poured into water and extracted with ethyl acetate (×3), dried (MgSO$_4$), and concentrated in vacuo to give a brown solid. This was purified by lobar chromatography [5% methanol in dichloromethane] to give a yellow solid. The solid was dissolved in diethyl ether and 1 equivalent of hydrogen chloride in diethyl ether added to give the hydrochloride salt which was filtered off and dried at 60° C. in vacuo.

m/z (ES$^+$) 527 ([M+H]$^+$).

EXAMPLE 64

(1R*,2R*,5R*)-2-{[3,5-Bis(trifluoromethyl)phenyl]methoxy}-8-(2-bromoacetyl)-1-phenyl-8-azabicyclo[3.2.1]octane (1R*,2R*,5R*)-2-{[3,5-Bis(trifluoromethyl)phenyl]methoxy}-1-phenyl-8-azabicyclo[3.2.1]octane (Example 60; 162 mg, 0.38 mmol) was dissolved in THF (3 ml) and triethylamine (0.059 ml, 0.42 mmol) added. The reaction mixture was cooled to 0° C. then bromoacetyl bromide (0.037 ml, 0.42 mmol) added, then the mixture warmed to room temperature. A further 1.1 equivalents of triethylamine (0.059 ml), and bromoacetyl bromide (0.037 ml) were added and the reaction mixture stirred at room temperature for 15 minutes. The reaction mixture was poured into water, extracted with ethyl acetate (×3), dried (MgSO$_4$), and concentrated in vacuo to give the title compound.

$\delta_H$(360 MHz, CDCl$_3$):, 7.80 (1H, s), 7.72 (2H, s), 7.55–7.48 (2H, m), 7.34–7.32 (2H, m), 7.19 (1H, m), 5.00 (1H, br s), 4.82 (1H, d, J 12.0 Hz), 4.65 (1H, d, J 12.0 Hz), 4.29 (1H, br s), 3.21 (1H, d, J 11.7 Hz), 3.05 (1H, d, J 11.8 Hz), 2.29–1.99 (6H, m), 1.71 (1H, m), 1.46–1.42 (1H, m).

EXAMPLE 65

(1R*,2R*,5R*)-2-{[3,5-Bis(trifluoromethyl)phenyl]methoxy}-1-phenyl-8-(pyrrolidin-1-yl)acetyl-8-azabicyclo[3.2.1]octane (1R*,2R*,5R*)-2-{[3,5-Bis(trifluoromethyl)phenyl]methoxy}-8-(2-bromoacetyl)-1-phenyl-8-azabicyclo[3.2.1]octane (Example 64; 143 mg, 0.26 mmol) was stirred with pyrrolidine (0.024 ml, 0.29 mmol), and triethylamine (0.040 ml, 0.29 mmol) in THF (2 ml) for 4 hours. The reaction mixture was concentrated in vacuo then purified by flash column chromatography [10% methanol in dichloromethane] to give a brown oil which when triturated in diethyl ether gave a pale brown solid. The solid was dissolved in diethyl ether and 1 equivalent of !N hydrogen chloride in diethyl ether added to a solution in diethyl ether to give the hydrochloride salt which was filtered off and dried in vacuo at 60° C.

m/z (ES$^+$) 541 ([M+H]$^+$).

EXAMPLE 66

(1R*,2R*,5R*)-2-{[3,5-Bis(trifluoromethyl)phenyl]methoxy}-8-[5-dimethylaminomethyl-(1,2,3,triazo-4-yl)methyl]-1-phenyl-8-azabicyclo[3.2.1]octane hydrochloride To (1R*,2R*,5R*)-8-(4-azidobut-2-ynyl)-2-{[3,5-bis(trifluoromethyl)phenyl]methoxy}-1-phenyl-8-azabicyclo[3.2.1]octane (Description 27; 256 mg, 0.54 mmol) in 1,4-dioxane (3 ml) was added an excess of dimethylamine. The reaction mixture was heated at 80° C. in a sealed tube for 3 hours after which the reaction was cooled and concentrated in vacuo to give a brown oil. This was purified by flash column chromatography [5%–20% methanol in dichloromethane] to give a brown solid. The solid was triturated in diethyl ether and the hydrochloride salt made by adding 1 equivalent of hydrogen chloride in diethyl ether (1N). The solid was filtered off and dried at 60° C. in vacuo. (65 mg, 20%).

m/z (ES$^+$) 568 ([M+H]$^+$).

EXAMPLE 67

(1R*,2R*,5R*)-2-{[3,5-Bis(trifluoromethyl)phenyl]methoxy}-8-(2-hydroxyethyl)-1-phenyl-8-azabicyclo[3.2.1]octane hydrochloride (1R*,2R*,5R*)-2-{[3,5-Bis(trifluoromethyl)phenyl]methoxy}-1-phenyl-8-azabicyclo[3.2.1]octane (Example 60; 345 mg, 0.80 mmol) was dissolved in dimethylformamide (3 ml) and potassium carbonate (331 mg, 2.40 mmol)

added. This was stirred for 5 minutes at room temperature then 2-bromoethanol (0.086 ml, 1.21 mmol) added and the reaction mixture heated for 5 days at 60° C. Only a small amount of starting material had converted to product so a further 25 equivalents of 2-bromoethanol (1.42 ml, 20 mmol) was added and the temperature increased to 80° C. overnight. The reaction mixture was poured into water and extracted with ethyl acetate (×3), dried (MgSO$_4$) and concentrated in vacuo to give a brown oil. This was purified by flash column chromatography [5%–20% ethyl acetate in iso-hexane] to give a yellow oil and the hydrochloride salt was made by adding 1 equivalent of hydrogen chloride in diethyl ether (1N). The title compound was filtered off and dried at 60° C. in vacuo.

m/z (ES$^+$) 474 ([M+H]$^+$).

EXAMPLE 68

(1R*,2R*,5R*)-2-{[3,5-Bis(trifluoromethyl)phenyl]methoxy}-8-(2-mesyloxyethyl)-1-phenyl-8-azabicyclo[3.2.1]octane (1R*,2R*,5R*)-2-{[3,5-Bis(trifluoromethyl)phenyl]methoxy}-8-(2-hydroxyethyl)-1-phenyl-8-azabicyclo[3.2.1]octane (Example 67; 173 mg, 0.37 mmol) was dissolved in dichloromethane (2 ml) and cooled to 0° C. Triethylamine (0.062 ml, 0.44 mmol) was added followed by methanesulphonyl chloride (0.029 ml, 0.37 mmol). The mixture was extracted between water and dichloromethane (×3) and the organics dried (MgSO$_4$) and concentrated in vacuo to give the title compound as a clear oil (201 mg, 100%).

m/z (ES$^+$) 492 ([M+H]$^+$).

EXAMPLE 69

(1R*,2R*,5R*)-2-{[3,5-Bis(trifluoromethyl)phenyl]methoxy}-1-phenyl-8-{2-(1,2,4-triazol-1-yl)ethyl}-8-azabicyclo[3.2.1]octane hydrochloride 1,2,4-Triazole (25 mg, 0.37 mmol) was dissolved in acetonitrile (2 ml) and sodium hydroxide (44 mg, 1.11 mmol). This was stirred at room temperature for 30 minutes then tetrabutylammonium hydrogen sulphate and (1R*,2R*,5R*)-2-{[3,5-bis(trifluoromethyl)phenyl]methoxy}-8-(2-mesyloxyethyl)-1-phenyl-8-azabicyclo[3.2.1]octane (Example 68; 201 mg, 0.37 mmol) added. The reaction was heated to reflux for 2.5 hours. The reaction mixture was diluted with water and extracted with ethyl acetate (×3), dried (MgSO$_4$), and concentrated in vacuo to give a brown oil. This was purified by flash column chromatography [5% methanol in dichloromethane] to give a brown oil and the hydrochloride salt was made by adding 1 equivalent of hydrogen chloride in diethyl ether (1N) and the title compound filtered off and dried in vacuo at 60° C.

m/z (ES$^+$) 525 ([M+H]$^+$).

EXAMPLE 70

(1R*,2R*,5R*)-8-Benzyl-2-{(1S*)-1-[3,5-bis(trifluoromethyl)phenyl]-(methoxycarbonyl)methoxy}-1-phenyl-8-azabicyclo[3.2.1]octane Slow addition of methyl 2-diazo-2-(3,5-bis(trifluoromethyl)phenyl)acetate (504 mg, 1.61 mmol) as a solution in benzene (3 ml) to (1R*,2R*,5R*)-8-benzyl-1-phenyl-8-azabicyclo[3.2.1]octan-2-ol (Description 9; 430 mg, 1.47 mmol) in benzene (3 ml) was carried out in the presence of catalytic rhodium acetate (5 mg) at reflux under N$_2$. The reaction mixture was concentrated in vacuo to give a green oil then purified by flash column chromatography [15% ethyl acetate in iso-hexane] to give the title compound as a yellow oil (mainly 1 isomer)(735 mg, 87%).

m/z (ES$^+$) 578 ([M+H]$^+$).

EXAMPLE 71

(1R*,2R*,5R*)-2-{(1S*)-1-[3,5-Bis(trifluoromethyl)phenyl]-(methoxycarbonyl)methoxy}-1-phenyl-8-azabicyclo[3.2.1]octane (1R*,2R*,5R*)-8-Benzyl-2-{(1S*)-1-[3,5-bis(trifluoromethyl)phenyl]-(methoxycarbonyl)methoxy}-1-phenyl-8-azabicyclo[3.2.1]octane (Example 70; 735 mg, 1.27 mmol) was dissolved in ethyl acetate (10 ml) with glacial acetic acid (0.5 ml) and 10% palladium hydroxide (40 mg) added. The mixture was hydrogenated on a Parr™ at 40 psi overnight. The mixture was filtered through Celite™, then concentrated in vacuo and the residue basified with saturated sodium hydrogen carbonate solution. The solution was then extracted with ethyl acetate (×3) and the extracts dried (MgSO$_4$) and concentrated in vacuo. The obtained oil was purified by flash column chromatography [10% methanol in dichloromethane) to give the title compound as a yellow oil. (5:1 desired:undesired). (323 mg, 52%).

m/z (ES$^+$) 488 ([M+H]$^+$).

EXAMPLE 72

(1R*,2R*,5R*)-2-{(1S*)-1-[3,5-Bis(trifluoromethyl)phenyl]-(methoxycarbonyl)methoxy}-1-phenyl-8-[(1,2,4-triazol-3-on-5-yl)methyl]-8-azabicyclo[3.2.1]octane (1R*,2R*,5R*)-2-{(1S*)-1-[3,5-Bis(trifluoromethyl)phenyl]-(methoxycarbonyl)methoxy}-1-phenyl-8-azabicyclo[3.2.1]octane (Example 71; 323 mg, 0.66 mmol), potassium carbonate (365 mg, 2.64 mmol), and N-methoxycarbonyl-2-chloroacetamidrazone (192 mg, 1.16 mmol) were heated at 60° C. in dimethylformamide for 1 hour. The reaction mixture was then cooled and washed with water (20 ml) and extracted with ethyl acetate (×2), dried (MgSO$_4$) and concentrated in vacuo to give an orange oil. This was dissolved in toluene (5 ml) and heated at 120° C. overnight. The reaction mixture was cooled and concentrated in vacuo to give a brown oil which was purified by flash column chromatography [5% methanol in dichloromethane] to give the title compound as an orange solid (164 mg, 42%).

m/z (ES$^+$) 585 ([M+H]$^+$).

EXAMPLE 73

(1R*,2R*,5R*)-2-{(1R*)-[3,5-Bis(trifluoromethyl)phenyl]-2-hydroxyethoxy)-1-phenyl-8-[(1,2,4-triazol-3-on-5-yl)methyl]-8-azabicyclo[3.2.1]octane hydrochloride (1R*,2R*,5R*)-2-(1R*)-1-[3,5-Bis(trifluoromethyl)phenyl]-(methoxycarbonyl)methoxy}-1-phenyl-8-[(1,2,4-triazol-3-on-5-yl)methyl]-8-azabicyclo[3.2.1]octane (prepared from the "undesired" isomer of Example 71 according to the method of Example 72; 164 mg, 0.28 mmol) was dissolved in diethyl ether (2 ml) and sodium borohydride added and the mixture stirred for 2 hours at room temperature. The reaction mixture was then quenched with water and extracted with diethyl ether (×3). The organics were dried (MgSO$_4$) and concentrated in vacuo to give a yellow solid which was purified by flash column chromatography [5% methanol in dichloromethane] to give a pale yellow solid and the hydrochloride salt made by adding 1 equivalent of hydrogen chloride (1N) in diethyl ether and the title compound filtered off and dried in vacuo at 60° C. (53 mg, 32%).

m/z (ES$^+$) 557+([M+H]$^+$).

EXAMPLE 74

(1R*,2R*,5R*)-2-{[3,5-Bis(trifluoromethyl)phenyl] methoxy})1-phenyl-8-[(2-methyl-1,2,4-triazol-5-yl) methyl]-8-azabicyclo[3.2.1]octane hydrochloride (1R*,2R*,5R*)-2-{[3,5-Bis(trifluoromethyl)phenyl] methoxy}-1-phenyl-8-azabicyclo[3.2.1]octane (Example 60; 99 mg, 0.23 mmol) was combined with potassium carbonate (127 mg, 0.92 mmol) and N-formyl-N-methyl-2-chloroacetamidrazone (59 mg, 0.39 mmol) in dimethylformamide and heated at 80° C. overnight. A further 0.78mmol (118 mg) of amidrazone was added and the mixture further stirred at 80° C. for 4 hours. The reaction mixture was poured into water and extracted with ethyl acetate (×3), dried (MgSO$_4$) and concentrated in vacuo to give a brown oil. This was purified by flash column chromatography [5% methanol in dichloromethane] to give a yellow oil. The oil was dissolved in methanol and purified using an SCX cartridge eluting with methanol then 10% ammonia in methanol. The ammonia containing fractions were concentrated to give a brown oil. The hydrochloride salt was made by adding 1 equivalent of hydrogen chloride in diethyl ether (1N) and the title compound was filtered off and dried at 60° C. in vacuo.

m/z (ES$^+$) 525+([M+H]$^+$).

EXAMPLE 75

(1R*,2R*,5S*,6R*)-8-Benzyl-2-{[3,5-bis (trifluoromethyl)phenyl]methoxy}-1-phenyl-8-azabicyclo[3.2.1]octan-6-carboxamide A solution of (1R*,2R*,5S*,6R*)-8-benzyl-2-{[3,5-bis (trifluoromethyl)phenyl]methoxy}-1-phenyl-8-azabicyclo [3.2.1]octan-6-carboxylic acid trifluoroacetate (Example 53; 2.7 mmol) was treated with ammonia solution in dioxane (0.5M, 10 ml, 5 mmol), triethylamine (0.6 ml, 4.3 mmol), 1-(3-dimethylaminopropyl)-3-ethylcarbodiimide hydrochloride (960 mg, 5.02 mmol), and 4-N,N-dimethylaminopyridine (120 mg, 1 mmol). The mixture was stirred for 24 hours, diluted with ethyl acetate (100 ml), washed with 10% aqueous citric acid, saturated aqueous NaHCO$_3$, dried (Na$_2$SO$_4$) and concentrated. The residue was purified by chromatography on silica gel (iso-hexane:ethyl acetate) to give the title compound (850 mg, 56%).

δ$_H$(360 MHz, CDCl$_3$): 7.74 (1H, s), 7.70 (2H, s), 7.55 (2H, m), 7.42 (2H, m), 7.36–7.27 (6H, m), 6.72 (1H, br), 4.93 (1H, br), 4.89 (1H, d, J 13.0 Hz), 4.60 (1H, d, J 12.6 Hz), 4.22 (1H, br s), 4.07 (1H, d, J 13.7 Hz), 3.83 (1H, d, J 14.0 Hz), 3.51 (1H, br s), 2.67 (1H, dd, J 3.9 Hz, 9.5 Hz), 2.41–2.30 (1H, m), 2.35 (1H, dd, J 9.8 Hz, 14.0 Hz), 2.16 (1H, dd, J 5.6 Hz, 15.8 Hz), 2.03 (1H, dd, J 4.2 Hz, 14.0 Hz), 1.96 (1H, m), 1.27 (1H, m).

EXAMPLE 76

(1R*,2R*,5S*,6R*)-8-Benzyl-2-{[3,5-bis (trifluoromethyl)phenyl]methoxy}-6-[4-methyloxazol-2-yl]-1-phenyl-8-azabicyclo[3.2.1] octane A mixture of (1R*,2R*,5S*,6R*)-8-benzyl-2-{[3,5-bis (trifluoromethyl) phenyl]methoxy}-1-phenyl-8-azabicyclo [3.2.1]octan-6-carboxamide (Example 75; 250 mg, 0.44 mmol), chloroacetone (1 ml) and N,N-dimethylformamide (4 ml) was stirred at 120° C. for 24 hours. After cooling to room temperature the reaction mixture was diluted with diethyl ether (70 ml), washed with saturated aqueous NaHCO$_3$, water and brine. The organic phase was dried (Na$_2$SO$_4$) and concentrated. The residue was purified by chromatography on silica gel (iso-hexane:ethyl acetate) to give the title compound (53 mg, 12%).

δ$_H$(400 MHz, CDCl$_3$): 7.75 (1H, s), 7.73 (2H, s), 7.59 (2H, d, J 7.4 Hz), 7.37–7.27 (5H, m), 7.26–7.13 (4H, m), 4.84 (1H, d, J 12.9 Hz), 4.57 (1H, d, J 12.9 Hz), 4.15 (1H, brs), 4.12 (1H, d, J 15.6 Hz), 3.86 (1H, d, J 15.6 Hz), 3.71 (1H, brs), 3.36 (1H, dd, J 4.7 Hz, 9.4 Hz), 2.57 (1H, dd, J 4.3 Hz, 13.3 Hz), 2.36 (1H, dd, J 9.4 Hz, 13.7 Hz), 2.22 (1H, m), 2.17 (3H, d, J 1.6 Hz), 2.15 (1H, m), 2.03 (1H, m), 1.31 (1H, m).

EXAMPLE 77

(1R*,2R*,5S*,6R*)-2-{[3,5-Bis(trifluoromethyl) phenyl]methoxy}-6-[4-methyloxazol-2-yl]-1-phenyl-8-azabicyclo[3.2.1]octane A mixture of (1R*,12R*,5S*,6R*)-8-benzyl-2-{[3,5-bis (trifluoromethyl)phenyl]methoxy}-6-[4-methyloxazol-2-yl]-1-phenyl-8-azabicyclo[3.2.1]octane (Example 76; 53 mg, 0.09 mmol), 10% palladium on charcoal (135 mg) ethanol (10 ml) was stirred under hydrogen atmosphere (1 atm) at +65° C. for 30 minutes. The reaction mixture was cooled to room temperature, flushed with nitrogen gas and filtered through a pad of Celite™. The filtrate was concentrated and purified by preparative TLC (dichloromethane:methanol) to give the title compound (38 mg, 84%). The hydrochloride salt of the title compound was prepared by treatment with ethereal HCl.

m/z (ES$^+$) 511 [M+H]$^+$.

EXAMPLE 78

(1R*,2R*,5S*,6R*)-8-Benzyl-2-{[3,5-bis (trifluoromethyl)phenyl]methoxy}-6-[4-methylthioazol-2-yl]-1-phenyl-8-azabicyclo[3.2.1] octane A mixture of (1R*,2R*,5S*,6S*)-8-benzyl-2-{[3,5-bis (trifluoromethyl)phenyl]-methoxy}-1-phenyl-8-azabicyclo [3.2.1]octan-6-carboxamide (Example 75; 300 mg, 0.53 mmol), Lawsson's reagent (128 mg) and toluene was stirred at 80° C. for 50 minutes and concentrated in vacuo. The residue was treated with N,N-dimethylformamide (2 ml) and chloroacetone (0.4 ml) and stirred at 110 C. for 20 minutes. After cooling to room temperature the reaction mixture was quenched with saturated aqueous NaHCO$_3$ and extracted into diethyl ether. The combined organic extracts were washed with water, dried (Na$_2$SO$_4$) and concentrated. The residue was purified by chromatography on silica gel (iso-hexane:diethyl ether) to give the title compound (50 mg, 18%).

δ$_H$(400 MHz, CDCl$_3$): 7.73 (1H, s), 7.70 (2H, s), 7.51 (2H, d, J 7.0 Hz), 7.44 (2H, d, J 7.4 Hz), 7.34 (4H, m), 7.24 (2H, m), 6.76 (1H, s), 4.78 (1H, d, J 12.9 Hz), 4.52 (1H, d, J 12.9 Hz), 4.18 (1H, br s), 4.20 (1H, d, J 15.3 Hz), 3.91 (1H, d, J 15.3 Hz), 4.01 (1H, dt, J 6.6 Hz, 11.7 Hz), 3.77 (1H, t, J 3.1 Hz), 2.56 (1H, dd, J 7.1 Hz, 13.3 Hz), 2.44 (1H, dd, J 4.3 Hz, 13.3 Hz), 2.42 (3H, d, J 0.8 Hz), 2.24–2.03(2H, m), 1.84 (1H, m), 1.15 (1H, m).

EXAMPLE 79

(1R*,2R*,5S*,6R*)-2-{[3,5-Bis(trifluoromethyl) phenyl]methoxy}-6-[4-methylthioazol-2-yl]-1-phenyl-8-azabicyclo[3.2.1]octane A solution of (1R*,2R*,5S*,6R*)-8-Benzyl-2-{[3,5-bis (trifluoromethyl)phenyl]-methoxy}-6-[4-methylthioazol-2- yl]-1-phenyl-8-azabicyclo[3.2.1]octane (Example 78; 50 mg, 0.081 mmol) in diethyl ether (2 ml) was treated 1M etheral HCl (0.3 ml). The mixture was concentrated in vacuo. The residue was treated with 10% palladium on charcoal (180 mg) ethanol (10 ml) was stirred under hydrogen atmosphere (1 atm) at +65° C. for 30 minutes. The reaction mixture was cooled to room temperature, flushed with nitrogen gas and filtered through a pad of Celite™. The filtrate was concentrated and purified by preparative TLC (dichloromethane:methanol) to give the title compound (15 mg, 35%). The hydrochloride salt of the title compound was prepared by treatment with ethereal HCl.

m/z (ES$^+$) 527 [M+H]$^+$

EXAMPLE 80

(1R*,2R*,5S*,6R*)-2-{[3,5-Bis(trifluoromethyl) phenyl]methoxy}-6-(tert-butoxycarbonyl)-1-phenyl-8-(prop-2-enyl)-8-azabicyclo[3.2.1]octane A mixture of (1R*,2R*,5S*,6R*)-2-{[3,5-bis (trifluoromethyl)phenyl]methoxy}-6-(tert-butoxycarbonyl)-1-phenyl-8-azabicyclo[3.2.1]octane (Example 25; 424 mg, 0.8 mmol), potassium carbonate (770 mg), allyl bromide (0.5 ml) and N,N-dimethylforamide (3 ml) was stirred at room temperature for 3 days. The reaction mixture was treated with 1:1 mixture diethyl ether:iso-hexane, washed with water, dried (Na$_2$SO$_4$) and concentrated. The residue was purified by chromatography on silica gel (iso-hexane:diethyl ether) to give the title compound (362 mg, 79%).

$\delta_H$(400 MHz, CDCl$_3$): 7.71 (1H, s), 7.58 (2H, s), 7.43 (2H, m), 7.31 (2H, m), 7.23 (1H, m), 5.86 (1H, dddd, J 5.1 Hz, 6.3 Hz, 10.2 Hz, 16.8 Hz), 5.19 (1H, ddt, J 1.6 Hz, 2.0 Hz, 17.2 Hz), 5.07 (1H, ddt, J 1.5 Hz, 1.8 Hz, 10.2 Hz), 4.63 (1H, d, J 12.9 Hz), 4.34 (1H, d, J 12.9 Hz), 3.82 (1H, br s), 3.75 (1H, br d, J 6.6 Hz), 3.54 (1H, ddt, J 1.2 Hz, 6.5 Hz, 15.6 Hz), 3.31 (1H, dt, J 6.2 Hz, 12.3 Hz), 3.03 (1H, ddt, J 1.6 Hz, J 5.4 Hz, 15.7 Hz), 2.40 (1H, dd, J 6.0 Hz, 13.7 Hz), 2.02 (1H, dd, J 9.0 Hz, 13.3 Hz), 2.10–2.01 (3H, m), 1.87 (1H, dd, J 2.5 Hz, 9.4 Hz), 1.49 (9H, s), 1.44 (1H, d, J 8.2 Hz).

EXAMPLE 81

(1R*,2R*,5S*,6RS*)-2-{[3,5-Bis(trifluoromethyl) phenyl]methoxy}-6-(tert-butoxycarbonyl)-1-phenyl-8-(prop-2-enyl)-8-azabicyclo[3.2.1]octane A solution of potassium bis(trimethylsilyl)amide in toluene (0.5M, 1.5 ml, 0.75 mmol) was added to a stirred solution of (1R*,2R*,5S*,6R*)-2-{[3,5-bis (trifluoromethyl)-phenyl]methoxy}-6-(tert-butoxycarbonyl)-1-phenyl-8-(prop-2-enyl)-8-azabicyclo [3.2.1]octane (Example 80; 362 mg, 0.635 mmol) in THF (5 ml) at +5° C. The mixture was stirred for 15 minutes and quenched with saturated aqueous NH$_4$Cl and extracted into diethyl ether. The organic extracts was washed with water, dried (Na$_2$SO$_4$) and concentrated to give the title compound as a 4.6:1 mixture diastereoisomers.

$\delta_H$(400 MHz, CDCl$_3$): 7.72 (1H, s), 7.62 (2H, s), 7.45 (2H, m), 7.31 (2H, m), 7.23 (1H, m), 5.76 (1H, dddd, J 4.3 Hz, 6.7 Hz, 10.5 Hz, 17.2 Hz), 5.22 (1H, dm, J 17.0 Hz), 5.03 (1H, dm, J 10.3 Hz), 4.71 (1H, d, J 12.9 Hz), 4.44 (1H, d, J 12.9 Hz), 3.95 (1H, dd, J 1.4 Hz, 3.6 Hz), 3.89 (1H, t, J 2.4 Hz), 3.46 (1H, ddt, J 1.1 Hz, 6.7 Hz, 16.0 Hz), 3.12 (1H, ddt, J 2.0 Hz, 3.9 Hz, 15.9 Hz), 2.73 (1H, dd, J 4.7 Hz, 9.4 Hz), 2.33 (1H, dd, J 5.0 Hz, 13.3 Hz), 2.13 (1H, m), 2.03 (1H, dd, J 9.6 Hz, 13.3 Hz), 1.88 (1H, m), 1.47 (9H, s), 1.27 (1H, m).

EXAMPLE 82

(1R*,2R*,5S*,6R*)-8-Benzyl-2-{[3,5-bis (trifluoromethyl)phenyl]methoxy}-1-phenyl-8-azabicyclo[3.2.1]octan-6-carboxylic acid 2-acetylhydrazide A mixture of (1R*,2R*,5S*,6RS*)-2-{[3,5-bis (trifluoromethyl)phenyl]methoxy}-6-(tert-butoxycarbonyl)-1-phenyl-8-(prop-2-enyl)-8-azabicyclo[3.2.1]octane (Example 81), trifluoroacetic acid (4 ml) and dichloromethane (6 ml) was stirred at room temperature overnight and concentrated in vacuo. The residue was treated with acetic hydrazide (164 mg, 2.21 mmol), triethylamine (0.5 ml, 3.6 mmol), 1-(3-dimethylaminopropyl)-3-ethylcarbodiimide hydrochloride (350 mg, 1.8 mmol), and 4-N,N-dimethylaminopyridine (47 mg, 0.38 mmol). The mixture was stirred for 5 hours, quenched with saturated aqueous NaHCO$_3$ and extracted into dichloromethane. The combined organic extracts were dried (Na$_2$SO$_4$) and concentrated. The residue was purified by chromatography on silica gel (iso-hexane:ethyl acetate) to give the title compound (180 mg, 50%).

$\delta_H$(360 MHz, CDCl$_3$): 10.01 (1H, d, J 6.0 Hz), 9.10 (1H, d, J 5.3 Hz), 7.73 (1H, s), 7.61 (2H, s), 7.48 (2H, m), 7.37 (2H, m), 7.26 (1H, m), 6.06 (1H, dddd, J 4.4 Hz, 9.0 Hz, 9.8 Hz, 17.0 Hz), 5.16 (1H, dm, J 17.2 Hz), 5.12 (1H, dm, J 10.2 Hz), 4.78 (1H, d, J 12.9 Hz), 4.51 (1H, d, J 12.9 Hz), 4.16 (1H, br s), 3.84 (1H, br s), 3.59 (1H, dd, J 8.8 Hz, 14.7 Hz), 3.47 (1H, ddt, J 1.8 Hz, 4.3 Hz, 14.8 Hz), 2.77 (1H, dd, J 4.2 Hz, 9.5 Hz), 2.31 (1H, dd, J 9.5 Hz, 14.0 Hz), 2.20 (1H, m), 2.06 (3H, s), 1.99 (1H, dd, J 4.2 Hz, 14.0 Hz), 1.93 (1H, m), 1.25 (1H, dd, J 4.6 Hz, 13.5 Hz).

EXAMPLES 83a AND 83b (1R*,2R*,5S*,6RS*)-2-{[3,5-Bis(trifluoromethyl) phenyl]methoxy}-6-(5-methyloxa-3,4-diazo-2-yl)-1-phenyl-8-(prop-2-enyl)-8-azabicyclo[3.2.1]octane A mixture of (1R*,2R*,5S*,6R*)-8-benzyl-2-{[3,5-bis (trifluoromethyl)phenyl]-methoxy}-1-phenyl-8-azabicyclo [3.2.1]octan-6-carboxylic acid 2-acetylhydrazide (Example 82; 180 mg, 0.32 mmol), phosphorus pentaoxide (140 mg) and xylene (3 ml) was stirred at reflux for 3 hours. The mixture was cooled to room temperature, treated with saturated aqueous NaHCO$_3$ and extracted into dichloromethane. The combined organic extracts were dried (Na$_2$SO$_4$) and concentrated. The residue was purified by chromatography on silica gel (iso-hexane:ethyl acetate 0–50%) to give the title compounds (6S*-isomer; 82 mg, 47%) and (6R*-isomer; 34 mg, 20%).

EXAMPLE 83a (6S*)-isomer $\delta_H$(360 MHz, CDCl$_3$): 7.73 (1H, s), 7.64 (2H, s), 7.48 (2H, m), 7.33 (2H, m), 7.24 (1H, m), 5.72 (1H, dddd, J 4.0 Hz, 7.1 Hz, 10.5 Hz, 17.3 Hz), 5.10 (1H, ddt, J 1.4 Hz, 2.1 Hz, 17.2 Hz), 4.98 (1H, ddt, J 1.1 Hz, 2.0 Hz, 10.3 Hz), 4.78 (1H, d, J 12.6 Hz), 4.52 (1H, d, J 12.6 Hz), 4.10 (1H, br s), 3.91 (1H, br s), 3.51 (1H, dd, J 7.4 Hz, 16.1 Hz), 3.43 (1H, dd, J 6.0 Hz, 8.4 Hz), 3.26 (1H, ddt, J 2.1 Hz, 3.9 Hz, 16.8 Hz), 2.53 (3H, s), 2.43–2.30 (2H, m), 2.29–2.09 (2H, m), 2.01 (1H, m), 1.36 (1H, dd, J 2.6 Hz, 5.4 Hz, 13.6 Hz).

EXAMPLE 83b (6R*-isomer $\delta_H$(360 MHz, CDCl$_3$): 7.71 (1H, s), 7.59 (2H, s), 7.47 (2H, m), 7.34 (2H, m), 7.25 (1H, m), 5.86 (1H, dddd, J 4.7

Hz, 7.0 Hz, 10.2 Hz, 17.2 Hz), 5.20 (1H, ddt, J 1.2 Hz, 1.9 Hz, 17.3 Hz), 5.09 (1H, ddt, J 1.3 Hz, 1.7 Hz, 10.3 Hz), 4.68 (1H, d, J 12.5 Hz), 4.40 (1H, d, J 12.5 Hz), 4.00 (1H, d, J 2.3 Hz), 3.94 (1H, dt, J 3.5 Hz, 6.3 Hz), 3.74 (1H, dt, J 6.7 Hz, 11.7 Hz), 3.59 (1H, ddt, J 1.3 Hz, 7.0 Hz, 15.7 Hz), 3.22 (1H, ddt, J 1.9 Hz, 4.7 Hz, 15.7 Hz), 2.71 (1H, dd, J 6.7 Hz, 13.7 Hz), 2.53 (3H, s), 2.35 (1H, dd, J 11.7 Hz, 13.3 Hz), 2.24–2.03 (2H, m), 1.84 (1H, dd, J 4.3 Hz, 14.5 Hz), 1.01 (1H, ddd, J 2.0 Hz, 4.7 Hz, 14.1 Hz).

EXAMPLE 84

(1R*,2R*,5S*,6S*)-2-{[3,5-Bis(trifluoromethyl) phenyl]methoxy}-6-(5-methyloxa-3,4-diazo-2-yl)-1-phenyl-8-azabicyclo[3.2.1]octane Tetrakis(triphenylphosphine)palladium(0) (28 mg, 0.024 mmol) was added to a stirred mixture of (1R*,2R*,5S*, 6S*)-2-{[3,5-bis(trifluoromethyl)phenyl]methoxy}-6-(5-methyloxa-3,4-diazo-2-yl)-1-phenyl-8-(prop-2-enyl)-8-azabicyclo[3.2.1]octane (Example 83a; 82 mg, 1.48 mmol), 1,3-dimethylbarbituric acid (130 mg, 0.84 mmol) in dichloromethane (3 ml) at room temperature. The reaction mixture was stirred at +40° C. for 35 minutes and treated with 2M aqueous NaOH (5 ml). The mixture was stirred for 5 minutes, then diluted with water (30 ml) and extracted into dichloromethane. The combined organic extracts were dried (Na$_2$SO$_4$) and concentrated. The residue was purified by preparative TLC on silica gel (dichloromethane:methanol 5%) to give the title compound (75 mg, 98%). The hydrochloride salt of the title compound was prepared by treatment with ethereal HCl.

m/z (ES$^+$) 512 [M+H]$^+$

EXAMPLE 85

(1R*,2R*,5S*,6S*)-8-Benzyl-2-{[3,5-bis(trifluoromethyl)phenyl]methoxy}-1-phenyl-8-azabicyclo[3.2.1]octan-6-carboxylic acid semicarbazide A mixture of (1R*,2R*,5S*,6S*)-8-benzyl-2-{[3,5-bis(trifluoromethyl)phenyl]methoxy}-6-(tert-butoxycarbonyl)-1-phenyl-8-azabicyclo[3.2.1]octane (Description 22; 250 mg, 0.4 mmol), trifluoroacetic acid (0.8 ml) and dichloromethane (1.2 ml) was stirred at room temperature overnight and concentrated in vacuo. The residue was treated with semicarbazide hydrochloride (355 mg, 3.2 mmol), triethylamine (1 ml, 7.2 mmol), 1-(3-dimethylaminopropyl)-3-ethylcarbodiimide hydrochloride (457 mg, 4.2 mmol), and 4-N,N-dimethylaminopyridine (35 mg, 0.28 mmol). The mixture was stirred at room temperature over weekend, quenched with saturated aqueous NaHCO$_3$ and extracted into dichloromethane. The combined organic extracts were dried (Na$_2$SO$_4$) and concentrated. The residue was purified by chromatography on silica gel (dichloromethane:methanol:ammonia) to give the title compound (278 mg, 55%).

δ$_H$(360 MHz, CDCl$_3$): 8.75 (1H, d, J 2.5 Hz), 7.75 (1H, s), 7.69 (2H, s), 7.58 (2H, m), 7.45 (2H, t, J 8.1 Hz), 7.39–7.22 (6H, m), 6.60 (1H, br), 4.88 (1H, d, J 12.6 Hz), 4.61 (1H, s), 4.60 (1H, d, J 12.6 Hz), 4.22 (1H, br s), 4.05 (1H, d, J 13.7 Hz), 3.85 (1H, d, J 13.7 Hz), 3.49 (1H, br s), 2.75 (1H, dd, J 4.6 Hz, 9.8 Hz), 2.35 (1H, dd, J 9.8 Hz, 14.0 Hz), 2.17 (1H, dd, J 5.3 Hz, 15.0 Hz), 2.04 (1H, dd, J 3.9 Hz, 14.0 Hz), 1.95 (1H, m), 2.06 (3H, s), 1.99 (1H, dd, J 4.2 Hz, 14.0 Hz), 1.28 (1H, m).

EXAMPLE 86

(1R*,2R*,5S*,6S*)-8-Benzyl-2-{[3,5-bis(trifluoromethyl)phenylmethoxy}-6-(2,4-dihydro-3H-1,2,4-triazol-3-on-5-yl)-1-phenyl-8-azabicyclo[3.2.1]octane A mixture of (1R*,2R*,5S*,6S*)-8-benzyl-2-{[3,5-bis(trifluoromethyl)phenyl]methoxy}-1-phenyl-8-azabicyclo[3.2.1]octan-6-carboxylic acid semicarbazide (Example 85; 273 mg, 0.44 mmol) and 1M aqueous NaOH (20 ml) was stirred at reflux for 40 minutes. After cooling to room temperature the mixture was acidified using 2M hydrochloric acid, treated with saturated aqueous NaHCO$_3$ and extracted into dichloromethane. The combined organic extracts were dried (Na$_2$SO$_4$) and concentrated. The crystalline residue was heated at reflux with a small amount of dichloromethane to give the title compound as a solid (120 mg, 45%).

δ$_H$(360 MHz, MeOH-d$_4$): 7.87 (2H, s), 7.81 (1H, s), 7.65 (2H, m), 7.32 (2H, t, J 7.9 Hz), 7.26–7.10 (6H, m), 4.98 (1H, d, J 13.4 Hz), 4.67 (1H, d, J 13.4 Hz), 4.30 (1H, br s), 4.12 (1H, d, J 15.5 Hz), 3.79 (1H, d, J 15.5 Hz), 3.46 (1H, br s), 3.14 (1H, dd, J 4.2 Hz, 9.2 Hz), 2.56 (1H, dd, J 4.2 Hz, 13.7 Hz), 2.27 (1H, dd, J 8.9 Hz, 13.4 Hz), 2.31–2.08 (3H, m), 1.31 (1H, ddd, J 2.0 Hz. 5.0 Hz, 13.2 Hz).

EXAMPLE 87

(1R*,2R*,5S*,6S*)-2-{[3,5-Bis(trifluoromethyl) phenyl]methoxy}-6-(2,4-dihydro-3H-1,2,4-triazol-3-on-5-yl)-1-phenyl-8-azabicyclo[3.2.1]octane A mixture of (1R*,2R*,5S*,6S*)-8-benzyl-2-{[3,5-bis(trifluoromethyl)phenyl]methoxy}-6-(2,4-dihydro-3H-1,2,4-triazol-3-on-5-yl)-1-phenyl-8-azabicyclo[3.2.1]octane (Example 86; 66 mg, 0.11 mmol), 10% palladium on charcoal (180 mg), ethanol (10 ml) was stirred under hydrogen atmosphere (1 atm) at +60° C. for 1.5 hour. The reaction mixture was cooled to room temperature, flushed with nitrogen gas and filtered through a pad of Celite™. The filtrate was concentrated to give the title compound. The hydrochloride salt of the title compound was prepared by treatment with ethereal HCl.

δ$_H$(400 MHz, MeOH-d$_4$): 7.81 (1H, s), 7.57 (2H, s), 7.41 (3H, m), 7.32 (2H, m), 4.73 (1H, d, J 12.6 Hz), 4.38 (1H, br s), 4.24 (1H, d, J 12.6 Hz), 3.91 (1H, br s), 3.71 (1H, dd, J 5.3 Hz, 9.6 Hz), 3.12 (1H,dd, J 9.6 Hz, 14.6 Hz), 2.78 (1H, dd, J 5.3 Hz, 14.6 Hz), 2.35–2.10 (3H, m), 1.99 (1H, m).

EXAMPLE 88

1-N,N-Dimethylaminoacetic acid 2-(1R*,2R*,5S*, 6R*)-8-benzyl-2-{[3,5-bis(trifluoromethyl)phenyl] methoxy}-1-phenyl-8-azabicyclo[3.2.1]octan-6-carbohydrazide A mixture of (1R*,2R*,5S*,6R*)-8-benzyl-2-{[3,5-bis(trifluoromethyl)phenyl]methoxy}-1-phenyl-8-azabicyclo[3.2.1]octan-6-carboxylic acid trifluoroacetate (Example 53; 212 mg, 0.31 mmol), triethylamine (0.3 ml, 2.15 mmol), 1-(3-dimethylaminopropyl)-3-ethylcarbodiimide hydrochloride (226 mg, 1.2 mmol), 4-N,N-dimethylaminopyridine (20 mg, 0.16 mmol), N,N-dimethylglycine hydrazide hydrochloride (185 mg, 0.97 mmol) and dichloromethane (4 ml) was stirred at room temperature for one hour and diluted with ethyl acetate. The organic solution was washed with saturated aqueous NaHCO$_3$, water and brine. The organic layer was dried (Na$_2$SO$_4$) and concentrated. The residue was purified by chromatography on silica gel (dichloromethane:methanol) to give the title compound (170 mg, 82%).

δ$_H$(360 MHz, CDCl$_3$): 9.15 (1H, s), 7.75 (1H, s), 7.74 (1H, s), 7.72 (2H, s), 7.46 (2H, t, J 7.2 Hz), 7.39 (2H, d, J 7.0 Hz), 7.35–7.19 (6H, m), 4.89 (1H, d, J 12.6 Hz), 4.63 (1H, d, J 12.6 Hz), 4.23 (1H, br s), 4.06 (1H, d, J 13.7 Hz), 3.86 (1H, d, J 13.7 Hz), 3.51 (1H, br s), 3.09 (2H, s), 2.75

(1H, dd, J 3.9 Hz, 9.5 Hz), 2.36 (1H, dd, J 9.5 Hz, 14.0 Hz), 2.33 (6H, s), 2.16 (1H, dd, J 4.2 Hz, 14.4 Hz), 1.96 (1H, m), 1.27 (1H, m).

EXAMPLE 89

(1R*,2R*,5S*,6R*)-8-Benzyl-2-{[3,5-bis(trifluoromethyl)phenyl]methoxy}-6-[(5-dimethylaminomethyl)oxa-3,4-diazo-2-yl]-1-phenyl-8-azabicyclo[3.2.1]octane A mixture of 1-N,N-dimethylaminoacetic acid 2-(1R*,2R*,5S*,6R*)-8-benzyl-2-{[3,5-bis(trifluoromethyl)phenyl]methoxy}-1-phenyl-8-azabicyclo[3.2.1]octan-6-carbohydrazide (Example 88; 162 mg, 0.24 mmol), phosphorus pentaoxide (50 mg) and xylene (4 ml) was stirred at reflux for 3.5 hours. After cooling to room temperature, the reaction mixture was quenched with saturated aqueous $NaHCO_3$ and extracted into ethyl acetate. The combined organic extracts were dried ($Na_2SO_4$) and concentrated. The residue was purified by chromatography on silica gel (dichloromethane:methanol) to give the title compound (58 mg, 37%).

$\delta_H$(400 MHz, $CDCl_3$): 7.76 (1H, s), 7.74 (2H, s), 7.62 (2H, m), 7.33 (2H, t, J 7.8 Hz), 7.30–7.12 (6H, m), 4.88 (1H, d, J 12.9 Hz), 4.63 (1H, d, J 12.9 Hz), 4.22 (1H, br s), 4.10 (1H, d, J 15.3 Hz), 3.88 (1H, d, J 15.6 Hz), 3.75 (2H, s), 3.67 (1H, br s), 3.44 (1H, dd, J 4.3 Hz, 9.4 Hz), 2.66 (1H, dd, J 4.3 Hz, 13.7 Hz), 2.40 (1H, dd, J 9.4 Hz, 13.7 Hz), 2.34 (6H, s), 2.28 (1H, ddt, J 2.7 Hz, 5.5 Hz, 13.3 Hz), 2.20 (1H, m), 2.07 (1H, ddd, J 3.5 Hz, 5.4 Hz, 13.1 Hz), 1.33 (1H, ddd, J 2.3 Hz, 5.6 Hz, 13.5 Hz).

EXAMPLE 90

(1R*,2R*,5S*,6R*)-2-{[3,5-Bis(trifluoromethyl)phenyl]methoxy}-6-[(5-dimethylaminomethyl)oxa-3,4-diazo-2-yl]-1-phenyl-8-azabicyclo[3.2.1]octane A mixture of (1R*,2R*,5S*,6R*)-8-benzyl-2-{[3,5-bis(trifluoromethyl)phenyl]methoxy}-6-[(5-dimethylaminomethyl)oxa-3,4-diazo-2-yl]-1-phenyl-8-azabicyclo[3.2.1]octane (Example 89; 58 mg, 0.09 mmol), 10% palladium on charcoal (121 mg), ethanol (20 ml) was stirred under hydrogen atmosphere (1 atm) at +65° C. for 1 hour. The reaction mixture was cooled to room temperature, flushed with nitrogen gas and filtered through a pad of Celite™. The filtrate was concentrated. The residue was purified by chromatography on silica gel (dichloromethane:methanol) to give the title compound (36 mg, 72%).

m/z (ES⁺) 555 [M+H]⁺.

EXAMPLE 91

(1R*,2R ,5S*,6R*)-8-Benzyl-2-{[3,5-bis(trifluoromethyl)phenyl]methoxy}-1-phenyl-8-azabicyclo[3.2.1]octan-6-carbohydrazide A mixture of (1R*,2R*,5S*,6R*)-8-benzyl-2-{[3,5-bis(trifluoromethyl)phenyl]methoxy}-1-phenyl-8-azabicyclo[3.2.1]octan-6-carboxylic acid trifluoroacetate (Example 53; 1.6 g, 2.35 mmol), triethylamine (1 ml, 7.1 mmol), 1-(3-dimethylaminopropyl)-3-ethylcarbodiimide hydrochloride (910 mg, 4.7 mmol), 4-N,N-dimethylaminopyridine (20 mg, 0.16 mmol), dichloromethane (15 ml) and hydrazine (1M solution in THF, 5 ml, 5 mmol) was stirred at room temperature over the weekend. The reaction mixture was diluted with ethyl acetate and washed with saturated aqueous $NaHCO$ , water and brine. The organic layer was dried ($Na_2SO_4$) and concentrated. The residue was purified by chromatography on silica gel (dichloromethane:methanol) to give the title compound (1 g, 74%).

$\delta_H$(400 MHz, $CDCl_3$): 7.91 (1H, s), 7.74 (1H, s), 7.69 (2H, s), 7.54 (2H, m), 7.43 (2H, t, J 7.4 Hz), 7.40–7.27 (6H, m), 4.88 (1H, d, J 12.9 Hz), 4.60 (1H, d, J 12.9 Hz), 4.21 (1H, br s), 4.06 (1H, d, J 13.7 Hz), 3.86 (1H, d, J 13.7 Hz), 3.68 (2H, br), 3.40 (1H, br s), 2.72 (1H, dd, J 4.3 Hz, 9.8 Hz), 2.34 (1H, dd, J 9.8 Hz, 14.1 Hz), 2.33 (1H, m), 2.15 (1H, dd, J 5.5 Hz, 15.7 Hz), 1.97 (1H, dd, J 3.9 Hz, 13.7 Hz), 1.94 (1H, m), 1.24 (1H, dd, J 5.5 Hz, 13.8 Hz).

EXAMPLE 92

(1R*,2R*,5S*,6R*)-8-Benzyl-2-{[3,5-bis(trifluoromethyl)phenyl]methoxy}-6-(5-trifluoromethyloxa-3,4-diazo-2-yl)-1-phenyl-8-azabicyclo[3.2.1]octane A mixture of (1R*,2R*,5S*,6R*)-8-benzyl-2-{[3,5-bis(trifluoromethyl)phenyl]methoxy}-1-phenyl-8-azabicyclo[3.2.1]octan-6-carbohydrazide (Example 91; 105 mg, 0.18 mmol), trifluoroacetic anhydride (0.05 ml), triethylamine (0.2 ml) and dichloromethane (2 ml) was stirred at room temperature for 30 minutes. The reaction mixture was quenched with saturated aqueous $NaHCO_3$ and extracted with dichloromethane. The combined organic extracts were dried ($Na_2SO_4$) and concentrated. The residue was treated with xylene (4 ml) and phosphorus pentaoxide (60 mg) and stirred at reflux for 3 hours. After cooling to room temperature, the reaction mixture was quenched with saturated aqueous $NaHCO_3$ and extracted into ethyl acetate. The combined organic extracts were dried ($Na_2SO_4$) and concentrated. The residue (2.5:1 mixture of diastereoisomers) was purified by chromatography on silica gel (iso-hexane-ethyl acetate 0–40%) to give the title compound (36 mg, 30%).

$\delta_H$(400 MHz, $CDCl_3$): 7.76 (1H, s), 7.73 (2H, s), 7.61 (2H, d, J 7.4 Hz), 7.36 (2H, t, J 7.4 Hz), 7.31–7.14 (6H, m), 4.89 (1H, d, J 12.6 Hz), 4.64 (1H, d, J 12.6 Hz), 4.26 (1H, br s), 4.11 (1H, d, J 15.4 Hz), 3.86 (1H, d, J 15.1 Hz), 3.66 (1H, br s), 3.56 (1H, dd, J 5.3 Hz, 8.4 Hz), 2.56–2.42 (2H, m), 2.38–2.17 (2H, m), 2.05 (1H, m), 1.35 (1H, ddd, J 2.8 Hz, 5.2 Hz, 13.2 Hz).

EXAMPLE 93

(1R*,2R*,5S*,6R*)-2-{[3,5-Bis(trifluoromethyl)phenyl]methoxy}-6-(5-trifluoromethyloxa-3,4-diazo-2-yl)-1-phenyl-8-azabicyclo[3.2.1]octane A mixture of (1R*,2R*,5S*,6R*)-8-benzyl-2-{[3,5-bis(trifluoromethyl)phenyl]methoxy}-6-(5-trifluoromethyloxa-3,4-diazo-2-yl)-1-phenyl-8-azabicyclo[3.2.1]octane (Example 92; 36 mg, 0.05 mmol), 10% palladium on charcoal (125 mg) and ethanol (10 ml) was stirred under hydrogen atmosphere (1 atm) at +65° C. for 3 hour. The reaction mixture was cooled to room temperature, flushed with nitrogen gas and filtered through a pad of Celite™. The filtrate was concentrated. The residue was purified by chromatography on silica gel (dichloromethane:methanol) to give the title compound. The hydrochloride salt of the title compound was prepared by treatment with ethereal HCl.

m/z (ES⁺) 566 [M+H]⁺.

EXAMPLE 94

(1R*,2R*,5S*,6R*)-8-Allyl-2-{[3,5-bis(trifluoromethyl)phenyl]methoxy}-6-(tert-butoxycarbonyl)-1-phenyl-8-azabicyclo[3.2.1]octane (1R*,2R*,5S*,6R*)-2-{[3,5-Bis(trifluoromethyl)phenyl]methoxy}-6-(tert-butoxycarbonyl)-1-phenyl-8-azabicyclo

[3.2.1]octane (Example 25; 2.1 g, 4.0 mmol), potassium carbonate (1.7 g, 12.0 mmol) and allyl bromide (0.42 ml, 4.8 mmol) in dimethylformamide (10 ml) were stirred at room temperature for 5 hours. The mixture was diluted with ethyl acetate and washed with water. The organics were collected, dried (MgSO$_4$) and concentrated in vacuo. The residue was purified by column chromatography, eluting with 10% ethyl acetate/iso-hexane, (1.8 g, 80%).

$\delta_H$(360 MHz, CDCl$_3$): 7.72 (1H, s), 7.63 (2H, m), 7.46 (2H, m), 7.34–7.21 (3H, m), 5.65 (1H, m), 5.20 (1H, m), 5.01 (1H, m), 4.71 (1H, d, J 12.7 Hz), 4.49 (1H, d, J 12.7 Hz), 3.96 (1H, s), 3.89 (1H, s), 3.47 (1H, m), 3.12 (1H, m), 2.72 (1H, m), 2.32 (1H, m), 2.02 (3H, m), 1.92 (1H, m), 1.46 (9H, s), 1.26 (1H, m).

EXAMPLE 95

(1R*,2R*,5S*,6R*)-8-Allyl-2-{[3,5-bis(trifluoromethyl)phenyl]methoxy}-6-(methoxycarbonyl)-1-phenyl-8-azabicyclo[3.2.1]octane Acetyl chloride (5 ml) was cautiously added to methanol (25 ml) and (1R*,2R*,5S*,6R*)-8-allyl-2-{[3,5-bis(trifluoromethyl)phenyl]methoxy}-6-(tert-butoxycarbonyl)-1-phenyl-8-azabicyclo[3.2.1]octane (Example 94; 1.23 g, 2.16 mmol) dissolved in the resulting solution. After standing for 4 weeks, the solvent was removed under reduced pressure and the residue partitioned between ethyl acetate (25 ml) and saturated aqueous sodium carbonate (2×15 ml), the organic layers dried (MgSO$_4$) and evaporated to leave the title compound as a gum. (1.07 g, 94%).

$\delta_H$(360 MHz, CDCl$_3$): 7.72 (1H, s), 7.62 (2H, s), 7.44 (2H, d, J 7.3 Hz), 7.33–7.20 (3H, m), 5.79–5.73 (1H, m), 5.17 (1H, dd, J 17.2 Hz, J 1.5 Hz), 5.03 (1H, dd, J 10.3 Hz, J 1.0 Hz), 4.71 (1H, d, J 12.8 Hz), 4.44 (1H, d, J 12.8 Hz), 3.95 (2H, s), 3.72 (3H, s), 3.46 (1H, dd, J 15.8 Hz, J 6.5 Hz), 3.10 (1H, dt, J 15.8 Hz, J 2.2 Hz), 2.83 (1H, dd, J 9.4 Hz, J 4.9 Hz), 2.38 (1H, dd J 13.6 Hz, J 4.9 Hz), 2.16–2.03 (3H, m), 1.95–1.82 (1H, m), 1.32–1.26 (1H, m).

EXAMPLE 96

(1R*,2R*,5S*,6R*)-8-Allyl-2-{[3,5-bis(trifluoromethyl)phenyl]methoxy}-6-(3-methyl-1,2,4-oxadiazol-5-yl])-1-phenyl-8-azabicyclo[3.2.1]octane Powdered 4A molecular sieves (100 mg), followed after 15 minutes by sodium hydride (60% dispersion in mineral oil; 30 mg, 0.75 mmol), were added to a suspension of acetamide oxime (55 mg, 0.75 mmol) in THF (5 ml). The mixture was stirred for 45 minutes before adding a solution of (1R*,2R*,5S*,6R*)-8-allyl-2-{[3,5-bis(trifluoromethyl)phenyl]methoxy}-6-(methoxycarbonyl)-1-phenyl-8-azabicyclo[3.2.1]octane (Example 95) in THF (10 ml). The resulting mixture was stirred under reflux for 2 hours, allowed to stand overnight at room temperature, and reflux resumed for a further 1.5 hours. The residue remaining after removal of solvent was partitioned between water (15 ml) and ethyl acetate (2×10 ml), the organic layers dried, (MgSO$_4$), evaporated, and the residue purified by column chromatography, eluting with 35% ethyl acetate in iso-hexane, to give the title compound as a gum (200 mg, 75%).

m/z (ES$^+$) 552 ([M+H]$^+$).

EXAMPLE 97

(1R*,2R*,5S*,6R*)-2-{[3,5-Bis(trifluoromethyl)phenyl]methoxy}-6-(3-methyl-1,2,4-oxadiazol-5-yl)-1-phenyl-8-azabicyclo[3.2.1]octane (1R*,2R*,5S*,6R-8-Allyl-2-{[3,5-bis(trifluoromethyl)phenyl]methoxy}-6-(3-methyl-1,2,4-oxadiazol-5-yl)-1-phenyl-8-azabicyclo[3.2.1]octane (Example 96; 81 mg, 0.15 mmol) was combined with tetrakis(triphenylphosphine)palladium(0) (10 mg) and N,N'-dimethylbarbituric acid (70 mg, 0.45 mmol) in dichloromethane and stirred at 35° C. for 3 hours. The reaction mixture was diluted with saturated sodium hydrogen carbonate solution and extracted with dichloromethane (×3). The organics were dried (MgSO$_4$) and concentrated in vacuo to give a dark red solid. The solid was purified by preparative thin layer chromatography [5% methanol in dichloromethane] to give the title compound as a yellow oil.

m/z (ES$^+$) 511 ([M+H]$^+$).

EXAMPLE 98

(1R*,2R*,5S*,6R*)-2-{[3,5-Bis(trifluoromethyl)phenyl]methoxy}-6-ethynyl-1-phenyl-8-azabicyclo[3.2.1]octane (1R*,2R*,5S*,6R*)-2-{(3,5-Bis(trifluoromethyl)phenyl]methoxy}-6-formyl-1-phenyl-8-azabicyclo[3.2.1]octane (Example 47; 165 mg, 0.3 mmol) in methanol (3 ml) at 0° C. was treated with potassium carbonate (83 mg, 0.6 mmol) and dimethyl 1-diazo-2-oxopropylphosphonate (81 mg, 0.5 mmol) and stirred for 18 hours at room temperature. The reaction mixture was concentrated in vacuo. The residue was partitioned between water and hexane. The organics were collected, dried (MgSO$_4$), filtered and concentrated in vacuo to afford the title compound as a white crystalline solid (123 mg, 75%).

m/z (ES$^+$) 544 ([M+H]$^+$).

EXAMPLE 99

(1R*,2R*,5S*,6R*)-2-{[3,5-Bis(trifluoromethyl)phenyl]methoxy}-6-(1,2,3-triazol-5-yl)-1-phenyl-8-azabicyclo[3.2.1]octane hydrochloride (1R*,2R*,5S*,6R*)-2-{[3,5-Bis(trifluoromethyl)phenyl]methoxy}-6-ethynyl-1-phenyl-8-azabicyclo[3.2.1]octane (Example 98; 136 mg, 0.3 mmol) and trimethylsilylazide (0.1 ml, 0.8 mmol) in toluene were heated in a sealed tube at 130° C. for 48 hours. The mixture was allowed to cool and quenched with methanol and water. The mixture was concentrated in vacuo, and the residue purified by flash column chromatography, eluting with 5% methanol/dichloromethane. The debenzylated product was treated with 1.0 eq HCl in ether and the title compound isolated as a white crystalline solid (20 mg, 13%).

m/z (ES$^+$) 497 ([M+H]$^+$).

EXAMPLE 100

(1R*,2R*,5S*,6R*)-2-{[3,5-Bis(trifluoromethyl)phenyl]methoxy}-6-(1-phenylthiomethyl-1,2,3-triazol-5-yl)-1-phenyl-8-azabicyclo[3.2.1]octane; and (1R*,2R*,5S*,6R*)-2-{[3,5-bis(trifluoromethyl)phenyl]methoxy}-6-(3-phenylthiomethyl-1,2,3-triazol-5-yl)-1-phenyl-8-azabicyclo[3.2.1]octane (1R*,2R*,5S*,6R*)-2-{[3,5-Bis(trifluoromethyl)phenyl]methoxy}-6-ethynyl-1-phenyl-8-azabicyclo[3.2.1]octane (Example 98; 96 mg, 0.2 mmol) and azidomethyl phenyl sulfide (30 μl, 0.2 mmol) in toluene (2 ml), were heated in a sealed tube at 110° C. for 18 hours. The mixture was allowed to cool and concentrated in vacuo. The residue was purified by flash column chromatography eluting with 10–50% ethyl acetate/hexane. The title compounds were isolated a brown solid (62 mg, 50%).

m/z (ES$^+$) 710 ([M+H]$^+$).

EXAMPLES 101a AND 101b (1R*,2R*,5S*,6R*)-2-{[3,5-Bis(trifluoromethyl)
phenyl]methoxy}-6-(1-methyl-1,2,3-triazol-5-yl)-1-
phenyl-8-azabicyclo[3.2.1]octane; and (1R*,2R*,5S*,6R*)-2-{[3,5-bis(trifluoromethyl)
phenyl]methoxy}-6-(3-methyl-1,2,3-triazol-5-yl)-1-
phenyl-8-azabicyclo[3.2.1]octane A mixture of (1R*,2R*,5S*,6R*)-2-{[3,5-bis (trifluoromethyl)phenyl]methoxy}-6-(1-phenylthiomethyl-1,2,3-triazol-5-yl)-1-phenyl-8-azabicyclo[3.2.1]octane and (1R*,2R*,5S*,6R*)-2-{[3,5-bis(trifluoromethyl)phenyl] methoxy}-6-(3-phenylthiomethyl-1,2,3-triazol-5-yl)-1-phenyl-8-azabicyclo[3.2.1]octane (Example 100; 99 mg, 0.1 mmol) and nickel(II)chloride hexahydrate (233 mg, 1.0 mmol) in methanol (6 ml) and THF (2 ml) at 0° C. was treated with sodium borohydride (112 mg, 2.9 mmol). A black precipitate was formed and the mixture was stirred for 20 minutes. The mixture was filtered through Celite™ and the filtrate concentrated in vacuo. The isomers were separated by preparative TLC eluting with 1:1 ethyl acetate/ hexane to afford the title compounds (3-methyl-1,2,3-triazol-5-yl isomer: 17 mg) and (1-methyl-1,2,3-triazol-5-yl isomer: 34 mg), in a combined yield of 61%.

EXAMPLE 101a $\delta_H$(400 MHz, CDCl$_3$): 7.72 (3H, m), 7.54 (2H, m), 7.45 (1H, s), 7.36 (1H, m), 7.30 (8H, m), 4.91 (1H, d, J 12.9 Hz), 4.64 (1H, d, J 12.5 Hz), 4.25 (1H, s), 4.11 (1H, d, J 14.9 Hz), 3.94 (1H, d, J 14.9 Hz), 3.89 (3H, s), 3.46 (1H, s), 3.16 (1H, m), 2.50 (1H, m), 2.37 (1H, m), 2.26 (1H, m), 2.12 (1H, m), 1.92 (1H, m).

EXAMPLE 101b $\delta_H$(400 MHz, CDCl$_3$): 7.73 (3H, m), 7.56 (2H, m), 7.29 (9H, m), 4.89 (1H, d, J 12.9 Hz), 4.61 (1H, d, J 12.8 Hz), 4.23 (1H, s), 4.10 (1H, d, J 14.7 Hz), 4.04 (3H, s), 3.89 (1H, J 14.7 Hz), 3.41 (2H, m), 2.50 (1H, m), 2.30 (1H, m), 2.17,(2H, m), 1.96 (1H, m), 1.26 (1H, m).

EXAMPLE 102

(1R*,2R*,5S*,6R*)-2-{[3,5-Bis
(trifluoromethylphenyl]methoxy}-6-(1-methyl-1,2,3-
triazol-5-yl)-1-phenyl-8-azabicyclo[3.2.1]octane
hydrochloride Prepared from (1R*,2R*,5S*,6R*)-2-{[3,5-bis (trifluoromethyl)phenyl]methoxy-6-(1-methyl-1,2,3-triazol-5-yl)-1-phenyl-8-azabicyclo[3.2.1]octane (Example 101a) by an analogous method to those previously described.

m/z (ES$^+$) 511 ([M+H]$^+$).

EXAMPLE 103

(1R*,2R*,5S*,6R*)-2-{[3,5-Bis(trifluoromethyl)
phenyl]methoxy}-6-(3-methyl-1,2,3-triazol-5-yl)-1-
phenyl-8-azabicyclo[3.2.1]octane hydrochloride Prepared from (1R*,2R*,5S*,6R*)-2-[3,5-bis (trifluoromethyl)phenyl]methoxy}-6-(3-methyl-1,2,3-triazol-5-yl)-1-phenyl-8-azabicyclo[3.2.1] octane (Example 101b) by an analogous method to those previously described.

m/z (ES$^+$) 511 ([M+H]$^+$).

EXAMPLE 104

(1R*,2R*,5S*,6R*)-6-Acetamidoazido-8-benzyl-2-{
[3,5-bis(trifluoromethyl)phenyl]methoxy}-1-phenyl-
8-azabicyclo[3.2.1]octane (1R*,2R*,5S*,6R*)-8-Benzyl-2-{[3,5-bis (trifluoromethyl)phenyl]methoxy}-1-phenyl-8-azabicyclo [3.2.1]octan-6-carboxylic acid (free base of Example 53; 377 mg, 0.67 mmol) was dissolved in dichloromethane (10 ml) and dimethylformamide (2 drops) and the mixture cooled to 0° C. then oxalyl chloride (0.063 ml, 0.72 mmol) added. The mixture was then left to warm to room temperature and stirred for 2 hours. The mixture was concentrated in vacuo then carried through crude. Acid chloride (389 mg, 0.67 mmol) was taken up in dichloromethane (10 ml) and sodium azide (48 mg, 0.74 mmol) added and the mixture stirred at room temperature for 3 days. A further 48 mg of sodium azide was added and the mixture further stirred overnight. The reaction mixture was then concentrated in vacuo and carried through crude. The isocyanate (394 mg, 0.70 mmol) was dissolved in THF (3 ml) and water (3 ml) and the mixture refluxed for 4 hours. The reaction mixture was then extracted with ethyl acetate (×2), dried (MgSO$_4$) and concentrated in vacuo to give the title compound as a beige solid (307 mg, 82%).

m/z (ES$^+$) 604 [M+H]$^+$).

EXAMPLE 105

(1R*,2R*,5S*,6R*)-6-Acetamidoazido-2-{[3,5-bis
(trifluoromethyl)phenyl]methoxy}-1-phenyl-8-
azabicyclo[3.2.1]octane hydrochloride (1R*,2R*,5S*,6R*)-6-Acetamidoazido-8-benzyl-2-{[3, 5-bis(trifluoromethyl)phenyl]methoxy}-1-phenyl-8-azabicyclo[3.2.1]octane (Example 104; 240 mg, 0.40 mmol) was dissolved in ethyl acetate (10 ml) and glacial acetic acid (1 ml) then 10% palladium hydroxide (30 mg) added and the mixture hydrogenated at 45 psi overnight. The reaction mixture was then filtered and the mixture further hydrogenated with fresh catalyst (30 mg) overnight. The reaction mixture was filtered then concentrated in vacuo, basified (saturated sodium hydrogen carbonate solution), extracted with dichloromethane (×3), dried (MgSO$_4$), and concentrated in vacuo. The crude product was purified by flash column chromatography [10% methanol in dichloromethane] to give an oil which when concentrated with iso-hexane gave a white solid. The hydrochloride salt was made by dissolving in diethyl ether and adding 1 equivalent of hydrogen chloride in diethyl ether. The title compound was filtered off and dried in vacuo at 60° C.

m/z (ES$^+$) 489 [M+H]$^+$).

EXAMPLE 106

(1R*,2R*,5S*,6R*)-8-Benzyl-2-{[3,5-bis
(trifluoromethyl)phenyl]methoxy}-1-phenyl-8-
azabicyclo[3.2.1]octan-6-carbamic acid methyl ester (1R*,2R*,5S*,6R*)-8-Benzyl-2-{[3,5-bis (trifluoromethyl)phenyl]methoxy}-1-phenyl-8-azabicyclo [3.2.1]octan-6-carboxamide (Example 75; 127 mg, 0.23 mmol) was stirred in methanol (5 ml). A solution of potassium hydroxide (5.36 g) in water (93 ml) was made up and bromine (1 g) added. 10 ml of the bromine solution was added to the amide in methanol then the reaction mixture heated to 70° C. for 3 hours. The reaction mixture was concentrated in vacuo then extracted with dichloromethane (×3), dried (MgSO$_4$), and concentrated in vacuo to give a yellow oil. This was purified by flash column chromatography [25% ethyl acetate in iso-hexane] to give the title compound (92 mg, 69%).

m/z (ES$^+$) 592 ([M+H]$^+$).

EXAMPLE 107

(1R*,2R*,5S*,6R*)-2-{[3,5-Bis(trifluoromethyl)
phenyl]methoxy}-1-phenyl-8-azabicyclo[3.2.1]
octan-6-carbamic acid methyl ester hydrochloride (1R*,2R*,5S*,6R*)-8-Benzyl-2-{[3,5-bis (trifluoromethyl)phenyl]methoxy}-1-phenyl-6- phenylsulfonyl-8-azabicyclo[3.2.1]octane (Example 1; 92 mg, 0.16 mmol), was dissolved in ethyl acetate (5 ml) and glacial acetic acid (0.5 ml), then 10% palladium hydroxide (20 mg) added and the reaction mixture hydrogenated at 40 psi overnight. The mixture was then filtered, washed with methanol and concentrated in vacuo. The oil was basified (saturated sodium hydrogen carbonate solution) then extracted with dichloromethane (×3) and the organics dried (MgSO$_4$) and concentrated in vacuo to give a clear oil. The hydrochloride salt was made by adding 1 equivalent of hydrogen chloride in diethyl ether to a solution in diethyl ether and the solid filtered off and dried at 60° C. in vacuo to give the title compound.

m/z (ES$^+$) 503 ([M+H]$^+$).

EXAMPLE 108

(1R*,2R*,5S*,6R*)-6-Amino-8-benzyl-2-{[3,5-bis(trifluoromethyl)phenyl]methoxy}-1-phenyl-8-azabicyclo[3.2.1]octane (1R*,2R*,5S*,6R*)-8-Benzyl-2-{[3,5-bis(trifluoromethyl)phenyl]methoxy}-1-phenyl-8-azabicyclo[3.2.1]octan-6-carboxamide (Example 75; 2.38 g, 4.23 mmol) was dissolved in 'butanol (27 ml). A solution of potassium hydroxide (10.72 g) in water (186 ml) was made up and bromine (2 g) added. 35 ml of the bromine solution was added to the amide in 'butanol and the mixture stirred at room temperature for 1 hour then at 70° C. for 30 minutes. The reaction mixture was then concentrated in vacuo, extracted with dichloromethane (×3), dried (MgSO$_4$) and concentrated in vacuo. The oil was purified by flash column chromatography [10%–20% methanol in dichloromethane] to give the title compound as a yellow solid (1.73 g, 76%).

m/z (ES$^+$) 535 ([M+H]$^+$).

EXAMPLE 109

(1R*,2R*,5S*,6R*)-6-Acetamido-8-benzyl-2-{[3,5-bis(trifluoromethyl)phenyl]methoxy}-1-phenyl-8-azabicyclo[3.2.1]octane (1R*,2R*,5S*,6R*)-6-Amino-8-benzyl-2-{[3,5-bis(trifluoromethyl)phenyl]methoxy}-1-phenyl-8-azabicyclo[3.2.1]octane (Example 108; 475 mg, 0.89 mmol), glacial acetic acid (0.076 ml, 1.34 mmol), triethylamine (0.14 ml, 0.98 mmol), 1-(3-dimethylaminopropyl)-3-ethyl-carbodiimide hydrochloride (257 mg, 1.34 mmol) and 4-dimethylaminopyridine (2 crystals) were combined in dichloromethane (4 ml) and stirred overnight at room temperature. The reaction mixture was washed with water and extracted with dichloromethane (×3). The organics were dried (MgSO$_4$), and concentrated in vacuo to give the title compound as a yellow oil (384 mg, 75%).

m/z (ES$^+$) 577 ([M+H]$^+$).

EXAMPLE 110

(1R*,2R*,5S*,6R*)-8-Benzyl-2-{[3,5-bis(trifluoromethyl)phenyl]methoxy}-6-(5-methyl-1H-tetrazol-1-yl)-1-phenyl-8-azabicyclo[3.2.1]octane (1R*,2R*,5S*,6R*)-6-Acetamido-8-benzyl-2-{[3,5-bis(trifluoromethyl)phenyl]methoxy}-1-phenyl-8-azabicyclo[3.2.1]octane (Example 109; 384 mg, 0.67 mmol) and sodium azide in dichloromethane (10 ml) were cooled to 0° C. and trifluoromethanesulphonic anhydride (0.11 ml, 0.67 mmol) added. The reaction was warmed to room temperature and stirred for 3 hours then quenched with saturated sodium hydrogen carbonate solution and extracted with dichloromethane (×3). The organics were dried (MgSO$_4$) and concentrated in vacuo to give a brown solid. This was purified by flash column chromatography [2.5% methanol in dichloromethane] to give the title compound as a cream-coloured solid (134 mg, 34%).

m/z (ES$^+$) 602 ([M+H]$^+$).

EXAMPLE 111

(1R*,2R*,5S*,6R*)-2-{[3,5-Bis(trifluoromethyl)phenyl]methoxy}-6-(5-methyl-1H-tetrazol-1-yl)-1-phenyl-8-azabicyclo[3.2.1]octane hydrochloride (1R*,2R*,5S*,6R*)-8-Benzyl-2-{[3,5-bis(trifluoromethyl)phenyl]methoxy}-6-(5-methyl-1H-tetrazol-1-yl)-1-phenyl-8-azabicyclo[3.2.1]octane (Example 110; 134 mg, 0.22 mmol) was dissolved in methanol (10 ml) and hydrochloric acid (2N) (1 ml) and 10% palladium hydroxide (50 mg) added and the mixture hydrogenated at 40 psi overnight. The reaction mixture was then filtered and concentrated in vacuo. The oil was partitioned between saturated sodium hydrogen carbonate solution and dichloromethane and the organics dried (MgSO$_4$) and concentrated in vacuo. The solid was purified by flash column chromatography [5% methanol in dichloromethane]. The hydrochloride salt was made by adding 1 equivalent of hydrogen chloride in diethyl ether to a solution in diethyl ether. The title compound was filtered off and dried in vacuo (32 mg, 26%).

m/z (ES$^+$) 512 ([M+H]$^+$).

EXAMPLE 112

(1R*,2R*,5S*,6R*)-8-Benzyl-2-{[3,5-bis(trifluoromethyl)phenyl]methoxy}-6-(3-methoxypropoxamido)-1-phenyl-8-azabicyclo[3.2.1]octane (1R*,2R*,5S*,6R*)-6-Amino-8-benzyl-2-{[3,5-bis(trifluoromethyl)phenyl]methoxy}-1-phenyl-8-azabicyclo[3.2.1]octane (Example 108; 527 mg, 0.99 mmol), 3-methoxypropionic acid (0.14 ml, 1.49 mmol), triethylamine (0.15 ml,1.09 mmol), 1-(3-dimethylaminopropyl)-3-ethyl-carbodiimide hydrochloride (286 mg, 1.49 mmol) and 4-dimethylaminopyridine (5 crystals) were combined in dichloromethane (4 ml) and stirred at room temperature overnight. The mixture was partitioned between dichloromethane and water and the organics collected. The aqueous was further extracted with dichloromethane (×2) and the organics combined and dried (MgSO$_4$) and concentrated in vacuo to give a yellow oil which was purified by flash column chromatography [2.5% methanol in dichloromethane] to give the title compound as a yellow oil (368 mg, 60%).

m/z (ES$^+$) 621 ([M+H]$^+$).

EXAMPLE 113

(1R*,2R*,5S*,6R*)-2-{[3,5-Bis(trifluoromethyl)phenyl]methoxy}-6-(3-methoxypropoxamide)-1-phenyl-8-azabicyclo[3.2.1]octane hydrochloride (1R*,2R*,5S*,6R*)-8-Benzyl-2-{[3,5-bis(trifluoromethyl)phenyl]methoxy}-6-(3-methoxypropoxamide)-1-phenyl-8-azabicyclo[3.2.1]octane (Example 112; 179 mg, 0.29 mmol) was dissolved in methanol (5 ml) with 2N hydrochloric acid (1 ml) and 10% palladium hydroxide (40 mg) added. The mixture was hydrogenated at 40 psi for 30 minutes. The reaction mixture was then filtered and concentrated in vacuo then partitioned between saturated sodium hydrogen carbonate solution and dichloromethane. The organic layer was collected and the aqueous further extracted with dichloromethane (×2). The organics were dried (MgSO$_4$) and concentrated in vacuo then the crude purified by flash column chromatography [5% methanol in dichloromethane] to give a cream-coloured solid. The hydrochloride salt was made by adding 1 equivalent of 1N hydrogen chloride in diethyl ether to a solution in diethyl ether and the title compound filtered and dried in vacuo at 60° C. (55 mg, 35%).

m/z (ES$^+$) 531 ([M+H]$^+$).

EXAMPLE 114

(1R*,2R*,5S*,6R*)-8-Benzyl-2-{[3,5-bis(trifluoromethyl)phenyl]methoxy}-1-phenyl-6-(1,2,4-triazol-4-yl)-8-azabicyclo[3.2.1]octane (1R*,2R*,5S*,6R*)-6-Amino-8-benzyl-2-{[3,5-bis(trifluoromethyl)phenyl]methoxy}-1-phenyl-8-azabicyclo[3.2.1]octane (Example 108; 211 mg, 0.40 mmol), N,N!-dimethylformamide azine (84 mg, 0.59 mg), and p-toluenesulphonic acid (38 mg, 0.20 mmol) were combined in toluene (4 ml) and heated at reflux under N$_2$ overnight. The reaction mixture was cooled and concentrated in vacuo. The crude was purified by flash column chromatography [7.5%–10% methanol in dichloromethane] to give the title compound as a brown oil (175 mg, 75%).

m/z (ES$^+$) 587 ([M+H]$^+$).

EXAMPLE 115

(1R*,2R*,5S*,6R*)-2-{[3,5-Bis(trifluoromethyl)phenyl]methoxy}-1-phenyl-6-(1,2,4-triazol-4-yl)-8-azabicyclo[3.2.1]octane hydrochloride (1R*,2R*,5S*,6R*)-8-Benzyl-2-{[3,5-bis(trifluoromethyl)phenyl]methoxy}-1-phenyl-6-(1,2,4-triazol-4-yl)-8-azabicyclo[3.2.1]octane (Example 114; 175 mg, 0.30 mmol), was dissolved in methanol (5 ml) and 2N hydrochloric acid (0.5 ml) and 10% palladium hydroxide (40 mg, 10%) added and the reaction mixture hydrogenated at 45 psi for 1 hour. The mixture was then filtered and concentrated in vacuo. The oil was partitioned between saturated sodium hydrogen carbonate solution and dichloromethane and the organic layer collected. The aqueous was further extracted with dichloromethane (×2) and the organics combined, dried (MgSO$_4$) and concentrated in vacuo to give a yellow oil. This was purified by flash column chromatography [5% methanol in dichloromethane] to give a cream-coloured solid (72 mg, 49%). The hydrochloride salt was made by adding 1 equivalent of hydrogen chloride in diethyl ether to a solution in diethyl ether and the title compound filtered and dried in vacuo at 60° C.

m/z (ES$^+$) 497 ([M+H]$^+$).

EXAMPLE 116

(1R*,2R*,5S*,6R*)-8-Benzyl-2-{[3,5-bis(trifluoromethyl)phenyl]methoxy}-1-phenyl-6-(1H-tetrazol-1-yl)-8-azabicyclo[3.2.1]octane (1R*,2R*,5S*,6R*)-6-Amino-8-benzyl-2-{[3,5-bis(trifluoromethyl)phenyl]methoxy}-1-phenyl-8-azabicyclo[3.2.1]octane (Example 108; 209 mg, 0.39 mmol) in triethylorthoformate (3.5 ml, 19.22 mmol) and glacial acetic acid (1 ml) was heated to 90° C. Sodium azide (250 mg, 3.85 mmol) was added and the mixture further heated at 90° C. overnight. The mixture was cooled and partitioned between saturated sodium hydrogen carbonate solution and dichloromethane. The organics were dried (MgSO$_4$) and concentrated in vacuo. The reaction mixture was purified by flash column chromatography [2.5% methanol in dichloromethane] to give the title compound as a cream-coloured foam (154 mg, 56%).

m/z (ES$^+$) 588 ([M+H]$^+$).

EXAMPLE 117

(1R*,2R*,5S*,6R*)-2-{[3,5-Bis(trifluoromethyl)phenyl]methoxy}-1-phenyl-6-(1H-tetrazol-1-yl)-8-azabicyclo[3.2.1]octane hydrochloride 1R*,2R*,5S*,6R*)-8-Benzyl-2-{[3,5-bis(trifluoromethyl)phenyl]methoxy}-1-phenyl-6-(1H-tetrazol-1-yl)-8-azabicyclo[3.2.1]octane. (Example 116; 154 mg, 0.26 mmol) was dissolved in methanol (30 ml) and 2N hydrochloric acid (0.5 ml) and 10% palladium hydroxide (40 mg, 10%) added. The mixture was hydrogenated at 35 psi for 1 hour. The reaction mixture was then filtered and concentrated in vacuo and the oil partitioned between saturated sodium hydrogen carbonate solution and dichloromethane. The organics were collected, dried (MgSO$_4$) and concentrated in vacuo to give an orange foam which was purified by flash column chromatography [7.5% methanol in dichloromethane] then further isolated by thin layer chromatography [7.5% methanol in dichloromethane] to give a clear oil. The hydrochloride salt was made by adding 1 equivalent of hydrogen chloride in diethyl ether (1.0M) to a solution in diethyl ether and the title compound filtered and dried in vacuo at 60° C. (25 mg, 18%).

m/z (ES$^+$) 498 ([M+H]$^+$).

EXAMPLE 118

(1R*,2R*,5S*,6R*)-6-Acetamido-8-benzyl-2-{[3,5-bis(trifluoromethyl)phenyl]methoxy}-1-phenyl-8-azabicyclo[3.2.1]octane To (1R*,2R*,5S*,6R*)-6-amino-8-benzyl-2-{[3,5-bis(trifluoromethyl)phenyl]methoxy}-1-phenyl-8-azabicyclo[3.2.1]octane (Example 108; 256 mg, 0.48 mmol) and sodium azide (75 mg, 1.15 mmol) in triethylorthoformate (0.25 ml) was added glacial acetic acid (2.5 ml) and the reaction mixture heated at 90° C. for 3 hours. The reaction mixture was cooled then concentrated in vacuo and partitioned between saturated sodium hydrogen carbonate solution and dichloromethane. The organics were dried (MgSO$_4$) and concentrated in vacuo to give a brown oil. This was purified by flash column chromatography [5% methanol in dichloromethane] to give the title compound (66 mg, 24%).

m/z (ES$^+$) 577 ([M+H]$^+$).

EXAMPLE 119

(1R*,2R*,5S*,6R*)-6-Acetamido-2-{[3,5-bis(trifluoromethyl)phenyl]methoxy}-1-phenyl-8-azabicyclo[3.2.1]octane hydrochloride (1R*,2R*,5S*,6R*)-6-Acetamido-8-benzyl-2-{[3,5-bis(trifluoromethyl)phenyl]methoxy}-1-phenyl-8-azabicyclo[3.2.1]octane (Example 118; 66 mg, 0.11 mmol) was dissolved in methanol (5 ml) and 2N hydrochloric acid (1 ml) and 10% palladium hydroxide (20 mg) added. The reaction mixture was hydrogenated at 40 psi for 1 hour. The mixture was then filtered and concentrated in vacuo then the oil basified (saturated sodium hydrogen carbonate solution) and extracted with dichloromethane (×3), dried (MgSO$_4$) and concentrated in vacuo to give a clear oil. The oil was purified by thin layer chromatography [10% methanol in dichloromethane] to give a white solid. The hydrochloride salt was made by adding 1 equivalent of hydrogen chloride in diethyl ether (1.0M) to a solution in diethyl ether and the title compound-filtered and dried in vacuo at 60° C.

m/z (ES$^+$) 487 ([M+H]$^+$).

EXAMPLE 120

(1R*,2R*,5S*,6R*)-8-Benzyl-2-{[3,5-bis(trifluoromethyl)phenyl]methoxy)-6-piperidinylcarbonyl-1-phenyl-8-azabicyclo[3.2.1]octane A 0.07M solution of (1R*,2R*,5S*,6R*)-8-benzyl-2-{[3,5-bis(trifluoromethyl)phenyl]methoxy}-1-phenyl-8-azabicyclo[3.2.1]octan-6-carboxylic acid trifluoroacetate (Example 53) in dichloromethane (2.5 ml, 0.18 mmol) was added to a mixture of piperidine (0.25 ml, 2.5 mmol), triethylamine (0.1 ml, 0.7 mmol), 1-(3-dimethylaminopropyl)-3-ethylcarbodiimide hydrochloride (66 mg, 0.34 mmol), and 4-N,N-dimethylaminopyridine (12 mg, 0.1 mmol). The mixture was stirred at room temperature overnight and purified by chromatography on silica gel (iso-hexane:ethyl acetate) to give the title compound (100 mg, 88%).

δ$_H$, (360 MHz, CDCl$_3$): 7.75 (3H, s), 7.61 (2H, d, J 8.1 Hz), 7.40 (2H, d, J 7.4 Hz), 7.35–7.13 (6H, m), 4.84 (1H, d, J 13.0 Hz), 4.60 (1H, d, J 13.0 Hz), 4.12 (1H, br s), 4.08 (1H, d, J 16.1 Hz), 3.82 (1H, d, J 15.8 Hz), 3.79 (1H, br), 3.52 (1H, s), 3.47–3.16 (3H, m), 2.96–2.84 (2H, m), 2.27–1.92 (4H, m), 1.69–1.17 (8H, m).

EXAMPLE 121

(1R*,2R*,5S*,6R*)-2-{[3,5-Bis(trifluoromethyl)phenyl]methoxy}-6-piperidinylcarbonyl-1-phenyl-8-azabicyclo[3.2.1]octane A mixture of (1R*,2R*,5S*,6R*)-8-benzyl-2-{[3,5-bis(trifluoromethyl)phenyl]methoxy}-6-piperidinylcarbonyl-1-phenyl-8-azabicyclo[3.2.1]octane (Example 120; 100 mg, 0.16 mmol), 10% palladium on charcoal (180 mg) and ethanol (10 ml) was stirred under hydrogen atmosphere (1 atm) at +65° C. for 1 hour. The reaction mixture was cooled to room temperature, flushed with nitrogen gas and filtered through a pad of Celite™. The filtrate was concentrated and purified chromatography on silica gel to give the title compound (83 mg, 90%). The hydrochloride salt of the title compound was prepared by treatment with ethereal HCl.

HCl salt:-δ$_H$(360 MHz, MeOH-d$_4$): 7.81 (1H, s), 7.58 (2H, s), 7.45–7.28 (5H, m), 4.72 (1H, d, J 12.6 Hz), 4.37 (1H, s), 4.23 (1H, d, J 12.6 Hz), 3.91 (1H, s), 3.69 (1H, dd, J 5.0 Hz, 9.9 Hz), 3.65–3.45 (4H, m), 3.21 (1H, dd, J 9.9 Hz, 14.0 Hz), 2.29–2.11 (4H, m), 1.89 (1H, m), 1.76–1.43 (6H, m).

Compounds listed in the Table 1 were prepared using the above protocol.

TABLE 1

| Structure (racemic mixture) | m/z (ES$^+$) (M + H)$^+$ |
|---|---|
| [structure] | 487 |
| [structure] | 517 |
| [structure] | 501 |

TABLE 1-continued
| Structure (racemic mixture) | m/z (ES+) (M + H)+ |
|---|---|
| 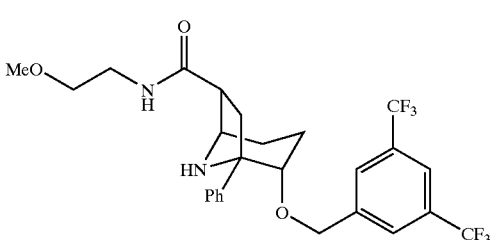 | 531 |
| 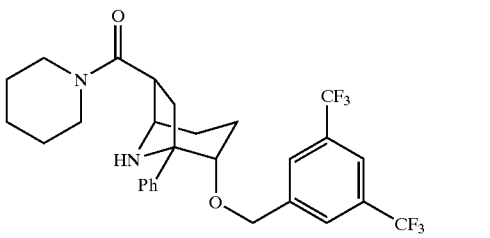 | 541 |
| 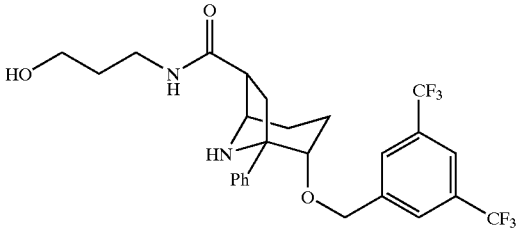 | 531 |
| 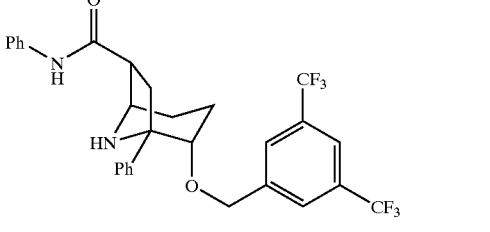 | 549 |
| 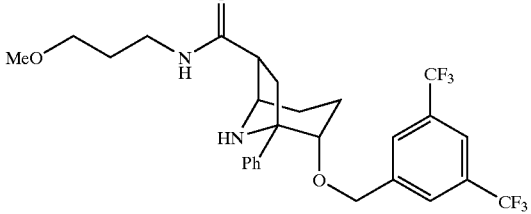 | 545 |
| 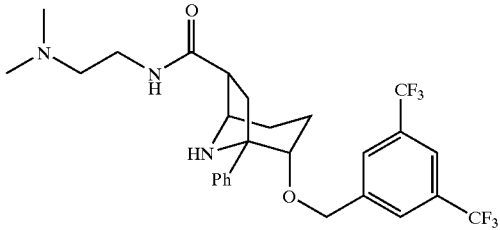 | 544 |

TABLE 1-continued
| Structure (racemic mixture) | m/z (ES+) (M + H)+ |
|---|---|
| 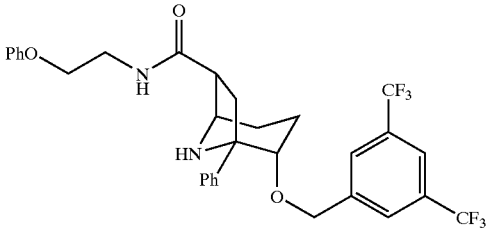 | 593 |
| 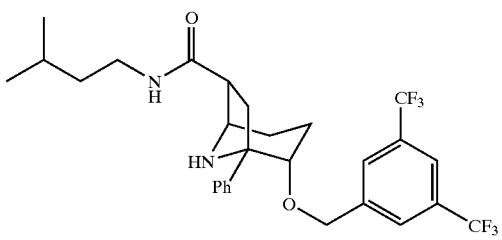 | 543 |
| 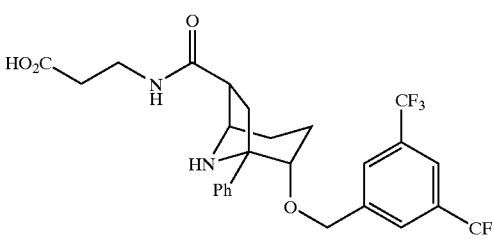 | 545 |
| 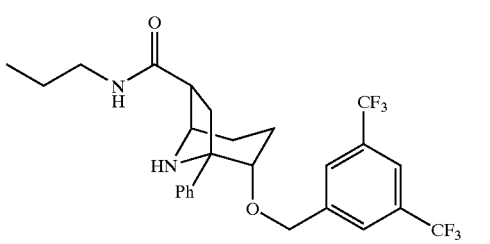 | 515 |
| 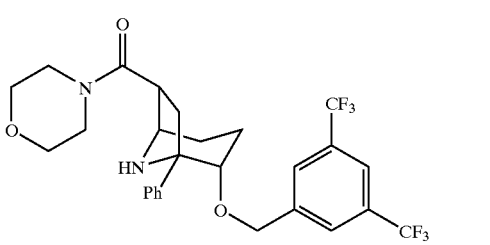 | 543 |
| 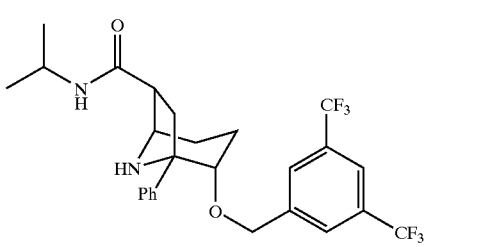 | 515 |

TABLE 1-continued
| Structure (racemic mixture) | m/z (ES+) (M + H)+ |
|---|---|
| 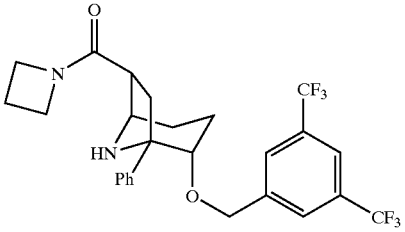 | 513 |
| 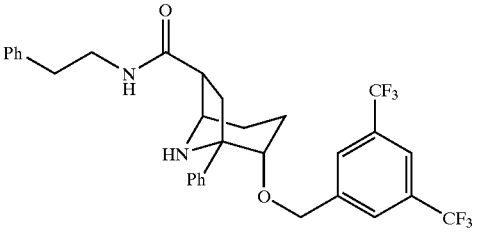 | 577 |
| 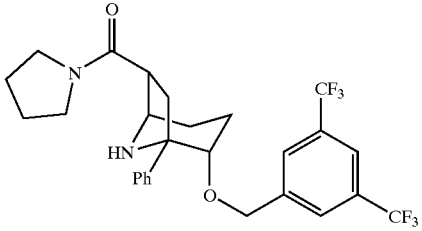 | 527 |
| 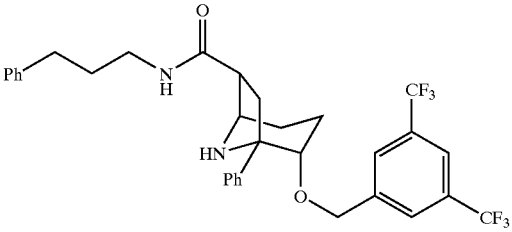 | 591 |
| 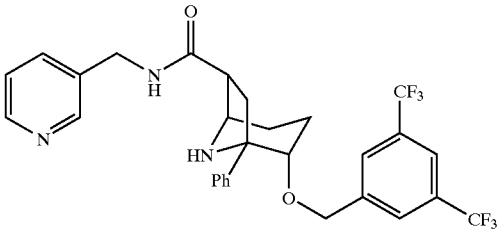 | 564 |
| 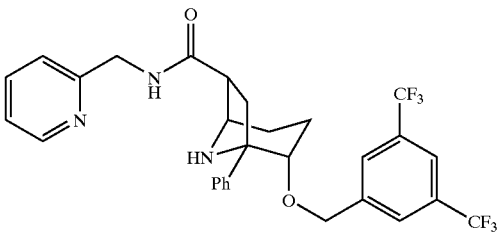 | 564 |

TABLE 1-continued
| Structure (racemic mixture) | m/z (ES+) (M + H)+ |
|---|---|
| 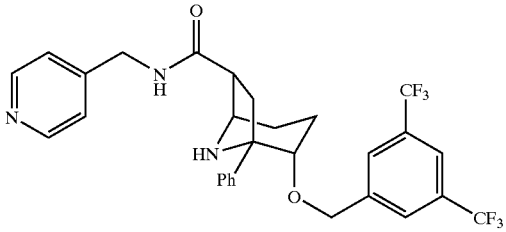 | 564 |
| 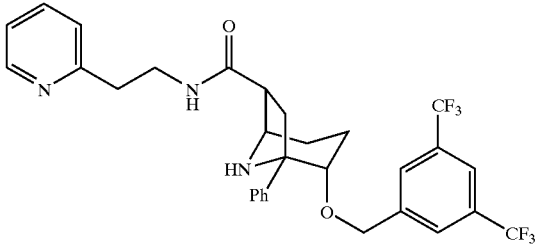 | 578 |
| 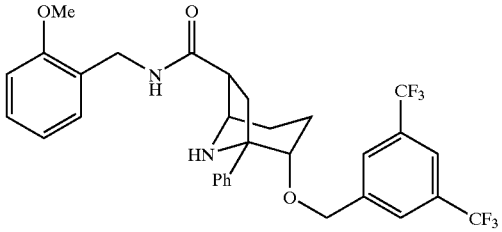 | 593 |
| 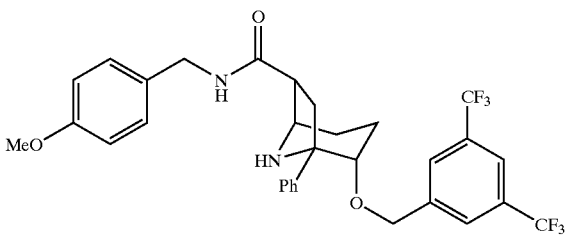 | 593 |
| 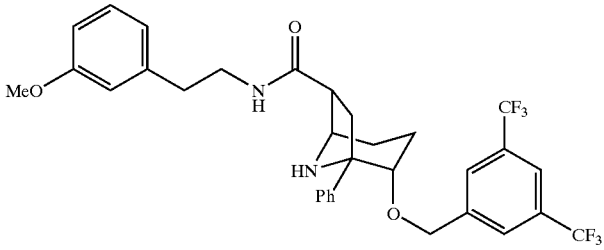 | 607 |
| 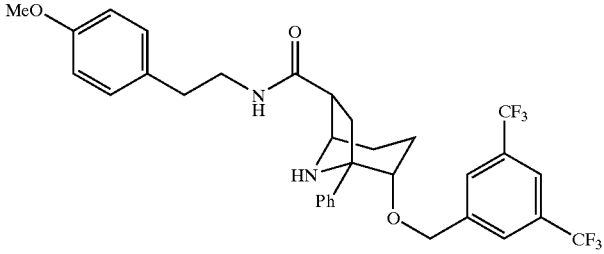 | 607 |

TABLE 1-continued

| Structure (racemic mixture) | m/z (ES+) (M + H)+ |
|---|---|
| [Structure: N-(2,3-dimethoxybenzyl) amide of 2-{[3,5-bis(trifluoromethyl)phenyl]methoxy}-1-phenyl-8-azabicyclo[3.2.1]octan-6-carboxylic acid] | 623 |
| [Structure: N-(2,4-dimethoxybenzyl) amide analogue] | 623 |
| [Structure: N-(3,4-dimethoxybenzyl) amide analogue] | 623 |
| [Structure: N-(2,4,6-trimethoxybenzyl) amide analogue] | 653 |
| [Structure: N-(3,5-dimethoxybenzyl) amide analogue] | 623 |

EXAMPLE 122

(1R*,2R*,5S*,6R*)-2-{[3,5-Bis(trifluoromethyl)phenyl]methoxy}-1-phenyl-8-azabicyclo[3.2.1]octan-6-carboxylic acid trifluoroacetate A mixture of (1R*,2R*,5S*,6R*)-8-benzyl-2-{[3,5-bis(trifluoromethyl)phenyl]methoxy}-1-phenyl-8-azabicyclo[3.2.1]octan-6-carboxylic acid trifluoroacetate (Example 53; 2.7 g, 4 mmol), 10% palladium on charcoal (500 mg) and ethanol (30 ml) was stirred under hydrogen atmosphere (1 atm) at +40° C. for 20 minutes. The reaction mixture was cooled to room temperature, flushed with nitrogen gas and filtered through a pad of Celite™. The filtrate was concentrated to give the title compound (2.6 g) as a white solid.

$\delta_H$(360 MHz, DMSO-$d_6$): 9.75 (1H, br d, J 8.8 Hz), 9.27 (1H, br d, J 8.4 Hz), 7.94 (1H, s), 7.66 (2H, s), 7.42–7.29 (5H, m), 4.73 (1H, d, J 13.0 Hz), 4.33 (1H, s), 4.20 (1H, d, J 13.0 Hz), 3.83 (1H, s), 3.40 (1H, dd, J 5.6 Hz, 10.2 Hz), 3.01 (1H, dd, J 10.5 Hz, 14.0 Hz), 2.37 (1H, dd, J 6.1 Hz, 14.4 Hz), 2.12–1.91 (3H, m), 1.79 (1H, m).

EXAMPLE 123

(1R*,2R*,5S*,6R*)-6-[(4-Benzylpiperazin-1-yl)carbonyl]-2-{[3,5-bis(trifluoromethyl)phenyl]methoxy}-1-phenyl-8-azabicyclo[3.2.1]octane A mixture of (1R*,2R*,5S*,6R*)-2-[3,5-bis(trifluoromethyl)phenyl]methoxy)-1-phenyl-8-azabicyclo[3.2.1]octan-6-carboxylic acid trifluoroacetate (Example 122; 100 mg, 0.19 mmol), N-benzylpiperazine (0.1 ml), triethylamine (0.1 ml, 0.7 mmol), 1-(3-dimethylaminopropyl)-3-ethylcarbodiimide hydrochloride (44 mg, 0.23 mmol) and 4-N,N-dimethylaminopyridine (12 mg, 0.1 mmol) was prepared. The mixture was stirred at room temperature for 20 hours and purified by chromatography on silica gel (dichloromethane:methanol) to give the title compound (102 mg, 85%).

$\delta_H$(400 MHz, CDCl$_3$): 7.65 (2H, s), 7.37–7.18 (6H, m), 4.43 (1H, d, J 12.1 Hz), 4.02 (1H, d, J 12.5 Hz), 3.80 (1H, br s), 3.59 (1H, br t), 3.55–3.38 (4H, m), 3.09 (1H, dd, J 4.7 Hz, 9.0 Hz), 2.51–2.35 (7H, m), 2.15 (1H, dd, J 4.3 Hz, 12.9 Hz), 2.06–1.93 (2H, m), 1.85 (1H, m), 1.50 (1H, m).

Compounds listed in the Table 2 were prepared using the above protocol.

TABLE 2

| Structure (racemic mixture) | m/z (ES$^+$) (M + H)$^+$ |
|---|---|
| [2-chlorobenzyl amide structure] | 597, 599 |
| [3-chlorobenzyl amide structure] | 597, 599 |
| [4-chlorobenzyl amide structure] | 597, 599 |
| [2,4-dichlorobenzyl amide structure] | 631, 633, 635 |
| [2,5-dimethoxybenzyl amide structure] | 623 |

TABLE 2-continued

| Structure (racemic mixture) | m/z (ES⁺) (M + H)⁺ |
|---|---|
| | 623 |
| | 553 |
| | 569 |
| | 567 |
| | 554 |
| | 569* |

TABLE 2-continued
| Structure (racemic mixture) | m/z (ES+) (M + H)+ |
|---|---|
| 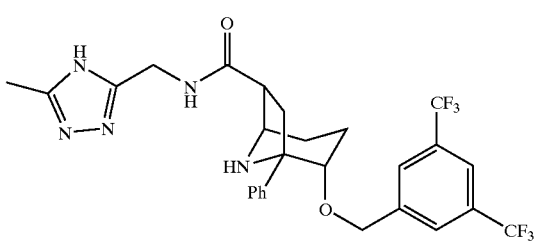 | 569* |
| 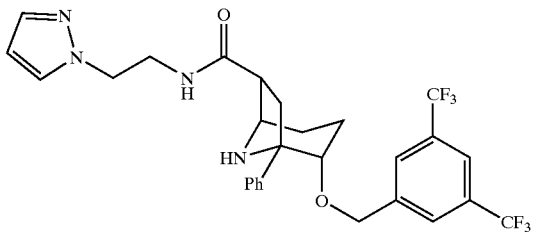 | 567 |
| 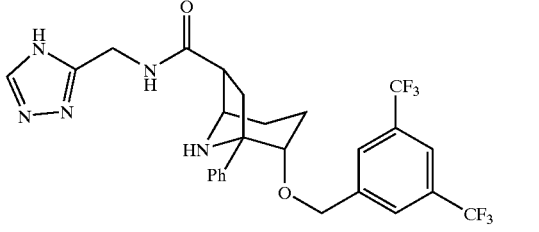 | 554 |
| 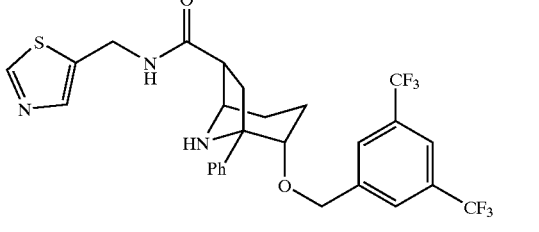 | 570 |
| 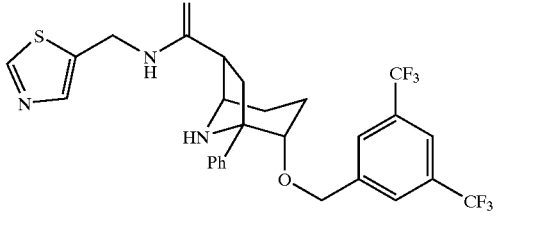 | 553 |
| 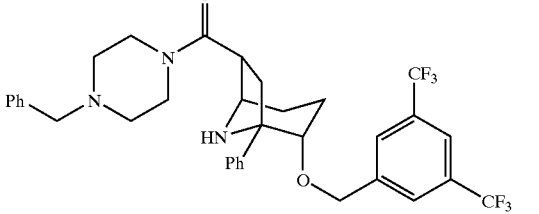 | 632 |

TABLE 2-continued
| Structure (racemic mixture) | m/z (ES+) (M + H)+ |
|---|---|
| 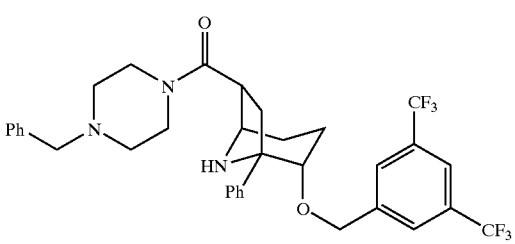 | 542 |
| 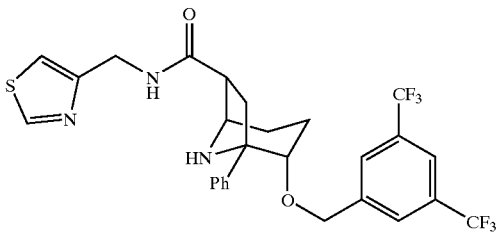 | 570 |
| 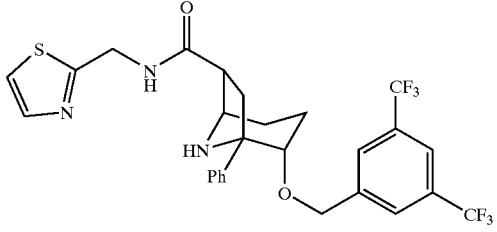 | 570 |
| 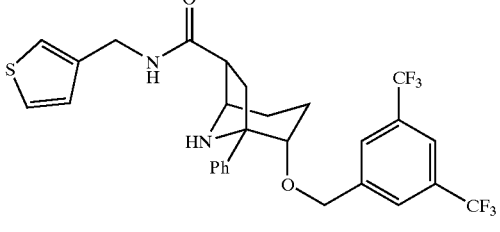 | 569 |
| 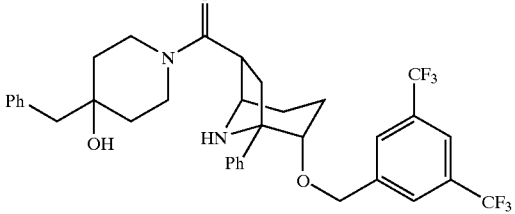 | 647 |
| 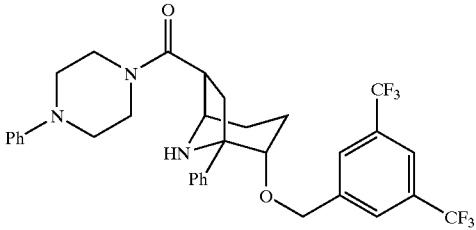 | 618 |

TABLE 2-continued
| Structure (racemic mixture) | m/z (ES+) (M + H)+ |
|---|---|
| 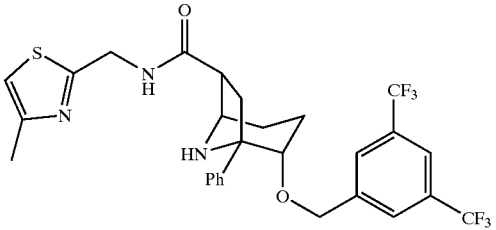 | 584 |
| 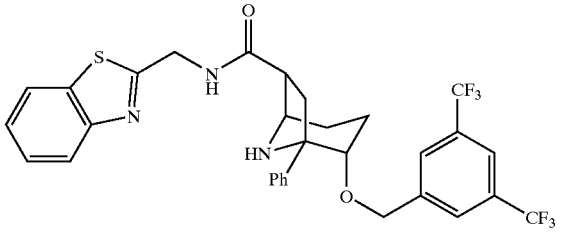 | 620 |
| 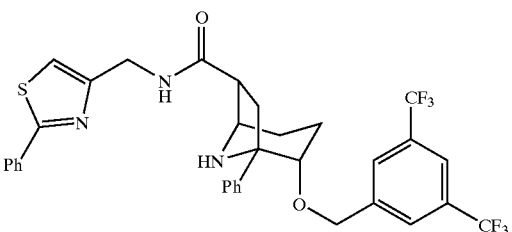 | 646 |
| 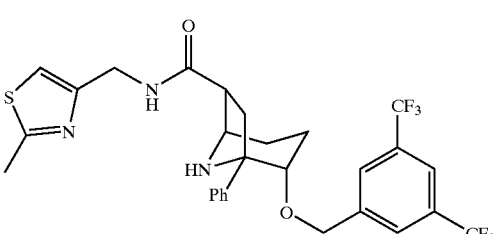 | 584 |
| 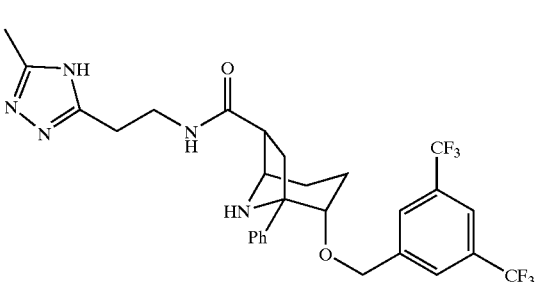 | 582 |
| 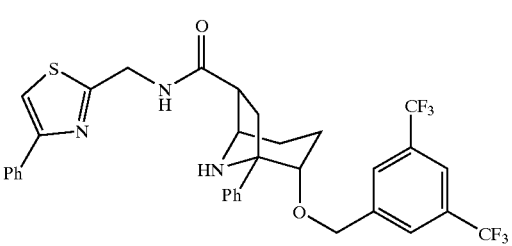 | 646 |

| Structure (racemic mixture) | m/z (ES+) (M + H)+ |
|---|---|
| 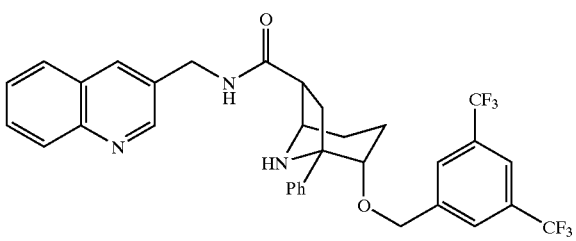 | 614 |

EXAMPLE 124

(1R*,2R*,5S*,6R*)-8-Benzyl-2-{(1S)-1-[3,5-bis (trifluoromethyl)phenyl]-(methoxycarbonyl) methoxy}-6-(tert-butoxycarbonyl)-1-phenyl-8-azabicyclo[3.2.1]octane; and (1R*,2R*,5S*,6R*)-8-benzyl-2-{(1R*)-1-[3,5-bis (trifluoromethyl)phenyl]-(methoxycarbonyl) methoxy}-6-(tert-butoxycarbonyl)-1-phenyl-8-azabicyclo[3.2.1]octane To a solution of (1R*,2R*,5S*,6R*)-8-Benzyl-6-(tert-butoxycarbonyl)-1-phenyl-8-azabicyclo[3.2.1]octan-2-ol (Description 21a; 0.57 g, 1.5 mmol) and catalytic rhodium acetate (9 mg, 0.02 mmol) in benzene (10 ml) at reflux under nitrogen, was added methyl 2-diazo-2-(3,5-bis (trifluoromethyl)phenyl)acetate [prepared by the method of R. T. Lewis et al. *J. Org. Chem.*, 2000, 65, 2615] slowly in benzene (5 ml). After evaporation and chromatography of the residue (eluent 10% ethyl acetate/hexane), the title compounds were isolated as a solid (836 mg, 85%).

$\delta_H$(400 MHz, CDCl$_3$): 1.43 (9H, s), 2.02 (3H, m), 2.23–2.53 (2H, m), 2.60 (1H, m) 3.63 and 3.77,(3H, s, diastereomers a and b), 3.70 (1H, br s), 3.78 (1H, d, J 15.9 Hz), 4.10 (1H, br s), 4.30 (1H, d, J 15.9 Hz), 4.86 and 5.18 (1H, s diastereomers b and a), 7.11–7.36 (10H, m), 7.70 and 7.82 (2H, s, diastereomers b and a), 7.78 and 7.95 (2H, s, diastereomers b and a).

EXAMPLE 125

(1R*,2R*,5S*,6R*)-8-Benzyl-2-{(1S*)-1-[3,5-bis (trifluoromethyl)phenyl]-(methoxycarbonyl) methoxy}-6-(tert-butoxycarbonyl)-1-phenyl-8-azabicyclo[3.2.1]octan-6-carboxylic acid trifluoroacetate; and (1R*,2R*,5S* 6R*)-8-benzyl-2-(1R*)-1-[3,5-bis (trifluoromethyl)phenyl]-(methoxycarbonyl) methoxy}-6-(tert-butoxycarbonyl)-1-phenyl-8-azabicyclo[3.2.1]octan-6-carboxylic acid trifluoroacetate (1R*,2R*,5S*,6R*)-8-Benzyl-2-{(1S*)-1-[3,5-bis (trifluoromethyl)phenyl]-(methoxycarbonyl)methoxy}-6-(tert-butoxycarbonyl)-1-phenyl-8-azabicyclo[3.2.1]octane and (1R*,2R*,5S*,6R*)-8-benzyl-2-{(1R*)-1-[3,5-bis (trifluoromethyl)phenyl]-(methoxycarbonyl)methoxy}-6-(tert-butoxycarbonyl)-1-phenyl-8-azabicyclo[3.2.1]octane (Example 124; 437 mg, 0.65 mmol) and trifluoroacetic acid (3 ml) in dichloromethane (10 ml), were stirred at room temperature for 18 hours. The mixture was concentrated in vacuo and the title compounds crystallised from ethyl acetate/hexane in quantitative yield.

m/z (ES+) 622 ([M+H]+).

EXAMPLE 126

(1R*,2R*,5S*,6R*)-2-{(1R*)-1-[3,5-bis (trifluoromethyl)phenyl]-2-hydroxyethoxy}-6-(1-morpholinocarbonyl)-1-phenyl-8-azabicyclo[3.2.1] octane hydrochloride (1R*,2R*,5S*,6R*)-8-Benzyl-2-{(1S*)-1-[3,5-bis (trifluoromethyl)phenyl]-(methoxycarbonyl)methoxy}-6-(tert-butoxycarbonyl)-1-phenyl-8-azabicyclo[3.2.1]octan-6-carboxylic acid trifluoroacetate and (1R*,2R*,5S*,6R*)-8-benzyl-2-{(1R*)-1-[3,5-bis(trifluoromethyl)phenyl]-(methoxycarbonyl)methoxy}-6-(tert-butoxycarbonyl)-1-phenyl-8-azabicyclo[3.2.1]octan-6-carboxylic acid trifluoroacetate (Example 125354 mg, 0.52 mmol), triethylamine (0.15 ml, 1.05 mmol), 4-dimethylaminopyridine (64 mg, 0.52 mmol), morpholine (0.1 ml, 1.05 mmol) and 1-(3-dimethylaminopropyl)-3-ethyl-carbodiimide hydrochloride were stirred at room temperature for 72 hours. The mixture was diluted with dichloromethane and washed with saturated sodium hydrogen carbonate and 10% citric acid. The organics were collected, dried (MgSO$_4$) and concentrated in vacuo to afford a white solid (279 mg). This material was treated with lithium borohydride (30 mg) in THF until the reduction was complete. The mixture was quenched with water and extracted with ethyl acetate. The organics were collected, dried (MgSO$_4$) and concentrated in vacuo. The product diastereomers were separated using preparative thin layer chromatography, eluting with 3:2 dichloromethane/diethyl ether. (1R*,2R*,5S*,6R*)-8-benzyl-2-{(1R*)-1-[-3,5-bis(trifluoromethyl)phenyl]-2-hydroxyethoxy)-6-(1-morpholinocarbonyl)-1-phenyl-8-azabicyclo[3.2.1]octane was isolated as a white solid (118 mg) and (1R*,2R*,5S*,6R*)-8-benzyl-2-1(1S*)-1-[3,5-bis (trifluoromethyl)phenyl]-2-hydroxyethoxy}-6-(1-morpholinocarbonyl)-1-phenyl-8-azabicyclo[3.2.1]octane (80 mg), total yield 96%. (1R*,2R*,5S*,6R*)-8-benzyl-2-{(1R*)-1-[3,5-bis(trifluoromethyl)phenyl]-2-hydroxyethoxy}-6-(1-morpholinocarbonyl)-1-phenyl-8-azabicyclo[3.2.1]octane was debenzylated and the hydrochloride salt prepared as described previously to afford the title compound.

m/z (ES+) 573 ([M+H]+).

EXAMPLE 127

(1R*,2R*,5S*,6R*)-8-Benzyl-2-{(1S*)-1-[3,5-bis(trifluoromethyl)phenyl]-2-hydroxyethoxy}-6-(tert-butoxycarbonyl)-1-phenyl-8-azabicyclo[3.2.1]octane; and (1R*,2R*,5S*,6R*)-8-Benzyl-2-{(1R*)-1-[3,5-bis(trifluoromethyl)phenyl]-2-hydroxyethoxy}-6-(tert-butoxycarbonyl)-1-phenyl-8-azabicyclo[3.2.1]octane (1R*,2R*,5S*,6R*)-8-Benzyl-2-{(1S*)-1-[3,5-bis(trifluoromethyl)phenyl]-(methoxycarbonyl)methoxy}-6-(tert-butoxycarbonyl)-1-phenyl-8-azabicyclo[3.2.1]octane and (1R*,2R*,5S*,6R*)-8-benzyl-2-{(1R*)-1-[3,5-bis(trifluoromethyl)phenyl]-(methoxycarbonyl)methoxy}-6-(tert-butoxycarbonyl)-1-phenyl-8-azabicyclo[3.2.1]octane (Example 125; 0.99 g, 1.5 mmol) in methanol (15 ml) at 0° C. was treated with sodium borohydride (55 mg, 1.4 mmol) and stirred at room temperature. The reaction was quenched with acetone and concentrated in vacuo. The residue was partitioned between ethyl acetate and water, the organics were separated, dried (MgSO$_4$), filtered and concentrated in vacuo to afford the title compounds as a clear foam (869 mg, 92%).

m/z(ES$^+$) 650 ([M+H]$^+$).

EXAMPLES 128a and 128b (1R*,2R*,5S*,6R*)-8-Benzyl-2-{(1S*)-1-[3,5-bis(trifluoromethyl)phenyl]ethoxy}-6-(tert-butoxycarbonyl)-1-phenyl-8-azabicyclo[3.2.1]octane; and (1R*,2R*,5S*,6R*)-8-Benzyl-2-{(1R*)-1-[3,5-bis(trifluoromethyl)phenyl]ethoxy}-6-(tert-butoxycarbonyl)-1-phenyl-8-azabicyclo[3.2.1]octane (1R*,2R*,5S*,6R*)-8-Benzyl-2-{(1S*)-1-[3,5-bis(trifluoromethyl)phenyl]-2-iodoethoxy}-6-(tert-butoxycarbonyl)-1-phenyl-8-azabicyclo[3.2.1]octane and (1R*,2R*,5S*,6R*)-8-benzyl-2-{(1R*)-11-[3,5-bis(trifluoromethyl)phenyl]-2-iodoethoxy}-6-(tert-butoxycarbonyl)-1-phenyl-8-azabicyclo[3.2.1]octane (Description 28; 306 mg, 0.40 mmol), triethylamine (61 mg, 0.6 mmol), palladium 10% on charcoal (100 mg), ethyl acetate (6 ml) and methanol (1 ml) were reacted with hydrogen using the Parr™ apparatus for 3 hours. The mixture was filtered and the catalyst washed with acetic acid. The filtrate was concentrated in vacuo, the residue was dissolved in dichloromethane and washed with saturated sodium hydrogen carbonate, 10% citric acid solution and 5% sodium thiosulphate solution. The organics were collected, dried (MgSO$_4$) and concentrated in vacuo. The title compounds were isolated as a white crystalline solid (230 mg, 90%).

EXAMPLES 128a AND 128b

δ$_H$(400 MHz, CDCl3): 1.33 and 1.48 (3H, d, J 6.5 Hz, diastereomers a and b), 1.42 (9H, s), 1.92 (2H, m), 2.30 (2H, m), 2.69 (1H, m), 3.65 (1H, d, J 16.3 Hz), 3.90 (2H, m), 4.18 (1H, m), 4.55 and 4.63 (1H, q, diastereomers a and b), 7.10–7.46 (10H, m), 7.59 and 7.85 (2H, s, diastereomers b and a), 7.70 and 7.77 (1H, s, diastereomers a and b); m/z (ES$^+$) 635 ([M+H]$^+$).

EXAMPLE 128a

δ$_H$(400 MHz, CDCl$_3$): 7.77 (1H, s), 7.59 (2H, s), 7.45 (2H, m), 7.33–7.10 (8H, m), 4.63 (1H, m), 4.18 (1H, d, J 16.2 Hz), 3.92 (1H, d, J 16.1 Hz), 3.88 (1H, br s), 3.69, (1H, br s), 2.68 (1H, m), 2.35–2.10 (2H, m), 1.91 (2H, m), 1.50 (3H, d), 1.25 (2H, m); m/z (ES$^+$) 634 ([M+H]$^+$).

EXAMPLE 129

(1R*,2R*,5S*,6R*)-8-Benzyl-2-{(1S*)-1-[3,5-bis(trifluoromethyl)phenyl]ethoxy}-6-(1-morpholinocarbonyl)-1-phenyl-8-azabicyclo[3.2.1]octane hydrochloride Prepared from a mixture of (1R*,2R*,5S*,6R*)-8-benzyl-2-{(1S*)-1-[3,5-bis(trifluoromethyl)phenyl]ethoxy}-6-(tert-butoxycarbonyl)-1-phenyl-8-azabicyclo[3.2.1]octane and (1R*,2R*,5S*,6R*)-8-benzyl-2-{(1R*)-1-[3,5-bis(trifluoromethyl)phenyl]ethoxy}-6-(tert-butoxycarbonyl)-1-phenyl-8-azabicyclo[3.2.1]octane (Example 128) in an analogous manner to that described for Example 126.

m/z (ES$^+$) 557 ([M+H]$^+$).

EXAMPLE 130

(1R*,2R*,5S*,6R*)-8-Benzyl-2-{(1S*)-1-[3,5-bis(trifluoromethyl)phenyl]ethoxy}-1-phenyl-8-azabicyclo[3.2.1]octan-6-carboxylic acid (1R*,2R*,5S*,6R*)-8-Benzyl-2-{(1S*)-1-[3,5-bis(trifluoromethyl)phenyl]ethoxy}-6-(tert-butoxycarbonyl)-1-phenyl-8-azabicyclo[3.2.1]octane (Example 128a; 3.28 g, 5.18 mmol) was dissolved in dichloromethane (30 ml) and trifluoroacetic acid added (8 ml) and the reaction mixture stirred overnight at room temperature. The reaction mixture was concentrated in vacuo then triturated with diethyl ether (×3) to give the title compound as a brown solid (4.82 g).

m/z (ES$^+$) 578 ([M+H]$^+$).

EXAMPLE 131

(1R*,2R*,5S*,6R*)-8-Benzyl-2-{(1S*)-1-[3,5-bis(trifluoromethyl)phenyl]ethoxy}-1-phenyl-8-azabicyclo[3.2.1]octan-6-carboxamide (1R*,2R*,5S*,6R*)-8-Benzyl-2-{(1S*)-1-[3,5-bis(trifluoromethyl)phenyl]ethoxy}-1-phenyl-8-azabicyclo[3.2.1]octan-6-carboxylic acid (Example 130; 4.82 g, 6.99 mmol), triethylamine (2.93 ml, 20.97 mmol), 1-(3-dimethylaminopropyl)-3-ethyl-carbodiimide hydrochloride (2.68 g, 13.98 mmol), 4-dimethylaminopyridine (10 mg), and ammonia in dioxane (41.94 ml, 20.97 mmol, 0.5M solution) were combined in dichloromethane (40 ml) and stirred in a sealed flask for 2 hours at room temperature. The reaction mixture was then diluted with water and the organics removed and the aqueous further extracted with dichloromethane (×2). All organics were combined, dried (MgSO$_4$) and concentrated in vacuo to give a brown oil which was purified by flash column chromatography [3% methanol in dichloromethane] to give the title compound as a cream-coloured solid (1.76 g, 60%).

m/z (ES$^+$) 577 ([M+H]$^+$).

EXAMPLE 132

(1R*,2R*,5S*,6R*)-6-Amino-8-benzyl-2-{(1S*)-1-[3,5-bis(trifluoromethyl)phenyl]ethoxy}-1-phenyl-8-azabicyclo[3.2.1]octane To a solution of potassium hydroxide (5.36 g) in water (93 ml) was added bromine (1 g) and 60 ml of this solution was added (1R*,2R*,5S*,6R*)-8-Benzyl-2-{(1S*)-1-[3,5-bis (trifluoromethyl)phenyl]ethoxy}-1-phenyl-8-azabicyclo [3.2.1]octan-6-carboxamide (Example 131; 1.76 g, 3.06 mmol) in t-butanol and the mixture stirred at room temperature for 30 minutes then at 70° C. for 2 hours. The reaction mixture was cooled and concentrated in vacuo. The aqueous was extracted with dichloromethane (×2), dried (MgSO$_4$) and concentrated in vacuo to give a cream-coloured foam. This was purified by flash column chromatography [3%–10%–15% methanol in dichloromethane] to give the title compound as a yellow solid (660 mg, 40%).

m/z (ES$^+$) 549 [M+H]$^+$).

EXAMPLE 133

(1R*,2R*,5S*,6R*)-8-Benzyl-2-{(1S*)-1-[3,5-bis (trifluoromethyl)phenyl]ethoxy}-1-phenyl-6-(1,2,4-triazol-4-yl)-8-azabicyclo[3.2.1]octane (1R*,2R*,5S*,6R*)-6-Amino-8-benzyl-2-{(1S*)-1-[3,5-bis(trifluoromethyl)phenyl]ethoxy}-1-phenyl-8-azabicyclo [3.2.1]octane (Example 132; 220 mg, 0.40 mmol), N,N'-dimethylformamide azine (84 mg, 0.59 mmol) and p-toluenesulphonic acid (38 mg, 0.20 mmol) were combined in toluene and heated at reflux for 4 hours under N$_2$. The reaction mixture was cooled and concentrated in vacuo to give a yellow oil which was purified by flash column chromatography [5% methanol in dichloromethane] to give the title compound as a yellow foam (185 mg, 77%).

m/z (ES$^+$) 601 ([M+H]$^+$).

EXAMPLE 134

(1R*,2R*,5S*,6R*)-2-{(1S*)-1-[3,5-Bis (trifluoromethyl)phenyl]ethoxy}-1-phenyl-6-(1,2,4-triazol-4-yl)-8-azabicyclo[3.2.1]octane hydrochloride (1R*,2R*,5S*,6R*)-8-Benzyl-2-{(1S*)-1-[3,5-bis (trifluoromethyl)phenyl]ethoxy}-1-phenyl-6-(1,2,4-triazol-4-yl)-8-azabicyclo[3.2.1]octane (Example 133; 185 mg, 0.31 mmol) was dissolved in methanol (5 ml) and 2N hydrochloric acid (0.5 ml) and 10% palladium hydroxide (50 mg) added. The mixture was hydrogenated at 45 psi for 1.5 hours. The reaction mixture was filtered then concentrated in vacuo. The residue was partitioned between saturated sodium hydrogen carbonate solution and dichloromethane and the organics removed, dried (MgSO$_4$) and concentrated in vacuo. The oil was purified by flash column chromatography [5% methanol in dichloromethane] and the hydrochloride salt was made by adding 1 equivalent of hydrogen chloride in diethyl ether (1.0M) to a solution in diethyl ether and the title compound filtered and dried in vacuo at 60° C. (27 mg, 16%).

m/z (ES$^+$) 511 ([M+H]$^+$).

EXAMPLE 135

(1R*,2R*,5S*,6R*)-8-Benzyl-2-{(1S*)-1-[3,5-bis (trifluoromethyl)phenyl]ethoxy}-1-phenyl-6-(1H-tetrazol-1-yl)-8-azabicyclo[3.2.1]octane (1R*,2R*,5S*,6R*)-6-Amino-8-benzyl-2-{(1S*)-1-[3,5-bis(trifluoromethyl)phenyl]ethoxy}-1-phenyl-8-azabicyclo [3.2.1]octane (Example 132; 150 mg, 0.27 mmol) in glacial acetic acid (2 ml) with triethylorthoformate (3 ml) was heated to 90° C. Sodium azide (178 mg, 2.74 mmol) was then added and the mixture stirred at 90° C. overnight. The reaction mixture was cooled and partitioned between saturated sodium hydrogen carbonate solution and dichloromethane and the organics dried (MgSO$_4$) and concentrated in vacuo to give the title compound as a yellow oil (158 mg, 95%).

m/z (ES$^+$) 602 ([M+H]$^+$).

EXAMPLE 136

(1R*,2R*,5S*,6R*)-2-{(1S*)-1-[3,5-Bis (trifluoromethyl)phenyl]ethoxy}-1-phenyl-6-(1H-tetrazol-1-yl)-8-azabicyclo[3.2.1]octane hydrochloride (1R*,2R*,5S*,6R*)-8-Benzyl-2-{(1S*)-1-[3,5-bis (trifluoromethyl)phenyl]ethoxy}-1-phenyl-6-(1H-tetrazol-1-yl)-8-azabicyclo[3.2.1]octane (Example 135; 158 mg, 0.26 mmol) was dissolved in methanol (5 ml) and 2N hydrochloric acid (0.5 ml) and 10% palladium hydroxide (40 mg) added and the mixture hydrogenated at 50 psi for 30 minutes. The reaction mixture was then filtered and concentrated in vacuo. The oil was partitioned between saturated sodium hydrogen carbonate solution and dichloromethane and the organics dried (MgSO$_4$) and concentrated in vacuo to give a yellow oil. This was purified by thin layer chromatography [5% methanol in dichloromethane] to give a white solid. The hydrochloride salt was made by adding 1 equivalent of hydrogen chloride in diethyl ether to a solution in diethyl ether and the title compound filtered and dried in vacuo at 60° C. (41 mg, 28%).

m/z (ES$^+$) 512 ([M+H]$^+$).

EXAMPLE 137

(1R*,2R*,5S*,6R*)-8-Benzyl-2-{[3,5-bis (trifluoromethyl)phenyl]methoxy}-6-cyano-1-phenyl-8-azabicyclo[3.2.1]octane Sodium hydride (0.3 g, 7.5 mmol, 60% in oil) was added portionwise to a solution of 3,5-bis(trifluoromethyl)benzyl bromide (2.5 g, 8.3 mmol) and (1R*,2R*,5S*,6R*)-8-benzyl-6-cyano-1-phenyl-8-azabicyclo[3.2.1]octan-2-ol (Description 31; 1.4 g, 4.4 mmol) in THF (20 ml). The mixture was stirred at 50° C. for 18 hours then cooled with an ice-bath and quenched by dropwise addition of water. The mixture was partitioned between brine and ethyl acetate. The organic layer was separated, dried (MgSO$_4$), filtered and concentrated. Chromatography on silica gel eluting with 2.5, 5, 10 and 20% ethyl acetate/iso-hexanes afforded the title compound (2.12 g, 88%).

δ$_H$(360 MHz, CDCl$_3$): 7.76 (1H, s), 7.70 (2H, s), 7.55–7.23 (10H, m), 4.81 (1H, d, J 12.7 Hz), 4.54 (1H, d, J 12.7 Hz), 4.15–4.07 (3H, m), 3.92 (1H, d, J 15.6 Hz), 3.83 (1H, s), 2.88 (1H, dd, J 4.5 Hz, 9.25 Hz), 2.42 (1H, dd, J 9.25 Hz, 13.7 Hz), 2.30 (1H, dd, J 4.5 Hz, 13.7 Hz), 2.22–2.10 (2H, m), 1.86–1.77 (1H, m).

EXAMPLE 138

(1R*,2R*,5S*,6R*)-8-Benzyl-2-{[3,5-bis (trifluoromethyl)phenyl]methoxy}-1-phenyl-6-(tetrazol-5-yl)-8-azabicyclo[3.2.1]octane (1R*,2R*,5S*,6R*)-8-Benzyl-2-{[3,5-bis (trifluoromethyl)phenyl]methoxy}-6-cyano-1-phenyl-8-azabicyclo[3.2.1]octane (Example 137; 4 g, 7.4 mmol), sodium azide (1.4 g, 22 mmol) and ammonium chloride (1.2 g, 22 mmol) were stirred at 120° C. in N,N-dimethylformamide (15 ml) for 20 hours. On cooling to room temperature the mixture was poured into water (250 ml) and extracted (×2) with ethyl acetate. The combined organic extracts were washed (×3) with water then dried (MgSO$_4$), filtered and concentrated. Residue was chromatographed on silica gel eluting with 1, 2 and 4% methanol/dichloromethane to give the title compound (2.7 g, 63%).

$\delta_H$(400 MHz, CDCl$_3$): 7.76 (1H, s), 7.72 (2H, s), 7.51–7.28 (10H, m), 4.92 (1H, d, J 12.6 Hz), 4.65 (1H, d, J 12.6 Hz), 4.28 (1H, s), 4.09 (1H, d, J 13.7 Hz), 3.91 (1H, d, J 13.7 Hz), 3.70 (1H, dd, J 3.6 Hz, 9.4 Hz), 3.45 (1H, s), 2.57 (1H, dd, J 9.4 Hz, 14.1 Hz), 2.47–2.38 (1H, m), 2.27 (1H, dd, J 5.0 Hz, 15.3 Hz), 2.15–2.09 (1H, m) 1.86 (1H, dd, J 3.2 Hz, 14.1 Hz), 1.44 (1H, dd, J 5.0 Hz, 13.4 Hz).

EXAMPLES 139a AND 139b (1R*,2R*,5S*,6R*)-8-Benzyl-2-{[3,5-bis(trifluoromethyl)phenyl]methoxy}-6-(1-methyl-1H-tetrazol-5-yl)-1-phenyl-8-azabicyclo[3.2.1]octane (isomer B); and (1R*,2R*,5S*,6R*)-8-benzyl-2-{[3,5-bis(trifluoromethyl)phenyl]methoxy}-6-(2-methyl-2H-tetrazol-5-yl)-1-phenyl-8-azabicyclo[3.2.1]octane (isomer A)

(1R*,2R*,5S*,6R*)-8-Benzyl-2-{[3,5-bis(trifluoromethyl)phenyl]methoxy}-1-phenyl-6-(tetrazol-5-yl)-8-azabicyclo[3.2.1]octane (Example 138; 0.5 g, 0.85 mmol), methyl iodide (0.3 g, 2.1 mmol) and potassium carbonate (0.29 g, 2.1 mmol) were stirred at 50° C. in acetonitrile (20 ml) for 2 hours. Concentrated in vacuo then partitioned between dichloromethane and water. The organic layer was separated, dried (MgSO$_4$), filtered and concentrated. The residue was chromatographed on silica gel eluting with 20, 50 and 75% ethyl acetate/iso-hexanes to afford the title compounds: isomer A (0.25 g, 49%) and isomer B (0.17 g, 33%).

EXAMPLE 139a

Isomer B $\delta_H$(400 MHz, CDCl$_3$): 7.76 (1H, s), 7.73 (2H, s), 7.69–7.67 (2H, d, J 8.6 Hz), 7.38–7.14 (8H, m), 4.89 (1H, d, J 12.8 Hz), 4.64 (1H, d, J 12.8 Hz), 4.25 (1H, s), 4.07 (1H, d, J 14.8 Hz), 3.92 (1H, d, J 14.8 Hz), 3.88 (3H, s), 3.49 (1H, s), 3.40 (1H, dd, J 4.7 Hz, 9.3 Hz), 2.86 (1H, dd, J 4.6 Hz, 13.6 Hz), 2.46 (1H, dd, 9.3 Hz, 13.6 Hz), 2.42–2.04 (3H, m), 1.27–1.25 (1H, m).

EXAMPLE 139b

Isomer A $\delta_H$(400 MHz, CDCl$_3$): 7.74 (3H, s), 7.63 (2H, d, J 7.3 Hz), 4.88 (1H, d, J 12.9 Hz), 4.62 (1H, d, J 12.8 Hz), 4.34 (3H, s), 4.22 (1H, s), 4.12 (1H, d, J 15.7 Hz), 3.89 (1H, d, J 15.7 Hz), 3.65 (1H, s), 3.53 (1H, dd, J 4.6 Hz, 9.3 Hz), 2.59 (1H, dd, J 4.7 Hz, 13.6 Hz), 2.47 (1H, dd, J 9.3 Hz, 13.6 Hz), 2.27–2.06 (3H, m), 1.38–1.33 (1H, m).

Compounds listed in the Table 3 were prepared in an analogous manner using appropriate halide.

TABLE 3

| No | Structure (racemic mixture) | m/z (ES+) (M + H)+ | No | Structure (racemic mixture) | m/z (ES+) (M + H)+ |
|---|---|---|---|---|---|
| 3a | 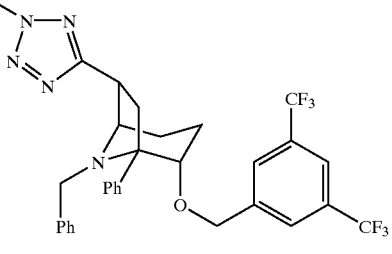 | 631 | 3b | 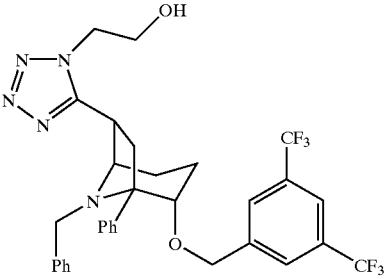 | 631 |
| 3c | 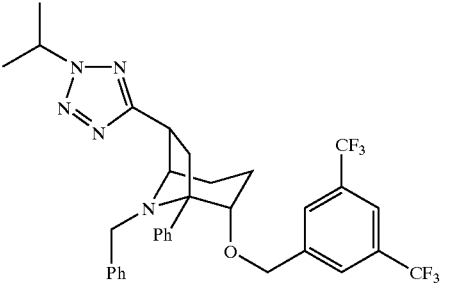 | 630 | 3d | 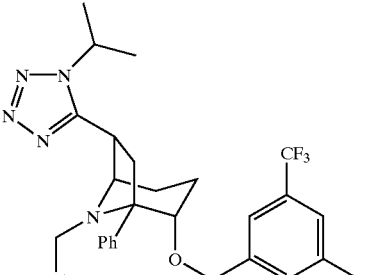 | 630 |

TABLE 3-continued

| No | Structure (racemic mixture) | m/z (ES+) (M + H)+ | No | Structure (racemic mixture) | m/z (ES+) (M + H)+ |
|---|---|---|---|---|---|
| 3e | | 632 | 3f | | 632 |
| 3g | | 648 | 3h | | 648 |
| 3i | | 644 | 3j | | 644 |
| 3k | | 634 | 3l | | 634 |
| 3m | | 652 | 3n | | 652 |

EXAMPLE 140

(1R*,2R*,5S*,6R*)-8-Benzyl-2-{[3,5-bis(trifluoromethyl)phenyl]methoxy}-6-{2-[2-(t-butoxycarbonylamino)ethyl]-2H-tetrazol-5-yl}-1-phenyl-8-azabicyclo[3.2.1]octane Diethylazodicarboxylate, 0.15 g, 0.86 mmol was added to a solution of (1R*,2 R*,5S*,6R*)-8-benzyl-2-{[3,5-bis(trifluoromethyl)phenyl]methoxyl 1-phenyl-6-(tetrazol-5-yl)-8-azabicyclo[3.2.1]octane (Example 138; 0.5 g, 0.85 mmol), [N-(t-butoxy-carbonyl)ethanolamine] (0.15 g, 0.93 mmol) and triphenylphosphine (0.23 g, 0.88 mmol) in dichloromethane (20 ml). The mixture was stirred at room temperature for 2 hours then concentrated in vacuo. The residue was chromatographed on silica gel eluting with 10, 20 and 30% ethyl acetate/iso-hexanes to yield the title compound (543 mg, 88%).

$\delta_H$(400 MHz, CDCl$_3$): 7.74 (3H, s), 7.65–7.63 (2H, m), 7.35–7.13 (8H, m), 4.89 (1H, d, J 12.9 Hz), 4.71–4.70 (2H, m), 4.63 (1H, d, J 12.9 Hz), 4.24–4.20 (1H, m), 4.13 (1H, d, J 15.6 Hz), 3.90 (1H, d, J 15.6 Hz), 3.76 (2H, m), 3.61 (1H, s), 3.54 (1H, dd, J 4.6 Hz, 9.4 Hz), 2.58 (1H, dd, J 4.5 Hz, 13.6 Hz), 2.46 (1H, dd, J 9.4 Hz, 13.6 Hz), 2.32–2.08 (3H, m), 1.44 (9H, s), 1.44–1.41 (1H, m).

EXAMPLE 141

(1R*,2R*,5S*,6R*)-6-[2-(2-Aminoethyl)-2H-tetrazol-5-yl]-8-benzyl-2-{[3,5-bis(trifluoromethyl)phenyl]methoxy}-1-phenyl-8-azabicyclo[3.2.1]octane (1R*,2R*,5S*,6R*)-8-Benzyl-2-{[3,5-bis(trifluoromethyl)phenyl]methoxy}-6-{2-[2-(t-butoxycarbonylamino)ethyl]-2H-tetrazol-5-yl}-1-phenyl-8-azabicyclo[3.2.1]octane (Example 140; 0.54 g) was stirred in 20% trifluoroacetic acid/dichloromethane for 90 minutes. The mixture was concentrated in vacuo. The residue was partitioned between saturated sodium carbonate and dichloromethane. The organic layer was separated, dried (MgSO$_4$), filtered and concentrated to yield the title compound (0.45 g, 96%).

$\delta_H$(400 MHz, CDCl$_3$): 7.74 (3H, s), 7.65–7.63 (2H, m), 7.35–7.13 (8H, m), 4.89 (1H, d, J 12.9 Hz), 4.67–4.61 (3H, m), 4.23–4.18 (1H, m), 4.14 (1H, d, J 15.7 Hz), 3.88 (1H, d, J 15.7 Hz), 3.64 (1H, s), 3.55 (1H, dd, J 4.6 Hz, 9.4 Hz), 3.35–3.32 (2H, m) 2.62 (1H, dd, J 4.6 Hz, 13.6 Hz), 2.45 (1H, dd, J 9.4 Hz, 13.6 Hz), 2.28–2.12 (3H, m), 1.39–1.35 (1H, m).

EXAMPLE 142

(1R*,2R*,5S*,6R*)-8-Benzyl-2-{[3,5-bis(trifluoromethyl)phenyl]methoxy}-6-{2-[2-(methylsulphonylamino)ethyl]-2H-tetrazol-5-yl}-1-phenyl-8-azabicyclo[3.2.1]octane Methanesulphonyl chloride (90 mg, 0.78 mmol) was added to a solution of (1R*,2R*,5S*6R*)-6-[2-(2-aminoethyl)-2H-tetrazol-5-yl]-8-benzyl-2-{[3,5-bis(trifluoromethyl)phenyl]methoxy}-1-phenyl-8-azabicyclo[3.2.1]octane (Example 141; 0.45 g, 0.71 mmol) and triethylamine (101 mg, 1 mmol) in dichloromethane (10 ml). The reaction mixture was stirred at room temperature for 3 hours then washed with water (×2). The organic layer was separated, dried (MgSO$_4$), filtered and concentrated to yield the title compound (0.47 g, 94%).

$\delta_H$(360 MHz, MeOH-d$_4$): 7.87 (2H, s), 7.80 (1H, s), 7.68–7.66 (2H, m), 7.33–7.10 (8H, m), 4.99 (1H, d, J 13.1 Hz), 4.81–4.70 (2H, m), 4.68 (1H, d, J 13.1 Hz), 4.34 (1H, s), 4.12 (1H, d, J 15.5 Hz), 3.81 (1H, d, J 15.5 Hz), 3.72–3.68 (2H, m), 3.59–3.55 (2H, m), 2.87 (3H, s), 2.55–2.52 (2H, m), 2.31–2.21 (3H, m), 1.37–1.35 (1H, m).

EXAMPLE 143

(1R*,2R*,5S*,6R*)-8-Benzyl-2-{[3,5-bis(trifluoromethyl)phenyl]methoxy}-6-{2-[2-(N,N-dimethylamino)ethyl]-2H-tetrazol-5-yl}-1-phenyl-8-azabicyclo[3.2.1]octane Prepared in analogous manner to (1R*,2R*,5S*,6R*)-8-benzyl-2-{[3,5-bis(trifluoromethyl)phenyl]methoxy}-6-(2-[2-(t-butoxycarbonylamino)ethyl]-2H-tetrazol-5-yl}-1-phenyl-8-azabicyclo[3.2.1]octane (Example 140) using N,N-dimethylethanolamine.

m/z (ES$^+$) 659 [M+H]$^+$.

EXAMPLES 144a AND 144b (1R*,2R*,5S*,6R*)-8-Benzyl-2-{[3,5-bis(trifluoromethyl)phenyl]methoxy}-6-(2-methoxycarbonylmethyl-2H-tetrazol-5-yl)-1-phenyl-8-azabicyclo[3.2.1]octane (isomer A); and (1R*,2R*,5S*,6R*)-8-Benzyl-2-{[3,5-bis(trifluoromethyl)phenyl]methoxy}-6-(1-methoxycarbonylmethyl-1H-tetrazol-5-yl)-1-phenyl-8-azabicyclo[3.2.1]octane (isomer B)

(1R*,2R*,5S*,6R*)-8-Benzyl-2-{[3,5-bis(trifluoromethyl)phenyl]methoxy}-1-phenyl-6-(tetrazol-5-yl)-8-azabicyclo[3.2.1]octane (Example 138; 2 g, 3.4 mmol), methyl bromoacetate (0.5 ml, 5.1 mmol) and potassium carbonate (0.75 g, 0.51 mmol) were stirred in acetonitrile (20 ml) at 45° C. for 90 minutes. After this time the mixture was concentrated in vacuo and the residue partitioned between brine and ethyl acetate. The organic layer was dried (MgSO$_4$), filtered and concentrated. The residual clear oil was chromatographed on silica gel eluting with 10, 20 and 50% ethyl acetate/iso-hexanes to yield the title compounds: isomer A (1.2 g, 54%) and isomer B (0.9 g, 40%).

EXAMPLE 144a

Isomer A

δH(400 MHz, CDCl$_3$): 7.74 (3H, s), 7.62–7.59 (2H, m), 7.33–7.13 (8H, m), 5.46–5.36 (2H, m), 4.88 (1H, d, J 12.8 Hz), 4.62 (1H, d, J 12.8 Hz), 4.22 (1H, s), 4.13 (1H, d, J 15.7 Hz), 3.89 (1H, dd, J 4.6 Hz, 9.4 Hz), 3.83 (3H, s), 3.71 (1H, s), 3.57 (1H, dd, J 4.6 Hz, 9.4 Hz), 2.66 (1H, dd, J 4.5 Hz, 13.6 Hz), 2.47 (1H, dd, J 9.4 Hz, 13.6 Hz), 2.32–2.08 (3H, m), 1.27–1.24 (1H, m).

EXAMPLE 144b

Isomer B $\delta_H$(400 MHz, CDCl$_3$): 7.75 (1H, s), 7.69 (2H, s), 7.67–7.64 (2H, m), 7.39–7.18 (8H, m), 5.38 (1H, d, J 17.6 Hz), 4.91 (1H, d, J 17.6 Hz), 4.88 (1H, d, J 12.7 Hz), 4.61 (1H, d, J 12.7 Hz), 4.25 (1H, s), 4.11 (1H, d, J 15.1 Hz), 3.62 (3H, s), 3.48–3.45 (2H, m), 2.59 (1H, dd, J 5.1 Hz, 13.8 Hz), 2.44 (1H, dd, J 9.5 Hz, 13.8 Hz), 2.41–2.22 (3H, m), 1.27–1.24 (1H, m).

EXAMPLE 145

(1R*,2R*,5S*,6R*)-8-Benzyl-2-{[3,5-bis(trifluoromethyl)phenyl]methoxy}-6-(2-carboxymethyl-2H-tetrazol-5-yl)-1-phenyl-8-azabicyclo[3.2.1]octane Lithium hydroxide (40 mg, 0.9 mmol) was added to a solution of (1R*,2 R*,5S*,6R*)-8-benzyl-2-{[3,5-bis (trifluoromethyl)phenyl]methoxy}-6-(2-methoxycarbonylmethyl-2H-tetrazol-5-yl)-1-phenyl-8-azabicyclo[3.2.1]octane (Example 144a; 0.6 g, 0.91 mmol) in water (5 ml) and THF (5 ml). The reaction mixture was stirred at room temperature for 30 minutes then partitioned between 5% citric acid solution and ethyl acetate. The organic layer was separated, dried (MgSO$_4$), filtered and concentrated to yield the title compound (0.55 g, 94%).

δ$_H$(400 MHz, CDCl$_3$): 7.74 (1H, s), 7.64 (2H, s), 7.57–7.55 (2H, m), 7.33–7.02 (8H, m), 5.35–5.21 (2H, m), 4.80 (1H, d, J 12.9 Hz), 4.48 (1H, d, J 12.9 Hz), 4.14 (1H, d, J 15.3 Hz), 4.00 (1H, s), 3.83 (1H, s), 3.67–3.52 (2H, m), 2.81–2.78 (1H, m), 2.58–2.52 (1H, m), 2.32–2.00 (3H, m), 1.43–1.39 (1H, m).

EXAMPLE 146

(1R*,2R*,5S*,6R*)-8-Benzyl-2-{[3,5-bis(trifluoromethyl)phenyl]methoxy}-6-{2-[(N,N-dimethylcarbamoyl)methyl]-2H-tetrazol-5-yl}-1-phenyl-8-azabicyclo[3.2.1]octane Prepared in analogous manner to (1R*,2R*,5S*,6R*)-8-benzyl-2-{[3,5-bis(trifluoromethyl)phenyl]methoxy}-1-phenyl-8-azabicyclo[3.2.1]octan-6-carboxamide (Example 75) using dimethylamine (2.0M solution in THF) and (1R*,2R*,5S*,6R*)-8-benzyl-2-{[3,5-bis(trifluoromethyl)phenyl]methoxy}-6-(2-carboxymethyl-2H-tetrazol-5-yl)-1-phenyl-8-azabicyclo[3.2.1]octane (Example 145).

δ$_H$(400 MHz, CDCl$_3$): 7.74 (3H, s), 7.62–7.60 (2H, m), 7.32–7.12 (8H, m), 5.51–5.42 (2H, m), 4.87 (1H, d, J 15.8 Hz), 4.61 (1H, d, J 12.9 Hz), 4.21 (1H, s), 4.12 (1H, d, J 15.8 Hz), 3.88 (1H, d, J 15.8 Hz), 3.72 (1H, s), 3.57 (1H, dd, J 4.6 Hz, 9.4 Hz), 3.10 (3H, s), 3.03 (3H, s), 2.67 (1H, dd, J 4.6 Hz, 13.6 Hz), 2.44 (1H, dd, J 9.4 Hz, 13.6 Hz), 2.25–2.11 (3H, m), 1.38–1.36 (1H, m).

EXAMPLE 147

(1R*,2R*,5S*,6R*)-8-Benzyl-2-{[3,5-bis(trifluoromethyl)phenyl]methoxy}-6-[2-(2-hydroxypropyl)-2H-tetrazol-5-yl]-1-phenyl-8-azabicyclo[3.2.1]octane Sodium borohydride (13 mg, 0.34 mmol) was added to a solution of (1R*,2R*,5S*,6R*)-8-benzyl-2-{[3,5-bis(trifluoromethyl)phenyl]methoxy}-6-[2-(2-oxopropyl)-2H-tetrazol-5-yl]-1-phenyl-8-azabicyclo[3.2.1]octane (Compound 3i in Table 3; 0.2 g, 0.31 mmol) in methanol (10 ml) and THF (2 ml). The mixture was stirred at room temperature for 18 hours. The reaction mixture was concentrated in vacuo and the residue partitioned between saturated sodium hydrogen carbonate and ethyl acetate. The organic layer was separated, dried (MgSO$_4$), filtered and concentrated. The residue was chromatographed on silica gel eluting with 25 and 35% ethyl acetate/iso-hexanes to yield the title compound (189 mg, 95%).

δ$_H$(400 MHz, CDCl$_3$): 7.67 (3H, s), 7.57–7.54 (2H, m), 7.28–7.24 (2H, m), 7.18–7.06 (6H, m), 4.81 (1H, d, J 12.8 Hz), 4.61–4.44 (3H, m), 4.31 (1H, br s), 4.17 (1H, s), 4.06 (1H, d, J 15.6 Hz), 3.82 (1H, d, J 15.6 Hz), 3.56 (1H, s), 3.50–3.47 (1H, m), 2.56–2.51 (1H, m), 2.41–2.35 (1H, m), 2.21–2.08 (3H, m), 1.36–1.31 (1H, m), 1.29–1.25 (3H, m).

EXAMPLE 148

(1R*,2R*,5S*,6R*)-8-Benzyl-2-{[3,5-bis(trifluoromethyl)phenyl]methoxy}-6-[2-(2-hydroxy-2-methylpropyl)-2H-tetrazol-5-yl]-1-phenyl-8-azabicyclo[3.2.1]octane Methylmagnesium bromide (3.0M solution in THF, 0.7 ml, 2.1 mmol) was added dropwise to a −78° C. solution of (1R*12R*,5S*,6R*)-8-benzyl-2-{[3,5-bis(trifluoromethyl)phenyl]methoxy}-6-[2-(2-oxopropyl)-2H-tetrazol-5-yl]-1-phenyl-8-azabicyclo[3.2.1]octane (Compound 3i in Table 3; 1.1 g, 1.7 mmol) in THF (25 ml). The mixture was warmed to 0° C. for 30 minutes then quenched by addition of saturated ammonium chloride. The mixture was partitioned between ethyl acetate and brine. The organic layer was separated, dried (MgSO$_4$), filtered and concentrated in vacuo. The residue was chromatographed on silica gel eluting with 2.5, 5 and 10% ethyl acetate/iso-hexanes to yield the title compound (0.43 g, 39%).

δ$_H$(400 MHz, CDCl$_3$): 7.67 (3H, s), 7.57–7.55 (2H, m), 7.28–7.24 (2H, m), 7.18–7.06 (6H, m), 4.82 (1H, d, J 12.9 Hz), 4.56 (1H, d, J 12.9 Hz), 4.53 (2H, s), 4.17 (1H, s), 4.04 (1H, d, J 15.5 Hz), 3.57 (1H, s), 3.50 (1H, dd, J 4.6 Hz, 9.4 Hz), 2.54 (1H, dd, J 4.6 Hz, 13.6 Hz), 2.38 (1H, dd, J 9.4 Hz, 13.6 Hz), 2.32–2.05 (3H, m), 1.38–1.31(1H, m), 1.18 (6H, s).

EXAMPLE 149

(1R*,2R*,5S*,6R*)-8-Benzyl-2-{[3,5-bis(trifluoromethyl)phenyl]methoxy}-6-(2-methanesulphonylmethyl-2H-tetrazol-5-yl)-1-phenyl-8-azabicyclo[3.2.1]octane Oxone® (370 mg, 0.6 mmol) was added to a suspension of (1R*,2R*,5S*,6R*)-8-benzyl-2-{[3,5-bis(trifluoromethyl)phenyl]methoxy}-6-(2-methylthiomethyl-2H-tetrazol-5-yl)-1-phenyl-8-azabicyclo[3.2.1]octane (Compound 3 g in Table 3; 130 mg, 0.2 mmol) and wet alumina (200 mg) in chloroform (10 ml). The mixture was heated to 50° C. for 18 hours, then filtered through Celite™ and the filtrate concentrated in vacuo to yield the title compound (92 mg, 68%).

δ$_H$(400 MHz, CDCl$_3$): 7.75 (1H, s), 7.73 (2H, s), 7.62–7.59 (2H, m), 7.34–7.12 (8H, m), 5.80–5.70 (2H, m), 4.88 (1H, d, J 12.9 Hz), 4.62 (1H, d, J 12.8 Hz), 4.26 (1H, s), 4.12 (1H, d, J 15.6 Hz), 3.88 (1H, d, J 15.6 Hz), 3.70 (1H, s), 3.58 (1H, dd, J 4.5 Hz, 9.3 Hz), 3.07 (3H, s), 2.62 (1H, dd, J 4.5 Hz, 13.7 Hz), 2.44 (1H, dd, J 9.4 Hz, 13.7 Hz), 2.32–2.14 (3H, m), 1.42–1.38 (1H, m).

EXAMPLE 150

(1R*,2R*,5S*,6R*)-8-Benzyl-2-{[3,5-bis(trifluoromethyl)phenyl]methoxy}-6-[2-(2-methoxyethyl)-2H-tetrazol-5-yl]-1-phenyl-8-azabicyclo[3.2.1]octane Iodomethane, 85 mg, 0.6 mmol was added to suspension of (1R*,2R*,5S*,6R*)-8-benzyl-2-{[3,5-bis(trifluoromethyl)phenyl]methoxy}-6-[2-(2-hydroxyethyl)-2H-tetrazol-5-yl]-1-phenyl-8-azabicyclo[3.2.1]octane (Compound 3a in Table 3; 250 mg, 0.4 mmol) and sodium hydride (24 mg, 0.6 mmol, 60% in oil). The reaction mixture was stirred at 50° C. for 2 hours then quenched by addition of saturated ammonium chloride. The mixture was partitioned between ethyl acetate and brine. The organic layer was dried (MgSO$_4$), filtered and concentrated in vacuo. The residue was chromatographed on silica gel eluting with 1:2 ethyl acetate/iso-hexanes to yield the title compound (246 mg, 95%).

δ$_H$(400 MHz, CDCl$_3$): 7.75 (3H, s), 7.64–7.62 (2H, m), 7.33–7.12 (8H, m), 4.87 (1H, d, J 12.9 Hz), 4.79–4.72 (2H, m), 4.62 (1H, d, J 12.9 Hz), 4.22 (1H, s), 4.11 (1H, d, J 15.7 Hz), 3.98–3.95 (2H, m), 3.88 (1H, d, J 15.8 Hz), 3.66 (1H, s), 3.54 (1H, dd, J 4.6 Hz, 9.3 Hz), 3.37 (3H, s), 2.65 (1H, dd, J 4.5 Hz, 13.6 Hz), 2.45 (1H, dd, J 9.4 Hz, 13.6 Hz), 2.25–2.15 (3H, m), 1.38–1.32 (1H, m).

EXAMPLE 151

(1R*,2R*,5S*,6R*)-2-{[3,5-Bis(trifluoromethyl) phenyl]methoxy}-6-(1-methyl-1H-tetrazol-5-yl)-1-phenyl-8-azabicyclo[3.2.1]octane Palladium on carbon (10%) 100 mg was added to a solution of (1R*,2R*,5S*,6R*)-8-benzyl-2-{[3,5-bis(trifluoromethyl)phenyl]methoxy}-6-(1-methyl-1H-tetrazol-5-yl)-1-phenyl-8-azabicyclo[3.2.1]octane (Example 139a; 170 mg, 0.3 mmol) in methanol (10 ml). The mixture was transferred to the Parr™ apparatus and hydrogenated at 45 psi. for 2 hours. The mixture was filtered through Celite™ and the filtrate concentrated in vacuo. The residue was chromatographed on silica gel eluting with 180:8:1 dichloromethane:methanol:ammonia to yield the title compound (84 mg, 58%). The hydrochloride salt was prepared by treatment with ethereal HCl.

m/z (ES$^+$) 512 [M+H]$^+$.

EXAMPLE 152

(1R*,2R*,5S*,6R*)-2-{[3,5-Bis(trifluoromethyl) phenyl]methoxy}-6-(2-methyl-2H-tetrazol-5-yl)-1-phenyl-8-azabicyclo[3.2.1]octane hydrochloride Prepared in an analogous manner to (1R*,2R*,5S*,6R*)-2-{[3,5-bis(trifluoromethyl)phenyl]methoxy}-6-(1-methyl-1H-tetrazol-5-yl)-1-phenyl-8-azabicyclo[3.2.1]octane (Example 151) from Example 139b.

$\delta_H$(360 MHz, MeOH-d$_4$): 7.80 (1H, s), 7.58 (2H, s), 7.44–7.31 (5H, m), 4.74 (1H, d, J 12.5 Hz), 4.60 (1H, s), 4.30 (3H, s), 4.26 (1H, d, J 12.5 Hz), 4.00 (1H, dd, J 5.1 Hz, 9.8 Hz), 3.97 (1H, s), 3.42 (1H, dd, J 9.9 Hz, 14.5 Hz), 2.85 (1H, dd, J 5.1 Hz, 14.6 Hz), 2.32–2.23 (3H, m), 2.10–2.07 (1H, m).

EXAMPLES 153a AND 153b (1R*,2R*,5S*,6R*)-2-{(1S*)-1-[3,5-Bis(trifluoromethyl)phenyl]ethoxy}-6-(1-methyl-1H-tetrazol-5-yl)-1-phenyl-8-azabicyclo[3.2.1]octane (isomer A); and
(1R*,2R*,5S*,6R*)-2-{(1R*)-1-[3,5-Bis(trifluoromethyl)phenyl]ethoxy}-6-(1-methyl-1H-tetrazol-5-yl)-1-phenyl-8-azabicyclo[3.2.1]octane (isomer B)

Palladium hydroxide, 100 mg was added as a slurry in water,1 ml to a solution of (1R*,2R*,5S*,6R*)-8-benzyl-2-{1-[3,5-bis(trifluoromethyl)phenyl]ethenyloxy}-6-(1-methyl-1H-tetrazol-5-yl)-1-phenyl-8-azabicyclo[3.2.1] octane (Description 34; 360 mg, 0.58 mmol) in methanol (10 ml). The mixture was transferred to the Parr™ apparatus and hydrogenated at 45 psi for one hour. The mixture was filtered through Celite ™ and the filtrate concentrated in vacuo. The residue was chromatographed using medium pressure Lo-Bar™ chromatography eluting with 1.5% methanol/dichloromethane to yield the title compounds: Isomer A (124 mg, 40%), isomer B (71 mg, 23%). The hydrochloride salts were prepared by treatment with ethereal HCl.

EXAMPLE 153a
Isomer A—HCl Salt $\delta_H$(400 MHz, MeOH-d$_4$): 7.89 (1H, s), 7.88 (2H, s), 7.56–7.41 (5H, m), 4.60 (1H, s), 4.21 (1H, q, J 6.4 Hz), 4.16–4.13 (1H, m), 4.10 (3H, s), 3.98 (1H, s), 3.46 (1H, dd, J 10 Hz, 14.4 Hz), 2.62 (1H, dd, J 5.4 Hz, 14.4 Hz), 2.31–2.16 (2H, m), 2.00 1.96 (1H, m), 1.72–1.69 (1H, m), 0.99 (3H, d, J 6.4 Hz); m/z (ES$^+$) 526 [M+H]$^+$.

EXAMPLE 153b
Isomer B)—HCl Salt $\delta_H$(400 MHz, MeOH-d$_4$): (isomer B) 7.74 (1H, s), 7.35 (2H, s), 7.32–7.29 (3H, m), 7.19–7.16 (2H, m), 4.67 (1H, q, J 6.4 Hz), 4.59 (1H, s), 4.15 (1H, dd, J 5.4 Hz, 9.9 Hz), 4.09 (3H, s), 3.71 (1H, s), 3.35 (1H, dd, J 9.8 Hz, 14.4 Hz), 2.51 (1H, dd, 5.4 Hz, 14.4 Hz), 2.35–2.09 (4H, m), 1.44 (3H, d, J 6.4 Hz); m/z (ES$^+$) 526 [M+H]$^+$.

Compounds listed in the Table 4 were prepared in an analogous manner.

TABLE 4

| Structure (racemic mixture) | m/z (ES$^+$) (M + H)$^+$ | Structure (racemic mixture) | m/z (ES$^+$) (M + H)$^+$ |
|---|---|---|---|
| 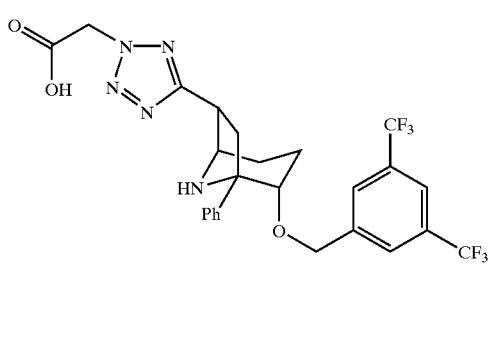 | 556 | 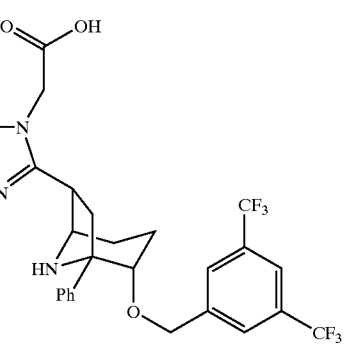 | 556 |

TABLE 4-continued

| Structure (racemic mixture) | m/z (ES+) (M + H)+ | Structure (racemic mixture) | m/z (ES+) (M + H)+ |
|---|---|---|---|
| (structure) | 541 | (structure) | 541 |
| (structure) | 589 | (structure) | 589 |
| (structure) | 542 | (structure) | 542 |
| (structure) | 540 | (structure) | 540 |

TABLE 4-continued
| Structure (racemic mixture) | m/z (ES+) (M + H)+ | Structure (racemic mixture) | m/z (ES+) (M + H)+ |
|---|---|---|---|
| 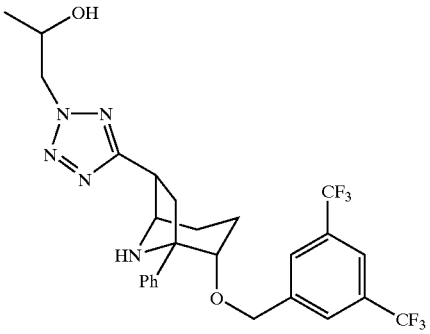 | 556 | 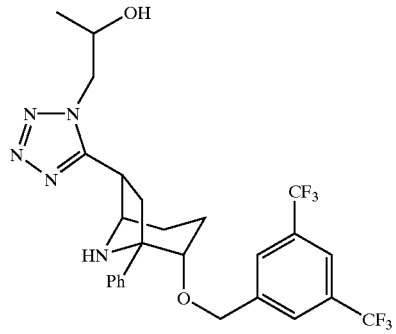 | 556 |
| 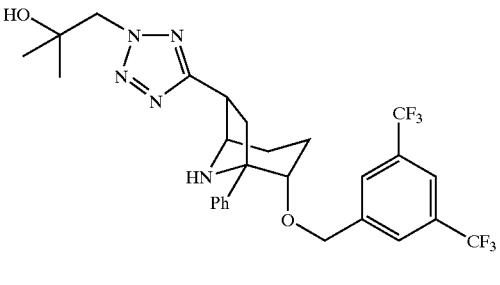 | 570 | 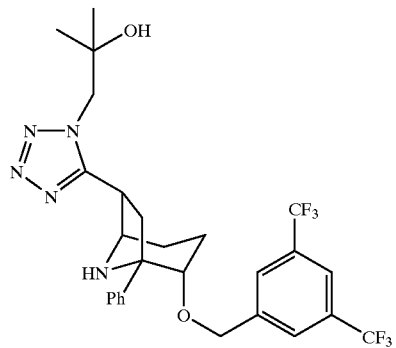 | 570 |
| 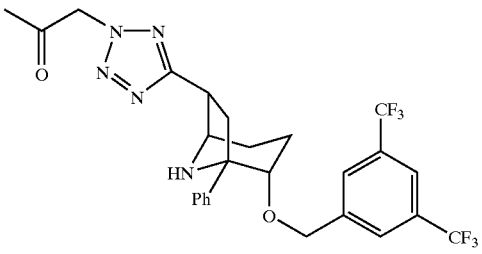 | 554 | 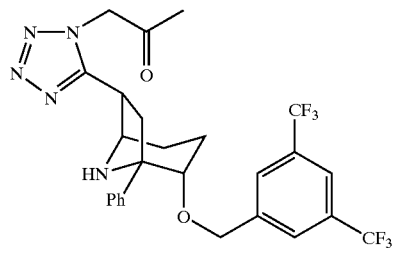 | 554 |
| 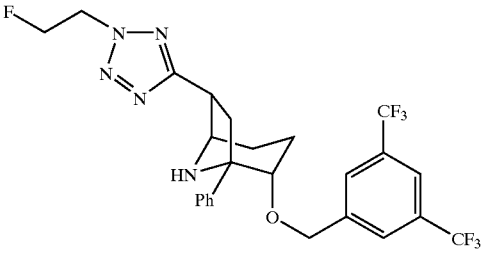 | 544 | 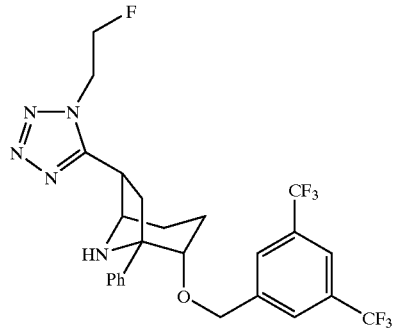 | 544 |

TABLE 4-continued

| Structure (racemic mixture) | m/z (ES⁺) (M + H)⁺ | Structure (racemic mixture) | m/z (ES⁺) (M + H)⁺ |
|---|---|---|---|
| 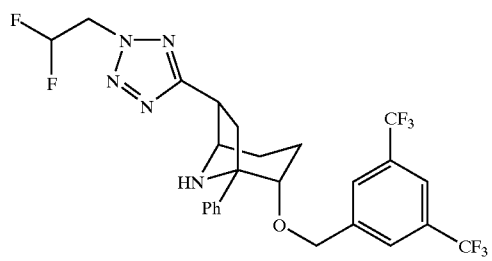 | 562 | 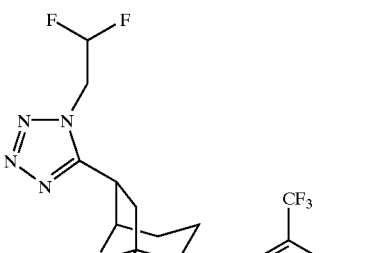 | 562 |
| 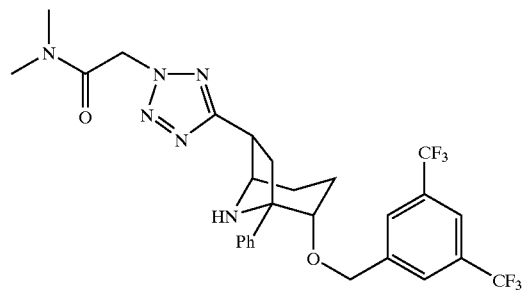 | 583 | 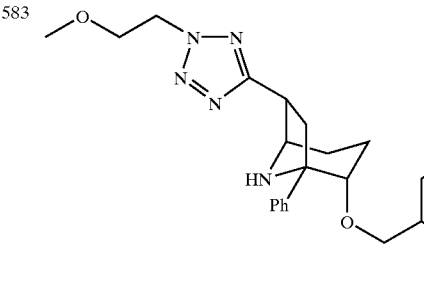 | 556 |

EXAMPLES 154a AND 154b (1R*,2R*,5S*,6R*)-2-{(1S*)-1-[3,5-Bis(trifluoromethyl)phenyl]ethoxy}-6-(2-methyl-2H-tetrazol-5-yl)-1-phenyl-8-azabicyclo[3.2.1]octane (isomer A); and (1R*,2R*,5S*,6R*)-2-{(1R*)-1-[3,5-bis(trifluoromethyl)phenyl]ethoxy}-6-(2-methyl-2H-tetrazol-5-yl)-1-phenyl-8-azabicyclo[3.2.1]octane (isomer B)

Prepared in an analogous manner to Example 153 from Description 35.

EXAMPLE 154a

Isomer A—HCl Salt $\delta_H$(400 MHz, MeOH-d$_4$): 7.89 (1H, s), 7.86 (2H, s), 7.55–7.42 (5H, m), 4.62 (1H, s), 4.30 (3H, s), 4.20 (1H, q, J 6.4 Hz), 4.02 (1H, dd, J 5.1 Hz, 9.9 Hz), 3.97 (1H, s), 3.38 (1H, dd, J 9.9 Hz, 14.6 Hz), 2.86 (1H, dd, J 5.1 Hz, 14.6 Hz), 2.27–1.91 (3H, m), 1.72–1.68 (1H, m), 0.99 (3H, d, J 6.4 Hz); m/z (ES⁺) 526 [M+H]⁺.

EXAMPLE 154b

Isomer B $\delta_H$(360 MHz, CDCl$_3$): 7.62 (1H, s), 7.15–7.13 (7H, m), 4.31 (1H, q, J 6.4 Hz), 4.21 (3H, s), 3.92 (1H, s), 3.56 (1H, dd, J 4.7 Hz, 9.1 Hz), 3.42 (1H, s), 2.62 (1H, dd, 9.4 Hz, 13.4 Hz), 2.28 (1H, dd, 4.6 Hz, 13.4 Hz), 2.06–1.97 (3H, m), 1.72–1.70 (1H, m), 1.36 (3H, d, J 6.4 Hz); m/z (ES⁺) 526 [M+H]⁺.

EXAMPLE 155

(1R*,2R*,5S*,6R*)-8-Benzyl-2-{(1R*)-1-[3,5-bis(trifluoromethyl)phenyl]-(methoxycarbonyl)methoxy}-6-cyano-1-phenyl-8-azabicyclo[3.2.1]octane A mixture of (1R*,2R*,5S*,6R*)-8-benzyl-6-cyano-1-phenyl-8-azabicyclo[3.2.1]octan-2-ol (Description 31; 7.186 g, 22.6 mmol) and rhodium(II) acetate dimer (0.216 g, 0.452 mmol) in benzene (30 ml) was heated to reflux, and treated slowly with a solution of methyl 2diazo-2-(3,5-bis(trifluoromethyl)phenyl)-acetate [prepared by the method of R. T. Lewis et al. *J. Org. Chem.*, 2000, 65, 2615] (7.7563 g, 24.86 mmol) in benzene (30 ml). After the addition was complete the mixture was concentrated in vacuo and the residue purified by flash column chromatography, eluting with 10–20% ethyl acetate/hexane to give a mixture of diastereomers (6.0 g, 2.6:1 ratio). The major diastereomer was separated by crystallisation with ethyl acetate/hexane to afford the title compound in two crops (3.81 g).

m/z (ES⁺) 590 ([M+H]⁺).

EXAMPLE 156

(1R*,2R*,5S*,6R*)-8-Benzyl-2-{(1R*)-1-[3,5-bis(trifluoromethyl)phenyl]-2-hydroxyethoxy}-6-cyano-1-phenyl-8-azabicyclo[3.2.1]octane (1R*,2R*,5S*,6R*)-8-Benzyl-2-{(1R*)-1-[3,5-bis(trifluoromethyl)phenyl]-(methoxycarbonyl)methoxy}-6-cyano-1-phenyl-8-azabicyclo[3.2.1]octane (Example 155; 2.408 g, 4 mmol) in methanol (25 ml) was treated with sodium borohydride (2.2698 g, 0.60 mmol) potionwise at 5–10° C. The reaction was quenched with acetone and concentrated in vacuo. The residue was partitioned between ethyl acetate and water, the organics separated and dried (MgSO$_4$) and concentrated in vacuo to afford the title compound as a white foam in quantitative yield.

δ$_H$(400 MHz, CDCl$_3$): 7.78 (1H, s), 7.53 (2H, m), 7.29–7.17 (10H, m), 4.60 (1H, m), 4.18 (1H, d, J 15.4 Hz), 3.93 (1H, d, J 15.4 Hz), 3.86 (1H, s), 3.64 (3H, m), 2.87 (1H, m), 2.38 (1H, m), 2.29–2.17 (3H, m), 1.69 (1H, m), 1.27 (1H, m).

EXAMPLE 157

(1R*,2R*,5S*,6R*)-8-Benzyl-2-{(1R*)-1-[3,5-bis (trifluoromethyl)phenyl]-2-phenylmethoxyethoxy}-6-cyano-1-phenyl-8-azabicyclo[3.2.1]octane (1R*,2R*,5S*,6R*)-8-Benzyl-2-{(1R*)-1-[3,5-bis (trifluoromethyl)phenyl]-2-hydroxyethoxy}-6-cyano-1-phenyl-8-azabicyclo[3.2.1]octane (Example 156; 0.7749 g, 1.35 mmol), benzyl bromide (0.4618 g, 0.321 ml, 2.7 mmol), 18-crown-6 (0.714 g, 2.7 mmol) and sodium hydride (0.1037 g, 4.32 mmol) in THF (6 ml) were heated at 60° C. for 1 hour. The mixture was diluted with water and extracted into ethyl acetate. The organics were collected and dried (MgSO$_4$) and concentrated in vacuo. The residue was purified by flash column chromatography eluting with 15% ethyl acetate/iso-hexane, to afford the title compound as a clear oil (712 mg, 79%).

δ$_H$(400 MHz, CDCl$_3$): 7.80 (1H, s), 7.51 (4H, m), 7.40–7.10 (13H, m), 4.67 (1H, m), 4.61 (1H, d, J 12.0 Hz), 4.52 (1H, d, J 11.9 Hz), 4.26 (1H, d, J 16.0 Hz), 4.03 (1H, d, J 16.0 Hz), 3.93 (1H, s), 3.81 (1H, s), 3.66 (1H, m), 3.46 (1H, m), 2.84 (1H, m), 2.31 (3H, m), 2.12 (1H, m), 1.73 (1H, m), 1.21 (1H, m).

EXAMPLE 158

(1R*,2R*,5S*,6R*)-8-Benzyl-2-{(1R*)-1-[3,5-bis (trifluoromethyl)phenyl]-2-phenylmethoxyethoxy}-1-phenyl-6-(tetrazol-5-yl)-8-azabicyclo[3.2.1]octane (1R*,2R*,5S*,6R*)-8-Benzyl-2-{(1R*)-1-[3,5-bis (trifluoromethyl)phenyl]-2-phenylmethoxyethoxy}-6-cyano-1-phenyl-8-azabicyclo[3.2.1]octane (Example 157; 0.7105 g, 1.07 mmol), sodium azide (0.2087 g, 3.21 mmol) and ammonium chloride (0.172 g, 3.21 mmol) in dimethylformamide (10 ml) were heated at 120° C. for 18 hours. A further 3.0 eq of sodium azide and 3.0 eq of triethylamine hydrochloride were added and the mixture heated for a further 18 hours. The mixture was diluted with ethyl acetate and washed with water. The organics were collected, dried (MgSO$_4$) and concentrated in vacuo. The residue was purified by flash column chromatography, eluting with 5% methanol/dichloromethane to give the title compound (400 mg, 53%).

δ$_H$(400 MHz, CDCl$_3$): 7.82 (1H, s), 7.58 (2H, s), 7.41–7.17 (15H, m), 4.78 (1H, m), 4.58 (1H, d, J 11.8 Hz), 4.56 (1H, d, J 11.9 Hz), 4.30 (1H, d, J 14.6 Hz), 4.13 (2H, m), 3.68 (1H, m), 3.61 (1H, m), 3.50 (1H, m), 3.46 (1H, s), 2.43 (3H, m), 2.02 (1H, m), 1.70 (1H, m), 1.35 (1H, m).

EXAMPLES 159a AND 159b (1R*,2R*,5S*,6R*)-8-Benzyl-2-{(1R*)-1-[3,5-bis (trifluoromethyl)phenyl]-2-phenylmethoxyethoxy}-6-(2-methyl-2H-tetrazol-5-yl)-1-phenyl-8-azabicyclo [3.2.1]octane (isomer A); and (1R*,2R*,5S*,6R*)-8-benzyl-2-{(1R*)-1-[3,5-bis (trifluoromethyl)phenyl]-2-phenylmethoxyethoxy}-6-(1-methyl-1H-tetrazol-5-yl)-1-phenyl-8-azabicyclo [3.2.1]octane (isomer B)

(1R*,2R*,5S*,6R*)-8-Benzyl-2-{(1R*)-1-[3,5-bis (trifluoromethyl)phenyl]-2-phenylmethoxyethoxy}1-phenyl-6-(tetrazol-5-yl)-8-azabicyclo[3.2.1]octane (Example 158; 0.403 g, 0.57 mmol), methyl iodide (0.2427 g, 0.107 ml, 1.71 mmol) and potassium carbonate (0.236 g, 1.71 mmol) in acetonitrile (10 ml) were heated at 60° C. for 2 hours. The mixture was quenched with water and concentrated in vacuo. The residue was partitioned between ethyl acetate and water. The organics were collected, dried (MgSO$_4$) and concentrated in vacuo. The residue was purified by flash column chromatography, eluting with 1% methanol/dichloromethane to give the title compounds (isomer A; 60 mg) and (isomer B; 70 mg), together with mixed fractions.

EXAMPLE 159a

Isomer A

δ$_H$(400 MHz, CDCl$_3$): 7.79 (1H, s), 7.58 (2H, s), 7.31–7.08 (15H, m), 4.72 (1H, m), 4.58 (1H, d, J 11.8 Hz), 4.53 (1H, d, J 11.9 Hz), 4.30 (3H, s) 4.22 (1H, d, J 14.6 Hz), 4.08 (1H, s), 4.01 (1H, d, J 14.8 Hz), 3.69 (2H, m), 3.49 (2H, m), 2.35 (4H, m), 2.01 (1H, m), 1.35 (1H, m).

EXAMPLE 159b

Isomer B

δ$_H$(400 MHz, CDCl$_3$): 7.80 (1H, s), 7.57 (2H, s), 7.32–7.12 (15H, m), 4.78 (1H, m), 4.58 (1H, d, J 11.8 Hz), 4.53 (1H, d, J 11.9 Hz), 4.22 (1H, d, J 14.6 Hz), 4.10 (1H, s), 4.01 (1H, d, J 14.8), 3.86 (3H, s), 3.69 (1H, m), 3.50 (2H, m), 3.46 (1H, s), 2.53 (1H, m), 2.35 (3H, m), 2.01 (1H, m), 1.35 (1H, m).

EXAMPLE 160

(1R*,2R*,5S*)-2-{(1R*)-1-[3,5-Bis(trifluoromethyl) phenyl]-2-hydroxyethoxy}-6-(1-methyl-1H-tetrazol-5-yl)-1-phenyl-8-azabicyclo[3.2.1]octane hydrochloride (1R*,2R*,5S*,6R*)-8-Benzyl-2-{(1R*)-1-[3,5-bis (trifluoromethyl)phenyl]-2-phenylmethoxyethoxy}-6-(1-methyl-1H-tetrazol-5-yl)-1-phenyl-8-azabicyclo[3.2.1] octane (Example 159b; 0.0721 g, 0.1 mmol), palladium 5% on charcoal (60 mg) and acetic acid (0.5 ml) in methanol (10 ml) were hydrogenated on the Parr™ apparatus for 48 hours. The mixture was filtered using a Whatman™ 0.2 micrometer filter. The filtrate was concentrated in vacuo, taken into dichloromethane and washed with saturated sodium hydrogen carbonate. The organic phase was separated using a bond elute cartridge and concentrated in vacuo. The product was isolated as the hydrochloride salt, recrystallised from methanol/diethyl ether to give the title compound as a white crystalline solid.

m/z (ES$^+$) 542 ([M+H]$^+$).

EXAMPLE 161

(1R*,2R*,5S*,6R*)-2-{(1R*)-1-[3,5-Bis (trifluoromethyl)phenyl]-2-hydroxyethoxy}-6-(2-methyl-2H-tetrazol-5-yl)-1-phenyl-8-azabicyclo [3.2.1]octane hydrochloride Prepared according to the method of Example 160 from Example 159a.

δ$_H$(400 MHz, MeOH-d$_4$): 7.77 (1H, s), 7.38 (3H, m), 7.24 (5H, m), 4.74 (1H, t, J 5.6 Hz), 4.62 (1H, s), 4.30 (3H, s), 4.04 (1H, m), 3.73 (1H, s), 3.59 (2H, d, J 5.72 Hz), 2.79 (1H, m), 2.40 (2H, m), 2.13 (2H, m); m/z (ES$^+$) 542 ([M+H]$^+$).

EXAMPLE 162

(1R*,2R*,5S*,6R*)-8-Benzyl-2-{[3,5-bis(trifluoromethyl)phenyl]methoxy}-1-phenyl-8-azabicyclo[3.2.1]octan-6-thioamide Lawesson's reagent (0.23 g, 0.57 mmol) was added to a solution of (1R*,2R*,5S*,6R*)-8-benzyl-2-{[3,5-bis(trifluoromethyl)phenyl]methoxyl}-1-phenyl-8-azabicyclo[3.2.1]octan-6-carboxamide (Example 75; 0.64 g, 1.14 mmol) in toluene (20 ml). The mixture was stirred at 100° C. for 1 hour then concentrated in vacuo. The residue was chromatographed on silica gel eluting with 2 and 3% methanol/dichloromethane to yield the title compound (0.162 g, 25%).

$\delta_H$(400 MHz, CDCl$_3$): 7.74 (1H, s), 7.68 (2H, s), 7.51–7.50 (2H, m), 7.45–7.41 (2H, m), 7.36–7.26 (6H, m), 4.90 (1H, d, J 12.7 Hz), 4.60 (1H, d, J 12.7 Hz), 4.24 (1H, s), 4.05 (1H, d, J 13.6 Hz), 3.83 (1H, d, J 13.6 Hz), 3.49 (1H, s), 3.36 (1H, dd, J 2.5 Hz, 9.6 Hz), 2.51 (1H, dd, J 9.6 Hz, 14.2 Hz), 2.39–2.35 (1H, m), 2.19–2.14 (1H, m), 2.02–1.97 (1H, m), 1.91 (1H, dd, J 4.1 Hz, 14.2 Hz), 1.35–1.32 (1H, m).

EXAMPLE 163

(1R*,2R*,5S*,6R*)-8-Benzyl-2-{[3,5-bis(trifluoromethyl)phenyl]methoxy}-6-(3-methyl-1,2,4-triazo-5-yl)-1-phenyl-8-azabicyclo[3.2.1]octane (1R*,2R*,5S*,6R*)-8-Benzyl-2-{[3,5-bis(trifluoromethyl)phenyl]methoxy}-1-phenyl-8-azabicyclo[3.2.1]octan-6-thioamide (Example 162; 0.16 g, 0.27 mmol), acetylhydrazide (0.2 g, 2.7 mmol) and crushed molecular sieves were stirred in xylenes at reflux for 24 hours. The mixture was filtered through Celite™ and the filtrate concentrated in vacuo. The residue was chromatographed on silica gel eluting with 1, 2 and 5% methanol/dichloromethane to yield the title compound (88 mg, 53%).

$\delta_H$(400 MHz, CDCl$_3$): 7.74 (1H, s), 7.72 (2H, s), 7.54–7.52 (2H, m), 7.41–7.34 (6H, m), 7.30–7.26 (2H, m), 4.90 (1H, d, J 12.8 Hz), 4.62 (1H, d, J 12.7 Hz), 4.23 (1H, s), 4.08 (1H, d, J 14.0 Hz), 3.88 (1H, d, J 14.0 Hz), 3.52 (1H, s), 3.37 (1H, dd, J 3.9 Hz, 9.5 Hz), 2.48 (1H, dd, J 9.5 Hz, 13.9 Hz), 2.44–2.42 (1H, m), 2.31 (3H, s), 2.23–2.18 (1H, m), 2.08–2.04 (1H, m), 1.95 (1H, dd, J 3.8 Hz, 13.8 Hz), 1.38–1.33 (1H, m).

EXAMPLE 164

(1R*,2R*,5S*,6R*)-8-Benzyl-2-{[3,5-bis(trifluoromethyl)phenyl]methoxy}-6-(1,3-imidazol-2-yl)-1-phenyl-8-azabicyclo[3.2.1]octane A solution of glyoxal (40% in water, 0.15 ml, 0.85 mmol) and (1R*,2R*,5S*,6R*)-8-benzyl-2-{[3,5-bis(trifluoromethyl)phenyl]methoxy}-6-formyl-1-phenyl-8-azabicyclo[3.2.1]octane (benzyl derivative of Example 47; 0.3 g, 0.55 mmol) in ethanol (20 ml) was added to a saturated solution of ammonia in ethanol (10 ml). Ammonia gas was bubbled through the solution for a further 5 minutes then left to stir for 18 hours. The reaction mixture was concentrated in vacuo and the residue partitioned between ethyl acetate and brine. The organic layer was separated, dried (MgSO$_4$), filtered and concentrated in vacuo to yield the title compound (307 mg, 96%).

$\delta_H$(400 MHz, CDCl$_3$): 7.74 (1H, s), 7.72 (2H, s), 7.55–7.53 (2H, m), 7.43–7.32 (6H, m), 7.31–7.25 (2H, m), 6.77 (2H, s), 4.91 (1H, d, J 12.7 Hz), 4.62 (1H, d, J 12.7 Hz), 4.25 (1H, s), 4.10 (1H, d, J 13.8 Hz), 3.88 (1H, d, J 13.8 Hz), 3.45 (1H, s), 3.38 (1H, dd, J 3.9 Hz, 9.4 Hz), 2.46 (1H, dd, J 9.4 Hz, 13.9 Hz), 2.40–2.32 (1H, m), 2.22–2.05 (2H, m), 1.87 (1H, dd, J 3.9 Hz, 13.9 Hz), 1.37–1.33 (1H, m).

EXAMPLE 165

(1R*,2R*,5S*,6R*)-8-Benzyl-2-{[3,5-bis(trifluoromethyl)phenyl]methoxy}-6-(4-methyl-1,3-imidazol-2-yl)-1-phenyl-8-azabicyclo[3.2.1]octane Prepared in an analogous manner to (1R*,2R*,5S*,6R*)-8-benzyl-2-{[3,5-bis(trifluoromethyl)phenyl]methoxy}-6-(1,3-imidazol-2-yl)-1-phenyl-8-azabicyclo[3.2.1]octane (Example 164) using methyl glyoxal.

$\delta_H$(400 MHz, CDCl$_3$): 7.74 (1H, s), 7.72 (2H, s), 7.55–7.52 (2H, m), 7.43–7.21 (8H, m), 6.42 (1H, s), 4.90 (1H, d, J 12.7 Hz), 4.62 (1H, d, J 12.7 Hz), 4.23 (1H, s), 4.06 (1H, d, J 13.6 Hz), 3.87 (1H, d, J 13.7 Hz), 3.43 (1H,s), 3.32–3.28 (1H, m), 2.45 (1H, dd, J 9.4 Hz, 13.9 Hz), 2.40–2.16 (3H, m), 2.12 (3H, s), 1.87 (1H, dd, J 3.8 Hz, 13.9 Hz), 1.35–1.32 (1H, m).

EXAMPLE 166

(1R*,2R*,5S*,6R*)-2-{[3,5-Bis(trifluoromethyl)phenyl]methoxy}-6-(3-methyl-1,2,4-triazol-5-yl)-1-phenyl-8-azabicyclo[3.2.1]octane hydrochloride Prepared in an analogous manner to Example 153a.
m/z (ES$^+$) 511 [M+H]$^+$.

EXAMPLE 167

(1R*,2R*,5S*,6R*)-2-{[3,5-Bis(trifluoromethyl)phenyl]methoxy}-6-(1,3-imidazol-2-yl)-1-phenyl-8-azabicyclo[3.2.1]octane dihydrochloride Prepared in an analogous manner to Example 153a.
m/z (ES$^+$) 496 [M+H]$^+$.

EXAMPLE 168

(1R*,2R*,5S*,6R*)-2-{[3,5-Bis(trifluoromethyl)phenyl]methoxy}-6-(1-methyl-1,3-imidazol-2-yl)-1-phenyl-8-azabicyclo[3.2.1]octane dihydrochloride Prepared in an analogous manner to Example 153a.
m/z (ES$^+$) 510 [M+H]$^+$.

EXAMPLE 169

(1R*,2R*,5S*,6R*)-2-{[3,5-Bis(trifluoromethyl)phenyl]methoxy}-6-(4-methyl-1,3-imidazol-2-yl)-1-phenyl-8-azabicyclo[3.2.1]octane dihydrochloride Prepared in an analogous manner to Example 153a.
m/z (ES$^+$) 510 [M+H]$^+$.

EXAMPLE 170

(1R*,2R*,5S*,6S*)-8-Benzyl-2-{[3,5-bis(trifluoromethyl)phenyl]methoxy}-6-ethoxycarbonyl-6-fluoro-1-phenyl-8-azabicyclo[3.2.1]octane Sodium hydride (60% in oil, 100 mg, 2.5 mmol) was washed twice with iso-hexane and added as a suspension in THF (3 ml) to a stirred mixture of (1R*,2R*,5S*,6S*)-8-benzyl-6-ethoxycarbonyl-6-fluoro-1-phenyl-8-azabicyclo

[3.2.1]octan-2-ol (Description 38; 512 mg, 1.3 mmol), 3,5-bis(trifluoromethyl)benzyl bromide (0.5 ml, 2.7 mmol), 18-crown-6 (360 mg, 1.37 mmol) in THF (5 ml) at room temperature. The reaction mixture was stirred for 40 hours, quenched with saturated aqueous NH$_4$Cl and extracted into a 1:1 mixture of iso-hexane:diethyl ether. The combined organic extracts were washed with water, dried (Na$_2$SO$_4$) and concentrated. The residue was purified by chromatography on silica gel (iso-hexane:diethyl ether) to give the title compound (494 mg, 61%).

$\delta_H$(400 MHz, CDCl$_3$): 7.75 (1H, s), 7.74 (2H, s), 7.61 (2H, m), 7.39–7.17 (8H, m), 4.92 (1H, d, J 12.6 Hz), 4.65 (1H, d, J 13.0 Hz), 4.39–4.19 (3H, m), 4.12 (1H, d, J 15.4 Hz), 3.89 (1H, d, J 15.4 Hz), 3.69 (1H, s), 2.95 (1H, dd, J 12.3 Hz, 15.1 Hz), 2.37–2.12 (3H, m), 2.18 (1H, dd, J 14.7 Hz, 24.6 Hz), 1.55 (1H, m), 1.30 (3H, t, J 7.0 Hz).

EXAMPLE 171

(1R*,2R*,5S*,6S*)-2-{[3,5-Bis(trifluoromethyl)phenyl]methoxy}-6-ethoxycarbonyl-6-fluoro-1-phenyl-8-azabicyclo[3.2.1]octane A mixture of ((1R*,2R*,5S*,6S*)-8-benzyl-2-{[3,5-bis(trifluoromethyl)phenyl]methoxy}-6-ethoxycarbonyl-6-fluoro-1-phenyl-8-azabicyclo[3.2.1]octane (Example 170; 52 mg, 0.085 mmol), 10% palladium on charcoal (123 mg), ethanol (10 ml) was stirred under hydrogen atmosphere (1 atm) at +65° C. for 40 minutes. The reaction mixture was cooled to room temperature, flushed with nitrogen gas and filtered through a pad of Celite™. The filtrate was concentrated. The residue was purified by chromatography on silica gel (dichloromethane:methanol) to give the title compound (13 mg, 30%). The hydrochloride salt of the title compound was prepared by treatment with ethereal HCl.

m/z (ES$^+$) 520 [M+H]$^+$.

EXAMPLE 172

(1R*,2R*,5S*,6S*)-8-Benzyl-2-{[3,5-bis(trifluoromethyl)phenyl]methoxy}-6-fluoro-6-[1-(2-methoxyethoxymethyl)-1H-tetrazol-5-yl]-1-phenyl-8-azabicyclo[3.2.1]octane (1R*,2R*,5S*,6S*)-8-benzyl-6-fluoro-6-[1-(2-methoxyethoxymethyl)-1H-tetrazol-5-yl]-1-phenyl-8-azabicyclo[3.2.1]octan-2-ol (Description 45; 205 mg, 0.44 mmol) was added to a stirred mixture of sodium hydride (60% in oil, 60 mg, 1.5 mmol, washed twice with iso-hexane) in THF (2 ml) followed by 18-crown-6 (40 mg, 1.5 mmol) and 3,5-bis(trifluoromethyl)benzyl bromide (0.4 ml, 2.16 mmol) at room temperature. The reaction mixture was warm up to reflux and stirred at room temperature overnight, then quenched with saturated aqueous NH$_4$Cl and extracted into diethyl ether. The combined organic extracts were washed with brine, dried (Na$_2$SO$_4$) and concentrated. The residue was purified by chromatography on silica gel (iso-hexane:diethyl ether 10–70%) to give the title compound (303 mg, 97%).

$\delta_H$(360 MHz, CDCl$_3$): 7.81 (5H, m), 7.40 (2H, t, J 8.1 Hz), 7.28 (1H, m), 7.14–6.96 (5H, m), 5.89 (1H, d, J 11.2 Hz), 5.70 (1H, dd, J 1.4 Hz, 11.2 Hz), 4.95 (1H, d, J 13.0 Hz), 4.72 (1H, d, J 12.6 Hz), 4.40 (1H, br s), 4.05 (1H, d, J 15.1 Hz), 3.85 (1H, d, J 14.7 Hz), 3.68 (1H, dd, J 12.6 Hz, 14.7 Hz), 3.64 (1H, s), 3.47 (1H, ddd, J 2.5 Hz, 8.1 Hz, 10.5 Hz), 3.21 (3H, s), 3.08 (1H, ddd, J 2.5 Hz, 4.6 Hz, 11.2 Hz), 2.95 (1H, ddd, J 2.5 Hz, 4.6 Hz, 10.9 Hz), 2.84 (1H, ddd, J 2.5 Hz, 8.1 Hz, 10.9 Hz), 2.53 (1H, dd, J 15.1 Hz, 26.3 Hz), 2.44–2.15 (3H, m), 1.69 (1H, m).

EXAMPLES 173a AND 173b (1R*,2R* 5S*,6S*)-8-Benzyl-2-{[3,5-bis(trifluoromethyl)phenyl]methoxy}-6-fluoro-6-(1-methyl-1H-tetrazol-5-yl)-1-phenyl-8-azabicyclo[3.2.1]octane (isomer A); and (1R*,2R*,5S*,6S*)-8-benzyl-2-{[3,5-bis(trifluoromethyl)phenyl]methoxy}-6-fluoro-6-(2-methyl-2H-tetrazol-5-yl)-1-phenyl-8-azabicyclo[3.2.1]octane (isomer B)

A mixture of (1R*,2R*,5S*,6S*)-8-benzyl-2-{[3,5-bis(trifluoromethyl)phenyl]-methoxy}-6-fluoro-6-[1-(2-methoxyethoxymethyl)-1H-tetrazol-5-yl]-1-phenyl-8-azabicyclo[3.2.1]octane (Example 172; 150 mg, 0.22 mmol), 1M solution of hydrogen chloride in ether (3 ml) and methanol (3 ml) was stirred at reflux for 9 hours. The reaction mixture was concentrated. The residue (170 mg) was treated with dichloromethane (3 ml), methanol (0.5 ml), triphenylphosphine (220 mg, 0.83 mmol) and diethyl azodicarboxylate (0.12 ml, 0.56 mmol). The reaction mixture was stirred at room temperature for 1 hour and concentrated in vacuo to give a 1:3.3 mixture of isomers A and B, respectively. Both isomers were separated by chromatography on silica gel (iso-hexane:ethyl acetate 0–20%).

EXAMPLE 173a

Isomer A $\delta_H$(400 MHz, CDCl$_3$): 7.77 (3H, s), 7.71 (2H, d, J 7.1 Hz), 7.38 (2H, t, J 7.8 Hz), 7.27 (1H, m), 7.13 (3H, m), 6.99 (2H, m), 4.95 (1H, d, J 12.9 Hz), 4.72 (1H, d, J 12.9 Hz), 4.40 (1H, br s), 4.09 (1H, d, J 15.3 Hz), 3.97 (3H, d, J 2.0 Hz), 3.89 (1H, d, J 14.5 Hz), 3.64 (1H, dd, J 12.1 Hz, 14.9 Hz), 3,56 (1H, br s), 2.54 (1H, dd, J 14.9 Hz, 26.2 Hz), 2.43–2.21 (2H, m), 1.66 (1H, m).

EXAMPLE 173b

Isomer B $\delta_H$(360 MHz, CDCl$_3$): 7.75 (3H, s), 7.57 (2H, d, J 7.4 Hz), 7.33 (2H, t, J 8.1 Hz), 7.24 (1H, m), 7.13 (3H, m), 6.93 (2H, m), 4.95 (1H, d, J 13.0 Hz), 4.67 (1H, d, J 12.6 Hz), 4.38 (4H, br s), 4.13 (1H, d, J 15.4 Hz), 3.91 (1H, s), 3.87 (1H, d, J 16.8 Hz), 3.02 (1H, dd, J 11.2 Hz, 14.7 Hz), 2.54 (1H, dd, J 15.1 Hz, 24.6 Hz), 2.44 (1H, m), 2.34–2.17 (2H, m), 1.73 (1H, m).

EXAMPLE 174

(1R*,2R*,5S*,6S*)-2-{[3,5-Bis(trifluoromethyl)phenyl]methoxy}-6-fluoro-6-(2-methyl-2H-tetrazol-5-yl)-1-phenyl-8-azabicyclo[3.2.1]octane A mixture of (1R*,2R*,5S*,6S*)-8-benzyl-2-{[3,5-bis(trifluoromethyl)phenyl]-methoxy}-6-fluoro-6-(2-methyl-2H-tetrazol-5-yl)-1-phenyl-8-azabicyclo[3.2.1]octane (Example 173b; 74 mg, 0.12 mmol) was treated with an etheral solution of hydrogen chloride and concentrated. The residue was dissolved in ethanol (20 ml) and 10% palladium on charcoal (109 mg) was added. The mixture was stirred under hydrogen atmosphere (1 atm) at +60° C. for 30 minutes. The reaction mixture was cooled to room temperature, flushed with nitrogen gas and filtered through a pad of Celite™. The filtrate was concentrated and the residue was purified by chromatography on silica gel (dichloromethane:methanol:ammonia) to give the title compound (52 mg, 82%). The hydrochloride salt of the title compound was prepared by treatment with ethereal HCl.

m/z (ES$^+$) 530 [M+H]$^+$

EXAMPLE 175

(1R*,2R*,5S*,6S*)-8-Benzyl-2-{(1R,S)-1-[3,5-bis(trifluoromethyl)phenyl]-(methoxycarbonyl)methoxy}-6-fluoro-6-[1-(2-methoxyethoxymethyl)-1H-tetrazol-5-yl]-1-phenyl-8-azabicyclo[3.2.1]octane Slow addition of methyl 2-diazo-2-[3,5-bis(trifluoromethyl)phenyl]acetate (1.86 g, 5.9 mmol) as a solution in 1.2-dichloroethane (10 ml) to (1R*,2R*,5S*,6S*)-8-benzyl-6-fluoro-6-[1-(2-methoxyethoxymethyl)-1H-tetrazol-5-yl]-1-phenyl-8-azabicyclo[3.2.1]octan-2-ol (Description 45; 10.2 g, 2.2 mmol) in 1,2-dichloroethane (10 ml) was carried out in the presence of catalytic rhodium(II) acetate dimer (45 mg) at reflux under N$_2$. The reaction mixture was concentrated in vacuo to give a green oil then purified by flash column chromatography [15% ethyl acetate in iso-hexane] to give a yellow oil (550 mg) as a mixture of diastereoisomers.

EXAMPLE 176

(1R*,2R*,5S*,6S*)-8-Benzyl-2-{(1R*)-1-[3,5-bis(trifluoromethyl)phenyl]-2-hydroxyethoxy}-6-fluoro-6-[1-(2-methoxyethoxymethyl)-1H-tetrazol-5-yl]-1-phenyl-8-azabicyclo[3.2.1]octane Lithium borohydride (15 mg, 0.69 mmol) was added to a solution of (1R*,2R*,5S*,6S*)-8-benzyl-2-{(1R,S)-1-[3,5-bis(trifluoromethyl)phenyl]-(methoxycarbonyl)methoxy}-6-fluoro-6-[1-(2-methoxyethoxymethyl)-1H-tetrazol-5-yl]-1-phenyl-8-azabicyclo[3.2.1]octane (Example 175; 0.5 g, 0.66 mmol) in diethyl ether (20 ml). After one hour the mixture was partitioned between saturated sodium hydrogen carbonate and ethyl acetate. The organic layer was dried (MgSO$_4$), filtered and concentrated in vacuo. The residue was chromatographed on silica gel eluting with 5 and 10% ethyl acetate/dichloromethane to yield the title compound (0.203 g, 43%).

$\delta_H$(360 MHz, CDCl$_3$): 7.85 (1H, s), 7.62 (2H, s), 7.18–7.05 (8H, m), 5.99–5.91 (2H, m), 4.78–4.74 (1H, m), 4.27 (1H, s), 4.25 (1H ,d, J 15.5 Hz), 4.13 (1H, d, J 15.5 hz), 3.97 (1H, s), 3.80–3.71 (4H, m), 3.55–3.53 (2H, m), 3.37 (3H, s), 3.23–3.16 (1H, m), 2.51–2.34 (3H, m), 1.98–1.96 (2H, m), 1.81–1.78 (1H, m).

EXAMPLE 177

(1R*,2R*,5S*,6S*)-8-Benzyl-2-{(1S*)-1-[3,5-bis(trifluoromethyl)phenyl]ethoxy}-6-fluoro-1-phenyl-6-(tetrazol-5-yl)-8-azabicyclo[3.2.1]octane Palladium on charcoal (60 mg) was added to a solution of (1R*,2R*,5S*,6S*)-8-benzyl-2-{(1R*)-1-[3,5-bis(trifluoromethyl)phenyl]-2-iodoethoxy}-6-fluoro-6-[1-(2-methoxyethoxymethyl)-1H-tetrazol-5-yl]-1-phenyl-8-azabicyclo[3.2.1]octane (Description 46; 193 mg, 0.23 mmol) and triethylamine (38 mg, 0.38 mmol) in methanol (3 ml) and ethyl acetate (5 ml). The mixture was hydrogenated at 40 psi. for 3 hours using the Parr™ apparatus. The mixture was filtered through Celite™ and the filtrate concentrated in vacuo. The residue was taken up in a mixture of 1.0M Hydrochloric acid in diethyl ether (5 ml) and methanol (5 ml) and stirred at reflux for 18 hours. The mixture was concentrated in vacuo to yield the title compound (90 mg, 78%).

$\delta_H$(400 MHz, CDCl$_3$): 7.81 (1H, s), 7.63 (2H, s), 7.28–7.15 (10H, m), 4.77 (1H, q, J 6.4 Hz), 4.31–4.11 (3H, m), 3.64 (1H, s), 2.84–2.72 (1H, m), 2.54–2.31 (4H, m), 1.75–1.67 (1H, m),1.56 (3H, d, J 6.4 Hz).

EXAMPLE 178

(1R*,2R*,5S*,6S*)-8-Benzyl-2-{(1S*)-1-[3,5-bis(trifluoromethyl)phenyl]ethoxy}-6-fluoro-6-(2-methyl-2H-tetrazol-5-yl)-1-phenyl-8-azabicyclo[3.2.1]octane Prepared in an analogous manner to Example 140.

$\delta_H$(400 MHz, CDCl$_3$): 7.72 (1H, s), 7.54 (2H, s), 7.18–7.00 (10H, s), 4.70 (1H, q, J 6.4 Hz), 4.28 (3H, s), 4.19 (1H, d, J 15.9 Hz), 4.14 (1H, s), 4.00 (1H, d, J 15.4 Hz), 3.88 (1H, s), 3.09 (1H, dd, J 11.3 Hz, 14.8 Hz), 2.41–2.20 (4H, m), 1.68–1.65 (1H, m), 1.47 (3H, d, J 6.5 Hz).

EXAMPLE 179

(1R*,2R*,5S*,6S*)-2-{(1S*)-1-[3,5-Bis(trifluoromethyl)phenyl]ethoxy}-6-fluoro-6-(2-methyl-2H-tetrazol-5-yl)-1-phenyl-8-azabicyclo[3.2.1]octane hydrochloride Prepared in an analogous manner to Example 153a.

m/z (ES$^+$) 544 [M+H]$^+$.

EXAMPLE 180

(1R,2R,5R)-8-Benzyl-2-{[3,5-bis(trifluoromethyl)phenyl]methoxy}-1-phenyl-8-azabicyclo[3.2.1]octane Sodium hydride (60% in oil, 90 mg, 2.25 mmol) was washed twice with THF and treated with a solution of (1R,2R,5R)-8-benzyl-1-phenyl-8-azabicyclo[3.2.1]octan-2-ol (Description 53; 79 mg, 0.25 mmol), 3,5-bis(trifluoromethyl)benzyl bromide (350 mg, 1.14 mmol), 18-crown-6 (110 mg, 0.41 mmol) in THF (5 ml). The reaction mixture was stirred at room temperature for 24 hours, quenched with saturated aqueous NH$_4$Cl and extracted into diethyl ether. The combined organic extracts were washed with water, dried (Na$_2$SO$_4$) and concentrated. The residue was purified by chromatography on silica gel (iso-hexane:diethyl ether) to give the title compound (165 mg).

$\delta_H$(360 MHz, CDCl$_3$): 7.73 (1H, s), 7.71 (2H, s), 7.53 (2H, m), 7.43 (2H, d, J 7.7 Hz), 7.37–7.15 (6H, m), 4.72 (1H, d, J 13.0 Hz), 4.41 (1H, d, J 13.0 Hz), 4.1 (1H, d, J 15.4 Hz), 3.89 (1H, br s), 3.67 (1H, d, J 15.4 Hz), 3.43 (1H, m), 2.25–1.90 (6H, m), 1.65 (1H, m), 1.14 (1H, m).

EXAMPLE 181

(1R,2R,5R)-2-{[3,5-Bis(trifluoromethyl)phenyl]methoxy}-1-phenyl-8-azabicyclo[3.2.1]octane A mixture of (1R,2R,5R)-8-benzyl-2-{[3,5-bis(trifluoromethyl)phenyl]methoxy}-1-phenyl-8-azabicyclo[3.2.1]octane (Example 180; 165 mg), 10% palladium on charcoal (215 mg) and ethanol (15 ml) was stirred under hydrogen atmosphere (1 atm) at +65° C. for 45 minutes. The reaction mixture was cooled to room temperature, flushed with nitrogen gas and filtered through a pad of Celite™. The filtrate was concentrated. The residue was purified by chromatography on silica gel (dichloromethane:methanol:ammonia) to give the title compound (64 mg, 59%). The hydrochloride salt of the title compound was prepared by treatment with ethereal HCl.

m/z (ES$^+$) 430 [M+H]$^+$.

EXAMPLE 182

(1S,2S,5S)-2-{[3,5-Bis(trifluoromethyl)phenyl]methoxy}-1-phenyl-8-(prop-2-enyl)-8-azabicyclo[3.2.1]octane Sodium hydride (60% in oil, 67 mg, 1.67 mmol) was washed twice with THF and treated with a solution 1S,2S,5S)-1-phenyl-8-(prop-2-enyl)-8-azabicyclo[3.2.1]octan-2-ol (Description 57; 116 mg, 0.47 mmol), 3,5-bis(trifluoromethyl)benzyl bromide (430 mg, 1.4 mmol), 18-crown-6 (33 mg, 1.25 mmol) in THF (2 ml). The reaction mixture was stirred at room temperature overnight, quenched with saturated aqueous NH$_4$Cl and extracted into diethyl ether. The combined organic extracts were washed with water, dried (Na$_2$SO$_4$) and concentrated. The residue was purified by chromatography on silica gel (iso-hexane:diethyl ether) to give the title compound.

$\delta_H$(360 MHz, MeOH-d$_4$): 7.77 (1H, s), 7.72 (2H, s), 7.44 (2H, m), 7.28 (2H, m), 7.19 (1H, m), 5.89 (1H, dddd, J 5.8 Hz, 6.4 Hz, 10.2 Hz, 16.7 Hz), 5.15 (1H, dq, J 1.5 Hz, 17.2 Hz), 5.07 (1H, d, J 9.9 Hz), 4.69 (1H, d, J 12.9 Hz), 4.25 (1H, d, J 12.6 Hz), 3.68 (1H, br s), 3.60 (1H, br s), 3.50 (1H, dd, J 5.9 Hz, 14.6 Hz), 2.89 (1H, d, J dd, J 6.7 Hz, 14.9 Hz), 2.19–1.90 (6H, m), 1.74 (1H, m), 1.31 (1H, d, J 12.9 Hz).

EXAMPLE 183

(1S,2S,5S)-2-{[3,5-Bis(trifluoromethyl)phenyl]methoxy}-1-phenyl-8-azabicyclo[3.2.1]octane Tetrakis(triphenylphosphine)palladium(0) (97 mg, 0.084 mmol) was added to a stirred mixture of (1S,2S,5S)-2-{[3,5-bis(trifluoromethyl)phenyl]methoxy}-1-phenyl-8-(prop-2-enyl)-8-azabicyclo[3.2.1]octane (Example 182), 1,3-dimethylbarbituric acid (270 mg, 1.9 mmol) in dichloromethane (10 ml) at room temperature. The reaction mixture was stirred at 30–35° C. overnight and treated with 2M aqueous NaOH (5 ml). The mixture was stirred for 30 minutes, then treated with water (30 ml) and extracted into dichloromethane. The combined organic extracts were dried (Na$_2$SO$_4$) and concentrated. The residue was purified by chromatography on silica gel to give the title compound (166 mg, 81% two steps). The hydrochloride salt of the title compound was prepared by treatment with ethereal HCl.

m/z (ES$^+$) 430 [M+H]$^+$.

EXAMPLE 184

(1S,2S,5R,6S,9S)-6-(tert-Butoxycarbonyl)-2-hydroxy-1-phenyl-8-(1-phenylethyl)-8-azabicyclo[3.2.1]octane Sodium borohydride (0.63 g, 16.7 mmol) was added portionwise to a solution of (1S,5R,6S,9S)-6-(tert-butoxycarbonyl)-1-phenyl-8-(1-phenylethyl)-8-azabicyclo[3.2.1]octan-2-one (Description 61; 6.79 g, 16.7 mmol) in THF/methanol (1:1, 150 ml). The mixture was stirred at room temperature under nitrogen for fifty minutes, concentrated in vacuo and diluted with water (250 ml). The mixture was extracted with ethyl acetate (2×250 ml), washed the combined extracts with saturated brine (250 ml), combined, dried (MgSO$_4$) and evaporated to afford the title compound (6.78 g, 98%) as a white solid.

m/z (ES$^+$) 408 ([M+H]$^+$).

EXAMPLE 185

(1S,2S,5R,6S,9S,11S)-2-(1-(3,5-Bis(trifluoromethyl)phenyl)-2-hydroxy)ethoxy-6-(tert-butoxycarbonyl)-1-phenyl-8-(1-phenylethyl)-8-azabicyclo[3.2.1]octane A solution of methyl 2-diazo-2-(3,5-bis(trifluoromethyl)phenyl)acetate [prepared by the method of R. T. Lewis et al. *J. Org. Chem.*, 2000, 65, 2615] (7.41 g, 23.7 mmol) in 1,2-dichloroethane (50 ml) was added dropwise over three hours to a refluxing solution of (1S,2S,5R,6S,9S)-6-(tert-butoxycarbonyl)-2-hydroxy-1-phenyl-8-(1-phenylethyl)-8-azabicyclo[3.2.1]octane (Example 184; 6.32 g, 15.5 mmol) and rhodium(II) acetate dimer (322.4 mg, 0.73 mmol) in 1,2-dichloroethane (100 ml). After the addition was complete, the mixture was stirred at reflux for a further thirty minutes, allowed to cool, filtered and concentrated in vacuo. The residue was dissolved in 10% ethyl acetate in iso-hexane and treated with silica. Filtered and washed silica with 10% ethyl acetate in iso-hexane. The filtrate was evaporated to give an orange foam (12.77 g). This was dissolved in methanol (250 ml) and treated in three portions with sodium borohydride (9.10 g, 0.24 mol), with the exotherm being moderated by use of a cold water bath. The resulting mixture was stirred at room temperature for an hour, concentrated to a small volume, diluted with water (500 ml) and extracted with ethyl acetate (2×250 ml). The extracts were washed with saturated brine (250 ml), combined, dried (MgSO$_4$) and evaporated. The residue was purified by flash chromatography, eluting with 0–5% diethyl ether in dichloromethane, iso-hexane crystallisation of impure fractions and further chromatography of the mother liquors to afford the title compound as the more polar diastereoisomer (5.62 g, 55%).

m/z (ES$^+$) 664 ([M+H]$^+$); [α]$_D$+23.1°. (c 0.65, CH$_2$Cl$_2$).

EXAMPLE 186

(1S,2S,5R,6S,9S,11R)-2-(1-(3,5-Bis(trifluoromethyl)phenyl))ethoxy-6-(tert-butoxycarbonyl)-1-phenyl-8-(1-phenylethyl)-8-azabicyclo[3.2.1]octane 20% Palladium hydroxide on carbon (0.62 g) was added to a solution of (1S,2S,5R,6S,9S,11S)-6-(tert-butoxycarbonyl)-2-(1-(3,5-bis(trifluoromethyl)phenyl)-2-iodo)ethoxy-1-phenyl-8-(1-phenylethyl)-8-azabicyclo[3.2.1]octane (Description 62; 3.07 g, 4.52 mmol) and triethylamine (1 ml) in ethyl acetate/methanol (1:1, 80 ml) and the mixture hydrogenated on a Parr™ apparatus (40 psi max.) for three hours. The mixture was filtered and concentrated in vacuo. The residue was treated with saturated aqueous sodium hydrogen carbonate (50 ml) and saturated aqueous sodium thiosulfate (50 ml) then extracted with dichloromethane (2×50 ml). The combined extracts were dried (MgSO$_4$), diluted with iso-hexane and evaporated to give the title compound (2.35 g, 91%) as a pale cream-coloured solid.

m/z (ES$^+$) 648 ([M+H]$^+$).

EXAMPLE 187

(1S,2S,5R,6S,9S,11R)-2-(1-(3,5-Bis(trifluoromethyl)phenyl))ethoxy-6-(methylaminocarbonyl)-1-phenyl-8-(1-phenylethyl)-8-azabicyclo[3.2.1]octane Trifluoroacetic acid (30 ml) was added to a solution of (1S,2S,5R,6S,9S,11R)-2-(1-(3,5-bis(trifluoromethyl)phenyl))ethoxy-6-(tertbutoxycarbonyl)-1-phenyl-8-(1- phenylethyl)-8-azabicyclo[3.2.1]octane (Example 186; 1.93 g, 2.98 mmol) in dichloromethane (70 ml) and the mixture stirred at room temperature overnight (17 hours). The mixture was concentrated in vacuo, diluted with toluene (5 ml) and evaporated to an oil. This was dissolved in diethyl ether and evaporated to give a foam (2.44 g). A portion of this material (0.75 g, ~0.92 mmol) was dissolved in dichloromethane (15 ml), treated with triethylamine (0.50 ml, 3.6 mmol) and DMAP (23.1 mg, 0.19 mmol) and the mixture cooled to 0° C. Methylamine in THF (2.0M; 2.5 ml, 5.0 mmol) followed by 1-(3-dimethylamino)propyl)-3-ethylcarbodiimide hydrochloride (0.44 g, 2.30 mmol) were added, the flask capped and the mixture stirred at room temperature overnight (16 hours). The mixture was poured into water (50 ml) and extracted with dichloromethane (2×25 ml). The organic extracts were washed with 0.5M hydrochloric acid (50 ml), saturated sodium hydrogen carbonate (25 ml) then saturated brine (50 ml), combined, dried ($MgSO_4$) and evaporated. Purification by flash chromatography, eluting with 2.5 to 5% methanol in dichloromethane, gave the title compound (293.2 mg, 53%) as a white solid.

m/z ($ES^+$) 606 ([M+H]$^+$), 501 ([M-PhCHCH$_3$+2H]$^+$).

EXAMPLE 188

(1S,2S,5R,6S,9S,11R)-2-(1-(3,5-Bis(trifluoromethyl) phenyl))ethoxy-6-(1-methyltetrazol-5-yl)-1-phenyl-8-(1-phenylethyl)-8-azabicyclo[3.2.1]octane Trifluoromethanesulfonic anhydride (100 μl, 0.59 mmol) was added to a cooled mixture of (1S,2S,5R,6S,9S,11R)-2-(1-(3,5-bis(trifluoromethyl)phenyl))ethoxy-6-(methylaminocarbonyl)-1-phenyl-8-(1-phenylethyl)-8-azabicyclo[3.2.1]octane (Example 187; 288.8 mg, 0.478 mmol) and sodium azide (51.8 mg) in dichloromethane (5 ml) [CAUTION: explosions have been reported with reactions involving sodium azide and dichloromethane]. The mixture was allowed to warm up from 0° C. to room temperature over 10 minutes then stirred overnight (21 hours). The reaction mixture was poured into saturated sodium hydrogen carbonate (25 ml) and extracted with dichloromethane (2×20 ml). The combined extracts were dried ($MgSO_4$), evaporated and the residue purified by flash chromatography, eluting with 1:1 ethyl acetate-iso-hexane, to give the title compound (143.2 mg, 48%) and recovered starting material (47.5 mg, 16%).

m/z ($ES^+$) 630 ([M+H]$^+$), 526 ([M-PhCHCH$_3$+2H]$^+$).

EXAMPLE 189

(1S,2S,5R,6S,9R)-2-(1-(3,5-Bis(trifluoromethyl) phenyl))ethoxy-6-(1-methyl-1H-tetrazol-5-yl)-1-phenyl-8-azabicyclo[3.2.1]octane hydrochloride 20% Palladium hydroxide on carbon (71.5 mg) was added to a solution of (1S,2S,5R,6S,9S,11R)-2-(1-(3,5-bis(trifluoromethyl)phenyl))ethoxy-6-(1-methyltetrazol-5-yl)-1-phenyl-8-(1-phenylethyl)-8-azabicyclo[3.2.1]octane (Example 188; 140.6 mg, 0.223 mmol) in methanol (10 ml) containing 1M hydrogen chloride in diethyl ether (250 μl, 0.25 mmol). The mixture was hydrogenated on Parr™ apparatus (50 psi max.) for 3 hours, filtered, evaporated and the residue recrystallized from methanol-diethyl ether to give the title compound in two crops (106.6 mg, 85%).

m/z ($ES^+$) 526 ([M+H]$^+$); [α]$_D$ +61° (c 0.2, MeOH).

EXAMPLE 190

(1S,2S,5R,6S,9R)-2-(1-(3,5-Bis(trifluoromethyl) phenyl))ethoxy-6-(methylaminocarbonyl)-1-phenyl-8-azabicyclo[3.2.1]octane hydrochloride Prepared in an analogous manner to Example 189 from (1S,2S,5R,6S,9S,11R)-2-(1-(3,5-bis(trifluoromethyl) phenyl))ethoxy-6-(methylaminocarbonyl)-1-phenyl-8-(1-phenylethyl)-8-azabicyclo[3.2.1]octane (Example 187).

m/z ($ES^+$) 501 ([M+H]$^+$).

EXAMPLE 191

(1S,2S,5R,6S,9R)-2-(1-(3,5-Bis(trifluoromethyl) phenyl))ethoxy-6-[(methylamino)(methylimino) methyl]-1-phenyl-8-azabicyclo[3.2.1]octane dihydrochloride Trimethylaluminium in hexanes (2.0M; 1.8 ml, 3.6 mmol) was added via syringe to a suspension of methylamine hydrochloride (226.5 mg, 3.35 mmol) in toluene (5 ml) at 0° C. Stirred at 0° C. for 5 minutes, removed cooling bath and allowed to warm to room temperature. Stirred at room temperature for 30 minutes to give a colourless solution. This solution was added via syringe to a solution of (1S,2S,5R,6S,9S,11R)-6-(tert-butoxycarbonyl)-2-(1-(3,5-bis(trifluoromethyl)phenyl))ethoxy-1-phenyl-8-(1-phenylethyl)-8-azabicyclo[3.2.1]octane (Example 186; 408.5 mg, 0.63 mmol) in toluene (5 ml). The resulting mixture was stirred at 90° C. under nitrogen for 24 hours. The reaction mixture was cooled to 0° C. and quenched by the addition of saturated aqueous potassium sodium tartrate. Stirred at room temperature for one hour, diluted with 2M sodium hydroxide and extracted with ethyl acetate (2×50 ml). The extracts were washed with saturated brine (25 ml), combined, dried ($MgSO_4$) and evaporated to give a pale yellow foam (429.1 mg). This material was dissolved in THF (50 ml) and treated with 2M hydrochloric acid (50 ml). The resulting mixture was stirred at reflux for 2 days, poured into water (50 ml) and extracted with dichloromethane (3×25 ml). The aqueous phase was basified by the addition of 4M sodium hydroxide (5 ml) and extracted with dichloromethane (2×25 ml). The extracts were washed with saturated brine (25 ml), combined, dried ($MgSO_4$) and evaporated. The residue was dissolved in diethyl ether and treated with excess 1M hydrogen chloride in diethyl ether to give a gum. Purification was effected by chromatography on a Varian C-18 Mega Bond Elut™ cartridge (10 g) with gradient elution from 10%–80% methanol in water. Fractions containing pure title compound were combined and evaporated. The residue was dissolved in methanol, diluted with diethyl ether and filtered. The filtrate was evaporated and the residue dried in vacuo to afford the title compound (75.1 mg) as a foam.

m/z ($ES^+$) 514 ([M+H]$^+$).

EXAMPLE 192

(1S,2S,5R,6S,9S,11S)-2-(1-(3,5-Bis(trifluoromethyl) phenyl)-2-phenylmethoxy)ethoxy-6-(tert-butoxycarbonyl)-1-phenyl-8-(1-phenylethyl)-8-azabicyclo[3.2.1]octane Sodium hydride (60% dispersion in oil; 0.18 g, 4.5 mmol) was added to a THF (25 ml) solution of (1S,2S,5R,6S,9S,11S)-2-(1-(3,5-Bis(trifluoromethyl)phenyl)-2-hydroxy) ethoxy-6-(tert-butoxycarbonyl)-1-phenyl-8-(1-phenylethyl)-8-azabicyclo[3.2.1]octane (Example 185) and 18-crown-6 (0.10 g, 0.38 mmol). The resulting mixture was stirred at room temperature under nitrogen for 20 minutes, treated with benzyl bromide (0.50 ml, 4.2 mmol) and stirred at 60° C. (oil bath temperature) for 2 hours. The reaction mixture was poured into water (125 ml) and extracted with ethyl acetate (2×50 ml). The extracts were washed with saturated brine (50 ml), combined, dried ($MgSO_4$) and evaporated. Crystallisation from iso-hexane gave the title compound (2.66 g, 93%) in three crops.

m/z (ES$^+$) 754 ([M+H]$^+$).

EXAMPLE 193

(1S,2S,5R,6S,9S,11S)-2-(1-(3,5-Bis(trifluoromethyl) phenyl)-2-phenylmethoxy)ethoxy-6-(1-(2-cyanoethyl)-1H-tetrazol-5-yl)-1-phenyl-8-(1-phenylethyl)-8-azabicyclo[3.2.1]octane Trifluoroacetic acid (30 ml) was added to a solution (1S,2S,5R,6S,9S,11S)-6-(tert-butoxycarbonyl)-2-(1-(3,5-bis(trifluoromethyl)phenyl)-2-phenylmethoxy)ethoxy-1-phenyl-8-(1-phenylethyl)-8-azabicyclo[3.2.1]octane (Example 192; 2.54 g, 3.37 mmol) in dichloromethane (70 ml) and the mixture stirred at room temperature for 16 hours. The mixture was concentrated in vacuo, diluted with toluene (5 ml) and evaporated to an oil. This was dissolved in diethyl ether and evaporated to give a foam (3.21 g). This material was dissolved in dichloromethane (50 ml), treated with triethylamine (2.35 ml, 16.9 mmol), 3-aminopropionitrile (0.62 ml, 8.4 mmol) and 4-dimethylaminopyridine (88.3 mg, 0.72 mmol) and the mixture cooled to 0° C. 1-(3-Dimethylamino)propyl)-3-ethylcarbodiimide hydrochloride (1.62 g, 8.45 mmol) was added and the mixture stirred at room temperature for 16 hours. The mixture was poured into 1M hydrochloric acid (100 ml) and extracted with dichloromethane (2×50 ml). The organic extracts were washed with saturated sodium hydrogen carbonate (100 ml) then saturated brine (50 ml), combined, dried (MgSO$_4$) and evaporated to a yellow foam (2.62 g). This crude amide was dissolved in dichloromethane (35 ml), sodium azide (0.27 g, 4.15 mmol) added and the mixture cooled to 0° C. Trifluoromethanesulfonic anhydride (0.70 ml, 4.16 mmol) was added and the mixture stirred at 0° C. for 10 minutes. The cooling bath was removed and the reaction mixture stirred at room temperature for 26 hours. The reaction mixture was poured into saturated sodium hydrogen carbonate (100 ml) and extracted with dichloromethane (2×25 ml). The combined extracts were dried (MgSO$_4$), evaporated and the residue purified by flash chromatography, eluting with 40% ethyl acetate-iso-hexane, to give the title compound (0.85 g, 33%).

m/z (ES$^+$) 775 ([M+H]$^+$), 671 ([M-PhCHCH$_3$+2H]$^+$).

EXAMPLE 194

(1S,2S,5R,6S,9S,11S)-2-(1-(3,5-Bis(trifluoromethyl) phenyl)-2-phenylmethoxy)ethoxy-1-phenyl-6-(tetrazol-5-yl)-8-(1-phenylethyl)-8-azabicyclo[3.2.1] octane (1S,2S,5R,6S,9S,11S)-2-(1-(3,5-Bis(trifluoromethyl) phenyl)-2-phenylmethoxy)ethoxy-6-(1-(2-cyanoethyl)-1H-tetrazol-5-yl)-1-phenyl-8-(1-phenylethyl)-8-azabicyclo [3.2.1]octane (Example 193; 0.85 g, 1.1 mmol) in methanol (20 ml) was treated with 10% sodium hydroxide (4 ml) and stirred at room temperature overnight. The mixture was concentrated in vacuo, the residue dissolved in water and extracted with dichloromethane. The organics were dried (MgSO$_4$) and concentrated in vacuo to give the title compound as a pale yellow solid (0.595 g, 84%).

m/z (ES$^+$) 722 ([M+H]$^+$).

EXAMPLES 195a AND 195b (1S,2S,5R,6S,9S,11S)-2-(1-(3,5-Bis(trifluoromethyl) phenyl)-2-phenylmethoxy)ethoxy-6-(1-methyl-1H-tetrazol-5-yl)-1-phenyl-8-(1-phenylethyl)-8-azabicyclo[3.2.1]octane (isomer A); and (1S,2S,5R,6S,9S,11S)-2-(1-(3,5-bis(trifluoromethyl) phenyl)-2-phenylmethoxy)ethoxy-6-(2-methyl-2H-tetrazol-5-yl)-1-phenyl-8-(1-phenylethyl)-8-azabicyclo[3.2.1]octane (isomer B)

(1S,2S,5R,6S,9S,11S)-2-(1-(3,5-Bis(trifluoromethyl) phenyl)-2-phenylmethoxy)ethoxy-1-phenyl-6-(tetrazol-5-yl)-8-(1-phenylethyl)-8-azabicyclo[3.2.1]octane (Example 194; 0.3245 g, 0.45 mmol), methyl iodide (0.84 ml, 1.35 mmol) and potassium carbonate (0.19 g, 1.35 mmol) in dimethylformamide (15 ml) were heated at 60° C. for 2 hours. The mixture was diluted with water and extracted with ethyl acetate. The organics were collected, dried (MgSO$_4$) and concentrated in vacuo. The residue was purified by flash column chromatography, eluting with 40% ethyl acetate/iso-hexane to afford isomer B as an oil (136 mg) and isomer A as a white solid (89 mg).

EXAMPLE 195a

Isomer A $\delta_H$(400 MHz, CDCl$_3$): 7.92 (1H, s), 7.85 (2H, s), 7.51 (2H, m), 7.34–7.26 (6H, m), 7.14–7.09 (7H, m), 4.91 (1H, m), 4.75 (1H, m), 4.58 (2H, d, J 11.9 Hz), 4.20 (1H, s), 3.82 (1H, m), 3.71 (3H, s), 3.60 (1H, m), 3.17 (1H, s), 3.08 (1H, m), 2.59 (1H, d, J 4.1 Hz), 2.45–2.30 (4H, m), 2.04 (1H, m), 1.18 (1H, m), 0.83 (3H, d, J 6.5 Hz); m/z (ES$^+$) 736 ([M+H]$^+$).

EXAMPLE 195b

Isomer B $\delta_H$(400 MHz, CDCl$_3$): 7.90 (1H, s), 7.85 (2H, s), 7.48 (2H, m), 7.33–7.09 (13H, m) 4.90 (1H, m), 4.75 (1H, m), 4.58 (2H, d, J 11.9 Hz), 4.33 (3H, s), 4.17 (1H, s), 3.83 (1H, m), 3.60 (1H, m), 3.37 (1H, s), 3.28 (1H, m), 2.59 (1H, d, J 4.1 Hz), 2.35 (3H, m), 2.04 (1H, m), 1.18 (1H, m), 0.83 (3H, d, J 6.5 Hz); m/z (ES$^+$) 736 ([M+H]$^+$).

EXAMPLE 196

(1S,2S,5R,6S,9S)-2-(1-(3,5-Bis(trifluoromethyl) phenyl)-2-hydroxy)ethoxy-6-(1-methyl-1H-tetrazol-5-yl)-1-phenyl-8-azabicyclo[3.2.1]octane hydrochloride (1S,2S,5R,6S,9S,11S)-2-(1-(3,5-Bis(trifluoromethyl) phenyl)-2-phenylmethoxy)ethoxy-6-(1-methyl-1H-tetrazol-5-yl)-1-phenyl-8-(1-phenylethyl)-8-azabicyclo[3.2.1]octane (Example 195a; 0.09 g, 0.12 mmol) and palladium hydroxide 20% on carbon (80 mg) in methanol (8 ml) were hydrogenated using the Parr™ apparatus for 2 hours. The mixture was filtered using a Whatman™ 0.2 micrometer filter. The filtrate was concentrated in vacuo, taken into dichloromethane and washed with saturated sodium hydrogen carbonate. The organic phase was separated using a bond elute cartridge and concentrated in vacuo. The hydrochloride salt was made in the usual manner and recrystallized from methanol/diethyl ether to give the title compound (37 mg, 54%).

m/z (ES$^+$) 542 ([M+H]$^+$).

EXAMPLE 197

(1S,2S,5R,6S,9S)-2-(1-(3,5-Bis(trifluoromethyl) phenyl)-2-hydroxy)ethoxy-6-(2-methyl-2H-tetrazol-5-yl)-1-phenyl-8-azabicyclo[3.2.1]octane (1S,2S,5R,6S,9S,11S)-2-(1-(3,5-Bis(trifluoromethyl) phenyl)-2-phenylmethoxy)ethoxy-6-(2-methyl-2H-tetrazol-5-yl)-1-phenyl-8-(1-phenylethyl)-8-azabicyclo[3.2.1]octane (Example 195b; 0.14 g, 0.19 mmol) and palladium hydroxide 20% on carbon (118 mg) in methanol (8 ml) were hydrogenated using the Parr™ apparatus for 2 hours. The mixture was filtered using a Whatman™ 0.2 micrometer filter. The filtrate was concentrated in vacuo, taken into dichloromethane and washed with saturated sodium hydrogen carbonate. The organic phase was separated using a bond elute cartridge and concentrated in vacuo to afford the title compound as a white foam (93 mg, 93%).

m/z (ES$^+$) 542 ([M+H]$^+$).

EXAMPLE 198

(1R*,2R*,5S*,6R*)-8-Benzyl-2-{(1R*)-1-[3,5-bis (trifluoromethyl)phenyl]-2-methoxyethoxy}-6-cyano-1-phenyl-8-azabicyclo[3.2.1]octane (1R*,2R*,5S*,6R*)-8-Benzyl-2-{(1R*)-1-[3,5-bis (trifluoromethyl)phenyl]-2-hydroxyethoxy}-6-cyano-1-phenyl-8-azabicyclo[3.2.1]octane (Example 156; 0.3 g, 0.5 mmol), methyl iodide (0.04 g, 0.02 ml, 0.3 mmol), sodium hydride (0.04 g, 1.6 mmol) and 18-crown-6 (0.3 g, 1 mmol) in N,N-dimethylformamide (3 ml) was heated at 60° C. for 1 hour. The mixture was quenched with water and extracted with ethyl acetate. The organics were collected, dried (MgSO$_4$) and concentrated in vacuo. The residue was purified by flash column chromatography, eluting with 30% ethyl acetate/hexane. The title compound was isolated as a white crystalline solid (285 mg, 97%).

$\delta_H$(400 MHz, CDCl$_3$): 7.79 (1H, s), 7.54 (4H, m), 7.38 (2H, m), 7.20 (3H, m), 7.14 (3H, m), 4.59 (1H, m), 4.27 (1H, d, J 15.9 Hz), 4.03 (1H, d, J 16.0 Hz), 3.94 (1H, s), 3.82 (1H, s), 3.55 (1H, m), 3.40 (4H, m), 2.84 (1H, m), 2.32 (3H, m), 2.16 (1H, m), 1.69 (1H, m).

EXAMPLE 199

(1R*,2R*,5S*,6R*)-8-Benzyl-2-{(1R*)-[3,5-bis (trifluoromethyl)phenyl]-2-methoxyethoxy}-1-phenyl-6-(tetrazol-5-yl)-8-azabicyclo[3.2.1]octane (1R*,2R*,5S*,6R*)-8-Benzyl-2-{(1R*)-1-[3,5-bis (trifluoromethyl)phenyl]-2-methoxyethoxy}-6-cyano-1-phenyl-8-azabicyclo[3.2.1]octane (Example 198; 0.3 g, 0.5 mmol), sodium azide (0.2 g, 1.4 mmol), ammonium chloride (0.1 g, 1.4 mmol) and N,N-dimethylformamide (3 ml) were heated under nitrogen at 120° C. for 48 hours. The mixture was allowed to cool and diluted with water, the organics were extracted into ethyl acetate and concentrated in vacuo. The residue was purified by flash column chromatography, eluting with 5% methanol/dichloromethane to afford the title compound (56 mg, 19%).

$\delta_H$(400 MHz, CDCl$_3$): 7.84 (1H, s), 7.60 (2H, s), 7.46–7.15 (10H, m), 4.75 (1H, m), 4.33 (1H, d, J 14.1 Hz), 4.15 (1H, s), 4.10 (1H, d, J 14.1 Hz), 3.56 (1H, m), 3.54 (1H, m), 3.48 (1H, m), 3.42 (4H, m), 2.89 (1H, m), 2.52 (1H, m), 2.40 (3H, m), 2.01 (1H, m).

EXAMPLE 200

(1R*,2R*,5S*,6R*)-8-Benzyl-2-{(1R*)-1-[3,5-bis (trifluoromethyl)phenyl]-2-methoxyethoxy}-6-(2-methyl-1H-tetrazol-5-yl)-1-phenyl-8-azabicyclo [3.2.1]octane (1R*,2R*,5S*,6R*)-8-Benzyl-2-{(1R*)-1-[3,5-bis (trifluoromethyl)phenyl]-2-methoxyethoxy}-1-phenyl-6-(tetrazol-5-yl)-8-azabicyclo[3.2.1]octane (Example 199; 0.05 g, 0.1 mmol), methyl iodide (0.04 g 0.02 ml, 0.3 mmol) and potassium carbonate (0.04 g, 0.3 mmol) in acetonitrile were heated at 60° C. for 1.5 hours. The mixture was quenched with water and concentrated in vacuo, the residue was partitioned between water and dichloromethane using a bond elute cartridge. The organics were collected and concentrated in vacuo and the residue purified by preparative thin layer chromatography eluting with 5% methanol/dichloromethane. The title compound was isolated as a white solid (33 mg, 58%).

m/z (ES$^+$) 646 ([M+H]$^+$).

EXAMPLE 201

(1R*,2R*,5S*,6R*)-2-{(1R*)-1-[3,5-Bis (trifluoromethyl)phenyl]-2-methoxyethoxy}-6-(2-methyl-1H-tetrazol-5-yl)-1-phenyl-8-azabicyclo [3.2.1]octane (1R*,2R*,5S*,6R*)-8-Benzyl-2-{(1R*)-1-[3,5-bis (trifluoromethyl)phenyl]-2-methoxyethoxy}-6-(2-methyl-1H-tetrazol-5-yl)-1-phenyl-8-azabicyclo[3.2.1]octane (Example 200; 0.03 g, 0.05 mmol), palladium, 5% on carbon (20 mg) and acetic acid (0.5 ml) were placed on the Parr™ apparatus for 2 hours. The mixture was filtered using a Whatman™ 0.2·m filter and concentrated in vacuo. The residue was taken into dichloromethane and washed with NaHCO$_3$ and the phases separated using a bond elute cartridge. The organics were concentrated in vacuo and the title compound isolated as the hydrochloride salt.

m/z (ES$^+$) 556 ([M+H]$^+$).

What is claimed is:

1. A compound of the formula (I):

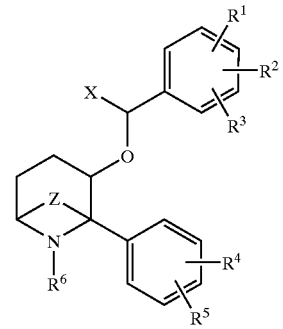

wherein

X represents hydrogen, C$_{1-4}$alkyl optionally substituted by a hydroxy, methoxy or benzyloxy group, or CO$_2$(C$_{1-2}$alkyl);

Z is —CR$^9$R$^{10}$CH$_2$— or —CH$_2$CR$^9$R$^{10}$—;

R$^1$ is hydrogen, halogen, C$_{1-6}$alkyl, C$_{1-6}$alkoxy, fluoroC$_{1-6}$alkyl, fluoroC$_{1-6}$alkoxy, C$_{3-7}$cycloalkyl, C$_{3-7}$cycloalkylC$_{1-4}$alkyl, NO$_2$, CN, SR$^a$, SOR$^a$, SO$_2$R$^a$, CO$_2$R$^a$, CONR$^a$R$^b$, C$_{2-6}$alkenyl, C$_{2-6}$alkynyl or C$_{1-4}$alkyl substituted by C$_{1-4}$alkoxy, wherein R$^a$ and R$^b$ each independently represent hydrogen or C$_{1-4}$alkyl;

R$^2$ is hydrogen, halogen, C$_{1-6}$alkyl, fluoroC$_{1-6}$alkyl or C$_{1-6}$alkoxy substituted by C$_{1-4}$alkoxy;

R$^3$ is hydrogen, halogen or fluoroC$_{1-6}$alkyl;

R$^4$ represents hydrogen, halogen, C$_{1-6}$alkyl, C$_{1-6}$alkoxy, CF$_3$, OCF$_3$, NO$_2$, CN, SR$^a$, SOR$^a$, SO$_2$R$^a$, CO$_2$R$^a$, CONR$^a$R$^b$, C$_{2-6}$alkenyl, C$_{2-6}$alkynyl or C$_{1-4}$alkyl substituted by C$_{1-4}$alkoxy, where R$^a$ and R$^b$ are as previously defined;

R$^5$ represents hydrogen, halogen, C$_{1-6}$alkyl, CF$_3$ or C$_{1-6}$alkoxy substituted by C$_{1-4}$alkoxy;

R$^6$ represents hydrogen, hydroxy, COR$^a$, CO$_2$R$^a$, COCONR$^a$R$^b$, COCO$_2$R$^a$, C$_{1-6}$alkyl, C$_{2-6}$alkenyl, or $C_{1-6}$alkyl substituted by a group selected from $CO_2R^a$, $CONR^aR^b$, hydroxy, CN, $COR^a$, $NR^aR^b$, $C(NOH)NR^aR^b$, $CONHphenyl(C_{1-4}alkyl)$, $COCO_2R^a$, $CONHNR^aR^b$, $C(S)NR^aR^b$, $CONR^aC_{1-6}alkylR^{14}$, $CONR^{11}C_{2-6}alkenyl$, $CONR^{11}C_{2-6}alkynyl$, $COCONR^aR^b$, $CONR^aC(NR^b)NR^aR^b$, $CONR^a$heteroaryl, (wherein heteroaryl is selected from the group consisting of pyrrolyl, furanyl, thienyl, pyridyl, pyrazolyl, imidazolyl, oxazolyl, isoxazolyl, thiazolyl, isothiazolyl, pyrazinyl, pyrimidinyl, pyridazinyl, triazolyl, oxadiazolyl, thiadiazolyl, triazinyl, tetrazolyl, indole, benzofuran, benzthiophene, benzimidazole, benzoxazole, benzthiazole and quinolinyl), and phenyl, optionally substituted by one, two or three substituents selected from $C_{1-6}$alkyl, $C_{1-6}$alkoxy, halogen and trifluoromethyl;

or $R^6$ represents a group of the formula —$CH_2C\equiv CCH_2NR^7R^8$ where $R^7$ and $R^8$ are as defined below;

or $R^6$ represents $C_{1-6}$alkyl, optionally substituted by oxo, substituted by heterocyclic ring which is selected from the group consisting of 1,3-imidazol-4-yl, 1,2,4-triazol-3-yl, 1,2,3-triazol-4-yl, 2-oxo-1,3-imidazol-4-yl and 3-oxo-1,2,4-triazol-5-yl, which is unsubstituted or substituted by =O or =S or a group of the formula —Y—$NR^7R^8$ where Y is $C_{1-6}$alkylene or $C_{3-6}$cycloalkyl;

$R^7$ represents hydrogen or $C_{1-4}$alkyl, $C_{3-7}$cycloalkyl, $C_{3-7}$cycloalkyl$C_{1-4}$alkyl, or $C_{2-4}$alkyl substituted by $C_{1-4}$alkoxy or hydroxyl;

$R^8$ represents hydrogen or $C_{1-6}$alkyl, $C_{1-6}$alkoxy, $C_{3-7}$cycloalkyl, $C_{3-7}$cycloalkyl$C_{1-4}$alkyl, phenyl or $C_{1-4}$alkyl substituted by a group selected from $C_{1-4}$alkoxy, hydroxyl, $CO_2R^a$, $NR^aR^b$, phenyl, phenyloxy, pyrrolyl, furanyl, thienyl, pyridyl, pyrazolyl, imidazolyl, oxazolyl, isoxazolyl, thiazolyl, isothiazolyl, pyrazinyl, pyrimidinyl, pyridazinyl, triazolyl, oxadiazolyl, thiadiazolyl, triazinyl, tetrazolyl, indole, benzofuran, benzthiophene, benzimidazole, benzoxazole, benzthiazole, quinolinyl, azetidinyl, pyrrolidino, piperidino, piperazino, morpholino, or thiomorpholino;

or $R^7$, $R^8$ and the nitrogen atom to which they are attached form azetidinyl, pyrrolidinyl, piperidinyl, morpholino, or piperazinyl which is unsubstituted or substituted by one or two groups selected from methyl, hydroxy, $CO_2(C_{1-2}alkyl)$, phenyl, benzyl or $C_{1-4}$alkoxy optionally substituted by a $C_{1-4}$alkoxy or hydroxyl group, and optionally containing a double bond, which ring may optionally contain an oxygen or sulphur ring atom, a group S(O) or $S(O)_2$ or a second nitrogen atom which will be part of a NH or $NR^c$ moiety where $R^c$ is $C_{1-4}$alkyl, hydroxy$C_{1-4}$alkyl, $C_{1-4}$alkoxy$C_{1-4}$alkyl, phenyl or benzyl;

or $R^7$, $R^8$ and the nitrogen atom to which they are attached form 5-azabicyclo[2.1.1]hexyl, 5-azabicyclo[2.2.1]heptyl, 6-azabicyclo[3.2.1]octyl, 2-azabicyclo[2.2.2]octyl, 6-azabicyclo[3.2.2]nonyl, 6-azabicyclo[3.3.1]nonyl, 6-azabicyclo[3.2.2]decyl, 7-azabicyclo[4.3.1]decyl, 7-azabicyclo[4.4.1]undecyl or 8-azabicyclo[5.4.1]dodecyl;

or Y, $R^7$ and the nitrogen atom to which they are attached form a azetidinyl, pyrrolidinyl or morpholinyl ring;

$R^9$ represents hydrogen, hydroxy, oxo, $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, fluoro$C_{1-6}$alkyl, $C_{1-6}$alkoxy, fluoro$C_{1-6}$alkoxy, hydroxy$C_{1-6}$alkyl, $C_{1-6}$alkoxy$C_{1-4}$alkyl, $C_{1-6}$alkoxy$C_{1-4}$alkoxy, fluoro$C_{1-6}$alkoxy$C_{1-4}$alkyl, $C_{2-6}$alkenyloxy, $C_{2-6}$alkynyloxy, $C_{3-7}$cycloalkoxy, $C_{3-7}$cycloalkyl$C_{1-4}$alkoxy, phenyl, phenyl($CH_2$), phenyloxy, phenyl($CH_2$)oxy, cyano, halogen, $NR^7R^8$, $CH_2NR^7R^8$, $SR^{12}$, $SOR^{12}$, $SO_2R^{12}$, $OSO_2R^{12}$, $NR^aCOR^{12}$, $CH(OH)R^{12}$, $COR^{12}$, $CO_2R^{12}$, $CONR^7R^8$, $CONHNH_2$, $CH_2OR^{13}$, pyrrolyl, furanyl, thienyl, pyridyl, pyrazolyl, imidazolyl, oxazolyl, isoxazolyl, thiazolyl, isothiazolyl, pyrazinyl, pyrimidinyl, pyridazinyl, triazolyl, oxadiazolyl, thiadiazolyl, triazinyl, tetrazolyl, indole, benzofuran, benzthiophene, benzimidazole, benzoxazole, benzthiazole, quinolinyl, pyrrolyl$C_{1-4}$alkyl, furanyl $C_{1-4}$alkyl, thienyl$C_{1-4}$alkyl, pyridyl$C_{1-4}$alkyl, pyrazolyl$C_{1-4}$alkyl, imidazolyl$C_{1-4}$alkyl, oxazoly$C_{1-4}$alkyll, isoxazolyl$C_{1-4}$alkyl, thiazolyl$C_{1-4}$alkyl, isothiazolyl$C_{1-4}$alkyl, pyrazinyl$C_{1-4}$alkyl, pyrimidinyl$C_{1-4}$alkyl, pyridazinyl$C_{1-4}$alkyl, triazolyl$C_{1-4}$alkyl, oxadiazolyl$C_{1-4}$alkyl, thiadiazolyl$C_{1-4}$alkyl, triazinyl$C_{1-4}$alkyl, tetrazolyl $C_{1-4}$alkyl, indole$C_{1-4}$alkyl, benzofuran$C_{1-4}$alkyl, benzthiophene$C_{1-4}$alkyl, benzimidazole$C_{1-4}$alkyl, benzoxazole$C_{1-4}$alkyl, benzthiazole$C_{1-4}$alkyl and quinolinyl$C_{1-4}$alkyl;

$R^{10}$ represents hydrogen, halogen or hydroxy;

$R^{11}$ represents hydrogen or $C_{1-6}$alkyl;

$R^{12}$ represents hydrogen, $C_{1-6}$alkyl, $C_{1-6}$alkoxy, fluoro$C_{1-6}$alkyl or phenyl optionally substituted by one, two or three substituents selected from $C_{1-6}$alkyl, $C_{1-6}$alkoxy, halogen or trifluoromethyl;

$R^{13}$ represents $C_{1-4}$alkyl substituted by a group selected from hydroxy, $COR^a$, $CO_2R^a$, $CONR^aR^b$, pyrrolyl, furanyl, thienyl, pyridyl, pyrazolyl, imidazolyl, oxazolyl, isoxazolyl, thiazolyl, isothiazolyl, pyrazinyl, pyrimidinyl, pyridazinyl, triazolyl, oxadiazolyl, thiadiazolyl, triazinyl, tetrazolyl, indole, benzofuran, benzthiophene, benzimidazole, benzoxazole, benzthiazole, quinolinyl;

$R^{14}$ represents $OR^a$, $CONR^aR^b$, pyrrolyl, furanyl, thienyl, pyridyl, pyrazolyl, imidazolyl, oxazolyl, isoxazolyl, thiazolyl, isothiazolyl, pyrazinyl, pyrimidinyl, pyridazinyl, triazolyl, oxadiazolyl, thiadiazolyl, triazinyl, tetrazolyl, indole, benzofuran, benzthiophene, benzimidazole, benzoxazole, benzthiazole, or quinolinyl;

or a pharmaceutically acceptable salt or N-oxide thereof.

2. The compound of claim 1 wherein $R^1$ is hydrogen, $C_{1-4}$alkyl, $C_{1-4}$alkoxy, halogen or $CF_3$.

3. The compound of claim 1 wherein $R^2$ is hydrogen, $C_{1-4}$alkyl, $C_{1-4}$alkoxy, halogen or $CF_3$.

4. The compound of claim 1 wherein $R^3$ is hydrogen, fluorine, chlorine or $CF_3$.

5. The compound of claim 1 wherein $R^4$ is hydrogen or fluorine.

6. The compound of claim 1 wherein $R^5$ is hydrogen.

7. The compound of claim 1 wherein $R^6$ is hydrogen or $C_{1-6}$alkyl, or a $C_{1-3}$alkyl group substituted by 1,3-imidazol-4-yl, 1,2,4-triazol-3-yl, 1,2,3-triazol-4-yl, 2-oxo-1,3-imidazol-4-yl or 3-oxo-1,2,4-triazol-5-yl.

8. The compound of claim 1 wherein Z is —$CR^9R^{10}CH_2$—.

9. The compound of claim 1 wherein $R^9$ is hydrogen, hydroxy, oxo, $C_{1-6}$alkoxy, $C_{1-6}$alkoxy$C_{1-4}$alkyl, hydroxy $C_{1-4}$alkyl, cyano, $NR^7R^8$, $CH_2NR^7R^8$, $SO_2R^d$, $CH(OH)R^{12}$, $COR^{12}$, $CO_2R^{12}$, $CONR^7R^8$, phenyl, pyrrolyl, furanyl, thienyl, pyridyl, pyrazolyl, imidazolyl, oxazolyl, isoxazolyl, thiazolyl, isothiazolyl, pyrazinyl, pyrimidinyl, pyridazinyl, triazolyl, oxadiazolyl, thiadiazolyl, triazinyl, tetrazolyl, indole, benzofuran, benzthiophene, benzimidazole, benzoxazole, benzthiazole, quinolinyl, pyrrolyl$C_{1-4}$alkyl, furanyl$C_{1-4}$alkyl, thienyl$C_{1-4}$alkyl, pyridyl$C_{1-4}$alkyl, pyrazolyl$C_{1-4}$alkyl, imidazolyl$C_{1-4}$alkyl, oxazoly$C_{1-4}$alkyll, isoxazolyl$C_{1-4}$alkyl, thiazolyl$C_{1-4}$alkyl, isothiazolyl $C_{1-4}$alkyl, pyrazinyl$C_{1-4}$alkyl, pyrimidinyl$C_{1-4}$alkyl, pyridazinyl$C_{1-4}$alkyl, triazolyl$C_{1-4}$alkyl, oxadiazolyl $C_{1-4}$alkyl, thiadiazolyl$C_{1-4}$alkyl, triazinyl$C_{1-4}$alkyl, tetrazolyl$C_{1-4}$alkyl, indole$C_{1-4}$alkyl, benzofuran$C_{1-4}$alkyl, benzthiophene$C_{1-4}$alkyl, benzimidazole$C_{1-4}$alkyl, benzoxazole$C_{1-4}$alkyl, benzthiazole$C_{1-4}$alkyl and quinolinyl$C_{1-4}$alkyl, or $CH_2OR^{13}$, where said phenyl is optionally substituted by one or two substituents selected from $C_{1-4}$alkyl, $C_{1-4}$alkoxy, halogen or trifluoromethyl.

10. The compound of claim 1 wherein $R^{10}$ is hydrogen, fluorine or hydroxy.

11. The compound of claim 1 wherein X is hydrogen, methyl or hydroxymethyl.

12. The compound of claim 1 of the formula (Ia):

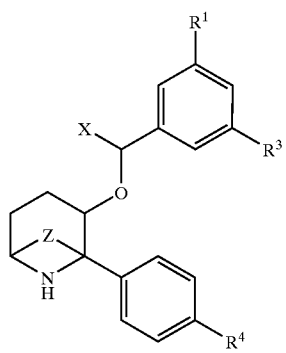

(Ia)

wherein Z is —$CR^9R^{10}CH_2$—;

or a pharmaceutically acceptable salt thereof.

13. The compound of claim 1 wherein the stereochemistry of the 1-, 2-, and 5-positions is as shown in formula (Ib):

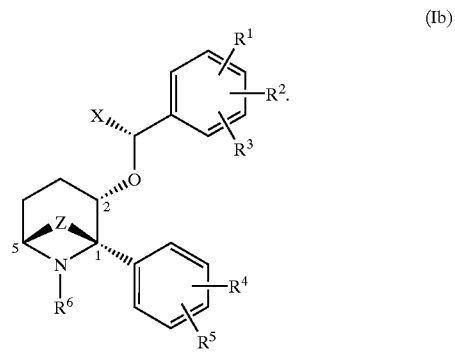

(Ib)

14. A pharmaceutical composition comprising the compound of claim 1 and at least one pharmaceutically acceptable carrier or excipient.

15. A method for the treatment of physiological disorders associated with an excess of tachykinins, which method comprises administration to a patient in need thereof of a tachykinin, reducing amount of the compound of claim 1.

16. The method according to claim 15 for the treatment, migraine, emesis, postherpetic neuralgia, depression or anxiety.

* * * * *